US009701681B2

(12) United States Patent
Kim et al.

(10) Patent No.: US 9,701,681 B2
(45) Date of Patent: Jul. 11, 2017

(54) FUSED RING HETEROARYL COMPOUNDS AND THEIR USE AS TRK INHIBITORS

(71) Applicants: CMG Pharmaceutical Co., Ltd., Seongnam-si, Gyeonggi-do (KR); HANDOK INC., Seoul (KR)

(72) Inventors: Moonsoo Kim, Seoul (KR); Chaewoon Lee, Seoul (KR); Gilnam Lee, Seoul (KR); Cheol Hwan Yoon, Seongnam (KR); Jeongbeob Seo, Seongnam (KR); Je Hak Kim, Anyang (KR); MinWoo Lee, Hwaseong-si (KR); Hankyul Jeong, Yangju-si (KR); Hyang Choi, Seoul (KR); Myung Eun Jung, Yongin (KR); Kinam Lee, Yongin (KR); Hyun Jung Kim, Yongin (KR); Hye Kyoung Kim, Yongin (KR); Jae Il Lee, Yongin (KR); Misoon Kim, Yongin (KR); Soongyu Choi, Yongin (KR)

(73) Assignees: CMG PHARMACEUTICAL CO., LTD., Seongnam, Gyeonggi-Do (KR); HANDOK INC., Seoul (KR)

(*) Notice: Subject to any disclaimer, the term of this patent is extended or adjusted under 35 U.S.C. 154(b) by 0 days.

(21) Appl. No.: 14/968,208

(22) Filed: Dec. 14, 2015

(65) Prior Publication Data

US 2016/0168156 A1    Jun. 16, 2016

Related U.S. Application Data

(60) Provisional application No. 62/092,193, filed on Dec. 15, 2014.

(51) Int. Cl.
*C07D 487/04*    (2006.01)

(52) U.S. Cl.
CPC ................... *C07D 487/04* (2013.01)

(58) Field of Classification Search
CPC .................................................. C07D 487/04
See application file for complete search history.

(56) References Cited

FOREIGN PATENT DOCUMENTS

| WO | 2009/140128 A2 | 11/2009 |
| WO | 2010/048314 A1 | 4/2010 |
| WO | 2011/006074 A1 | 1/2011 |
| WO | 2011/029027 A1 | 3/2011 |
| WO | 2011/146336 A1 | 11/2011 |
| WO | 2012/034095 A1 | 3/2012 |

OTHER PUBLICATIONS

Patapoutian et al., "Trk receptors: mediators of neurotrophin action", Current Opinion in Neurobiology, 2001, vol. 11, pp. 272-280.

Woolf et al. "Nerve Growth Factor Contributes To The Generation Of Inflammatory Sensory Hypersensitivity", Neuroscience, 1994, vol. 62, No. 2, pp. 327-331.
Zahn et al., "Effect of Blockade of Nerve Growth Factor and Tumor Necrosis Factor on Pain Behaviors After Plantar Incision", The Journal of Pain, 2004, vol. 5, No. 3, pp. 157-163.
McMahon, et al. "The biological effects of endogenous nerve growth factor on adult sensory neurons revealed by a trkA-IgG fusion molecule", Nature Medicine, Aug. 1995, vol. 1, No. 8, pp. 774-780.
Ma et al., "The progressive tactile hyperalgesia induced by peripheral inflammation is nerve growth factor dependent", NeuroReport, 1997, vol. 8, pp. 807-810.
Shelton et al. "Nerve growth factor mediates hyperalgesia and cachexia in auto-immune arthritis", Pain, 2005, vol. 116, pp. 8-16.
Delafoy et al., "Role of nerve growth factor in the trinitrobenzene sulfonic acid-induced colonic hypersensitivity", Pain, 2003, vol. 105, pp. 489-497.
Lamb et al., "Nerve growth factor and gastric hyperalgesia in the rat", Neurogastroenterol Motil, 2003, vol. 15, pp. 355-361.
Jaggar et al., "Inflammation of the rat urinary bladder is associated with a referred thermal hyperalgesia which is nerve growth factor dependent", British Journal of Anaesthesia, 1999, vol. 83, No. 3, pp. 442-448.
Matayoshi et al., "Actions of brain-derived neurotrophic factor on spinal nociceptive transmission during inflammation in the rat", J Physiol., 2005, vol. 569.2, pp. 685-695.

(Continued)

*Primary Examiner* — Rebecca Anderson
(74) *Attorney, Agent, or Firm* — Knobbe Martens Olson & Bear LLP

(57) ABSTRACT

The disclosure provides novel chemical compounds represented by Formula I or a pharmaceutically acceptable salt, solvate, polymorph, ester, tautomer or prodrug thereof. The compounds can be used as an inhibitor of Trk and are useful in the treatment of pain, cancer, inflammation, neurodegenerative disease and certain infectious diseases.

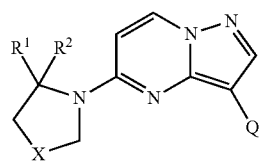

In some compounds of Formula I, Q is —CH=CR³C(O)NR⁴R⁵, —C≡CC(O)NR⁴R⁵, or

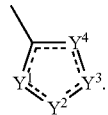

19 Claims, No Drawings

(56) References Cited

OTHER PUBLICATIONS

Thompson et al., "Brain-derived neurotrophic factor is an endogenous modulator of nociceptive responses in the spinal cord", Proc. Natl. Acad. Sci. USA, Jul. 1999, vol. 96, pp. 7714-7718.
Li et al., Brain derived neurotrophic factor (BDNF) contributes to the pain hypersensitivity following surgical incision in the rats, Molecular Pain, 2008, vol. 4, No. 27, pp. 1-11.
Brodeur, "Neuroblastoma: Biological Insights Into a Clinical Enigma", Nature Reviews Cancer, 2003, vol. 3, pp. 203-216.
Kruttgen et al., "The Dark Side of the NGF Family: Neurotrophins in Neoplasias", Brain Pathology, 2006, vol. 16, pp. 304-310.
Dionne et al., "Cell Cycle-independent Death of Prostate Adenocarcinoma Is Induced by the trk Tyrosine Kinase Inhibitor CEP-751 (KT6587)", Clinical Cancer Research, 1998, vol. 4, pp. 1887-1898.
Dang et al., "Expression of nerve growth factor receptors is correlated with progression and prognosis of human pancreatic cancer", Journal of Gastroenterology and Hepatology, 2006, vol. 21, pp. 850-858.
Marchetti et al., "Frequent Mutations in the Neurotrophic Tyrosine Receptor Kinase Gene Family in Large Cell Neuroendocrine Carcinoma of the Lung", Human Mutation, 2008, vol. 29, No. 5, pp. 609-616.
Bardelli et al., "Mutational Analysis of the Tyrosine Kinome in Colorectal Cancers", Science, 2003, vol. 300, p. 949.
Nakagawara, "Trk receptor tyrosine kinases: A bridge between cancer and neural development", Cancer Letters, 2001, vol. 169, pp. 107-114.
Meyer et al., "Remarkable leukemogenic potency and quality of a constitutively active neurotrophin receptor, DTrkA", Leukemia, 2007, vol. 21, pp. 2171-2180.
Pierotti et al., "Oncogenic rearrangements of the NTRK1/NGF receptor", Cancer Letters, 2006, vol. 232, pp. 90-98.
Adriaenssens et al., "Nerve Growth Factor Is a Potential Therapeutic Target in Breast Cancer", Cancer Res, 2008, vol. 68, No. 2, pp. 346-351.
Freund-Michel. et. al., "The nerve growth factor and its receptors in airway inflammatory diseases", Pharmacology & Therapeutics, 2008, vol. 117, pp. 52-76.
Hu et. al., "Decrease in Bladder Overactivity With REN1820 In Rats With Cyclophosphamide Induced Cystitis", The Journal of Urology, 2005, vol. 173, pp. 1016-1021.
Di Mola et. al., "Nerve growth factor and Trk high affinity receptor (TrkA) gene expression in inflammatory bowel disease", Gut, 2000, vol. 46, pp. 670-678.
Dou et. al., "Increased nerve growth factor and its receptors in atopic dermatitis: an immunohistochemical study", Archives of Dermatological Research, 2006, vol. 298, pp. 31-37.
Raychaudhuri et. al., "K252a, a High-Affinity Nerve Growth Factor Receptor Blocker, Improves Psoriasis: An In Vivo Study Using the Severe Combined Immunodeficient Mouse-Human Skin Model", The Journal of Investigative Dermatology, 2004, vol. 122, pp. 812-819.
Sohrabji et al., "Estrogen—BDNF interactions: Implications for neurodegenerative diseases", Frontiers in Neuroendocrinology, 2006, vol. 27, pp. 404-414.
Vaishnavi et. al., "Oncogenic and drug-sensitive NTRK1 rearrangements in lung cancer", Nature Medicine, 2013, vol. 19, No. 11, pp. 1469-1472.
Heller, "Electrical Wiring of Redox Enzymes", Acc. Chem. Res., 1990, vol. 23, No. 5, pp. 128-134.
Berge et al., "Pharmaceutical Salts", Journal of Pharmaceutical Sciences, Jan. 1977, vol. 66, No. 1, pp. 1-19.
Written Opinion dated Apr. 19, 2016 of PCT/IB2015/002521 which is the parent application—6 pages.

FUSED RING HETEROARYL COMPOUNDS AND THEIR USE AS TRK INHIBITORS

FIELD

This disclosure relates to new chemical entities and use of the entities as TRK inhibitors.

BACKGROUND

Trk's are high affinity tyrosine kinase receptors that are activated by Neurotrophins (NT). The Trk receptor family has three members: TrkA, TrkB and TrkC. Among the neurotrophins are a group of soluble growth factors Nerve Growth Factor (NGF) which activates TrkA, Brain-Derived Neurotrophic Factor (BDNF) and NT-4/5 which activates TrkB, and Neurotrophin-3 (NT3) which activates TrkC. Trk's are widely expressed in neuronal tissue and are implicated in the maintenance, signaling and survival of neuronal cells (Patapoutian, A. et al., *Current Opinion in Neurobiology*, 2001, 11, 272-280).

Inhibitors of the Trk/neutrophin pathway have been demonstrated to be effective in numerous pre-clinical animal models of pain. Antagonistic NGF and TrkA antibodies have been shown to be efficacious in inflammatory and neuropathic pain animal models and in human clinical trials. (Woolf, C. J. et al. *Neuroscience* 1994, 62, 327-331; Zahn, P. K. et al. *J. Pain* 2004, 5, 157-163; McMahon, S. B. et al. *Nat. Med.* 1995, 1, 774-780; Ma, Q. P. and Woolf, C. J. *Neuroreport* 1997, 8, 807-810; Shelton, D. L. et al. *Pain* 2005, 116, 8-16; Delafoy, L. et al. *Pain* 2003, 105, 489-497; Lamb, K. et al. *Neurogastroenterol. Motil.* 2003, 15, 355-361; Jaggar, S. I. et al. *Br. J. Anaesth.* 1999, 83, 442-448.)

It has been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. Activation of the BDNF/TrkB pathway has been implicated in numerous studies as a modulator of marious types of pain including inflammatory pain (Matayoshi, S., *J. Physiol.* 2005, 569:685-695), neuropathic pain (Thompson, S. W. *Proc. Natl. Acad. Sci. USA* 1999, 96:7714-7718) and surgical pain (Li, C.-Q. et al. *Molecular Pain*, 2008, 4(28), 1-11). Because TrkA and TrkB kinases may serve as a mediator of NGF driven biological responses, inhibitors of TrkA and/or other Trk kinases may provide an effective treatment for chronic pain states.

The association between overexpression, activation, amplification and/or mutation of Trk kinases and several cancers as seen with studies conduct on neuroblastoma (Brodeur, G. M. *Nat. Rev. Cancer* 2003, 3, 203-216), ovarian cancer (Kruettgen et al. *Brain Pathology* 2006, 16:304-310), prostate cancer (Dionne et al. *Clin. Cancer Res.* 1998, 4(8), 1887-1898), pancreatic cancer (Dang et al. *j of Gastroenterology and Hepatology* 2006, 21(5), 850-858), large cell neuroendocrine tumors (Marchetti et al. *Human Mutation* 2008, 29(5), 609-616), and colorectal cancer (Bardelli, A. *Science* 2003, 300, 949) support the reasoning that therapeutic implications of an effective Trk inhibitor may extend far beyond pain therapy. In preclinical models of cancer, non-selective small molecule inhibitors of TrkA, B and C were efficacious in both inhibiting tumor growth and stopping tumor metastasis (Nakagawara, A. *Cancer Letters* 2001, 169:107-114; Meyer, J. et al. *Leukemia* 2007, 1-10; Pierottia, M. A. and Greco A. *Cancer Letters*, 2006, 232: 90-98; Eric Adriaenssens, E. et al. *Cancer Res* 2008, 68(2), 346-351).

Also, inhibition of the neurotrophin/Trk pathway has been shown to be effective in treatment of inflammatory lung diseases including asthma (Freund-Michel, V. et. al. *Pharmacology & Therapeutics* 2008, 117(1), 52-76), interstitial cystitis (Hu Vivian Y, et. al. *The Journal of Urology* 2005, 173(3), 1016-1021), inflammatory bowel diseases including ulcerative colitis and Crohn's disease (Di Mola, F. F, et. al. *Gut* 2000, 46(5), 670-678) and inflammatory skin diseases such as atopic dermatitis (Dou, Y. C. et. al. *Archives of Dermatological Research* 2006, 298(1), 31-37), eczema and psoriasis (Raychaudhuri, S. P. et. al. *J. Investigative Dermatology* 2004, 122(3), 812-819).

Modulation of the neutrophin/Trk pathway has also been shown to have an effect in the etiology neurodegenerative diseases including multiple sclerosis, Parkinson's disease and Alzheimer's disease (Sohrabji, F. et. al. Neuroendocrinology 2006, 27(4), 404-414).

Recent literature has identified new gene fusions in patients with lung cancer harboring the kinase domain of the NTRK1 gene that encodes the high-affinity nerve growth factor receptor-TrkA protein (Vaishnavi, A. et. al. *Nature Medisine* 2013, 19(11), 1469-1472).

The foregoing information is provided as background for understanding features of the invention and does not constitute an admission of prior art.

SUMMARY

The present application discloses new chemical entities. These new chemical entities can work Trk inhibitors and are believed to be useful in the treatment of multiple types of acute and chronic pain including but not limited to inflammatory pain, neuropathic pain, and pain associated with cancer, surgery and bone fracture. The compounds are also believed to be useful in the treatment of cancer, inflammation, neurodegenerative diseases and certain infectious diseases.

One aspect of the invention provides a compound of Formula I or a pharmaceutically acceptable salt, solvate, polymorph, ester, tautomer or prodrug thereof:

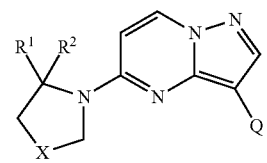

Formula I

In some embodiments, $R^1$ of Formula I is a phenyl ring optionally substituted with one or more substituent groups or a 5-6 membered heteroaryl ring optionally substituted with one or more substituent groups, wherein the one or more substituent groups are independently selected from the group consisting of halogen, —$CF_3$, —$CHF_2$, $NH_2$, hydroxyl, linear C1-C4 alkyl, branched C1-C4 alkyl, linear C1-C4 alkoxy, and branched C1-C4 alkoxy. Further, in Formula I, $R^2$ is selected from the group consisting of hydrogen, linear C1-C4 alkyl and branched linear C1-C4 alkyl. Further, in Formula I, X is selected from the group consisting of —$CH_2$—, —$CH_2CH_2$—, —$CH_2O$—, —$CH_2NH$—, —$CH_2N$(C1-C4 alkyl)-, —CH(F)—, —$CF_2$—, —CH(Cl)—, —CH(OH)—, —CH(OCH_3)—, —CH(NH$_2$)—, or —C(CH$_3$)$_2$—. Further, in Formula I, Q is selected from the group consisting of —CH=CR$^3$C(O)NR$^4$R$^5$, —CH=CR$^3$NR$^4$C(O)R$^5$, —CH=CR$^3$NR$^4$C(O)NR$^4$R$^5$, —CH=CR$^3$R$^5$, —C≡CC(O)NR$^4$R$^5$, —C≡CR$^5$, and

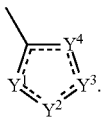

In Q of Formula I, R$^3$ is selected from the group consisting of hydrogen, halogen, linear C1-C6 alkyl and branched C1-C6 alkyl. In Q of Formula I, —NR$^4$R$^5$ either forms a 4-7 membered heterocyclic ring or does not form a ring structure, the heterocylic ring being either heteroaryl or heterocycloalkyl ring. When —NR$^4$R$^5$ forms a 4-7 membered heterocyclic ring, the 4-7 membered heterocyclic ring includes an optional second heteroatom in addition to the nitrogen of —NR$^4$R$^5$ and is optionally substituted with one or more substituent groups independently selected from the group consisting of linear C1-C6 alkyl, branched C1-C6 alkyl, hydroxyl, carboxylic acid, linear C1-C4 alkyl carboxylic acid, and branched C1-C4 alkyl carboxylic acid branched. When —NR$^4$R$^5$ does not form a ring structure, R$^4$ is selected from the group consisting of hydrogen, linear C1-C6 alkyl and branched C1-C6 alkyl, and R$^5$ is selected from the group consisting of hydrogen, linear C1-C6 alkyl optionally substituted with at least one fluorine or at least one hydroxyl, branched C1-C6 alkyl optionally substituted with at least one fluorine or at least one hydroxyl, and C1-C6 cycloalkyl optionally substituted with at least one fluorine or at least one hydroxyl. Further in Q of Formula I, Y$^1$, Y$^2$, Y$^3$, and Y$^4$ are each independently selected from the group consisting of —CH, N, O, S, —CR$^6$, and —NR$^6$, wherein R$^6$ is selected from the group consisting of hydrogen, linear C1-C4 alkyl, branched C1-C4 alkyl, 5-6 membered aryl ring, 5-6 membered heteroaryl ring, 3-7 membered heterocycloalkyl ring, 3-7 membered cycloalkyl ring, —NHCO-(aryl ring), and —CH$_2$CO—(C3-C6 membered heterocylic ring).

In other embodiments, R$^1$ of Formula I is a 6-membered aryl or heteroaryl ring optionally substituted with one or more substituent groups independently selected from the group consisting of halogen, hydroxyl, linear C1-C4 alkyl, branched C1-C4 alkyl, linear C1-C4 alkoxy, and branched C1-C4 alkoxy. Further, in Formula I, R$^2$ is hydrogen, linear C1-C4 alkyl or branched linear C1-C4 alkyl; and X is —CH$_2$—, —CH$_2$CH$_2$—, —CH$_2$O— or —CH(Z)—, wherein Z is halogen; and Q is —CH=CR$^3$C(O)NR$^4$R$^5$, —C≡CC(O)NR$^4$R$^5$, or

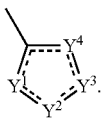

Further, in Q of Formula I, R$^3$ is hydrogen or halogen. Further, in Q of Formula I, —NR$^4$R$^5$ either forms a 4-7 membered heterocyclic ring or does not form a ring structure, the heterocylic ring being either heteroaryl or heterocycloalkyl ring. When —NR$^4$R$^5$ forms a 4-7 membered heterocyclic ring, the 4-7 membered heterocyclic ring includes an optional second heteroatom in addition to the nitrogen of —NR$^4$R$^5$ and is optionally substituted with one or more substituent groups independently selected from the group consisting of linear C1-C6 alkyl, branched C1-C6 alkyl, hydroxyl, carboxylic acid, linear C1-C4 alkyl carboxylic acid, and branched C1-C4 alkyl carboxylic acid branched. When —NR$^4$R$^5$ does not form a ring structure, R$^4$ is selected from the group consisting of hydrogen, linear C1-C6 alkyl and branched C1-C6 alkyl, and R$^5$ is selected from the group consisting of hydrogen, linear C1-C6 alkyl optionally substituted with at least one fluorine or at least one hydroxyl, branched C1-C6 alkyl optionally substituted with at least one fluorine or at least one hydroxyl, and C1-C6 cycloalkyl optionally substituted with at least one fluorine or at least one hydroxyl. In Q of Formula I, Y$^1$, Y$^2$, Y$^3$ and Y$^4$ are each independently selected from the group consisting of —CH, N, O, S, —CR$^6$, and —NR$^6$, wherein R$^6$ is selected from the group consisting of hydrogen, linear C1-C4 alkyl, branched C1-C4 alkyl, 5-6 membered aryl ring, 5-6 membered heteroaryl ring, 3-7 membered heterocycloalkyl ring, 3-7 membered cycloalkyl ring, —NHCO-(aryl ring), and —CH$_2$CO—(C3-C6 membered heterocylic ring).

In the forgoing compound of Formula I, R$^1$ a phenyl ring substituted with one or more substituent groups may be independently selected from the group consisting of fluorine, methoxy and ethoxy; R$^2$ and R$^3$ are H; R$^5$ may be selected from the group consisting of H, methyl, ethyl, iso-propyl, cyclopropyl, t-butyl, methoxyethyl and hydroxyethyl. In the compound of Formula I, R$^1$ may be a pyridine ring substituted with at least one selected from the group consisting of fluorine and methoxy; R$^2$ and R$^3$ are H; R$^5$ may be selected from the group consisting of H, methyl, ethyl, iso-propyl, cyclopropyl, t-butyl, methoxyethyl and hydroxyethyl. In the compound of Formula I, R$^1$ may be a pyrid-2-on-3-yl ring optionally substituted with one or more substituent groups independently selected from the group consisting of halogen and C1-C4 alkyl.

In the compound of Formula I, when —NR$^4$R$^5$ does not form a ring structure, R$^4$ is selected from the group consisting of hydrogen, linear C1-C6 alkyl and branched C1-C6 alkyl, and R$^5$ is selected from the group consisting of linear C1-C6 fluoroalkyl, branched C1-C6 fluoroalkyl, linear C1-C6 difluoroalkyl, branched C1-C6 difluoroalkyl, linear C1-C6 trifluoroalkyl, branched C1-C6 trifluoroalkyl, linear C1-C6 hyroxyalkyl, branched C1-C6 hyroxyalkyl, linear C2-C6 difluoroalkyl, and branched C2-C6 difluoroalkyl. In the compound of Formula I, —NR$^4$R$^5$ forming a 4-7 membered heterocyclic ring may be a 4-7 membered heterocycloalkyl ring. In the compound of Formula I, when —NR$^4$R$^5$ forms a 4-7 membered heterocyclic ring, the second heteroatom in the 4-7 membered heterocyclic ring may be selected from the group consisting of nitrogen, oxygen and sulfur.

The compound of Formula I is a compound of Formula II:

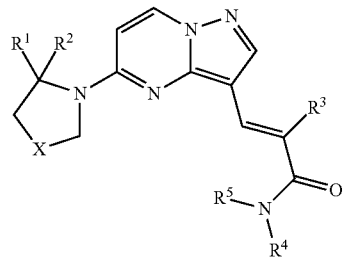

Formula II

The compound of Formula I is a compound of Formula III:

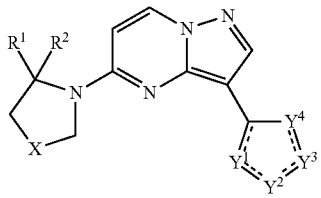

Formula III

The compound of Formula I is a compound of Formula IV:

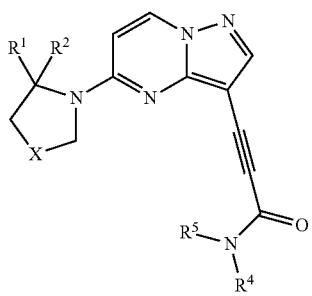

Formula IV

The salt of the compound of Formula I may be selected from the group consisting of acetate, benzoate, besylate, bitartrate, bromide, carbonate, chloride, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, oxalate, pamoate, phosphate, diphosphate, salicylate, disalicylate, stearate, succinate, sulfate, tartrate, tosylate, triethiodide, trifluoroacetate and valerate.

Another aspect of the invention provides a method of treating or prophylaxis of a TRK mediated disease selected from the group consisting of papillary thyroid carcinoma, pancreatic cancer, lung cancer, colon cancer, breast carcinoma, neuroblastoma, pain, cachexia, dermatitis and asthma. The method comprises administering a pharmaceutically effective amount of the compound of Formula I or a pharmaceutically acceptable salt thereof to a subject in need of such treatment.

Still another aspect of the invention provides a method of inhibiting a TRK enzyme. The method comprises administering a pharmaceutically effective amount of the compound of Formula I or a pharmaceutically acceptable salt thereof to a subject in need of such inhibition.

DETAILED DESCRIPTION OF EMBODIMENTS

The novel features of the invention are set forth with particularity in the appended claims. A better understanding of the features and advantages of the present invention will be obtained by reference to the following detailed description that sets forth illustrative embodiments, in which the principles of the invention are utilized. While some embodiments of the present invention have been shown and described herein such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Definitions

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, Formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical Formulas, written from left to right, they equally encompass the chemically identical substituents that would result from writing the structure from right to left. As a non-limiting example, $CH_2O$ is equivalent to $OCH_2$. Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, *Acc. Chem. Res.* 1990, 23, 128.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., $CH_2CH_3$), fully substituted (e.g., $CF_2CF_3$), mono-substituted (e.g., $CH_2CH_2F$) or substituted at a level anywhere in-between fully substituted and mono-substituted (e.g., $CH_2CHF_2$, $CF_2CH_3$, $CFHCHF_2$, etc.) It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-Cn, includes $C_1$-$C_2$, $C_1$-$C_3$, ... $C_1$-Cn. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, isobutyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The terms "heteroatom" or "hetero" as used herein, alone or in combination, refer to an atom other than carbon and hydrogen. Heteroatoms are independently selected from among oxygen, nitrogen, sulfur, phosphorous, silicon, selenium and tin but are not limited to these atoms. When two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkylene" as used herein, alone or in combination, refers to a diradical derived from the above-defined monoradical, alkyl. Examples include, but are not limited to methylene (—$CH_2$), ethylene (—$CH_2CH_2$), propylene (—$CH_2CH_2CH_2$), isopropylene (—CH($CH_3$)$CH_2$) and the like.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (CH=$CH_2$), 1-propenyl ($CH_2$CH=$CH_2$), isopropenyl [C($CH_3$)=$CH_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkynyl" as used herein, alone or in combination, refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. When two or more hydrogen atoms may be replaced with halogen atoms that are the same as each another (e.g. difluoromethyl). When two or more hydrogen atoms may be replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl).

A non-limiting example of "cycloalkyl" includes azinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl and quinolizinyl and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized $\pi$-electron system containing 4n+2 $\pi$ electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "heteroaryl" as used herein, alone or in combination, refers to optionally substituted aromatic mono-radicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. When two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide and the like.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Heterocycles can be optionally substituted. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom. The term "alkoxy" as used herein, alone or in combination, refers to an alkyl ether radical, O-alkyl, including the groups O-aliphatic and O-carbocycle, wherein the alkyl, aliphatic and carbocycle groups may be optionally substituted, and wherein the terms alkyl, aliphatic and carbocycle are as defined herein. Non-limiting examples of alkoxy radicals include methoxy, ethoxy, n-propoxy, iso-propoxy, n-butoxy, iso-butoxy, sec-butoxy, tertbutoxy and the like.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "solvate" as used herein refers to a combination of a compound of this invention with a solvent molecule formed by solvation. In some situations, the solvate refers to a hydrate, i.e., the solvent molecule is a water molecule, the combination of a compound of this invention and water forms a hydrate.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., *J. Pharm. Sci.* 1977, 66, 1-19.). Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, IV' ($C_{1-4}$ alkyl)$_4$, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The term "polymorph" or "polymorphism" as used herein refers to a compound of this invention present in different crystal lattice forms.

The term "ester" as used herein refers to a derivative of a compound of this invention derived from an oxoacid group and a hydroxyl group, either one of which can be present at the compound of this invention.

The term "tautomer" as used herein refers to an isomer readily interconverted from a compound of this invention by e.g., migration of a hydrogen atom or proton.

The term "pharmaceutically acceptable derivative or prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference. The prodrugs described herein include, but are not limited to, the following groups and combinations of these groups; amine derived prodrugs: Hydroxy prodrugs include, but are not limited to acyloxyalkyl esters, alkoxycarbonyloxyalkyl esters, alkyl esters, aryl esters and disulfide containing esters.

The term "Trk inhibitor" as used herein refers to a compound that exhibits an $IC_{50}$, with respect to Trk activity, of no more than about 100 μm activity, of no more than about 50 μM, as measured in the pan-Trk kinase assay described generally herein. "$IC_{50}$" is that concentration of inhibitor which reduces the activity of an enzyme (e.g., Trk) to half-maximal level. Compounds described herein have been discovered to exhibit inhibition against Trk. Compounds of the present invention preferably exhibit an $IC_{50}$ with respect to Trk of no more than about 10 μM, more preferably, no more than about 5 μm preferably, no more than about 1 μM, and most preferably, not more than about 200 nM, as measured in the Trk kinase assay described herein.

The term "selective," "selectively," or "selectivity" as used herein refers to a compound of this invention having a lower $IC_{50}$ value for a Trk enzyme as compared to any other enzymes (e.g., at least 2, 5, 10 or more-fold lower).

The term "subject", "patient" or "individual" as used herein in reference to individuals suffering from a disorder, a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, *Pharmaceutical Sciences* (current edition), Mack Publishing Co., Easton, Pa. In preferred embodiments, the compounds and compositions described herein are administered orally.

The term "acceptable" as used herein, with respect to a Formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "carrier" as used herein, refers to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent (s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

Novel Compounds

According to embodiments of the invention, novel chemical compounds include a compound of Formula I or a pharmaceutically acceptable salt, solvate, polymorph, ester, tautomer or prodrug thereof.

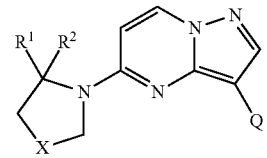

Formula I

In some embodiments, $R^1$ of Formula I is a phenyl ring optionally substituted with one or more substituent groups or a 5-6 membered heteroaryl ring optionally substituted with one or more substituent groups, wherein the one or more substituent groups are independently selected from the group consisting of halogen, $-CF_3$, $-CHF_2$, $NH_2$, hydroxyl, linear C1-C4 alkyl, branched C1-C4 alkyl, linear C1-C4 alkoxy, and branched C1-C4 alkoxy.

In some embodiments, $R^2$ is selected from the group consisting of hydrogen, linear C1-C4 alkyl and branched linear C1-C4 alkyl. Further, in Formula I, X is selected from the group consisting of $-CH_2-$, $-CH_2CH_2-$, $-CH_2O-$, $-CH_2NH-$, $-CH_2N(C1-C4\ alkyl)-$, $-CH(F)-$, $-CF_2-$, $-CH(Cl)-$, $-CH(OH)-$, $-CH(OCH_3)-$, $-CH(NH_2)-$, or $-C(CH_3)_2-$. Further, in Formula I, Q is selected from the group consisting of $-CH=CR^3C(O)NR^4R^5$, $-CH=CR^3NR^4C(O)R^5$, $-CH=CR^3NR^4C(O)NR^4R^5$, $-CH=CR^3R^5$, $-C\equiv CC(O)NR^4R^5$, $-C\equiv CCR^5$, and

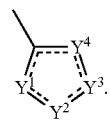

In some embodiments, $R^3$ is selected from the group consisting of hydrogen, halogen, linear C1-C6 alkyl and branched C1-C6 alkyl.

In some embodiments, $-NR^4R^5$ either forms a 4-7 membered heterocyclic ring or does not form a ring structure, the heterocylic ring being either heteroaryl or heterocycloalkyl ring.

In embodiments where $-NR^4R^5$ forms a 4-7 membered heterocyclic ring, the 4-7 membered heterocyclic ring includes an optional second heteroatom in addition to the nitrogen of $-NR^4R^5$ and is optionally substituted with one or more substituent groups independently selected from the group consisting of linear C1-C6 alkyl, branched C1-C6 alkyl, hydroxyl, carboxylic acid, linear C1-C4 alkyl carboxylic acid, and branched C1-C4 alkyl carboxylic acid branched.

In embodiments where $-NR^4R^5$ does not form a ring structure, $R^4$ is selected from the group consisting of hydrogen, linear C1-C6 alkyl and branched C1-C6 alkyl, and $R^5$ is selected from the group consisting of hydrogen, linear C1-C6 alkyl optionally substituted with at least one fluorine or at least one hydroxyl, branched C1-C6 alkyl optionally substituted with at least one fluorine or at least one hydroxyl, and C1-C6 cycloalkyl optionally substituted with at least one fluorine or at least one hydroxyl.

In some embodiments, $Y^1$, $Y^2$, $Y^3$, and $Y^4$ are each independently selected from the group consisting of —CH, N, O, S, —CR$^6$, and —NR$^6$, wherein R$^6$ is selected from the group consisting of hydrogen, linear C1-C4 alkyl, branched C1-C4 alkyl, 5-6 membered aryl ring, 5-6 membered heteroaryl ring, 3-7 membered heterocycloalkyl ring, 3-7 membered cycloalkyl ring, —NHCO-(aryl ring), and —CH$_2$CO—(C3-C6 membered heterocylic ring).

In some embodiments, the compound of Formula I is a compound of Formula II, III or IV:

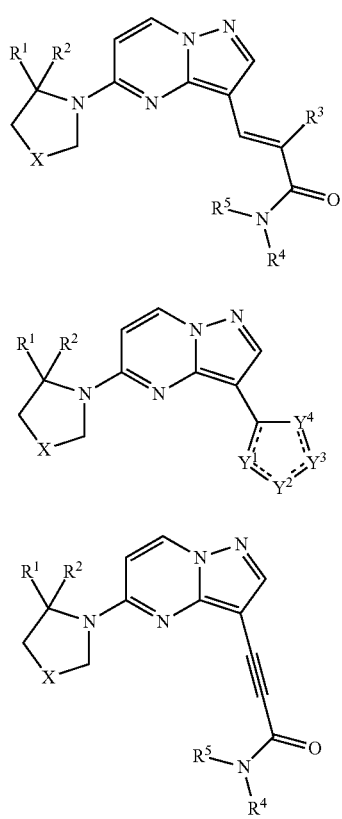

Formula II

Formula III

Formula IV

In some embodiments, some compounds of Formula I or a pharmaceutically acceptable salt, solvate, polymorph, ester, tautomer or prodrug thereof have a structure wherein, Q is 5-6 membered heteroaryl rings including, but are not limited to, the following structures:

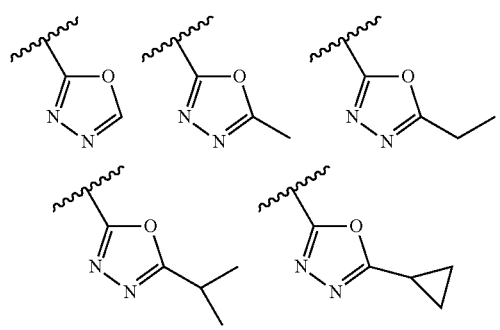

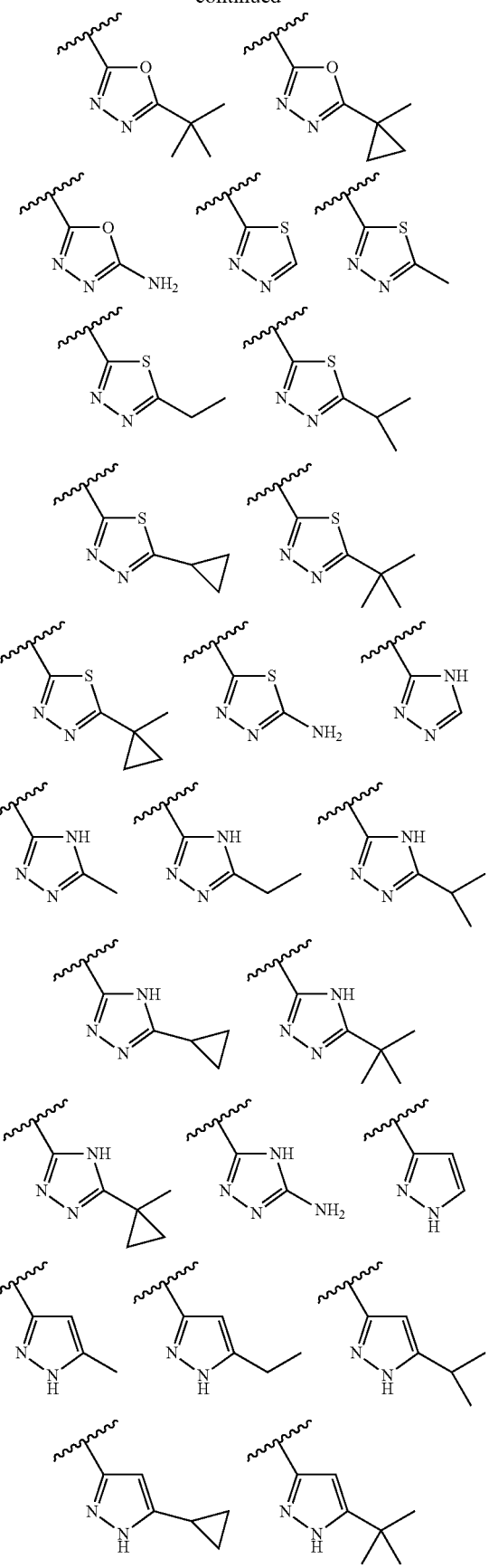

-continued

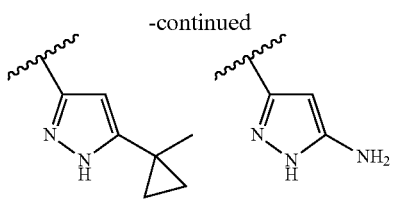

and tautomers of the foregoing ones.

Additional examples of Q include the following structures:

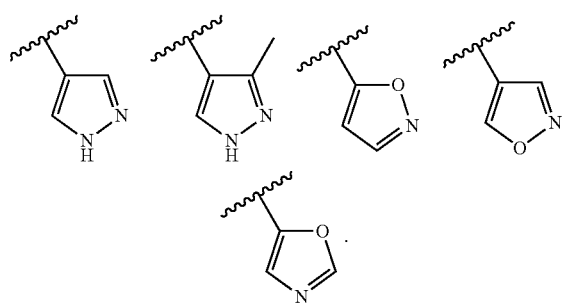

In certain embodiments, $R^5$ is selected from methyl, ethyl, propyl, isopropyl, tert-butyl, isobutyl, —C(CH$_3$)$_2$CH$_2$F, —CHCF$_2$, CH$_2$CHF$_2$, CF$_3$, CH$_2$CF$_3$ and CH(CH$_3$)CF$_3$.

In certain embodiments, $R^5$ is —(C1-C6)hydroxyalkyl or [(C1-C6)alkoxy](C1-C6)alkyl-. Examples include —CH$_2$CH$_2$OH, —CH$_2$CH$_2$CH$_2$OH, —CH$_2$CH$_2$CH$_2$CH$_2$OH, —CH$_2$CH(OH)CH$_3$, —C(CH$_3$)$_2$CH$_2$OH, —CH$_2$C(CH$_3$)$_2$OH, —CH(CH$_3$)CH$_2$OH, —CH$_2$C(CH$_3$)$_2$CH$_2$OH, —CH(CH$_2$OH)CH(CH$_3$)$_2$, —CH(CH$_2$CH$_3$)CH$_2$OH, —CH(CH$_2$OH)C(CH$_3$)$_3$, —CH$_2$CH$_2$OCH$_3$, —CH$_2$CH$_2$CH$_2$OCH$_3$, —CH$_2$CH$_2$CH$_2$CH$_2$OCH$_3$, —CH$_2$CH(OCH$_3$)CH$_3$, —C(CH$_3$)$_2$CH$_2$OCH$_3$, —CH$_2$C(CH$_3$)$_2$OCH$_3$, —CH(CH$_3$)CH$_2$OCH$_3$, —CH$_2$C(CH$_3$)$_2$CH$_2$OCH$_3$, —CH(CH$_2$OCH$_3$)CH(CH$_3$)$_2$, —CH(CH$_2$CH$_3$)CH$_2$OCH$_3$, and —CH(CH$_2$OCH$_3$)C(CH$_3$)$_3$. A particular example is —CH$_2$CH$_2$OH or CH$_2$CH$_2$OCH$_3$.

In one embodiment, $R^5$ is —(C1-C6)hydroxyalkyl or [(C1-C6)alkoxy](C1-C6)alkyl- and $R^4$ is hydrogen.

In one embodiment, $R^5$ is —(C1-C6)hydroxyalkyl or [(C1-C6)alkoxy](C1-C6)alkyl- and $R^4$ is —(C1-C6)alkyl.

In certain embodiments, $R^5$ is —(C2-C6)dihydroxyalkyl. Examples include —CH$_2$CH(OH)CH$_2$OH, —C(CH$_3$)(CH$_2$OH)$_2$, —CH(CH$_2$OH)$_2$ and —CH(CH$_2$OH)(CHOHCH$_3$). Particular examples include —CH$_2$CH(OH)CH$_2$OH and —C(CH$_3$)(CH$_2$OH)$_2$. In one embodiment, $R^5$ is —(C2-C6)dihydroxyalkyl and $R^4$ is hydrogen. In one embodiment, $R^5$ is —(C2-C6)dihydroxyalkyl and $R^4$ is —(C1-C6)alkyl.

In certain embodiments, $R^5$ is —O(C1-C6)alkyl which is optionally substituted with OH or (C1-C4)alkoxy, and $R^4$ is hydrogen. Examples of $R^5$ include —OMe, —OEt, —OCH$_2$CH$_2$OH, —OCH$_2$CH$_2$CH$_2$OH, —OCH$_2$CH(OH)CH$_3$, —OCH$_2$C(CH$_3$)$_2$OH, —OCH$_2$CH$_2$OCH$_3$, —OCH$_2$CH$_2$CH$_2$OCH$_3$, and —OCH$_2$CH(OCH$_3$)CH$_3$.

In certain embodiments $R^5$ is:

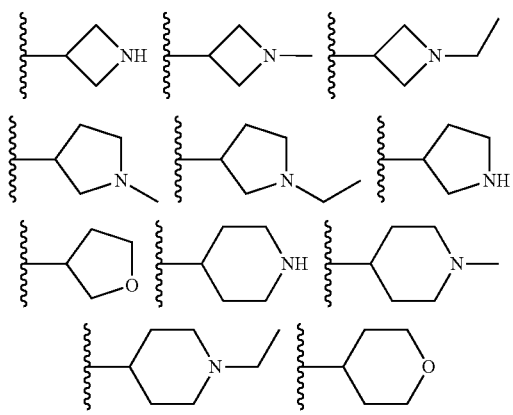

In certain embodiments $R^5$ is:

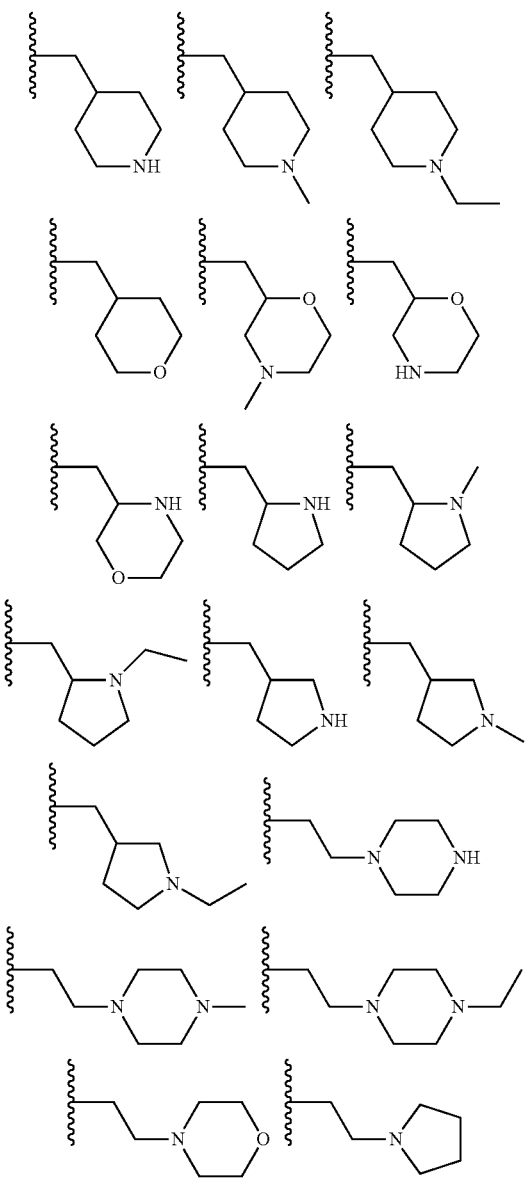

-continued

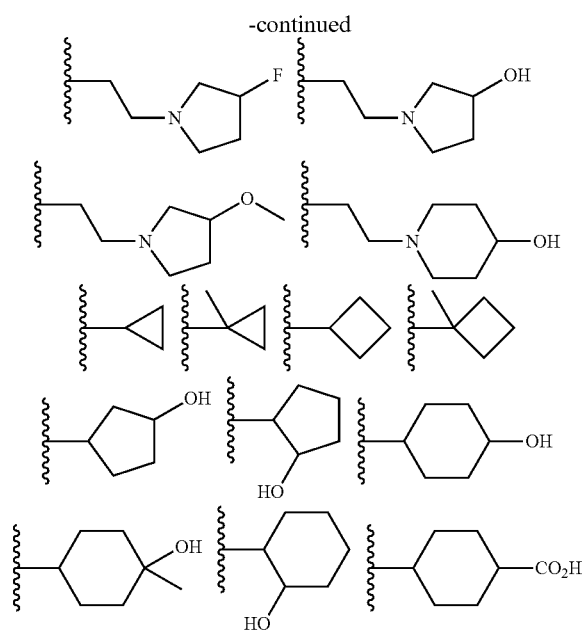

In certain embodiments, NR⁴R⁵ forms a 4-7 membered heterocyclic ring having a ring nitrogen atom and optionally having a second ring heteroatom selected from N and O, wherein said ring is optionally substituted with one or more substituents independently selected from (C1-C6)alkyl, OH, COOH, and (C1-C3 alkyl)COOH. In certain embodiments, the heterocyclic ring is optionally substituted with one or two of said substituents. Particular examples include, but are not limited to, the following structures:

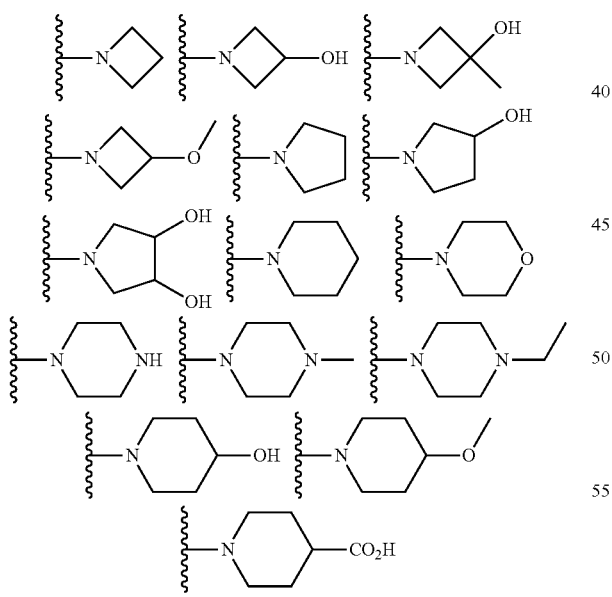

In some embodiments, R¹ is phenyl optionally substituted with one or more substituents independently selected from halogen, (C1-C4)alkoxy, —CF₃, —CHF₂, —O(C1-C4 alkyl), —(C1-C4)alkyl and NH₂, or a 5-6 membered heteroaryl ring having a ring heteroatom selected form N and S, wherein said heteroaryl ring is optionally substituted with one or more substituents independently selected from halo- gen, —O(C1-C4 alkyl), (C1-C4)alkyl and NH₂, or a pyrid-2-on-3-yl ring optionally substituted with one or more substituents independently selected from halogen and (C1-C4)alkyl. Particular examples include, but are not limited to, the following structures:

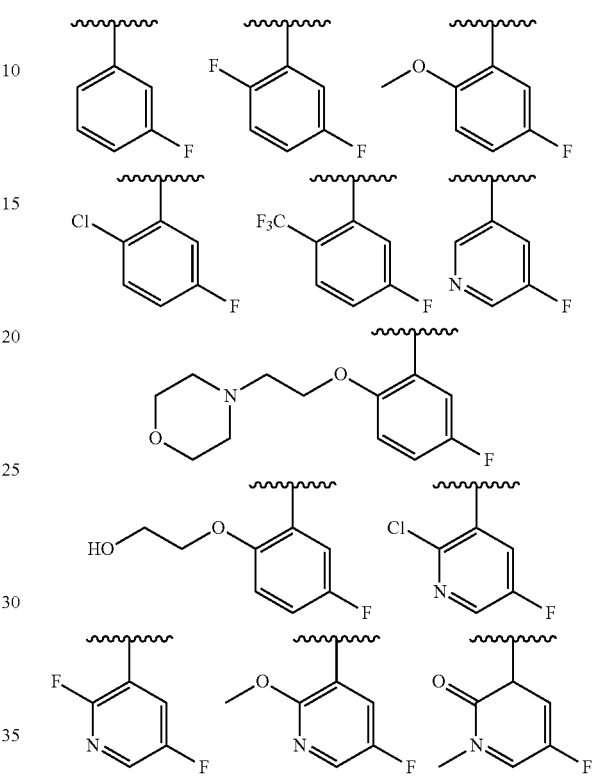

In embodiments, Formulas I, II, III, and IV include the compounds shown below:

1

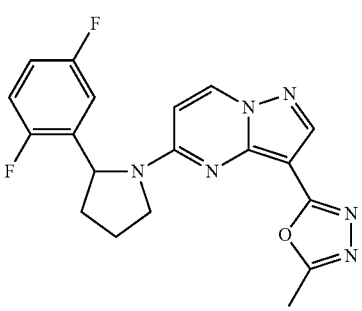

2

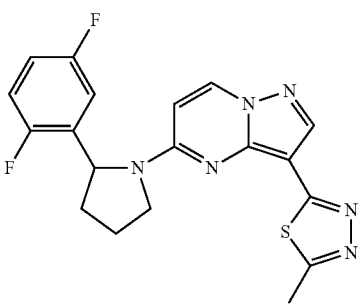

3
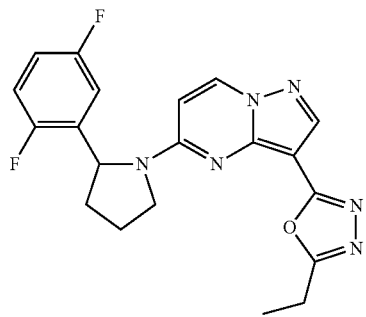
4
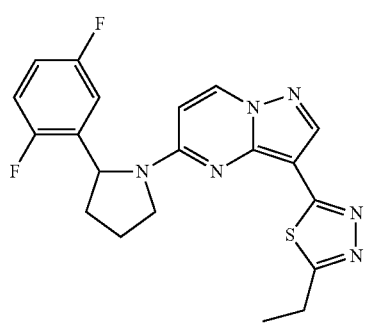
5
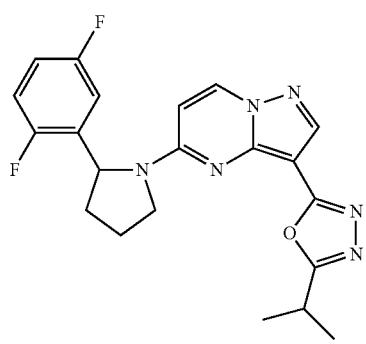
6
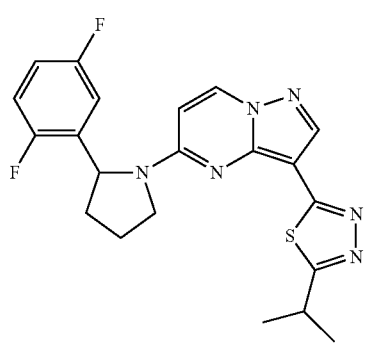
7
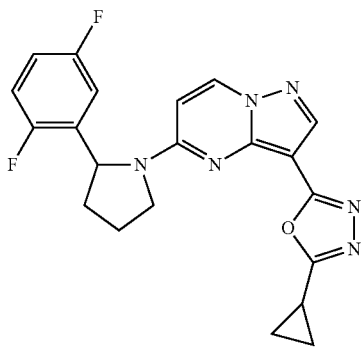
8
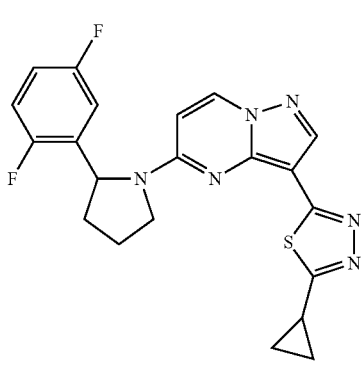
9
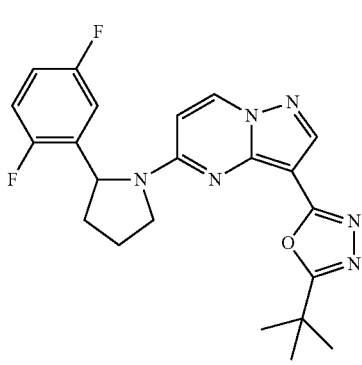
10
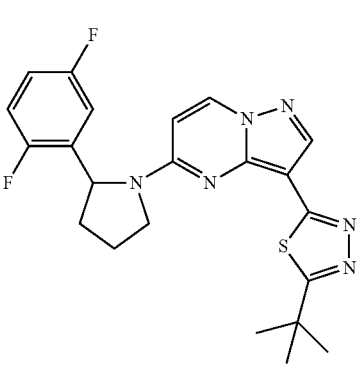

11
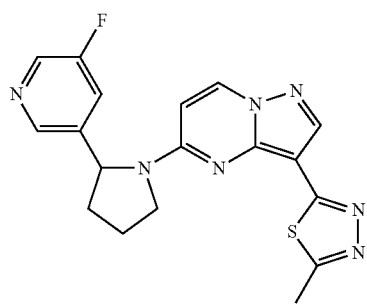
12
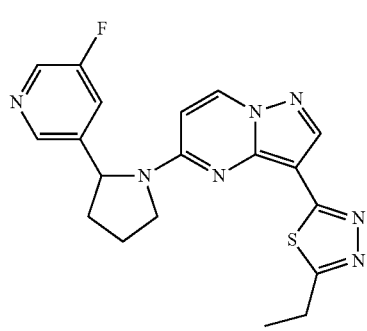
13
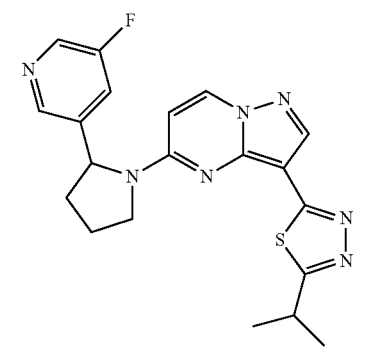
14
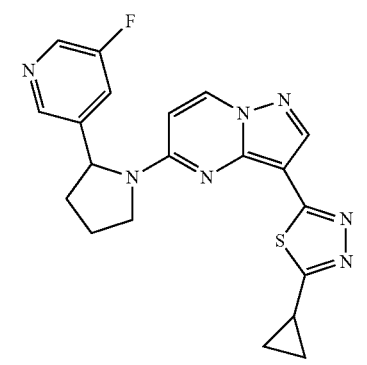
15
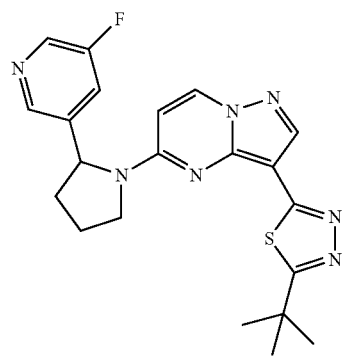
16
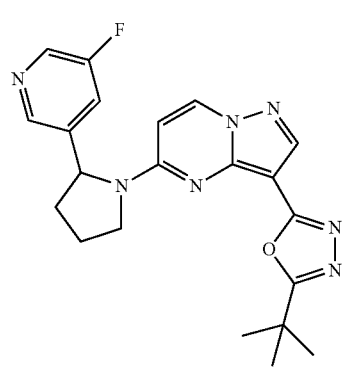
17
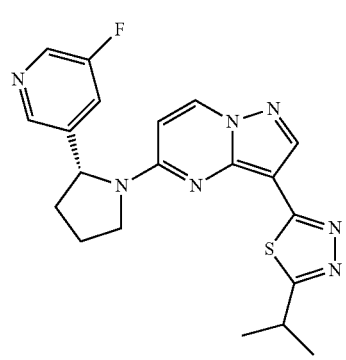
18
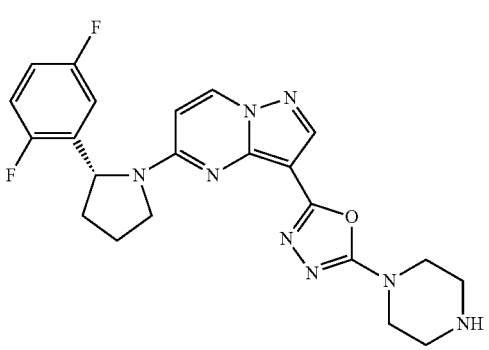

19
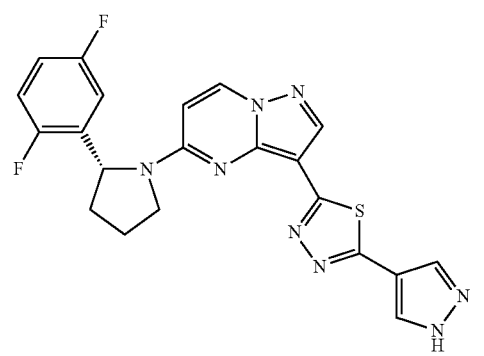
20
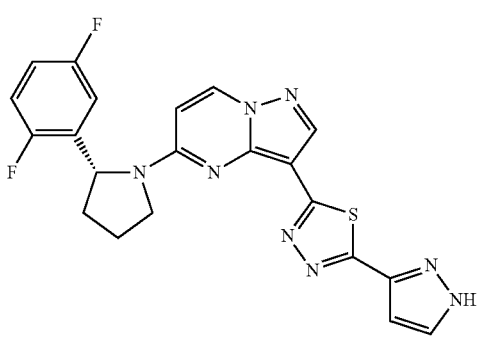
21
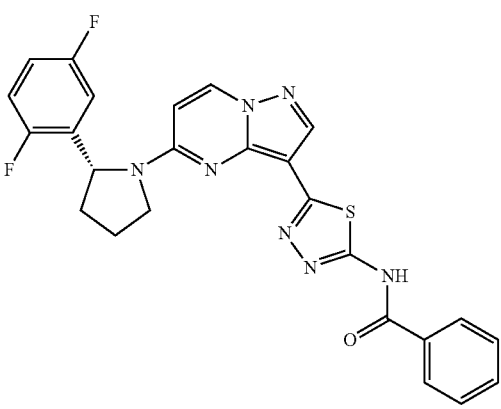
22
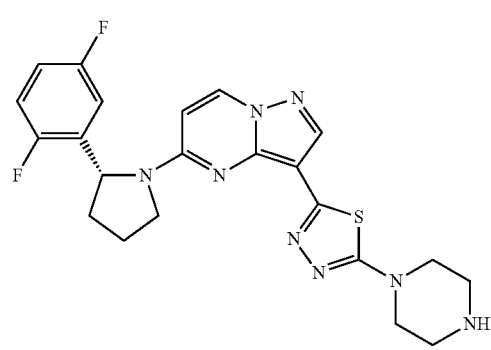
23
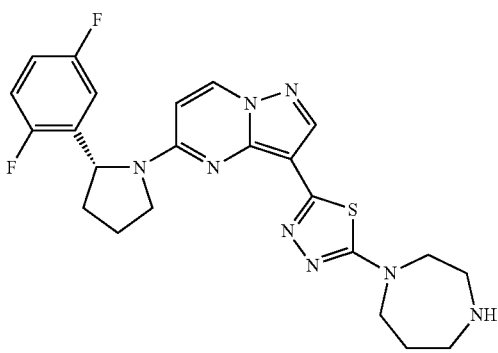
24
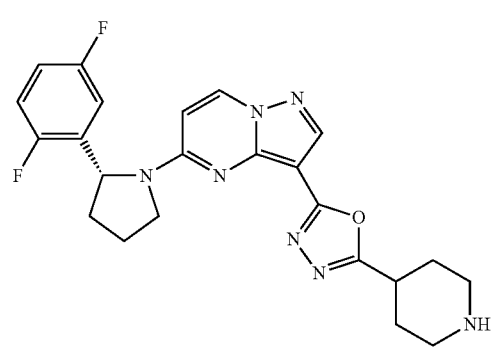
25
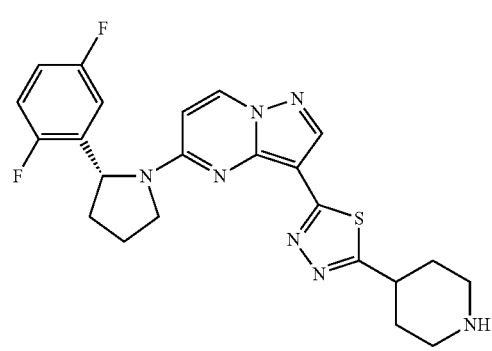
26
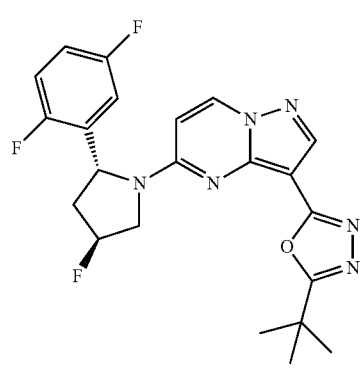

27
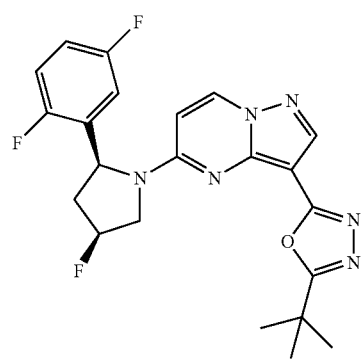
28
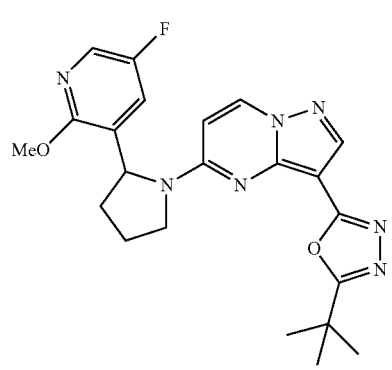
29
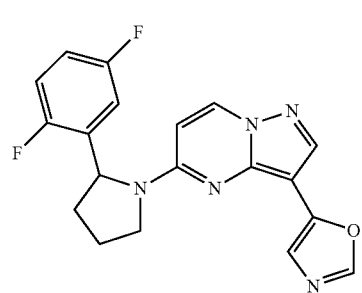
30
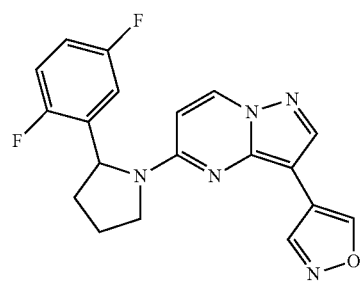
31
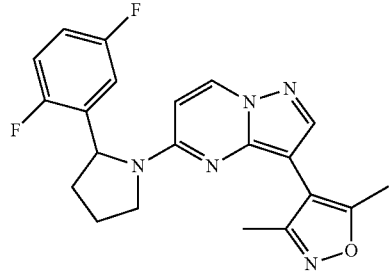
32
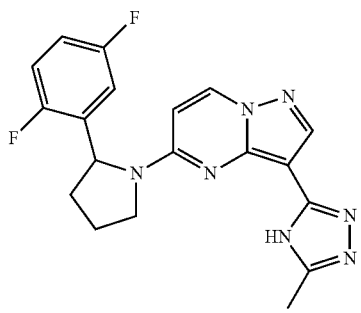
33
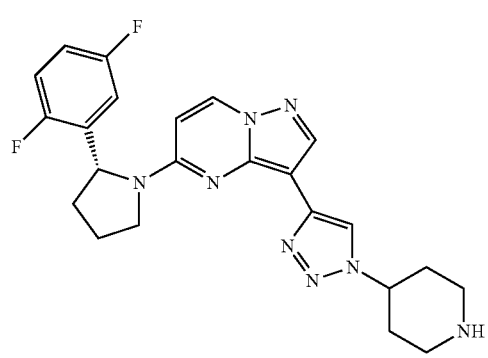
34
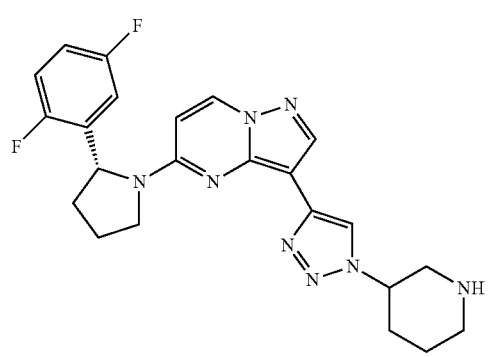
35
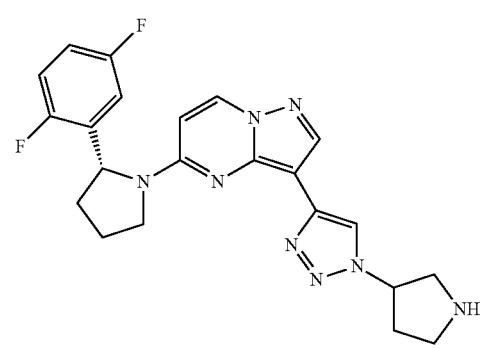

-continued
36
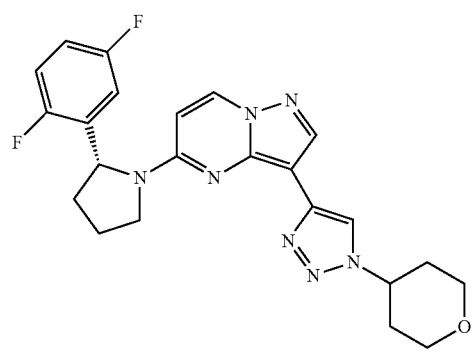
37
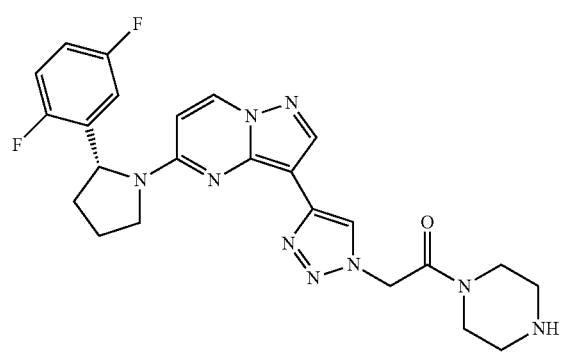
38
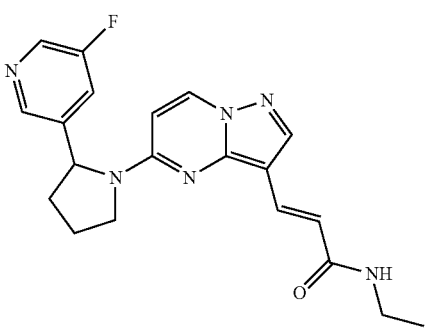
39
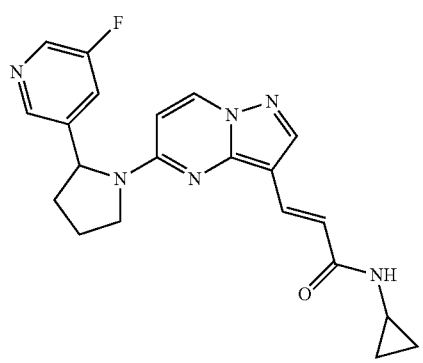
-continued
40
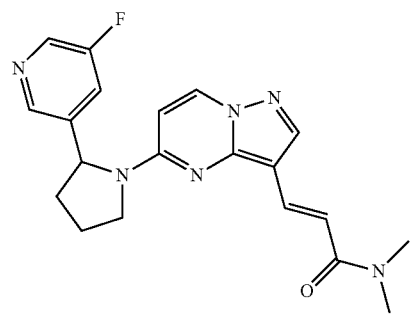
41
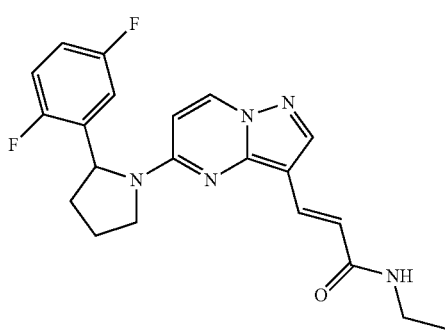
42
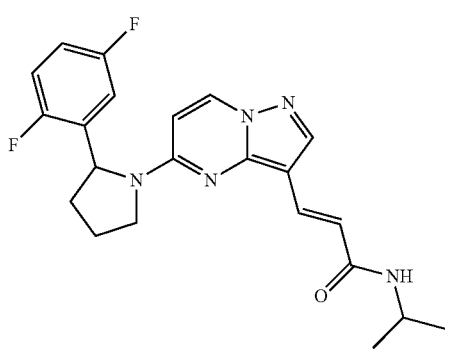
43
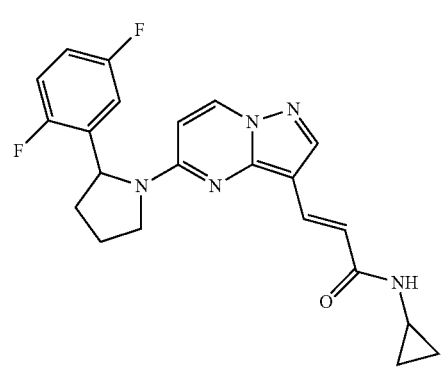

44
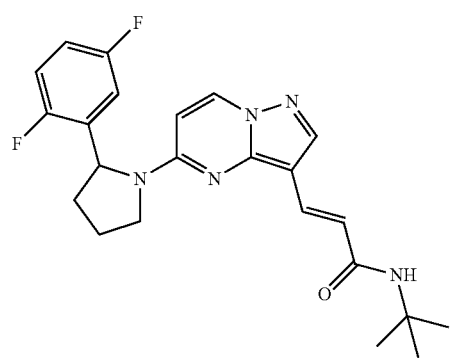
45
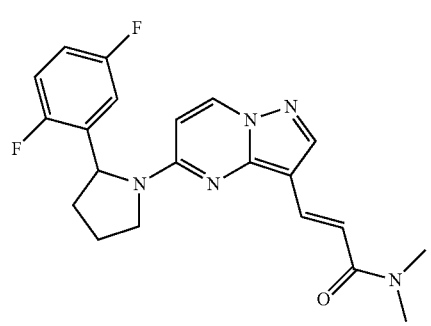
46
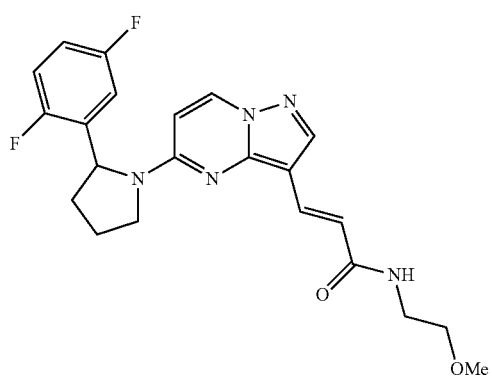
47
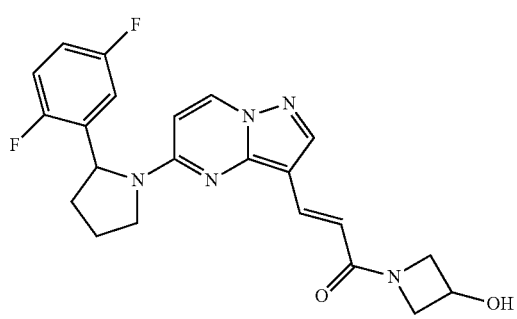
48
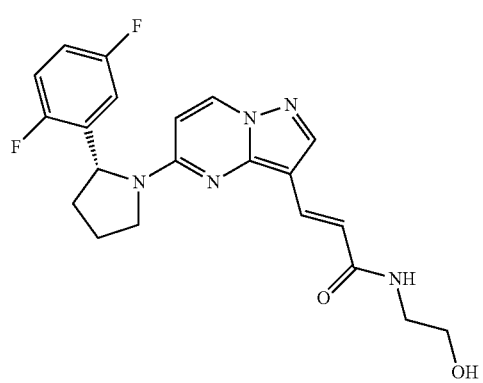
49
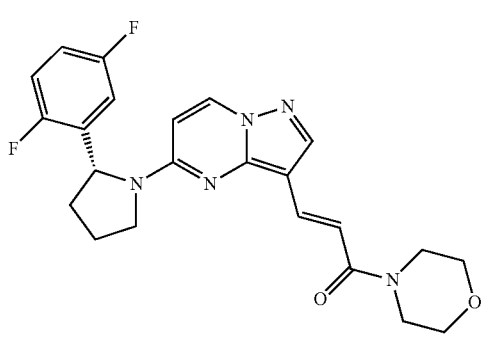
50
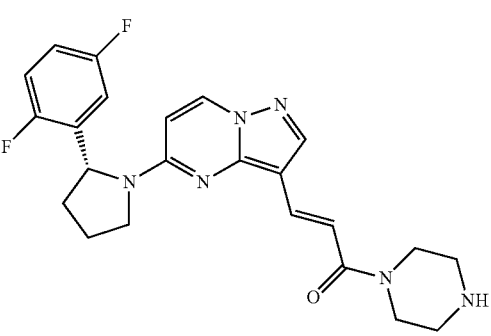
51
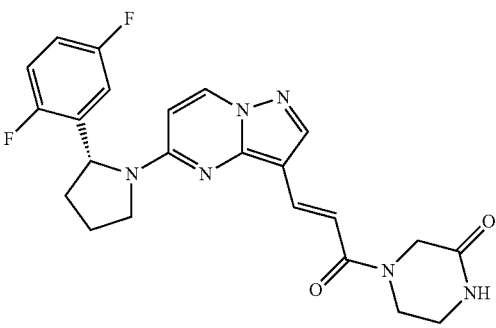

52
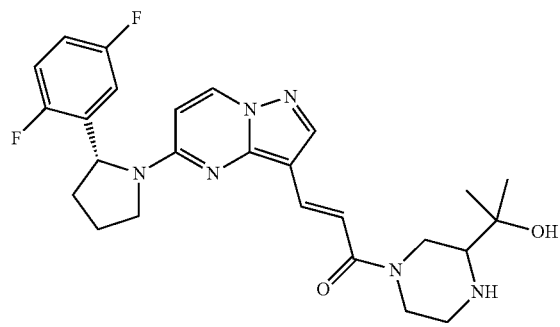
53
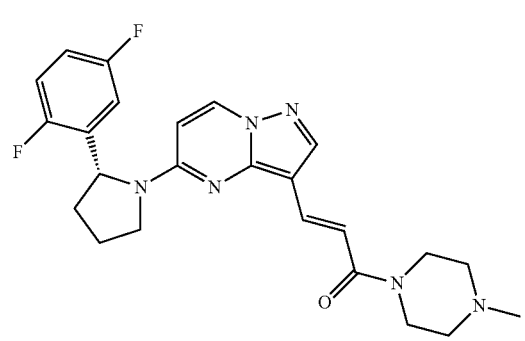
54
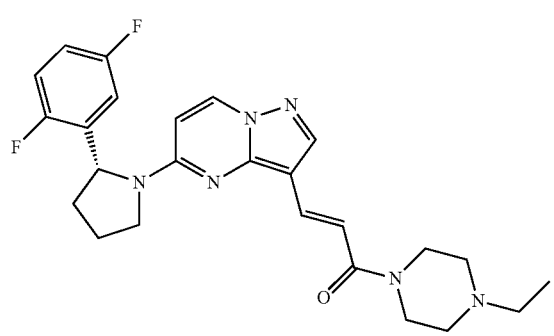
55
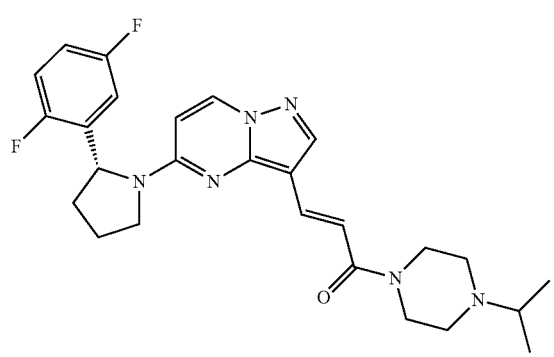
56
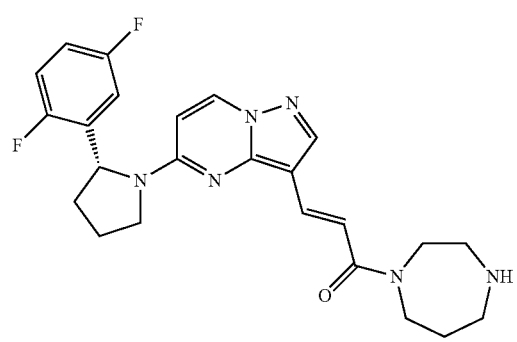
57
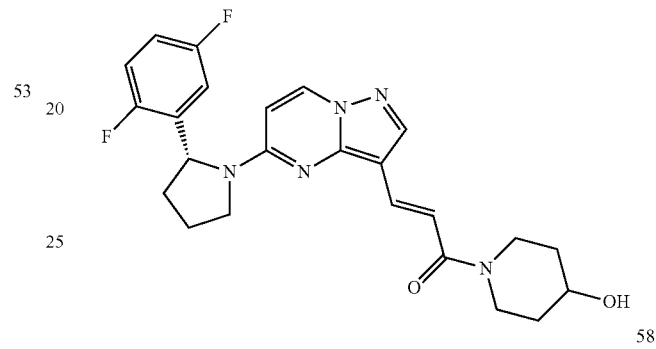
58
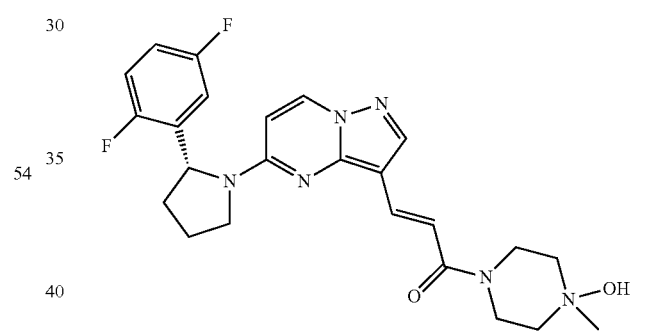
59
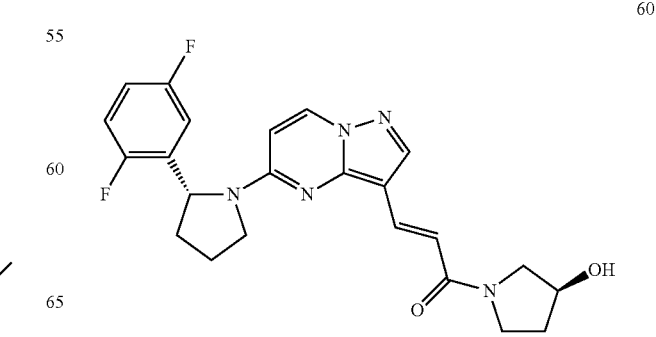

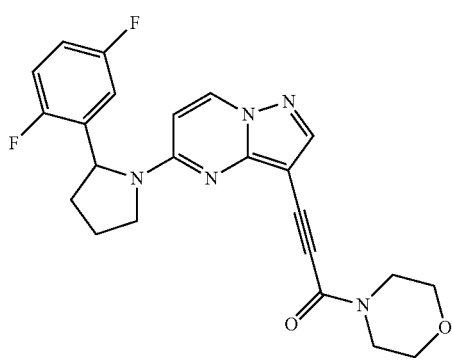

61

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Pharmaceutical Compositions, Treating Diseases, Administration

The novel compounds disclosed above are inhibitors of TrkA, TrkB and/or TrkC and are useful for treating pain, cancers and other hyperproliferative diseases. In one aspect, the present invention provides a pharmaceutical composition including one or more of the chemical compounds of Formula I or their pharmaceutically acceptable salts, solvates, polymorphs, esters, tautomers or prodrugs for use in treating pain cancers and other hyperproliferative diseases.

In embodiments, the pharmaceutical composition includes an effective amount of a compound of Formula I or a pharmaceutically acceptable salt, solvate, polymorph, ester, tautomer or prodrug thereof. Further, the pharmaceutical composition further includes a pharmaceutically acceptable carrier, adjuvants and/or excipients. In some embodiments, such a composition may contain at least one of preservatives, agents for delaying absorption, fillers, binders, adsorbents, buffers, disintegrating agents, solubilizing agents, and other carriers, adjuvants and/or excipients as inert ingredients. The composition may be Formulated with a method well-known in the art.

In some embodiments, the pharmaceutical composition is in a form suitable for oral administration. In further or additional embodiments, the pharmaceutical composition is in the form of a tablet, capsule, pill, powder, sustained release Formulation, solution and suspension. In some embodiments, the pharmaceutical composition is in a form suitable for parenteral injection, such as a sterile solution, suspension or emulsion; for topical administration as an ointment or cream or for rectal administration as a suppository.

In some embodiments, the composition comprising a compound of Formula I is administered orally, intraduodenally, parenterally (including intravenous, subcutaneous, intramuscular, intravascular or by infusion), topically or rectally. In some embodiments, the pharmaceutical composition is in a form suitable for oral administration. In further or additional embodiments, the pharmaceutical composition is in the form of a tablet, capsule, pill, powder, sustained release Formulations, solution and suspension for oral administration, for parenteral injection as a sterile solution, suspension or emulsion, for topical administration as an ointment or cream, or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant.

In another aspect, the present invention provides a method of admininstering a therapeutically effective amount of the pharmaceutical composition to a subject for the treatment of pain, inflammation, neurodegenerative diseases, certain infectious diseases, cancer, other hyperproliferative diseases or conditions modulated by the Trk cascade in a mammal including human.

In another aspect, the present invention provides a method for inhibiting a Trk enzyme. The method comprises contacting said Trk enzyme with an amount of a composition comprising a compound of Formula I or a pharmaceutically acceptable salt, solvate, polymorph, ester, tautomer or prodrug thereof, sufficient to inhibit said enzyme, wherein said enzyme is inhibited. In some embodiments, the present invention is directed to a method for selectively inhibiting a Trk enzyme.

In another aspect, the present invention is directed to use of a compound of Formula I or a pharmaceutically acceptable salt, solvate, polymorph, ester, tautomer or prodrug thereof in the preparation of a pharmaceutical composition for inhibiting a Trk enzyme.

In embodiments, the Trk enzyme is Trk kinase. In some embodiments the Trk enzyme is TrkA. In some embodiments the Trk enzyme is TrkB. In some embodiments, the Trk enzyme is TrkC.

In some embodiments, the compounds of Formula I can selectively inhibit a TrkA enzyme, TrkB enzyme or TrkC enzyme. In some other embodiments, the compounds of Formula I may not have a selectivity from TrkA enzyme, TrkB enzyme and TrkC enzyme.

In some embodiments, the contacting occurs within a cell. In further or additional embodiments the cell is a mammalian cell. In further or additional embodiments the mammalian cell is a human cell. In further or additional embodiments, the Trk enzyme is inhibited with a composition comprising a pharmaceutically acceptable salt of a compound of Formula I.

In some embodiments, the present invention is directed to a method of treatment of a Trk mediated disorder in an individual suffering from said disorder comprising administering to said individual an effective amount of a composition comprising a compound of Formula I or a pharmaceutically acceptable salt, solvate, polymorph, ester, tautomer or prodrug thereof.

In some embodiments, the present invention is directed to use of a compound of Formula I or a pharmaceutically acceptable salt, solvate, polymorph, ester, tautomer or prodrug thereof in the preparation of a pharmaceutical composition for treating a Trk mediated disorder.

In further or additional embodiments, the pharmaceutical composition is in unit dosage forms suitable for single administration of precise dosages. In further or additional embodiments, the amount of compound of Formula I is in the range of about 0.001 to about 1000 mg/kg body weight/day. In further or additional embodiments, the amount of compound of Formula I is in the range of about 0.5 to about 50 mg/kg body weight/day. In further or additional embodiments the amount of compound of Formula I is about 0.001 to about 7 g/day. In further or additional embodiments the amount of compound of Formula I is about 0.002 to about 6 g/day. In further or additional embodiments the amount of compound of Formula I is about 0.005 to about 5 g/day. In further or additional embodiments the amount of compound of Formula I is about 0.01 to about 5 g/day. In further or additional embodiments the amount of compound of Formula I is about 0.02 to about 5 g/day. In further or additional embodiments the amount of compound of Formula I is about 0.05 to about 2.5 g/day. In further or additional embodiments the amount of compound of Formula I is about 0.1 to about 1 g/day.

In further or additional embodiments, dosage levels below the lower limit of the aforesaid range may be more than adequate. In further or additional embodiments, dosage levels above the upper limit of the aforesaid range may be required. In further or additional embodiments the compound of Formula I is administered in a single dose, once daily. In further or additional embodiments the compound of Formula I is administered in multiple doses, more than once per day. In further or additional embodiments the compound of Formula I is administered twice daily. In further or additional embodiments the compound of Formula I is administered three times per day. In further or additional embodiments the compound of Formula I is administered four times per day. In further or additional embodiments the compound of Formula I is administered more than four times per day. In some embodiments, the pharmaceutical composition is for administration to a mammal.

In further or additional embodiments, the pharmaceutical composition further comprises at least one therapeutic agent. In further or additional embodiments, the therapeutic agent is selected from the group consisting of cytotoxic agents, anti-angiogenesis agents and anti-neoplastic agents.

In further or additional embodiments, the anti-neoplastic agent is selected from the group consisting of alkylating agents, anti-metabolites, epidophyllotoxins; antineopiastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is taxol, bortezomib or both. In further or additional embodiments, the pharmaceutical composition is administered in combination with an additional therapy. In further or additional embodiments, the additional therapy is radiation therapy, chemotherapy or a combination of both. In further or additional embodiments, the pharmaceutical composition comprises a pharmaceutically acceptable salt of a compound of Formula I.

In further or additional embodiments the enzyme is at least about 1% inhibited. In further or additional embodiments the enzyme is at least about 2% inhibited. In further or additional embodiments the enzyme is at least about 3% inhibited. In further or additional embodiments the enzyme is at least about 4% inhibited. In further or additional embodiments the enzyme is at least about 5% inhibited. In further or additional embodiments the enzyme is at least about 10% inhibited. In further or additional embodiments the enzyme is at least about 20% inhibited. In further or additional embodiments the enzyme is at least about 25% inhibited. In further or additional embodiments the enzyme is at least about 30% inhibited. In further or additional embodiments the enzyme is at least about 40% inhibited. In further or additional embodiments the enzyme is at least about 50% inhibited. In further or additional embodiments the enzyme is at least about 60% inhibited. In further or additional embodiments the enzyme is at least about 70% inhibited. In further or additional embodiments the enzyme is at least about 75% inhibited. In further or additional embodiments the enzyme is at least about 80% inhibited. In further or additional embodiments the enzyme is at least about 90% inhibited. In further or additional embodiments the enzyme is essentially completely inhibited.

In further or additional embodiments the amount of compound of Formula I is in the range of about 0.001 to about 1000 mg/kg body weight/day. In further or additional embodiments the amount of compound of Formula I is in the range of about 0.5 to about 50 mg/kg body weight/day. In further or additional embodiments the amount of compound of Formula I is about 0.001 to about 7 g/day. In further or additional embodiments the amount of compound of Formula I is about 0.01 to about 7 g/day. In further or additional embodiments the amount of compound of Formula I is about 0.02 to about 5 g/day. In further or additional embodiments the amount of compound of Formula I is about 0.05 to about 2.5 g/day. In further or additional embodiments the amount of compound of Formula I is about 0.1 to about 1 g/day.

In further or additional embodiments, dosage levels below the lower limit of the aforesaid range may be more than adequate. In further or additional embodiments, dosage levels above the upper limit of the aforesaid range may be required. In further or additional embodiments the compound of Formula I is administered in a single dose, once daily. In further or additional embodiments the compound of Formula I is administered in multiple doses, more than once per day. In further or additional embodiments the compound of Formula I is administered twice daily. In further or additional embodiments the compound of Formula I is administered three times per day. In further or additional embodiments the compound of Formula I is administered four times per day. In further or additional embodiments the compound of Formula I is administered more than four times per day.

In some embodiments, the individual suffering from the Trk mediated disorder is a mammal. In further or additional embodiments, the individual is a human. In some embodiments, the composition comprising a compound of Formula I is administered in combination with an additional therapy. In further or additional embodiments, the additional therapy is radiation therapy, chemotherapy or a combination of both. In further or additional embodiments, the composition comprising a compound of Formula I is administered in combination with at least one therapeutic agent. In further or additional embodiments, the therapeutic agent is selected from the group of cytotoxic agents, anti-angiogenesis agents and anti-neoplastic agents.

In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors.

In further or additional embodiments, the therapeutic agent is selected from taxol, bortezomib or both. In some embodiments, the Trk mediated disorder is selected from the group consisting of inflammatory diseases, infections, autoimmune disorders, stroke, ischemia, cardiac disorder, neurological disorders, fibrogenic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma and wide angle glaucoma.

In further or additional embodiments, the Trk mediated disorder is an inflammatory disease. In further or additional embodiments, the Trk mediated disorder is a hyperproliferative disease. In further or additional embodiments, the Trk mediated disorder is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, an effective amount of a composition comprising a pharmaceutically acceptable salt of a compound of Formula I is administered.

In some embodiments, the present invention is directed to a method for degrading, inhibiting the growth of or killing a cancer cell comprising contacting said cell with an amount of a composition effective to degrade, inhibit the growth of or to kill said cell, the composition comprising a compound of Formula I or a pharmaceutically acceptable salt, solvate, polymorph, ester, tautomer or prodrug thereof.

In some embodiments, the present invention is directed to use of a compound of Formula I or a pharmaceutically acceptable salt, solvate, polymorph, ester, tautomer or prodrug thereof in the preparation of a pharmaceutical composition for degrading and/or inhibiting the growth of or killing a cancer cell.

In some embodiments, the cancer cells comprise brain, breast, lung, ovarian, pancreatic, prostate, renal, or colorectal cancer cells. In further or additional embodiments, the composition is administered with at least one therapeutic agent. In further or additional embodiments, the therapeutic agent is taxol, bortezomib or both. In further or additional embodiments, the therapeutic agent is selected from the group consisting of cytotoxic agents, anti-angiogenesis agents and anti-neoplastic agents. In further or additional embodiments, the anti-neoplastic agents selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors.

In some embodiments, the cancer cells are degraded. In further or additional embodiments, 1% of the cancer cells are degraded. In further or additional embodiments, 2% of the cancer cells are degraded. In further or additional embodiments, 3% of the cancer cells are degraded. In further or additional embodiments, 4% of the cancer cells are degraded. In further or additional embodiments, 5% of the cancer cells are degraded. In further or additional embodiments, 10% of the cancer cells are degraded. In further or additional embodiments, 20% of the cancer cells are degraded. In further or additional embodiments, 25% of the cancer cells are degraded. In further or additional embodiments, 30% of the cancer cells are degraded. In further or additional embodiments, 40% of the cancer cells are degraded. In further or additional embodiments, 50% of the cancer cells are degraded. In further or additional embodiments, 60% of the cancer cells are degraded. In further or additional embodiments, 70% of the cancer cells are degraded. In further or additional embodiments, 75% of the cancer cells are degraded. In further or additional embodiments, 80% of the cancer cells are degraded. In further or additional embodiments, 90% of the cancer cells are degraded. In further or additional embodiments, 100% of the cancer cells are degraded. In further or additional embodiments, essentially all of the cancer cells are degraded.

In some embodiments, the cancer cells are killed. In further or additional embodiments, 1% of the cancer cells are killed. In further or additional embodiments, 2% of the cancer cells are killed. In further or additional embodiments, 3% of the cancer cells are killed. In further or additional embodiments, 4% of the cancer cells are killed. In further or additional embodiments, 5% of the cancer cells are killed. In further or additional embodiments, 10% of the cancer cells are killed. In further or additional embodiments, 20% of the cancer cells are killed. In further or additional embodiments, 25% of the cancer cells are killed. In further or additional embodiments, 30% of the cancer cells are killed. In further or additional embodiments, 40% of the cancer cells are killed. In further or additional embodiments, 50% of the cancer cells are killed. In further or additional embodiments, 60% of the cancer cells are killed. In further or additional embodiments, 70% of the cancer cells are killed. In further or additional embodiments, 75% of the cancer cells are killed. In further or additional embodiments, 80% of the cancer cells are killed. In further or additional embodiments, 90% of the cancer cells are killed. In further or additional embodiments, 100% of the cancer cells are killed. In further or additional embodiments, essentially all of the cancer cells are killed.

In further or additional embodiments, the growth of the cancer cells is inhibited. In further or additional embodiments, the growth of the cancer cells is about 1% inhibited. In further or additional embodiments, the growth of the cancer cells is about 2% inhibited. In further or additional embodiments, the growth of the cancer cells is about 3% inhibited. In further or additional embodiments, the growth of the cancer cells is about 4% inhibited. In further or additional embodiments, the growth of the cancer cells is about 5% inhibited. In further or additional embodiments, the growth of the cancer cells is about 10% inhibited. In further or additional embodiments, the growth of the cancer cells is about 20% inhibited. In further or additional embodiments, the growth of the cancer cells is about 25% inhibited. In further or additional embodiments, the growth of the cancer cells is about 30% inhibited. In further or additional embodiments, the growth of the cancer cells is about 40% inhibited. In further or additional embodiments, the growth of the cancer cells is about 50% inhibited. In further or additional embodiments, the growth of the cancer cells is about 60% inhibited. In further or additional embodiments, the growth of the cancer cells is about 70% inhibited. In further or additional embodiments, the growth of the cancer cells is about 75% inhibited. In further or additional embodiments, the growth of the cancer cells is about 80% inhibited. In further or additional embodiments, the growth of the cancer cells is about 90% inhibited. In further or additional embodiments, the growth of the cancer cells is about 100% inhibited. In further or additional embodiments, a composition comprising a pharmaceutically acceptable salt of a compound of Formula I is used.

In some embodiments, the present invention is directed to a method for the treatment or prophylaxis of a proliferative disease in an individual comprising administering to said individual an effective amount of a composition comprising a compound of Formula I or a pharmaceutically acceptable salt, solvate, polymorph, ester, tautomer or pro-drug thereof.

In some embodiments, the present invention is directed to use of a compound of Formula I or a pharmaceutically acceptable salt, solvate, polymorph, ester, tautomer or pro-drug thereof in the preparation of a pharmaceutical composition for the treatment or prophylaxis of a proliferative disease.

In some embodiments, the proliferative disease is cancer, psoriasis, restenosis, autoimmune disease, or atherosclerosis. In further or additional embodiments, the proliferative disease is a hyperproliferative disease. In further or additional embodiments, the proliferative disease is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer.

In some embodiments, the composition comprising a compound of Formula I is administered in combination with an additional therapy. In further or additional embodiments, the additional therapy is radiation therapy, chemotherapy or a combination of both. In further or additional embodiments, the composition comprising a compound of Formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally.

In further or additional embodiments the amount of compound of Formula I is in the range of about 0.001 to about 1000 mg/kg body weight/day. In further or additional embodiments the amount of compound of Formula I is in the range of about 0.5 to about 50 mg/kg body weight/day. In further or additional embodiments the amount of compound of Formula I is about 0.001 to about 7 g/day. In further or additional embodiments the amount of compound of Formula I is about 0.01 to about 7 g/day. In further or additional embodiments the amount of compound of Formula I is about 0.02 to about 5 g/day. In further or additional embodiments the amount of compound of Formula I is about 0.05 to about 2.5 g/day. In further or additional embodiments the amount of compound of Formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of Formula I is administered in a single dose, once daily. In further or additional embodiments the compound of Formula I is administered in multiple doses, more than once per day. In further or additional embodiments the compound of Formula I is administered twice daily. In further or additional embodiments the compound of Formula I is administered three times per day. In further or additional embodiments the compound of Formula I is administered four times per day. In further or additional embodiments the compound of Formula I is administered more than four times per day. In some embodiments, the individual suffering from the proliferative disease is a mammal. In further or additional embodiments, the individual is a human. In further or additional embodiments, an effective amount of a composition comprising a pharmaceutically acceptable salt of a compound of Formula I is administered.

In some embodiments, the present invention is directed to a method for the treatment or prophylaxis of an inflammatory disease in an individual comprising administering to said individual an effective amount of a composition comprising a compound of Formula I or a pharmaceutically acceptable salt, solvate, polymorph, ester, tautomer or prodrug thereof.

In some embodiments, the present invention is directed to use of a compound of Formula I or a pharmaceutically acceptable salt, solvate, polymorph, ester, tautomer or prodrug thereof in the preparation of a pharmaceutical composition for the treatment or prophylaxis of an inflammatory disease.

In further or additional embodiments, the inflammatory disease is selected from chronic inflammatory diseases, rheumatoid arthritis, spondyloarthropathies, gouty arthritis, osteoarthritis, juvenile arthritis, acute rheumatic arthritis, enteropathic arthritis, neuropathic arthritis, psoriatic arthritis, pyogenic arthritis, atherosclerosis, systemic lupus erythematosus, inflammatory bowel disease, irritable bowel syndrome, ulcerative colitis, reflux esophagitis, Crohn's disease, gastritis, asthma, allergies, respiratory distress syndrome, pancreatitis, chronic obstructive pulmonary disease, pulmonary fibrosis, psoriasis, eczema or scleroderma. In some embodiments, the composition comprising a compound of Formula is administered in combination with an additional therapy. In further or additional embodiments, the composition comprising a compound of Formula is administered in combination with at least one therapeutic agent. In some embodiments, the composition is administered orally, intraduodenally, parenterally (including intravenous, subcutaneous, intramuscular, intravascular or by infusion), topically or rectally.

In further or additional embodiments the amount of compound of Formula I is in the range of about 0.001 to about 1000 mg/kg body weight/day. In further or additional embodiments the amount of compound of Formula I is in the range of about 0.5 to about 50 mg/kg body weight/day. In further or additional embodiments the amount of compound of Formula I is about 0.001 to about 7 g/day. In further or additional embodiments the amount of compound of Formula I is about 0.01 to about 7 g/day. In further or additional embodiments the amount of compound of Formula I is about 0.02 to about 5 g/day. In further or additional embodiments the amount of compound of Formula I is about 0.05 to about 2.5 g/day. In further or additional embodiments the amount of compound of Formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of Formula I is administered in a single dose, once daily. In further or additional embodiments the compound of Formula I is administered in multiple doses, more than once per day. In further or additional embodiments the compound of Formula I is administered twice daily. In further or additional embodiments the compound of Formula I is administered three times per day. In further or additional embodiments the compound of Formula I is administered four times per day. In further or additional embodiments the compound of Formula I is administered more than four times per day. In some embodiments, the individual suffering from the inflammatory disease is a mammal. In further or additional embodiments, the individual is a human. In further or additional embodiments, an effective amount of a composition comprising a pharmaceutically acceptable salt of a compound of Formula I is administered.

In some embodiments, the present invention is directed to a method for the treatment or prophylaxis of cancer in an individual comprising administering to said individual an effective amount of a composition comprising a compound of Formula I or a pharmaceutically acceptable salt, solvate, polymorph, ester, tautomer or prodrug thereof.

In some embodiments, the present invention is directed to use of a compound of Formula I or a pharmaceutically acceptable salt, solvate, polymorph, ester, tautomer or prodrug thereof in the preparation of a pharmaceutical composition for the treatment or prophylaxis of a cancer.

In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer.

In some embodiments, the composition comprising a compound of Formula I is administered in combination with an additional therapy. In further or additional embodiments, the additional therapy is radiation therapy, chemotherapy or a combination of both. In further or additional embodiments, the composition comprising a compound of Formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally.

In further or additional embodiments the amount of compound of Formula I is in the range of about 0.001 to about 1000 mg/kg body weight/day. In further or additional embodiments the amount of compound of Formula I is in the range of about 0.5 to about 50 mg/kg body weight/day. In further or additional embodiments the amount of compound of Formula I is about 0.001 to about 7 g/day. In further or additional embodiments the amount of compound of Formula I is about 0.01 to about 7 g/day. In further or additional embodiments the amount of compound of Formula I is about 0.02 to about 5 g/day. In further or additional embodiments the amount of compound of Formula I is about 0.05 to about 2.5 g/day. In further or additional embodiments the amount of compound of Formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of Formula I is administered in a single dose, once daily. In further or additional embodiments the compound of Formula I is administered in multiple doses, more than once per day. In further or additional embodiments the compound of Formula I is administered twice daily. In further or additional embodiments the compound of Formula I is administered three times per day. In further or additional embodiments the compound of Formula I is administered four times per day. In further or additional embodiments the compound of Formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of Formula I is administered.

In some embodiments, the present invention is directed to a method of reducing the size of a tumor, inhibiting tumor size increase, reducing tumor proliferation or preventing tumor proliferation in an individual, comprising administering to said individual an effective amount of a composition comprising a compound of Formula I or a pharmaceutically acceptable salt, solvate, polymorph, ester, tautomer or prodrug thereof.

In some embodiments, the present invention is directed to use of a compound of Formula I or a pharmaceutically acceptable salt, solvate, polymorph, ester, tautomer or prodrug thereof in the preparation of a pharmaceutical composition for reducing the size of a tumor, inhibiting tumor size increase, reducing tumor proliferation or preventing tumor proliferation.

In some embodiments, the size of a tumor is reduced. In further or additional embodiments, the size of a tumor is reduced by at least 1%. In further or additional embodiments, the size of a tumor is reduced by at least 2%. In further or additional embodiments, the size of a tumor is reduced by at least 3%. In further or additional embodiments, the size of a tumor is reduced by at least 4%. In further or additional embodiments, the size of a tumor is reduced by at least 5%. In further or additional embodiments, the size of a tumor is reduced by at least 10%. In further or additional embodiments, the size of a tumor is reduced by at least 20%. In further or additional embodiments, the size of a tumor is reduced by at least 25%. In further or additional embodiments, the size of a tumor is reduced by at least 30%. In further or additional embodiments, the size of a tumor is reduced by at least 40%. In further or additional embodiments, the size of a tumor is reduced by at least 50%. In further or additional embodiments, the size of a tumor is reduced by at least 60%. In further or additional embodiments, the size of a tumor is reduced by at least 70%. In further or additional embodiments, the size of a tumor is reduced by at least 75%. In further or additional embodiments, the size of a tumor is reduced by at least 80%. In further or additional embodiments, the size of a tumor is reduced by at least 85%. In further or additional embodiments, the size of a tumor is reduced by at least 90%. In further or additional embodiments, the size of a tumor is reduced by at least 95%. In further or additional embodiments, the tumor is eradicated. In some embodiments, the size of a tumor does not increase.

In some embodiments, tumor proliferation is reduced. In some embodiments, tumor proliferation is reduced by at least 1%. In some embodiments, tumor proliferation is reduced by at least 2%. In some embodiments, tumor proliferation is reduced by at least 3%. In some embodiments, tumor proliferation is reduced by at least 4%. In some embodiments, tumor proliferation is reduced by at least 5%. In some embodiments, tumor proliferation is reduced by at least 10%. In some embodiments, tumor proliferation is reduced by at least 20%. In some embodiments, tumor proliferation is reduced by at least 25%. In some embodiments, tumor proliferation is reduced by at least 30%. In some embodiments, tumor proliferation is reduced by at least 40%. In some embodiments, tumor proliferation is reduced by at least 50%. In some embodiments, tumor proliferation is reduced by at least 60%. In some embodiments, tumor proliferation is reduced by at least 70%. In some embodiments, tumor proliferation is reduced by at least 75%. In some embodiments, tumor proliferation is reduced by at least 80%. In some embodiments, tumor proliferation is reduced by at least 90%. In some embodiments, tumor proliferation is reduced by at least 95%. In some embodiments, tumor proliferation is prevented.

In some embodiments, the composition comprising a compound of Formula I is administered in combination with an additional therapy. In further or additional embodiments, the additional therapy is radiation therapy, chemotherapy or a combination of both. In further or additional embodiments, the composition comprising a compound of Formula I is administered in combination with at least one therapeutic agent. In further or additional embodiments, the therapeutic agent is selected from the group of cytotoxic agents, anti-angiogenesis agents and anti-neoplastic agents.

In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/antihormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally.

In further or additional embodiments the amount of compound of Formula I is in the range of about 0.001 to about 1000 mg/kg body weight/day. In further or additional embodiments the amount of compound of Formula I is in the range of about 0.5 to about 50 mg/kg body weight/day. In further or additional embodiments the amount of compound of Formula I is about 0.001 to about 7 g/day. In further or additional embodiments the amount of compound of Formula I is about 0.01 to about 7 g/day. In further or additional embodiments the amount of compound of Formula I is about 0.02 to about 5 g/day. In further or additional embodiments the amount of compound of Formula I is about 0.05 to about 2.5 g/day. In further or additional embodiments the amount of compound of Formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of Formula I is administered in a single dose, once daily. In further or additional embodiments the compound of Formula I is administered in multiple doses, more than once per day. In further or additional embodiments the compound of Formula I is administered twice daily. In further or additional embodiments the compound of Formula I is administered three times per day. In further or additional embodiments the compound of Formula I is administered four times per day. In further or additional embodiments the compound of Formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of Formula I is administered.

In some embodiments, the present invention is directed to a method for achieving an effect in a patient comprising the administration of an effective amount of a composition comprising a compound of Formula I or a pharmaceutically acceptable salt, solvate, polymorph, ester, tautomer or prodrug thereof, to a patient, wherein the effect is selected from the group consisting of inhibition of various cancers, immunological diseases, and inflammatory diseases. In some embodiments, the effect is inhibition of various cancers. In further or additional embodiments, the effect is inhibition of immunological diseases. In further or additional embodiments, the effect is inhibition inflammatory diseases.

In some embodiments, the present invention is directed to use of a compound of Formula I or a pharmaceutically acceptable salt, solvate, polymorph, ester, tautomer or prodrug thereof in the preparation of a pharmaceutical composition for the inhibiting various cancers, immunological diseases, and/or inflammatory diseases.

In some embodiments, the composition comprising a compound of Formula I is administered in combination with an additional therapy. In further or additional embodiments, the additional therapy is radiation therapy, chemotherapy or a combination of both. In further or additional embodiments, the composition comprising a compound of Formula I is administered in combination with at least one therapeutic agent. In some embodiments, the composition is administered orally, intraduodenally, parenterally (including intravenous, subcutaneous, intramuscular, intravascular or by infusion), topically or rectally.

In further or additional embodiments the amount of compound of Formula I is in the range of about 0.001 to about 1000 mg/kg body weight/day. In further or additional embodiments the amount of compound of Formula I is in the range of about 0.5 to about 50 mg/kg body weight/day. In further or additional embodiments the amount of compound of Formula I is about 0.001 to about 7 g/day. In further or additional embodiments the amount of compound of Formula I is about 0.01 to about 7 g/day. In further or additional embodiments the amount of compound of Formula I is about 0.02 to about 5 g/day. In further or additional embodiments the amount of compound of Formula I is about 0.05 to about 2.5 g/day. In further or additional embodiments the amount of compound of Formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of Formula I is administered in a single dose, once daily. In further or additional embodiments the compound of Formula I is administered in multiple doses, more than once per day. In further or additional embodiments the compound of Formula I is administered twice daily. In further or additional embodiments the compound of Formula I is administered three times per day. In further or additional embodiments the compound of Formula I is administered four times per day. In further or additional embodiments the compound of Formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of Formula I is administered.

In some embodiments, the present invention is directed to a process for preparing a compound of Formula I or a pharmaceutically acceptable salt, solvate, polymorph, ester, tautomer or prodrug thereof.

Preparation of Compounds of Formula I

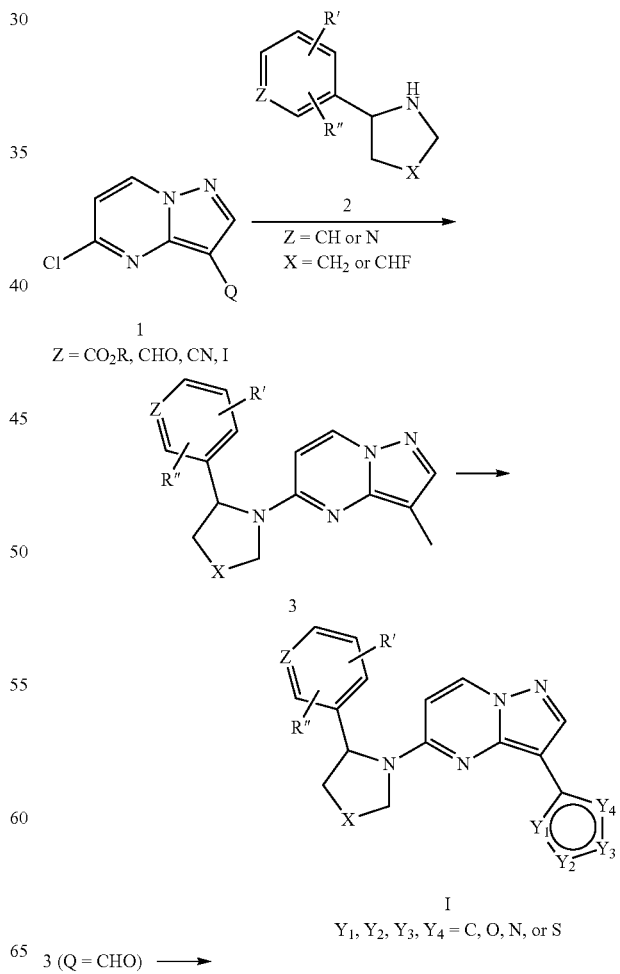

-continued

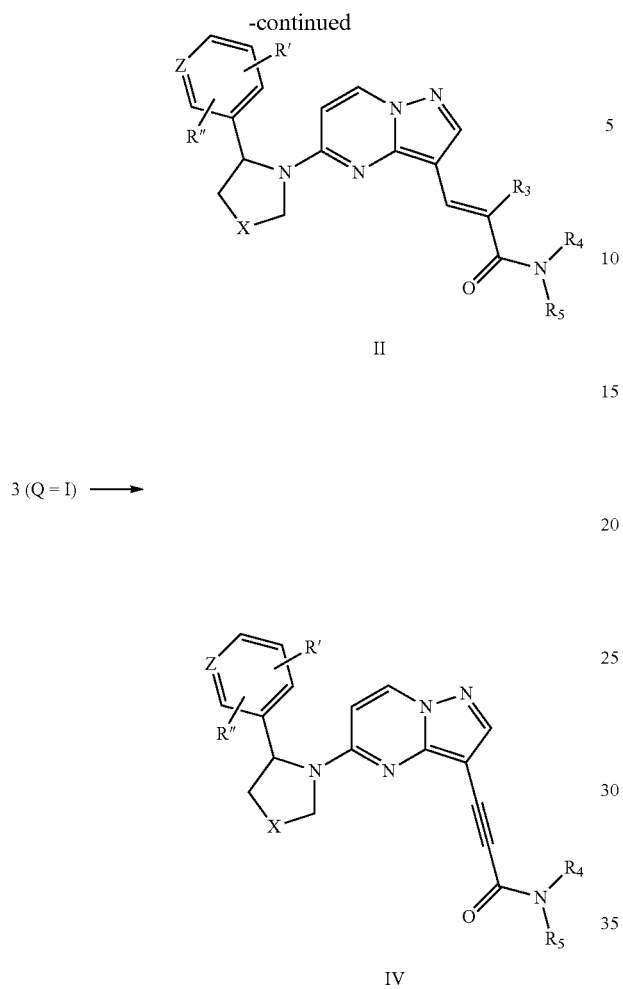

II 3 (Q = I) ⟶

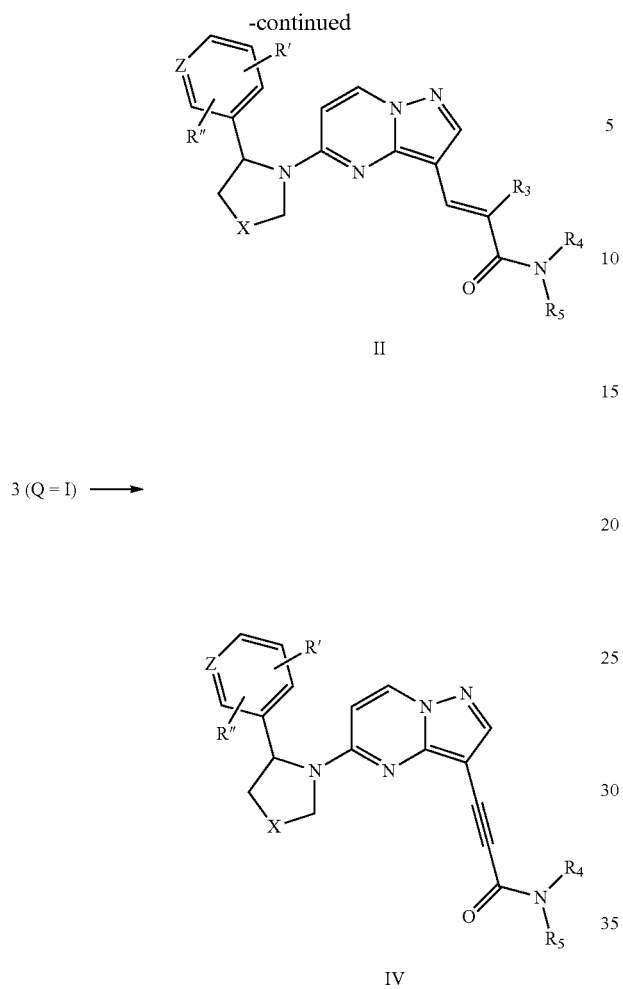

IV

The foregoing scheme provides general synthetic routes for the compounds of Formula I, II, and IV. The key intermediate compound 3 can be obtained via coupling reaction of cyclic amine compounds with the bicyclic hetero cyclic compound 1 containing various functional groups Q. The various five membered heterocyclic moieties in the compounds of Formula I are introduced via coupling reaction, condensation, or cyclization reactions from the compound 3. The compounds of Formula II can be prepared from the compound 3 containing aldehyde moiety through HEW reaction, hydrolysis followed by amide coupling reaction. In the case of Formula IV, Sonogashira reaction with iodo compound 3 afforded the desired compounds.

Experimental Procedures

NMR spectra were recorded in CDCl$_3$ and DMSO-d$_6$ solution in 5-mm o.d. tubes (Norell, Inc. 507-HP) at 30° C. and were collected on Varian VNMRS-400 at 400 MHz for $^1$H. The chemical shifts (δ) are relative to tetramethylsilane (TMS=0.00 ppm) and expressed in ppm. LC/MS was taken on Ion-trap Mass Spectrometer on FINNIGAN Thermo LCQ Advantage MAX, Agilent LC 1200 series (Column: YMC Hydrosphere (C18, Ø4.6×50 mm, 3 μm, 120 Å, 40° C.) operating in ESI(+) ionization mode; flow rate=1.0 mL/min. Mobile phase=0.01% heptafluorobutyric acid (HFBA) and 1.0% isopropyl alcohol (IPA) in water or CH$_3$CN.

Example 1: Preparation of Intermediate Compound 1

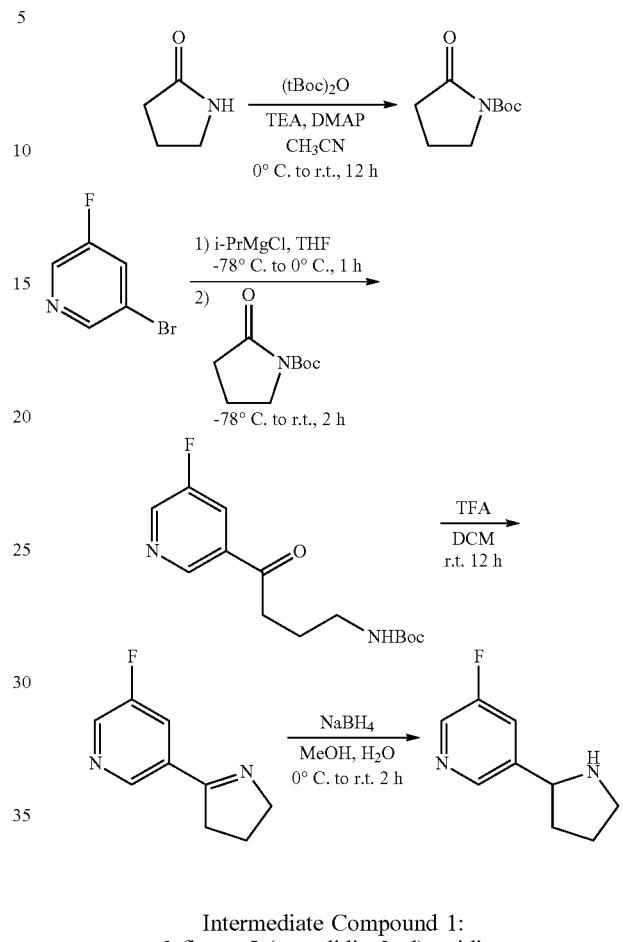

Intermediate Compound 1:
3-fluoro-5-(pyrrolidin-2-yl)pyridine

Step A: tert-butyl 2-oxopyrrolidine-1-carboxylate

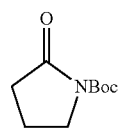 [SMILES: CC(C)(C)OC(=O)N1CCCC1=O]

To a solution of pyrrolidin-2-one (10.0 g, 118 mmol) in CH$_3$CN (118 mL) were added TEA (19.6 mL, 141 mmol), DMAP (7.18 g, 58.8 mmol) and (t-Boc)$_2$O (32.7 mL, 141 mmol) at 0° C. The reaction mixture was stirred at room temperature overnight and then partitioned between EtOAc and water. The separated organic layer was washed with 1 N aq. HCl, 1 N aq. NaOH and brine, dried over Na$_2$SO$_4$, filtered and concentrated in vacuo. The residue was purified by column chromatography on SiO$_2$ (Hex:EtOAc=1:1) to afford tert-butyl 2-oxopyrrolidine-1-carboxylate (21.0 g, 96%) as a pale yellow oil. $^1$H-NMR (CDCl$_3$, Varian, 400 MHz): δ 1.53 (9H, s), 2.00 (2H, quint, J=8.0 Hz), 2.52 (2H, t, J=8.0 Hz), 3.75 (2H, t, J=7.6 Hz).

Step B: tert-butyl 4-(5-fluoropyridin-3-yl)-4-oxobutylcarbamate

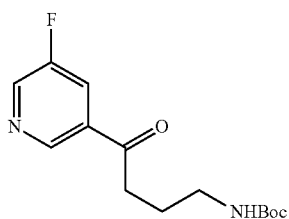 [SMILES: CC(C)(C)OC(=O)NCCCC(=O)c1cncc(F)c1]

To a solution of 3-bromo-5-fluoropyridine (4.26 g, 24.2 mmol) in dry THF (25 mL) was added isopropylmagnesium chloride (2.0 M in THF, 14.5 mL, 29.0 mmol) at −78° C. The mixture was slowly warmed to 0° C., stirred for 1 hour at 0° C. and then cooled to −78° C. After addition of a solution of tert-butyl 2-oxopyrrolidine-1-carboxylate (5.38 g, 29.0 mmol) in dry THF (10 mL) at −78° C., the reaction mixture was allowed to warm to room temperature, stirred at room temperature for 2 hours and quenched with saturated aq. NH$_4$Cl. The mixture was extracted with EtOAc twice. The combined organic layers were washed with brine, dried over Na$_2$SO$_4$, filtered and concentrated in vacuo. The residue was purified by column chromatography on SiO$_2$ (Hex:EtOAc=2:1 to 1:1) to afford tert-butyl 4-(5-fluoropyridin-3-yl)-4-oxobutylcarbamate (4.73 g, 69%) as a yellow oil.

Step C: 3-(3,4-dihydro-2H-pyrrol-5-yl)-5-fluoropyridine

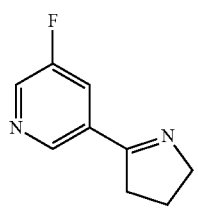 [SMILES: Fc1cncc(C2=NCCC2)c1]

To a solution of tert-butyl 4-(5-fluoropyridin-3-yl)-4-oxobutylcarbamate (4.73 g, 16.7 mmol) in DCM (17 mL) was added TFA (6.45 mL, 84 mmol) at 0° C. The reaction mixture was stirred at room temperature for 12 hours and then concentrated in vacuo. The residue was diluted with EtOAc, washed with saturated aq. NaHCO$_3$, dried over Na$_2$SO$_4$, filtered and concentrated in vacuo to afford 3-(3,4-dihydro-2H-pyrrol-5-yl)-5-fluoropyridine (1.83 g, 66.5%) as a yellow solid, which was used for the next reaction without further purification. $^1$H-NMR (CDCl$_3$, Varian, 400 MHz): δ 2.10 (2H, quint, J=8.0 Hz), 2.96 (2H, t, J=8.4 Hz), 4.10 (2H, t, J=7.6 Hz), 7.94 (1H, d, J=9.2 Hz), 8.53 (1H, d, J=2.4 Hz), 8.79 (1H, s).

Step D: 3-fluoro-5-(pyrrolidin-2-yl)pyridine

To a solution of 3-(3,4-dihydro-2H-pyrrol-5-yl)-5-fluoropyridine (1.83 g, 11.1 mmol) in MeOH (16 mL) and water (4.0 mL) was portionwise added sodium borohydride (0.843 g, 22.3 mmol) at 0° C. The reaction mixture was stirred for 2 hours at room temperature and then quenched with 2 N aq. HCl. After evaporation of MeOH, the residue was basified with 1 N aq. NaOH and extracted with DCM twice. The combined organic layers were dried over Na$_2$SO$_4$, filtered and concentrated in vacuo to afford 3-fluoro-5-(pyrrolidin-2-yl)pyridine (1.62 g, 87%) as a yellow oil. $^1$H-NMR (CDCl$_3$, Varian, 400 MHz): δ 1.60-1.69 (1H, m), 1.81-1.98 (3H, m), 2.20-2.29 (1H, m), 3.03-3.10 (1H, m), 3.15-3.20 (1H, m), 4.22 (1H, t, J=7.6 Hz), 7.49 (1H, d, J=10.0 Hz), 8.32 (1H, d, J=2.4 Hz), 8.40 (1H, s).

Example 2: Preparation of Intermediate Compound 2

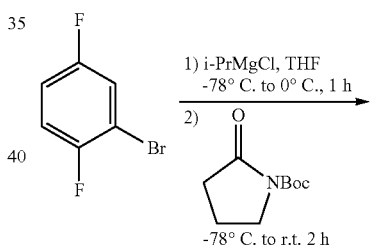

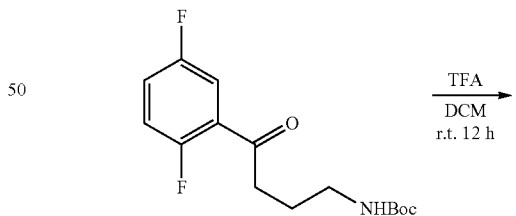

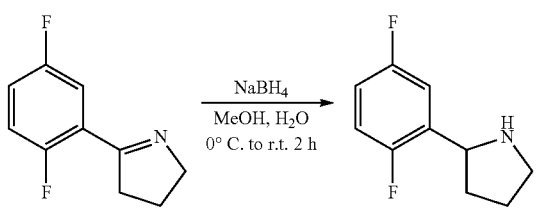

Intermediate Compound 2: 2-(2,5-difluorophenyl)pyrrolidine

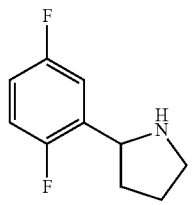 [SMILES: Fc1ccc(F)c(C2CCCN2)c1]

Step A: tert-butyl 4-(2,5-difluorophenyl)-4-oxobutylcarbamate

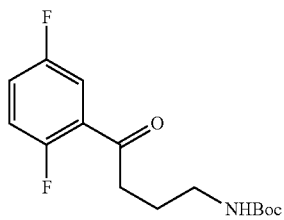 [SMILES: CC(C)(C)OC(=O)NCCCC(=O)c1cc(F)ccc1F]

To a solution of 2-bromo-1,4-difluorobenzene (5.81 mL, 51.8 mmol) in dry THF (50 mL) was added isopropylmagnesium chloride (2.0 M in THF, 31.1 mL, 62.2 mmol) at −78° C. The mixture was slowly warmed to 0° C., stirred for 1 hour at that temperature and then cooled to −78° C. again. After addition of a solution of tert-butyl 2-oxopyrrolidine-1-carboxylate (11.5 g, 62.2 mmol) in dry THF (20 mL) at −78° C., the reaction mixture was allowed to warm to room temperature with stirring for 2 hours and quenched with saturated aq. NH$_4$Cl. The mixture was extracted with EtOAc twice. The combined organic layers were washed with brine, dried over Na$_2$SO$_4$, filtered and concentrated in vacuo to afford tert-butyl 4-(2,5-difluorophenyl)-4-oxobutylcarbamate (15.5 g, 100%) as a pale green oil, which was used for the next reaction without further purification.

Step B: 5-(2,5-difluorophenyl)-3,4-dihydro-2H-pyrrole

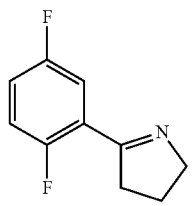 [SMILES: Fc1ccc(F)c(C2=NCCC2)c1]

To a solution of tert-butyl 4-(2,5-difluorophenyl)-4-oxobutylcarbamate (15.5 g, 51.8 mmol) in DCM (52 mL) was added TFA (19.9 mL, 259 mmol) at 0° C. The reaction mixture was stirred at room temperature for 12 hours and then concentrated in vacuo. The residue was diluted with EtOAc, washed with saturated aq. NaHCO$_3$, dried over Na$_2$SO$_4$, filtered and concentrated in vacuo to afford 5-(2,5-difluorophenyl)-3,4-dihydro-2H-pyrrole (6.17 g, 65.8%) as a reddish oil, which was used for the next reaction without further purification. $^1$H-NMR (CDCl$_3$, Varian, 400 MHz): δ 2.00-2.08 (2H, m), 2.97-3.02 (2H, m), 3.99-4.04 (2H, m), 7.04-7.08 (2H, m), 7.64-7.68 (1H, m).

Step C: 2-(2,5-difluorophenyl)pyrrolidine

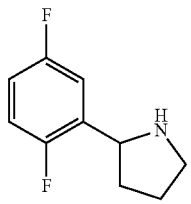 [SMILES: Fc1ccc(F)c(C2CCCN2)c1]

To a solution of 5-(2,5-difluorophenyl)-3,4-dihydro-2H-pyrrole (6.17 g, 34.1 mmol) in MeOH (60 mL) and water (15 mL) was portionwise added sodium borohydride (2.58 g, 68.1 mmol) at 0° C. The reaction mixture was stirred for 2 hours at room temperature and then quenched with 2 N aq. HCl. After evaporation of MeOH, the residue was basified with 1 N aq. NaOH and extracted with DCM twice. The combined organic layers were dried over Na$_2$SO$_4$, filtered and concentrated in vacuo to afford 2-(2,5-difluorophenyl)pyrrolidine (5.94 g, 95%) as a yellow oil. $^1$H-NMR (CDCl$_3$, Varian, 400 MHz): δ 1.56-1.65 (1H, m), 1.78-1.94 (3H, m), 2.21-2.30 (1H, m), 3.01-3.08 (1H, m), 3.13-3.18 (1H, m), 4.40 (1H, t, J=7.2 Hz), 6.82-6.88 (1H, m), 6.91-6.97 (1H, m), 7.22-7.26 (1H, m).

Example 3: Preparation of Intermediate Compound 3

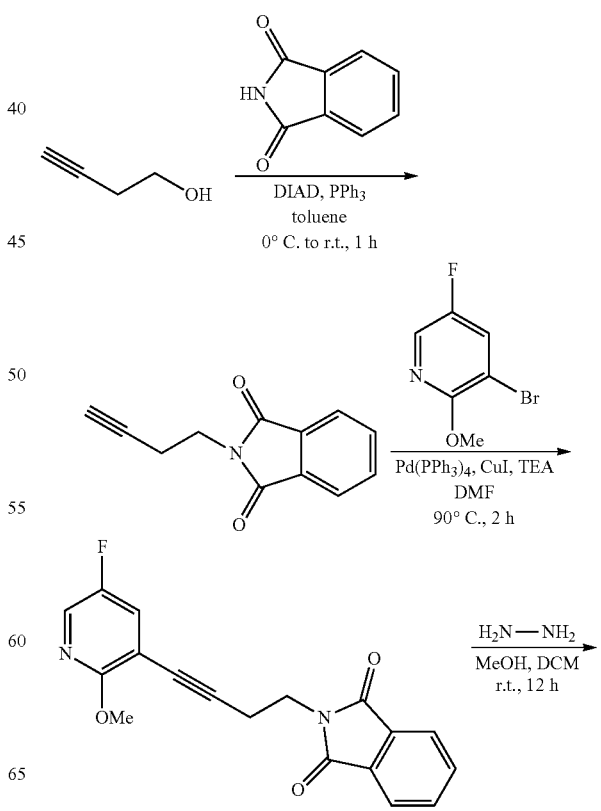

-continued

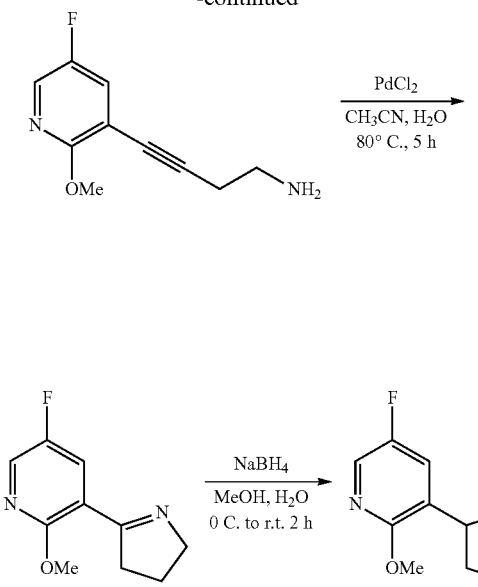

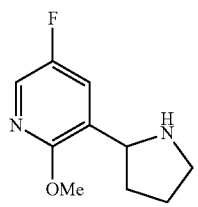 [SMILES: COc1ncc(F)cc1C1CCCN1]

Intermediate Compound 3:
5-fluoro-2-methoxy-3-(pyrrolidin-2-yl)pyridine

Step A: 2-(but-3-ynyl)isoindoline-1,3-dione

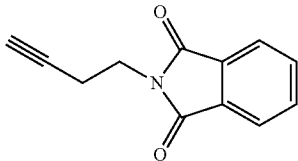

To a solution of phthalimide (10.0 g, 68.0 mmol), but-3-yn-1-ol (5.24 g, 74.8 mmol) and triphenylphosphine (19.6 g, 74.8 mmol) in toluene (136 mL) was slowly added DIAD (15.8 mL, 82.0 mmol) at 0° C. over 10 min. The reaction mixture was stirred at room temperature for 1 hour. After addition of MeOH (50 mL), the mixture was stirred for 30 min. A precipitated solid was collected by filtration and washed with MeOH. The filtrate was concentrated in vacuo and a residual solid was triturated with MeOH and collected by filtration to afford 2-(but-3-ynyl)isoindoline-1,3-dione (10.9 g, 81%) as a white solid. $^1$H-NMR (DMSO-$d_6$, Varian, 400 MHz): δ 2.52 (2H, dt, J=7.2, 2.4 Hz), 2.78-2.80 (1H, m), 3.68 (2H, t, J=6.8 Hz), 7.80-7.86 (4H, m).

Step B: 2-(4-(5-fluoro-2-methoxypyridin-3-yl)but-3-ynyl)isoindoline-1,3-dione

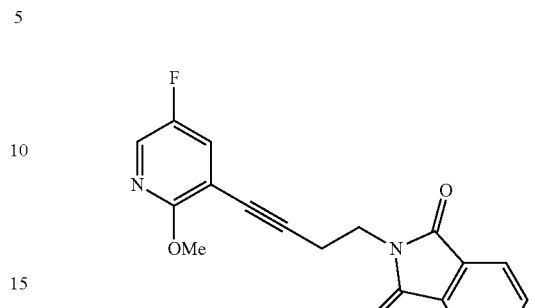

A solution 3-bromo-5-fluoro-2-methoxypyridine (4.00 g, 19.4 mmol), 2-(but-3-ynyl)isoindoline-1,3-dione (3.87 g, 19.4 mmol) and TEA (10.8 mL, 78 mmol) in DMF (40 mL) was degassed with argon. After addition of Pd(PPh$_3$)$_4$ (1.12 g, 0.971 mmol) and CuI (0.370 g, 1.94 mmol), the reaction mixture was heated at 90° C. for 2 hours and cooled to room temperature. After addition of MeOH, a precipitated solid was collected by filtration. The solid was washed with MeOH and dried under vacuum to afford 2-(4-(5-fluoro-2-methoxypyridin-3-yl)but-3-ynyl)isoindoline-1,3-dione (5.80 g, 92%) as a white fluffy solid. $^1$H-NMR (CDCl$_3$, Varian, 400 MHz): δ 2.90 (2H, t, J=6.8 Hz), 3.85 (3H, s), 3.99 (2H, t, J=6.8 Hz), 7.34 (1H, dd, J=7.6, 2.4 Hz), 7.73-7.75 (2H, m), 7.87-7.89 (3H, m).

Step C: 4-(5-fluoro-2-methoxypyridin-3-yl)but-3-yn-1-amine

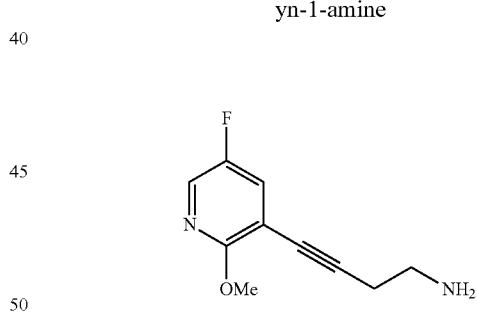

To a solution of 2-(4-(5-fluoro-2-methoxypyridin-3-yl)but-3-ynyl)isoindoline-1,3-dione (6.44 g, 19.8 mmol) in MeOH (20 mL) and DCM (100 mL) was added hydrazine (1.39 mL, 29.8 mmol) at room temperature. The reaction mixture was stirred at room temperature for 12 hours, while an insoluble solid was observed. The solid was filtered off and washed with DCM. The filtrate was washed with water. The aqueous layer was extracted with DCM. The combined organic layers were dried over Na$_2$SO$_4$, filtered and concentrated in vacuo to afford 4-(5-fluoro-2-methoxypyridin-3-yl)but-3-yn-1-amine (3.86 g, 100%) as a yellow solid, which was used for the next reaction without further purification. $^1$H-NMR (CDCl$_3$, Varian, 400 MHz): δ 1.41 (2H, br. s), 2.61 (2H, t, J=6.4 Hz), 2.95 (2H, t, J=6.4 Hz), 3.97 (3H, s), 7.40 (1H, dd, J=8.0, 2.8 Hz), 7.92 (1H, d, J=2.8 Hz).

Step D: 3-(3,4-dihydro-2H-pyrrol-5-yl)-5-fluoro-2-methoxypyridine

Example 4: Preparation of Intermediate Compound 4

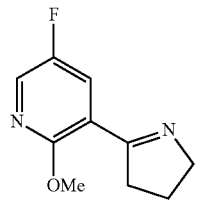 [SMILES: COc1ncc(F)cc1C1=NCCC1]

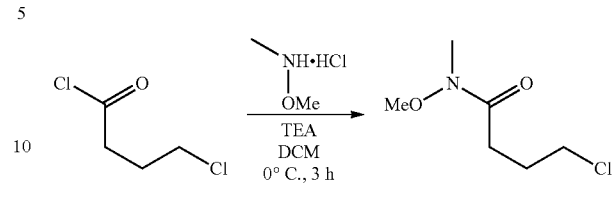

A mixture of 4-(5-fluoro-2-methoxypyridin-3-yl)but-3-yn-1-amine (3.86 g, 19.8 mmol) and PdCl$_2$ (35.0 mg, 0.199 mmol) in CH$_3$CN (50 mL) and water (17 mL) was heated at 80° C. for 5 hours and cooled to room temperature. After concentration in vacuo, the residue was partitioned between DCM and water. The aqueous layer was extracted with DCM. The combined organic layers were dried over Na$_2$SO$_4$, filtered and concentrated in vacuo. The residue was purified by column chromatography on SiO$_2$ (Hex:EtOAc=5:1 to 3:1) to afford 3-(3,4-dihydro-2H-pyrrol-5-yl)-5-fluoro-2-methoxypyridine (2.10 g, 54%) as a yellow solid. $^1$H-NMR (CDCl$_3$, Varian, 400 MHz): δ 2.01 (2H, quint, J=7.6 Hz), 3.01 (2H, t, J=7.6 Hz), 3.97 (3H, s), 3.99 (2H, t, J=7.6 Hz), 7.92 (1H, dd, J=8.4, 2.8 Hz), 8.04 (1H, d, J=2.8 Hz).

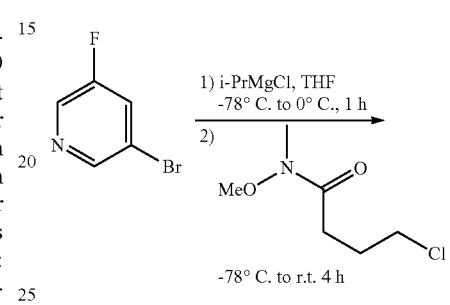

Step E:
5-fluoro-2-methoxy-3-(pyrrolidin-2-yl)pyridine

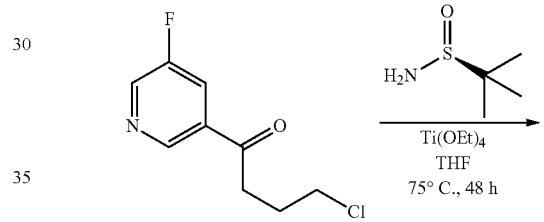

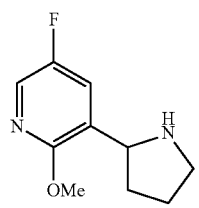 [SMILES: COc1ncc(F)cc1C1CCCN1]

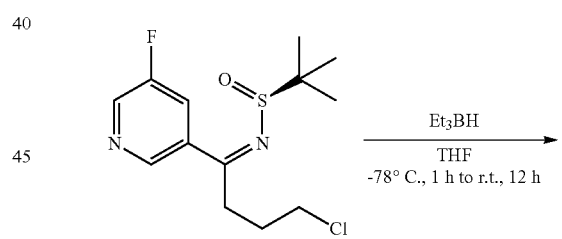

To a dispersion of 3-(3,4-dihydro-2H-pyrrol-5-yl)-5-fluoro-2-methoxypyridine (500 mg, 2.57 mmol) in MeOH (10 mL) and water (2.5 mL) was portionwise added sodium borohydride (195 mg, 5.15 mmol) at 0° C. The reaction mixture was stirred for 2 hours at room temperature and then quenched with 2 N aq. HCl. After evaporation of MeOH, the mixture was basified with 1 N aq. NaOH and extracted with DCM twice. The combined organic layers were dried over Na$_2$SO$_4$, filtered and concentrated in vacuo to afford 5-fluoro-2-methoxy-3-(pyrrolidin-2-yl)pyridine (437 mg, 87%) as a yellow oil, which was used for the next reaction without further purification. $^1$H-NMR (CDCl$_3$, Varian, 400 MHz): δ 1.50-1.59 (1H, m), 1.79-1.87 (2H, m), 1.93 (1H, br. s), 2.20-2.28 (1H, m), 3.01-3.15 (2H, m), 3.93 (3H, s), 4.29 (1H, t, J=7.6 Hz), 7.57 (1H, dd, J=8.8, 3.2 Hz), 7.83 (1H, d, J=3.2 Hz).

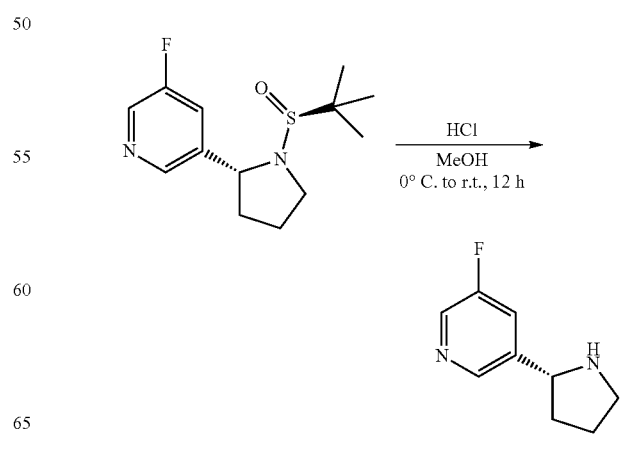

Intermediate Compound 4: (R)-3-fluoro-5-(pyrrolidin-2-yl)pyridine

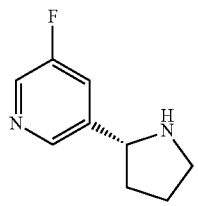

Step A: 4-chloro-N-methoxy-N-methylbutanamide

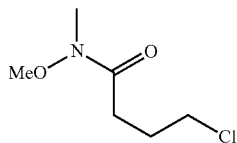

To a solution of 4-chlorobutanoyl chloride (50.0 g, 355 mmol) and N-MeO—N-Methyl amine HCl (34.6 g, 355 mmol) in DCM (709 mL) was slowly added TEA (109 mL, 780 mmol) at 0° C. over 30 minutes. The reaction mixture was stirred at 0° C. for 3 hours and then treated with water (250 mL). The separated organic layer was washed with brine, dried over Na$_2$SO$_4$, filtered and concentrated in vacuo to afford 4-chloro-N-methoxy-N-methylbutanamide (55.0 g, 94%) as yellow oil, which was used for the next reaction without further purification. $^1$H-NMR (CDCl$_3$, Varian, 400 MHz): δ 2.12 (2H, quint, J=6.4 Hz), 2.63 (2H, t, J=7.2 Hz), 3.19 (3H, s), 3.64 (2H, t, J=6.4 Hz), 3.71 (3H, s).

Step B: 4-chloro-1-(5-fluoropyridin-3-yl)butan-1-one

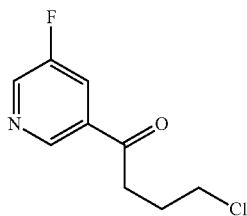 [SMILES: O=C(CCCCl)c1cncc(F)c1]

To a solution of 3-bromo-5-fluoropyridine (30.0 g, 170 mmol) in dry THF (170 mL) was added isopropylmagnesium chloride (2.0 M in THF, 102 mL, 205 mmol) at −78° C. The mixture was slowly warmed to 0° C., stirred for 1 hour at that temperature and then cooled to −78° C. again. After addition of a solution of 4-chloro-N-methoxy-N-methylbutanamide (31.1 g, 188 mmol) in dry THF (100 mL), the reaction mixture was allowed to warm to room temperature with stirring for 4 hours and quenched with saturated aq. NH$_4$Cl. The mixture was extracted with EtOAc twice. The combined organic layers were washed with brine, dried over Na$_2$SO$_4$, filtered and concentrated in vacuo. The residue was purified by column chromatography on SiO$_2$ (Hex: EtOAc=7:1 to 6:1) to afford 4-chloro-1-(5-fluoropyridin-3-yl)butan-1-one (25.1 g, 125 mmol, 73%) as a yellow oil. $^1$H-NMR (CDCl$_3$, Varian, 400 MHz): δ 2.27 (2H, quint, J=6.4 Hz), 3.22 (2H, t, J=6.8 Hz), 3.70 (2H, t, J=6.4 Hz), 7.93-7.97 (1H, m), 8.68 (1H, d, J=3.2 Hz), 9.03 (1H, t, J=1.6 Hz).

Step C: (S,Z)—N-(4-chloro-1-(5-fluoropyridin-3-yl)butylidene)-2-methylpropane-2-sulfinamide

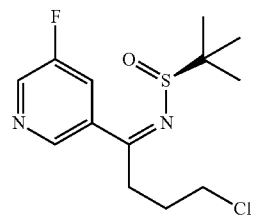 [SMILES: CC(C)(C)[S@](=O)/N=C(/CCCCl)c1cncc(F)c1]

A solution of 4-chloro-1-(5-fluoropyridin-3-yl)butan-1-one (25.1 g, 125 mmol), (S)-2-methylpropane-2-sulfinamide (22.6 g, 187 mmol) and tetraethoxytitanium (42.6 g, 187 mmol) in THF (249 mL) was heated at 75° C. for 48 hours and cooled to room temperature. After addition of EtOAc (100 mL) and brine (100 mL), the resulting mixture was stirred for 1 hour at room temperature. A precipitated solid was filtered off and washed with EtOAc. The filtrate was washed with water twice, dried over Na$_2$SO$_4$, filtered and concentrated in vacuo. The residue was purified by column chromatography on SiO$_2$ (Hex:EtOAc=3:1 to 2:1) to afford (S,Z)—N-(4-chloro-1-(5-fluoropyridin-3-yl)butylidene)-2-methylpropane-2-sulfinamide (30.0 g, 79%) as a yellow oil. $^1$H-NMR (CDCl$_3$, Varian, 400 MHz): δ 1.35 (9H, s), 2.09-2.26 (2H, m), 3.31-3.38 (1H, m), 3.44-3.51 (1H, m), 3.62-3.71 (2H, m), 7.87 (1H, d, J=9.2 Hz), 8.59 (1H, d, J=2.8 Hz), 8.92 (1H, s).

Step D: 3-((R)-1-((S)-tert-butylsulfinyl)-pyrrolidin-2-yl)-5-fluoropyridine

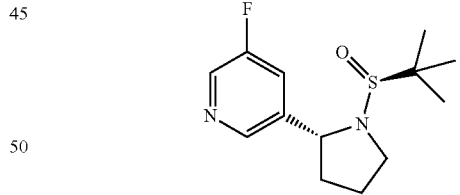

To a solution of (S,Z)—N-(4-chloro-1-(5-fluoropyridin-3-yl)butylidene)-2-methylpropane-2-sulfinamide (10.0 g, 32.8 mmol) in dry THF (131 mL) was added Super hydride (1 M in THF, 36.1 mL, 36.1 mmol) at −78° C. The reaction mixture was stirred at −78° C. for 1 hour, warmed to room temperature and stirred for 12 hours at room temperature. After being quenched with saturated aq. NH$_4$Cl, the mixture was extracted with EtOAc twice. The combined organic layers were washed with water, dried over Na$_2$SO$_4$, filtered and concentrated in vacuo. The residue was purified by column chromatography on SiO$_2$ (Hex:EtOAc=1:1 to 1:2 to 1:3 to EtOAc) to afford 3-((R)-1-((S)-tert-butylsulfinyl)-pyrrolidin-2-yl)-5-fluoropyridine (3.73 g, 42%) as a yellow oil. $^1$H-NMR (CDCl$_3$, Varian, 400 MHz): δ 1.13 (9H, s), 1.75-1.79 (1H, m), 1.79-2.04 (2H, m), 2.28-2.36 (1H, m), 2.97-3.03 (1H, m), 3.90-3.95 (1H, m), 4.71 (1H, t, J=7.2 Hz), 7.33-7.36 (1H, m), 8.38-8.39 (2H, m).

Step E: (R)-3-fluoro-5-(pyrrolidin-2-yl)pyridine

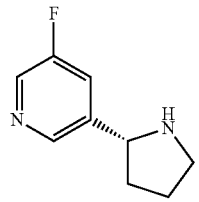 [SMILES: Fc1cncc([C@H]2CCCN2)c1]

To a solution of 3-((R)-1-((S)-tert-butylsulfinyl)-pyrrolidin-2-yl)-5-fluoropyridine (7.47 g, 27.6 mmol) in MeOH (55 mL) was added HCl (4 M in dioxane, 34.5 mL, 138 mmol) at 0° C. The reaction mixture was stirred for 12 hours at room temperature. After concentration in vacuo, the residue was dissolved in water (100 mL) and washed with EtOAc (100 mL). The separated aqueous layer was neutralized with 1 N aq. NaOH (150 mL), extracted with DCM (100 mL×3). The combined organic layers were washed with brine, dried over Na$_2$SO$_4$, filtered and concentrated in vacuo to afford (R)-3-fluoro-5-(pyrrolidin-2-yl)pyridine (4.35 g, 95%) as a reddish oil. $^1$H-NMR (CDCl$_3$, Varian, 400 MHz): δ 1.60-1.69 (1H, m), 1.83-1.97 (3H, m), 2.20-2.29 (1H, m), 3.04-3.10 (1H, m), 3.15-3.21 (1H, m), 4.23 (1H, t, J=7.6 Hz), 7.47-7.51 (1H, m), 8.33 (1H, d, J=2.8 Hz), 8.40 (1H, s).

Example 5: Preparation of Intermediate Compound 5

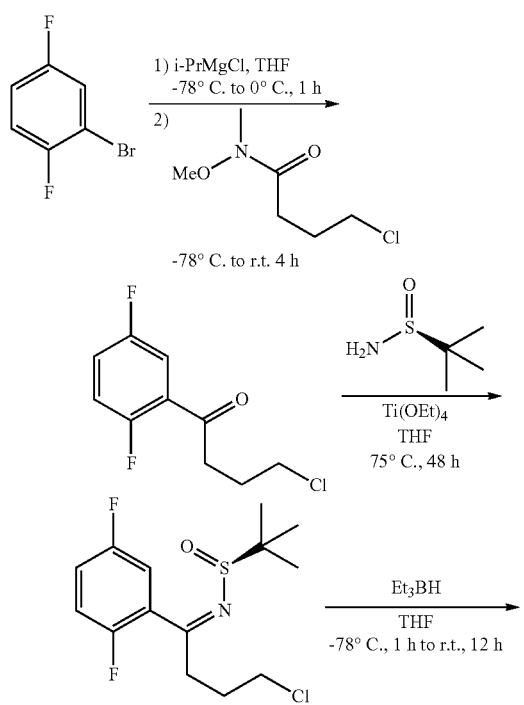

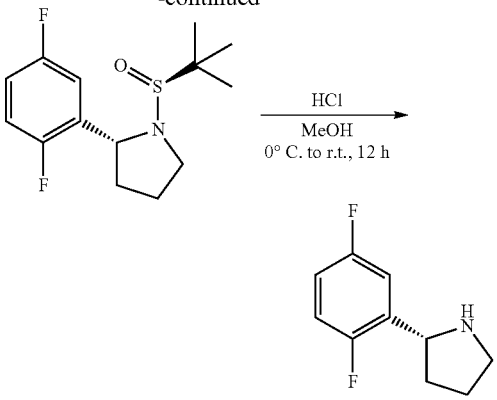

Intermediate Compound 5:
(R)-2-(2,5-difluorophenyl)pyrrolidine

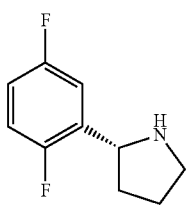

Step A: 4-chloro-1-(2,5-difluorophenyl)butan-1-one

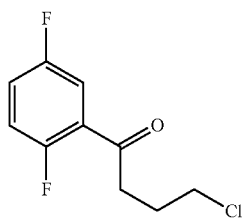 [SMILES: O=C(CCCCl)c1cc(F)ccc1F]

To a solution of 2-bromo-1,4-difluorobenzene (30.0 g, 155 mmol) in dry THF (155 mL) was added isopropylmagnesium chloride (2 M in THF, 93.0 mL, 187 mmol) at −78° C. The mixture was slowly warmed to 0° C., stirred for 1 hour at that temperature and then cooled to −78° C. again. After addition of a solution of 4-chloro-N-methoxy-N-methylbutanamide (28.3 g, 171 mmol) in THF (100 mL), the reaction mixture was allowed to warm to room temperature with stirring for 4 hours and quenched with saturated aq. NH$_4$Cl. The mixture was extracted with EtOAc twice. The combined organic layers were washed with brine, dried over Na$_2$SO$_4$, filtered and concentrated in vacuo. The residue was purified by column chromatography on SiO$_2$ (Hex: EtOAc=7:1 to 6:1) to afford 4-chloro-1-(2,5-difluorophenyl)butan-1-one (13.3 g, 39%) as a pale yellow oil. $^1$H-NMR (CDCl$_3$, Varian, 400 MHz): δ 2.22 (2H, quint, J=6.8 Hz), 3.16-3.20 (2H, m), 3.67 (2H, t, J=6.4 Hz), 7.11-7.17 (1H, m), 7.20-7.26 (1H, m), 7.55-7.59 (1H, m).

Step B: (S,Z)—N-(4-chloro-1-(2,5-difluorophenyl)butylidene)-2-methylpropane-2-sulfinamide

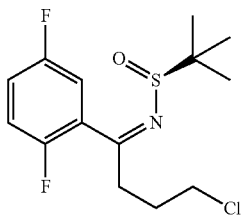 [SMILES: CC(C)(C)[S@](=O)/N=C(/CCCCl)c1cc(F)ccc1F]

A solution of 4-chloro-1-(2,5-difluorophenyl)butan-1-one (16.4 g, 75.0 mmol), (S)-2-methylpropane-2-sulfinamide (13.6 g, 113 mmol) and tetraethoxytitanium (25.7 g, 113 mmol) in THF (150 mL) was heated at 75° C. for 48 hours and cooled to room temperature. After addition of EtOAc (50 mL) and brine (50 mL), the resulting mixture was vigorously stirred for 1 hour at room temperature. A precipitated solid was filtered off and washed with EtOAc. The filtrate was washed with water twice, dried over Na$_2$SO$_4$, filtered and concentrated in vacuo. The residue was purified by column chromatography on SiO$_2$ (Hex:EtOAc=3:1 to 2:1) to afford (S,Z)—N-(4-chloro-1-(2,5-difluorophenyl)butylidene)-2-methylpropane-2-sulfinamide (16.3 g, 67%) as a yellow oil. $^1$H-NMR (DMSO-d$_6$, Varian, 400 MHz): δ 1.15 and 1.21 (9H, s and s), 1.86-2.12 (2H, m), 2.78-3.30 (2H, m), 3.60-3.76 (2H, m), 7.20-7.60 (3H, m).

Step C: (R)-1-((S)-tert-butylsulfinyl)-2-(2,5-difluorophenyl)pyrrolidine

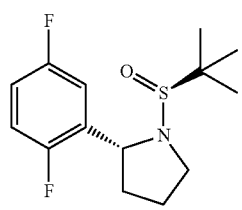 [SMILES: CC(C)(C)[S@](=O)N1CCC[C@@H]1c1cc(F)ccc1F]

To a solution of (S,Z)—N-(4-chloro-1-(2,5-difluorophenyl)butylidene)-2-methylpropane-2-sulfinamide (16.3 g, 50.7 mmol) in dry THF (203 mL) was added Super hydride (1 M sol in THF, 55.7 mL, 55.7 mmol) at −78° C. The reaction mixture was stirred at −78° C. for 1 hour, warmed to room temperature and stirred for 12 hours at room temperature. After being quenched with saturated aq. NH$_4$Cl, the mixture was extracted with EtOAc. The separated organic layer was washed with water, dried over Na$_2$SO$_4$, filtered and concentrated in vacuo. The residue was purified by column chromatography on SiO$_2$ (Hex:EtOAc=6:1 to 5:1 to 4:1) to afford (R)-1-((S)-tert-butylsulfinyl)-2-(2,5-difluorophenyl)pyrrolidine (8.60 g, 59%) as a yellow oil. $^1$H-NMR (CDCl$_3$, Varian, 400 MHz): δ 1.15 (9H, s), 1.75-1.80 (1H, m), 1.82-1.98 (2H, m), 2.24-2.32 (1H, m), 2.95-3.01 (1H, m), 3.87-3.93 (1H, m), 4.96 (1H, t, J=7.2 Hz), 6.87-6.93 (1H, m), 6.95-7.06 (2H, m).

Step D: (R)-2-(2,5-difluorophenyl)pyrrolidine

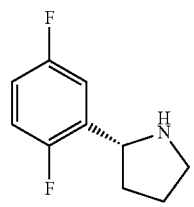 [SMILES: Fc1ccc(F)c([C@H]2CCCN2)c1]

To a solution of (R)-1-((S)-tert-butylsulfinyl)-2-(2,5-difluorophenyl)pyrrolidine (8.60 g, 29.9 mmol) in MeOH (60 mL) was added HCl (4 M in dioxane, 37.4 mL, 150 mmol) at 0° C. The reaction mixture was stirred for 12 hours at room temperature. After concentration in vacuo, the residue was dissolved in water (100 mL) and washed with EtOAc (100 mL). The separated aqueous layer was neutralized with 1 N aq. NaOH (150 mL), extracted with DCM (100 mL×3). The combined organic layers were washed with brine, dried over Na$_2$SO$_4$, filtered and concentrate in vacuo to afford (R)-2-(2,5-difluorophenyl)pyrrolidine (5.06 g, 92%) as a reddish oil. $^1$H-NMR (CDCl$_3$, Varian, 400 MHz): δ 1.56-1.65 (1H, m), 1.78-1.93 (3H, m), 2.21-2.30 (1H, m), 3.01-3.08 (1H, m), 3.13-3.18 (1H, m), 4.39 (1H, t, J=7.6 Hz), 6.82-6.88 (1H, m), 6.91-6.97 (1H, m), 7.22-7.26 (1H, m).

Example 6: Preparation of Intermediate Compounds 6 and 7

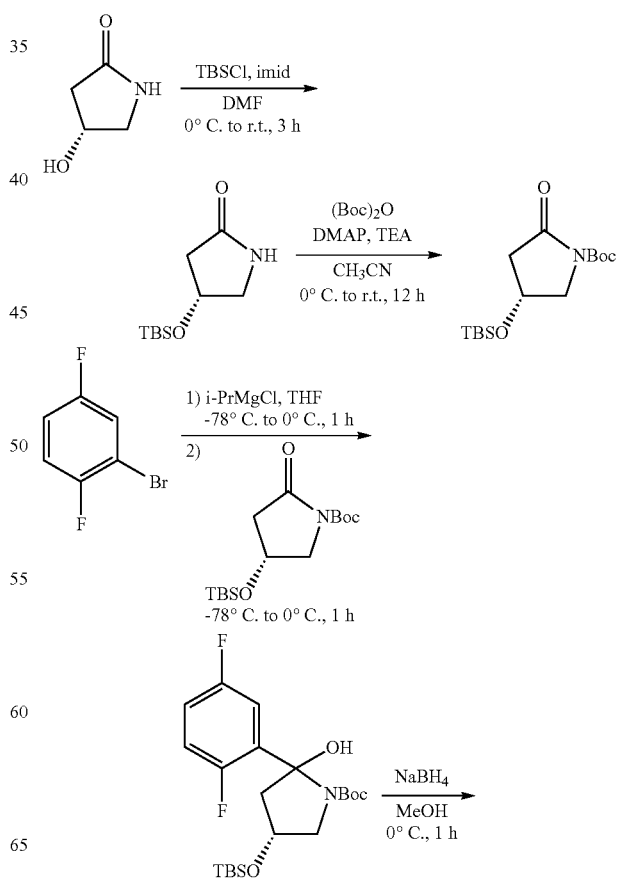

-continued

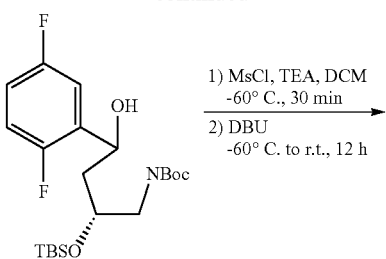

Intermediate Compounds 6 and 7: (2R,4S)-2-(2,5-difluorophenyl)-4-fluoropyrrolidine (6) and (2S,4S)-2-(2,5-difluorophenyl)-4-fluoropyrrolidine (7)

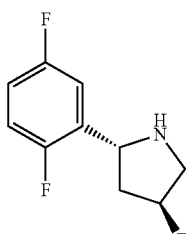

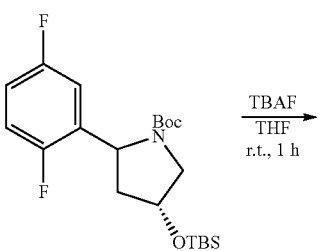

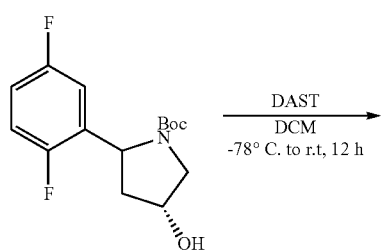

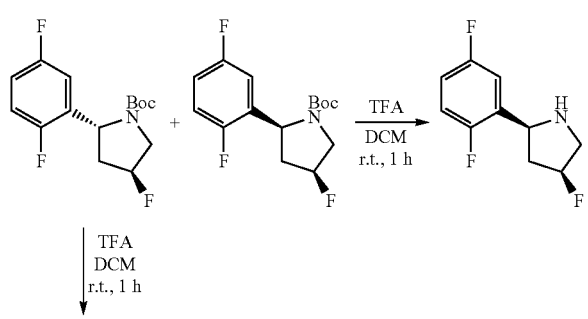

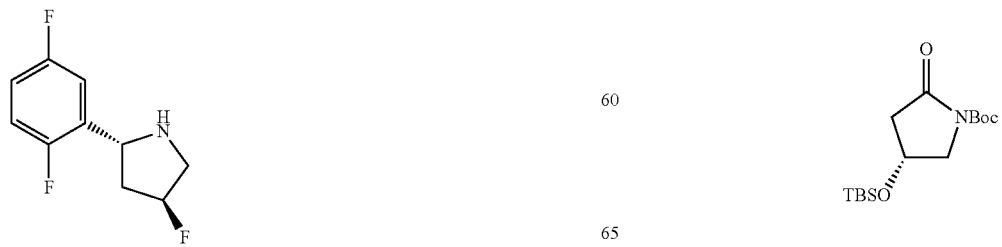

Step A: (R)-4-(tert-butyldimethylsilyloxy)pyrrolidin-2-one

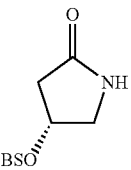

To a solution of (R)-4-hydroxypyrrolidin-2-one (5.00 g, 49.5 mmol) in DMF (24 mL) were added TBSCl (7.83 g, 51.9 mmol) and imidazole (5.05 g, 74.2 mmol) at 0° C. The reaction mixture was stirred at room temperature for 3 hours and poured into ice water. A precipitate solid was collected by filtration and dried under vacuum to give (R)-4-(tert-butyldimethylsilyloxy)pyrrolidin-2-one (9.64 g, 91%) as a white solid. $^1$H-NMR (CDCl$_3$, Varian 400 MHz): δ 0.07 (6H, s), 0.89 (9H, s), 2.27 and 2.54 (2H, ABq, J$_{AB}$=16.8 Hz), 3.24 and 3.59 (2H, ABq, J$_{AB}$=9.8 Hz), 4.53-4.58 (1H, m), 6.25 (1H, s).

Step B: (R)-tert-butyl 4-(tert-butyldimethylsilyloxy)-2-oxopyrrolidine-1-carboxylate

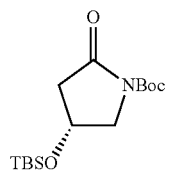 [SMILES: CC(C)(C)OC(=O)N1C[C@H](O[Si](C)(C)C(C)(C)C)CC1=O]

To a solution of (R)-4-(tert-butyldimethylsilyloxy)pyrrolidin-2-one (9.64 g, 44.8 mmol) in CH$_3$CN (90 mL) were added TEA (7.49 mL, 53.7 mmol), DMAP (5.47 g, 44.8 mmol) and (t-Boc)$_2$O (12.5 mL, 53.7 mmol) at 0° C. The reaction mixture was stirred at room temperature overnight and then partitioned between EtOAc and water. The separated organic layer was washed with saturated aq. NH$_4$Cl and brine, dried over Na$_2$SO$_4$, filtered and concentrated in vacuo. The residue was purified by column chromatography on SiO$_2$ (Hex:EtOAc=3:1) to afford (R)-tert-butyl 4-(tert-butyldimethylsilyloxy)-2-oxopyrrolidine-1-carboxylate (13.4 g, 95%) as a pale brown solid. $^1$H-NMR (CDCl$_3$, Varian 400 MHz): δ 0.077 (3H, s), 0.082 (3H, s), 0.88 (9H, s), 1.53 (9H, s), 2.47 and 2.71 (2H, ABq, J$_{AB}$=17.4 Hz), 3.62 and 3.86 (2H, ABq, J$_{AB}$=11.3 Hz), 4.37-4.41 (1H, m).

Step C: tert-butyl (2R)-2-(tert-butyldimethylsilyloxy)-4-(2,5-difluorophenyl)-4-hydroxybutylcarbamate

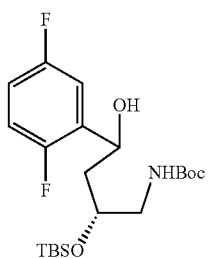 [SMILES: CC(C)(C)OC(=O)NC[C@@H](CC(O)c1cc(F)ccc1F)O[Si](C)(C)C(C)(C)C]

To a solution of 2-bromo-1,4-difluorobenzene (3.97 mL, 35.4 mmol) in dry THF (118 mL) was added isopropylmagnesium chloride (2.0 M in THF, 21.2 mL, 42.5 mmol) at −78° C. The mixture was slowly warmed to 0° C. and stirred for 1 hour at that temperature and then cooled to −78° C. again. After the addition of a solution of (R)-tert-butyl 4-(tert-butyldimethylsilyloxy)-2-oxopyrrolidine-1-carboxylate (13.4 g, 42.5 mmol) in dry THF (40 mL) at −78° C., the reaction mixture was allowed to warm to 0° C. with stirring for 1 hour. After addition of MeOH (118 mL) followed by NaBH$_4$ (2.01 g, 53.1 mmol) at 0° C., the resulting mixture was stirred for 1 hour and then quenched with saturated aq. NH$_4$Cl. The mixture was extracted with EtOAc twice. The combined organic layers were washed with brine, dried over Na$_2$SO$_4$, filtered and concentrated in vacuo. The residue was purified by column chromatography on SiO$_2$ (Hex:EtOAc=6:1) to afford tert-butyl (2R)-2-(tert-butyldimethylsilyloxy)-4-(2,5-difluorophenyl)-4-hydroxybutylcarbamate (10.2 g, 67%) as a white solid. $^1$H-NMR (CDCl$_3$, Varian 400 MHz): δ 0.09-0.14 (6H, m), 0.91-0.93 (9H, m), 1.44 (9H, s), 1.73-1.93 (2H, m), 3.22-3.44 (2H, m), 3.66-3.83 (1H, m), 4.06-4.15 (1H, m), 4.81 (1H, s), 5.15-5.21 (1H, m), 6.87-6.97 (2H, m), 7.22-7.29 (1H, m).

Step D: (4R)-tert-butyl 4-(tert-butyldimethylsilyloxy)-2-(2,5-difluorophenyl)pyrrolidine-1-carboxylate

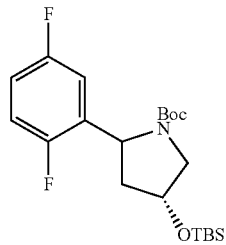 [SMILES: CC(C)(C)OC(=O)N1C[C@H](O[Si](C)(C)C(C)(C)C)CC1c1cc(F)ccc1F]

To a solution of (2R)-2-(tert-butyldimethylsilyloxy)-4-(2,5-difluorophenyl)-4-hydroxybutylcarbamate (10.0 g, 23.2 mmol) in DCM (116 mL) were added TEA (9.69 mL, 69.5 mmol) and MsCl (1.99 mL, 25.5 mmol) at −60° C. The mixture was stirred for 30 min at −60° C. After addition of DBU (5.24 mL, 34.8 mmol) at −60° C., the reaction mixture was slowly warmed to room temperature and stirred overnight. After treatment of water, the mixture was extracted with DCM twice. The combined organic layers were washed with brine, dried over Na$_2$SO$_4$, filtered and concentrated in vacuo. The residue was purified by column chromatography on SiO$_2$ (Hex:EtOAc=8:1) to afford (4R)-tert-butyl 4-(tert-butyldimethylsilyloxy)-2-(2,5-difluorophenyl)pyrrolidine-1-carboxylate as a colorless oil. $^1$H-NMR (CDCl$_3$, Varian 400 MHz): δ 0.00-0.34 (6H, m), 0.86-1.08 (9H, m), 1.36-1.62 (9H, m), 2.04-2.67 (2H, m), 3.60-3.93 (2H, m), 4.50-4.55 (1H, m), 5.17-5.49 (1H, m), 6.98-7.33 (3H, m).

Step E: (4R)-tert-butyl 2-(2,5-difluorophenyl)-4-hydroxypyrrolidine-1-carboxylate

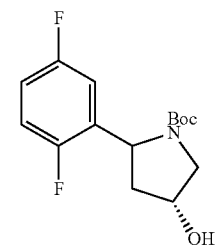 [SMILES: CC(C)(C)OC(=O)N1C[C@H](O)CC1c1cc(F)ccc1F]

To a solution of (4R)-tert-butyl 4-(tert-butyldimethylsilyloxy)-2-(2,5-difluorophenyl)-pyrrolidine-1-carboxylate (7.23 g, 17.5 mmol) in THF (35.0 mL) was added TBAF (1.0 M in THF, 22.7 mL, 22.7 mmol) at room temperature. After being stirred for 1 hour at room temperature, the reaction mixture was poured into ice water and extracted with EtOAc. The organic layer was washed with brine, dried over Na$_2$SO$_4$, filtered and concentrated in vacuo. The residue was purified by column chromatography on SiO$_2$ (Hex:EtOAc=2:1) to afford (4R)-tert-butyl 2-(2,5-difluorophenyl)-4-hydroxypyrrolidine-1-carboxylate (3.81 g, 73%) as a white solid. $^1$H-NMR (CDCl$_3$, Varian 400 MHz): δ 1.20-1.46 (9H, m), 1.94-2.13 (2H, m), 2.42-2.59 (1H, m), 3.56-3.81 (2H, m), 4.49-4.50 (1H, m), 5.06-5.30 (1H, m), 6.88-7.08 (3H, m).

Step F: (2R,4S)-tert-butyl 2-(2,5-difluorophenyl)-4-fluoropyrrolidine-1-carboxylate (6a) and (2S,4S)-tert-butyl 2-(2,5-difluorophenyl)-4-fluoropyrrolidine-1-carboxylate (7a)

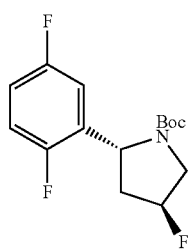 [SMILES: Fc1ccc(F)c([C@H]2C[C@H](F)CN2)c1]

6a

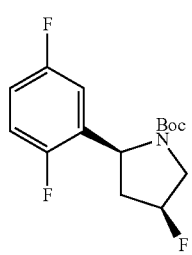 [SMILES: Fc1ccc(F)c([C@@H]2C[C@H](F)CN2)c1]

7a

To a solution of (4R)-tert-butyl 2-(2,5-difluorophenyl)-4-hydroxypyrrolidine-1-carboxylate (1.00 g, 3.34 mmol) in DCM (11 mL) was added DAST (0.883 mL, 6.68 mmol) at −78° C. After being stirred for 2 hours at −78° C., the reaction mixture was slowly warmed to room temperature and stirred overnight. After quenched by slow addition of saturated aq. NaHCO₃ solution, the mixture was extracted with DCM twice. The combined organic layers were dried over Na₂SO₄, filtered and concentrated in vacuo. The residue was purified by column chromatography on SiO₂ (Hex:EtOAc=10:1) to afford (2R,4S)-tert-butyl 2-(2,5-difluorophenyl)-4-fluoropyrrolidine-1-carboxylate (6a) (383 mg, 38%) and (2S,4S)-tert-butyl 2-(2,5-difluorophenyl)-4-fluoropyrrolidine-1-carboxylate (7a) (252 mg, 25%) as a colorless oil.

(The stereochemistry of each isomer was proposed by the comparison with reference (WO2012034095A1)

For (2R,4S)-tert-butyl 2-(2,5-difluorophenyl)-4-fluoropyrrolidine-1-carboxylate (6a)

¹H-NMR (CDCl₃, Varian 400 MHz): δ 1.21-1.46 (9H, m), 1.94-2.10 (1H, m), 2.71-2.79 (1H, m), 3.62-3.75 (1H, m), 3.98-4.14 (1H, m), 5.09-5.48 (2H, m), 6.92-7.01 (3H, m)

For (2S,4S)-tert-butyl 2-(2,5-difluorophenyl)-4-fluoropyrrolidine-1-carboxylate (7a)

¹H-NMR (CDCl₃, Varian 400 MHz): δ 1.20-1.49 (9H, s), 2.25-2.35 (1H, m), 2.48-2.60 (1H, m), 3.71-4.03 (1H, m), 5.19-5.33 (2H, m), 6.88-6.99 (3H, m).

Step G: (2R,4S)-2-(2,5-difluorophenyl)-4-fluoropyrrolidine (6)

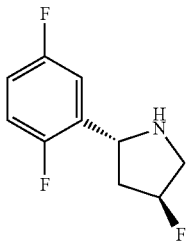

To a solution of (2R,4S)-tert-butyl 2-(2,5-difluorophenyl)-4-fluoropyrrolidine-1-carboxylate (383 mg, 1.27 mmol) in DCM (2.5 mL) was added TFA (1.96 mL, 25.4 mmol) at room temperature. After being stirred for 1 hour at room temperature, the reaction mixture was concentrated under reduced pressure. The residue was neutralized with saturated aq. NaHCO₃ and extracted with EtOAc. The organic layer was dried over Na₂SO₄, filtered and concentrated in vacuo to afford (2R,4S)-2-(2,5-difluorophenyl)-4-fluoropyrrolidine (100 mg, 39%) as a yellow solid. ¹H-NMR (CDCl₃, Varian 400 MHz): δ 1.66-1.83 (1H, m), 1.91 (1H, s), 2.58-2.69 (1H, m), 3.16-3.40 (2H, m), 4.71-4.75 (1H, m), 5.20-5.35 (1H, m), 6.84-6.90 (1H, m), 6.93-6.99 (1H, m), 7.28-7.31 (1H, m).

Step H: (2S,4S)-2-(2,5-difluorophenyl)-4-fluoropyrrolidine (7)

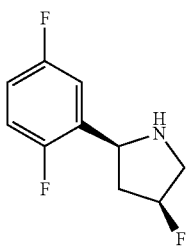

To a solution of (2S,4S)-tert-butyl 2-(2,5-difluorophenyl)-4-fluoropyrrolidine-1-carboxylate (252 mg, 0.836 mmol) in DCM (1.67 mL) was added TFA (1.29 mL, 16.7 mmol) at room temperature. After being stirred for 1 hour, the reaction mixture was concentrated under reduced pressure. The residue was neutralized with saturated aq. NaHCO₃ and extracted with EtOAc. The organic layer was dried over Na₂SO₄, filtered and concentrated under reduced pressure to give (2S,4S)-2-(2,5-difluorophenyl)-4-fluoropyrrolidine (117 mg, 70%) as a yellow solid. ¹H-NMR (CDCl₃, Varian 400 MHz): δ 1.90-2.05 (2H, m), 2.53-2.68 (1H, m), 2.98-3.11 (1H, m), 3.44-3.52 (1H, m), 4.42 (1H, t, J=7.8 Hz), 5.28 (1H, dt, J=52.4, 4.8 Hz), 6.87-6.92 (1H, m), 6.93-7.00 (1H, m), 7.28-7.31 (1H, m).

Example 7: Preparation of Intermediate Compound 8

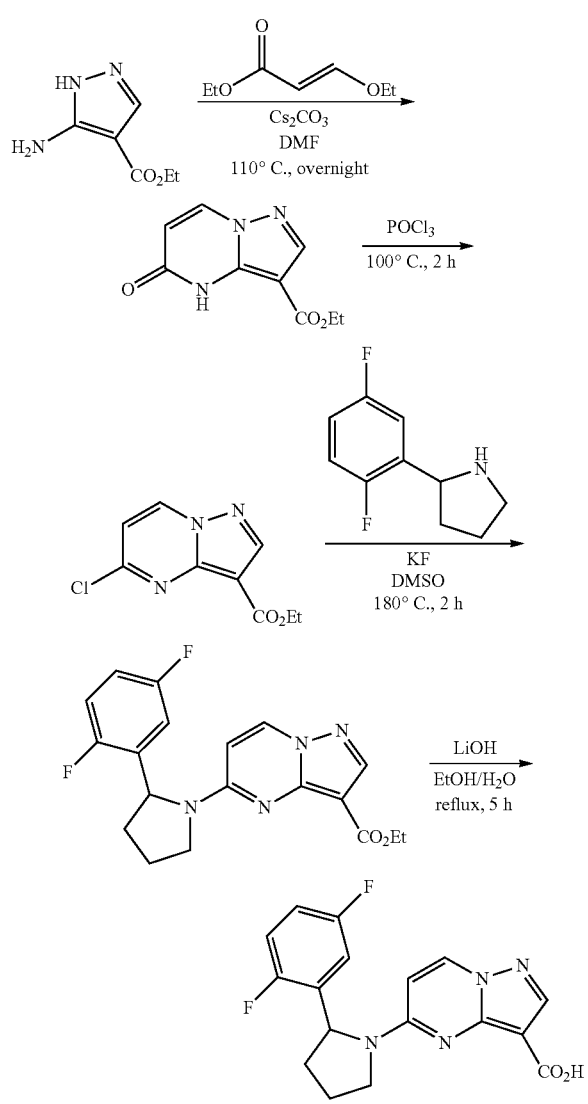

Intermediate Compound 8: 5-(2-(2,5-difluorophenyl)pyrrolidin-1-yl)pyrazolo[1,5-a]pyrimidine-3-carboxylic acid

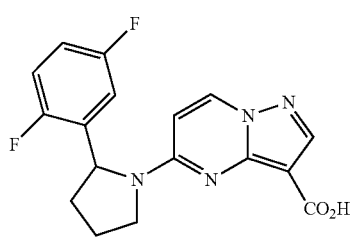

Step A: ethyl 5-oxo-4,5-dihydropyrazolo[1,5-a]pyrimidine-3-carboxylate

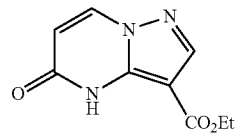 [SMILES: CCOC(=O)c1cnn2ccc(=O)[nH]c12]

A mixture of ethyl-5-amino-1H-pyrazole-4-carboxylate (20.0 g, 129 mmol), (E)-ethyl 3-ethoxyacrylate (22.4 mL, 155 mmol) and cesium carbonate (63.0 g, 193 mmol) in DMF (322 mL) was stirred at 110° C. overnight. After being cooled to 0° C., the reaction mixture was acidified with 2 N aq. HCl. A precipitated solid was collected by filtration and washed with water and EtOAc to afford ethyl 5-oxo-4,5-dihydropyrazolo[1,5-a]pyrimidine-3-carboxylate (24.7 g, 92%) as a pale yellow solid. $^1$H-NMR (DMSO-$d_6$, Varian, 400 MHz): δ 1.27 (3H, t, J=7.2 Hz), 4.80 (2H, q, J=6.8 Hz), 6.16 (1H, d, J=8.0 Hz), 8.14 (1H, s), 8.58 (1H, d, J=8.0 Hz), 11.7 (1H, br. s).

Step B: ethyl 5-chloropyrazolo[1,5-a]pyrimidine-3-carboxylate

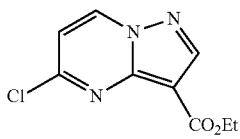 [SMILES: CCOC(=O)c1cnn2ccc(Cl)nc12]

A mixture of ethyl-5-oxo-4,5-dihydropyrazolo[1,5-a]pyrimidine-3-carboxylate (24.7 g, 119 mmol) and POCl$_3$ (111 mL, 1.19 mol) was refluxed for 2 hours. After being cooled to room temperature, the reaction mixture was concentrated in vacuo. The residue was purified by column chromatography on SiO$_2$ (Hex:EtOAc:DCM=3:1:1 to 2:1:1) to afford ethyl 5-chloropyrazolo[1,5-a]pyrimidine-3-carboxylate (15.6 g, 58%) as a white solid. $^1$H-NMR (CDCl$_3$, Varian, 400 MHz): δ 1.42 (3H, t, J=7.2 Hz), 4.42 (2H, q, J=7.2 Hz), 7.00 (1H, d, J=7.2 Hz), 8.64 (1H, s), 8.64 (1H, d, J=7.2 Hz).

Step C: ethyl 5-(2-(2,5-difluorophenyl)pyrrolidin-1-yl)pyrazolo[1,5-a]pyrimidine-3-carboxylate

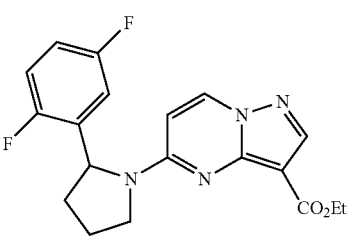 [SMILES: CCOC(=O)c1cnn2ccc(N3CCCC3c3cc(F)ccc3F)nc12]

A mixture of ethyl 5-chloropyrazolo[1,5-a]pyrimidine-3-carboxylate (1.00 g, 4.43 mmol), 2-(2,5-difluorophenyl)pyrrolidine (Intermediate 2, 853 mg, 4.65 mmol) and KF (1.28 g, 22.1 mmol) in DMSO (14 mL) was stirred at 180° C. for 2 hours. After being cooled to room temperature, the reaction mixture was poured into water. The mixture was stirred for 30 min. A precipitated solid was collected by filtration and dried under vacuum to afford ethyl 5-(2-(2,5-difluorophenyl)pyrrolidin-1-yl)pyrazolo[1,5-a]pyrimidine-3-carboxylate (1.51 g, 91%) as a yellow solid. $^1$H-NMR (CDCl$_3$, Varian, 400 MHz): δ 1.30-1.49 (3H, m), 1.98-2.18 (3H, m), 2.43-2.58 (1H, m), 3.95-4.20 (2H, m), 4.25-4.48 (2H, m), 5.18-5.23 (1H, m), 5.82-5.94 (1H, m), 6.68-6.80 (1H, m), 6.86-6.98 (1H, m), 7.00-7.12 (1H, m), 8.08-8.22 (1H, m), 8.29 (1H, s).

Step D: 5-(2-(2,5-difluorophenyl)pyrrolidin-1-yl)pyrazolo[1,5-a]pyrimidine-3-carboxylic acid

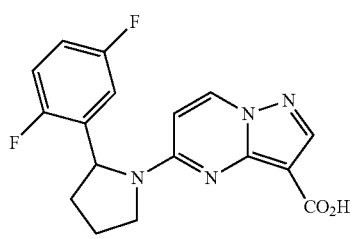

To a solution of ethyl 5-(2-(2,5-difluorophenyl)pyrrolidin-1-yl)pyrazolo[1,5-a]pyrimidine-3-carboxylate (1.51 g, 4.06 mmol) in EtOH (15 mL) and water (5.0 mL) was added LiOH (291 mg, 12.1 mmol) at 0° C. The reaction mixture was refluxed for 5 hours and cooled to room temperature. After evaporation of EtOH, the residue was acidified with 2 N aq. HCl until pH 5-6, and then extracted with EtOAc twice. The combined organic layers were washed with brine, dried over Na$_2$SO$_4$, filtered and concentrated in vacuo to afford 5-(2-(2,5-difluorophenyl)pyrrolidin-1-yl)pyrazolo[1,5-a]pyrimidine-3-carboxylic acid (1.33 g, 95%) as a pale yellow solid. $^1$H-NMR (DMSO-d$_6$, Varian, 400 MHz): δ 1.80-2.12 (3H, m), 2.35-2.46 (1H, m), 3.58-3.85 (1H, m), 3.94-4.06 (1H, m), 5.31 and 5.53 (1H, s+s), 6.07 and 6.67 (1H, s+s), 6.90-7.42 (3H, m), 8.10-8.24 (1H, m), 8.58 and 8.71 (1H, s+s), 11.4 (1H, br. s).

Example 8: Preparation of Intermediate Compound 9

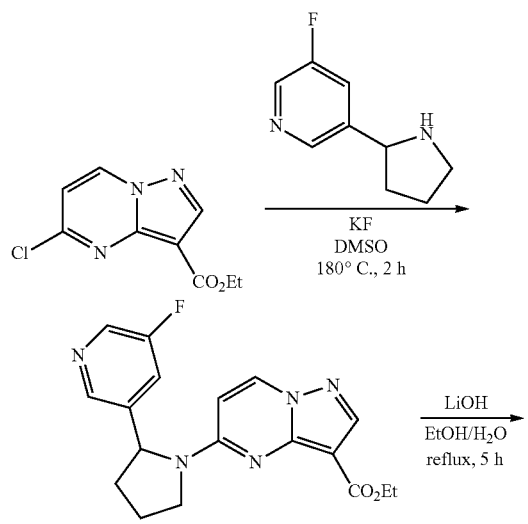

Intermediate Compound 9: 5-(2-(5-fluoropyridin-3-yl)pyrrolidin-1-yl)pyrazolo[1,5-a]pyrimidine-3-carboxylic acid

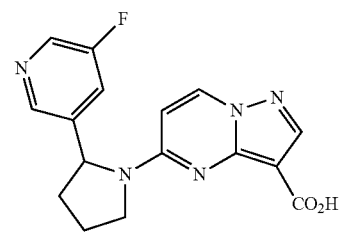

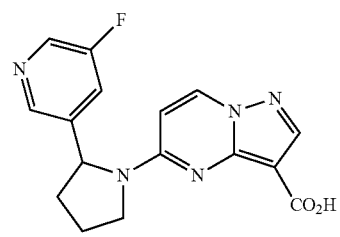 [SMILES: O=C(O)c1cnn2ccc(N3CCCC3c3cncc(F)c3)nc12]

Step A: ethyl 5-(2-(5-fluoropyridin-3-yl)pyrrolidin-1-yl)pyrazolo[1,5-a]pyrimidine-3-carboxylate

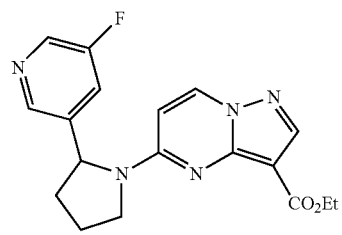 [SMILES: CCOC(=O)c1cnn2ccc(N3CCCC3c3cncc(F)c3)nc12]

A mixture of ethyl 5-chloropyrazolo[1,5-a]pyrimidine-3-carboxylate (1.05 g, 4.65 mmol), 2 3-fluoro-5-(pyrrolidin-2-yl)pyridine (Intermediate 1, 812 mg, 4.89 mmol) and KF (1.35 g, 23.3 mmol) in DMSO (15 mL) was stirred at 180° C. for 2 hours. After being cooled to room temperature, the reaction mixture was poured into water. The mixture was stirred for 30 min. A precipitated solid was collected by filtration and dried under vacuum to afford ethyl 5-(2-(5-fluoropyridin-3-yl)pyrrolidin-1-yl)pyrazolo[1,5-a]pyrimidine-3-carboxylate (1.53 g, 93%) as a yellow solid. 1H-NMR (CDCl$_3$, Varian, 400 MHz): δ 1.22-1.48 (3H, m), 2.01-2.28 (3H, m), 2.24-2.61 (1H, m), 3.51-4.20 (2H, m), 4.21-4.40 (2H, m), 5.02 and 5.62 (1H, s+s), 5.90 and 6.31 (1H, s+s), 7.20-7.50 (1H, m), 8.10-8.45 (4H, m).

Step B: 5-(2-(5-fluoropyridin-3-yl)pyrrolidin-1-yl)pyrazolo[1,5-a]pyrimidine-3-carboxylic acid

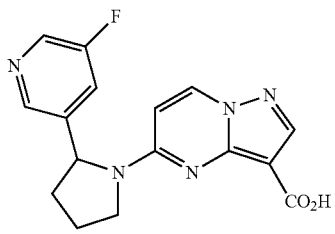 [SMILES: O=C(O)c1cnn2ccc(N3CCCC3c3cncc(F)c3)nc12]

To a solution of ethyl 5-(2-(5-fluoropyridin-3-yl)pyrrolidin-1-yl)pyrazolo[1,5-a]pyrimidine-3-carboxylate (1.53 g, 4.31 mmol) in EtOH (32 mL) and water (10 mL) was added LiOH (309 mg, 12.9 mmol) at 0° C. The reaction mixture was refluxed for 5 hours and cooled to room temperature. After evaporation of EtOH, the residue was acidified with 2 N aq. HCl until pH 5-6, and then extracted with EtOAc twice. The combined organic layers were washed with brine, dried over $Na_2SO_4$, filtered and concentrated in vacuo to afford 5-(2-(5-fluoropyridin-3-yl)pyrrolidin-1-yl)pyrazolo[1,5-a]pyrimidine-3-carboxylic acid (1.23 g, 87%) as a pale yellow solid. $^1$H-NMR (DMSO-$d_6$, Varian, 400 MHz): δ 1.19-2.20 (3H, m), 2.40-2.50 (1H, m), 3.60-3.82 (1H, m), 4.00-4.08 (1H, m), 5.25-5.48 (1H, m), 6.12 and 6.65 (1H, s+s), 7.66-7.80 (1H, m), 8.10-8.26 (1H, m), 8.40-8.80 (3H, m), 11.6 (1H, br. s).

Preparation of Chemical Compounds 1-10

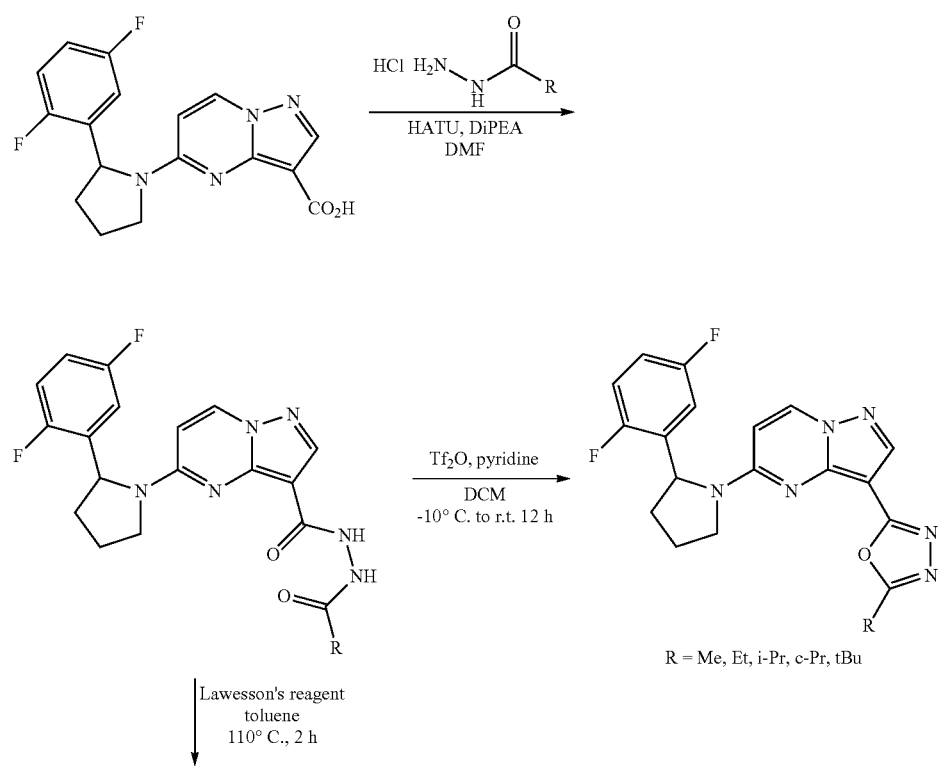

R = Me, Et, i-Pr, c-Pr, tBu

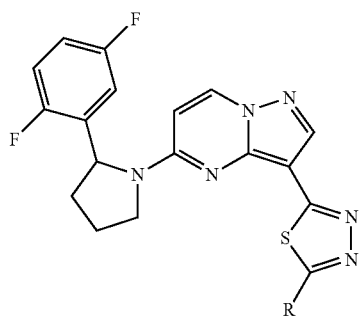

R = Me, Et, i-Pr, c-Pr, tBu

Example 9: Preparation of Chemical Compound 1: 2-(5-(2-(2,5-difluorophenyl)pyrrolidin-1-yl)pyrazolo[1,5-a]pyrimidin-3-yl)-5-methyl-1,3,4-oxadiazole

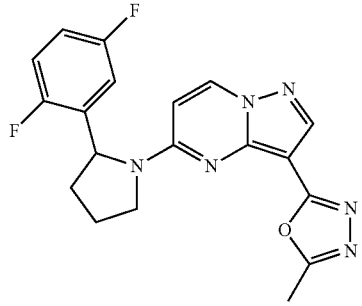

1

Step A: N'-acetyl-5-(2-(2,5-difluorophenyl)pyrrolidin-1-yl)pyrazolo[1,5-a]pyrimidine-3-carbohydrazide

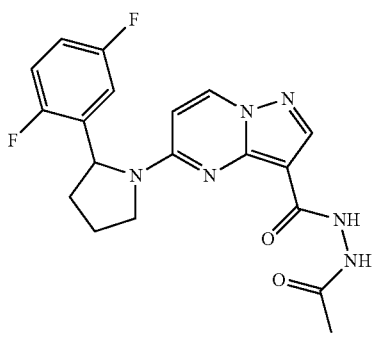 [SMILES: CC(=O)NNC(=O)c1cnn2ccc(N3CCCC3c3cc(F)ccc3F)nc12]

To a solution of 5-(2-(2,5-difluorophenyl)pyrrolidin-1-yl)pyrazolo[1,5-a]pyrimidine-3-carboxylic acid (Intermediate 8, 100 mg, 0.290 mmol) in DMF (2.0 mL) were added acetohydrazide (43.0 mg, 0.581 mmol), DIPEA (0.152 mL, 0.871 mmol), HATU (166 mg, 0.436 mmol) at room temperature. The reaction mixture was stirred at room temperature overnight and diluted with EtOAc. The mixture was washed with water and brine, dried over Na$_2$SO$_4$, filtered and concentrated in vacuo. The residue was purified by column chromatography on SiO$_2$ (EtOAc only to DCM:MeOH=20:1 to 10:1) to afford N'-acetyl-5-(2-(2,5-difluorophenyl)pyrrolidin-1-yl)pyrazolo[1,5-a]pyrimidine-3-carbohydrazide (72.0 mg, 62%) as a white solid. $^1$H-NMR (DMSO-d$_6$, Varian, 400 MHz): δ 1.80-1.92 (2H, m), 1.90-1.98 (1H, m), 2.10-2.16 (2H, m), 2.38-2.48 (1H, m), 3.66-3.78 (1H, m), 5.35-5.37 (1H, m), 6.26-6.27 and 6.69-6.71 (1H, m), 7.02-7.34 (3H, m), 8.14-8.28 (1H, m), 8.61-8.68 (1H, m), 8.82-8.93 (1H, m), 9.78 and 10.0 (1H, s+s). * Two protons from NHNH were not observed.

Step B: 2-(5-(2-(2,5-difluorophenyl)pyrrolidin-1-yl)pyrazolo[1,5-a]pyrimidin-3-yl)-5-methyl-1,3,4-oxadiazole

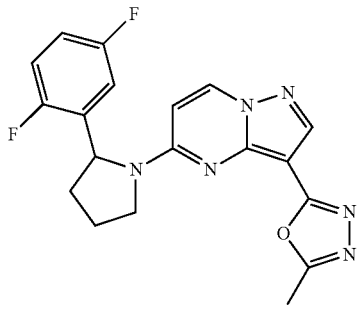

1

To a solution of N'-acetyl-5-(2-(2,5-difluorophenyl)pyrrolidin-1-yl)pyrazolo[1,5-a]pyrimidine-3-carbohydrazide (40.0 mg, 0.100 mmol) in DCM (0.6 mL) was added pyridine (0.0180 mL, 0.220 mmol) at 0° C. The mixture was cooled to −10° C., and then triflic anhydride (0.0350 mL, 0.210 mmol) was dropwise added to it. The reaction mixture was stirred at −10° C. for 1 hour and then at 0° C. for 1 hour. After quenched with water, the mixture was extracted with DCM twice. The combined organic layers were dried over Na$_2$SO$_4$, filtered and concentrate in vacuo. The residue was purified by column chromatography on SiO$_2$ (Hex:EtOAc=1:3 to 1:7) to afford 2-(5-(2-(2,5-difluorophenyl)pyrrolidin-1-yl)pyrazolo[1,5-a]pyrimidin-3-yl)-5-methyl-1,3,4-oxadiazole (15.0 mg, 40%) as a white solid. $^1$H-NMR (CDCl$_3$, Varian, 400 MHz): δ 2.04-2.25 (3H, m), 2.43-2.56 (3H, m), 4.05-4.30 (2H, m), 5.20 and 5.70 (1H, s+s), 5.93 and 6.37 (1H, s+s), 6.74-6.83 (1H, m), 6.85-7.20 (2H, m), 7.52-7.54 and 7.67-7.71 (1H, m+m), 8.19-8.56 (2H, m). MS: 383.3 [MH$^+$].

Example 10: Preparation of Chemical Compound 2: 2-(5-(2-(2,5-difluorophenyl)pyrrolidin-1-yl)pyrazolo[1,5-a]pyrimidin-3-yl)-5-methyl-1,3,4-thiadiazole

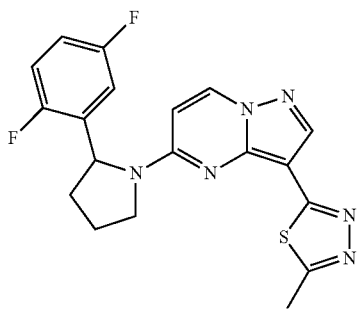

2

To a solution of N'-acetyl-5-(2-(2,5-difluorophenyl)pyrrolidin-1-yl)pyrazolo[1,5-a]pyrimidine-3-carbohydrazide (63.0 mg, 0.157 mmol) in toluene (3.0 mL) was added Lawesson's reagent (70.0 mg, 0.173 mmol) at room temperature. The reaction mixture was stirred at 110° C. for 2 hours, cooled to room temperature and partitioned between water and EtOAc. The separated organic layer was dried over Na$_2$SO$_4$, filtered and concentrated in vacuo.

The residue was purified by column chromatography on SiO₂ (DCM only to DCM:MeOH=10:1) to afford 2-(5-(2-(2,5-difluorophenyl)pyrrolidin-1-yl)pyrazolo[1,5-a]pyrimidin-3-yl)-5-methyl-1,3,4-thiadiazole (63.0 mg, 100%) as a white solid. ¹H-NMR (CDCl₃, Varian, 400 MHz): δ 2.04-2.30 (3H, m), 2.40-2.60 (1H, m), 2.32-2.94 (2H, m), 3.60-4.40 (3H, m), 5.22 and 5.66 (1H, s+s), 5.91 and 6.39 (1H, s+s), 6.65-7.18 (3H, m), 8.20-8.37 (1H, m), 8.50-8.60 (1H, m). MS: 399.3 [MH⁺].

Example 11: Preparation of Chemical Compound 3: 2-(5-(2-(2,5-difluorophenyl)pyrrolidin-1-yl)pyrazolo[1,5-a]pyrimidin-3-yl)-5-ethyl-1,3,4-oxadiazole

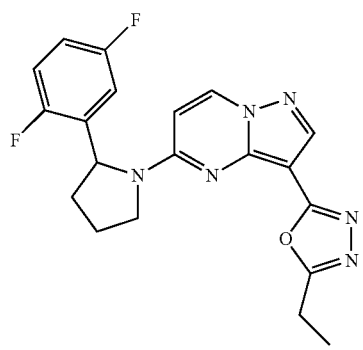

Step A: tert-butyl 2-propionylhydrazinecarboxylate

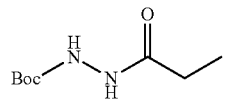

To a solution of tert-butyl hydrazinecarboxylate (3.00 g, 22.7 mmol), TEA (6.33 mL, 45.4 mmol) in DCM (51 mL) was added a solution of propionyl chloride (3.00 mL, 34.0 mmol) in DCM (10 mL) at 0° C. The reaction mixture was stirred at 0° C. for 2 hours and quenched with water. The mixture was extracted with DCM, washed with 1 N aq. HCl and brine, dried over Na₂SO₄, filtered and concentrated in vacuo. The residue was purified by column chromatography on SiO₂ (Hex:EtOAc=2:1 to 1:1) to afford tert-butyl 2-propionylhydrazinecarboxylate (2.03 g, 47%) as a white solid. ¹H-NMR (CDCl₃, Varian, 400 MHz): δ 1.19 (3H, t, J=7.6 Hz), 1.47 (9H, s), 2.26 (2H, q, J=7.6 Hz), 6.66 (1H, br. s), 7.67 (1H, br. s).

Step B: Propionohydrazide Hydrochloride

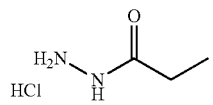

To a solution of tert-butyl 2-propionylhydrazinecarboxylate (615 mg, 3.27 mmol) in dioxane (11 mL) was added HCl (4 N in dioxane, 6.53 mL, 26.1 mmol) at room temperature. The reaction mixture was stirred at room temperature overnight and concentrated in vacuo. The residue was treated with ether. A precipitated solid was collected by filtration and dried under vacuum to afford propionohydrazide hydrochloride (272 mg, 66%) as a pale yellow solid. ¹H-NMR (DMSO-d₆, Varian, 400 MHz): δ 1.00 (3H, t, J=7.6 Hz), 2.20 (2H, q, J=7.6 Hz), 10.4 (3H, br. s), 11.0 (1H, br. s).

Step C: 5-(2-(2,5-difluorophenyl)pyrrolidin-1-yl)-N'-propionylpyrazolo[1,5-a]pyrimidine-3-carbohydrazide

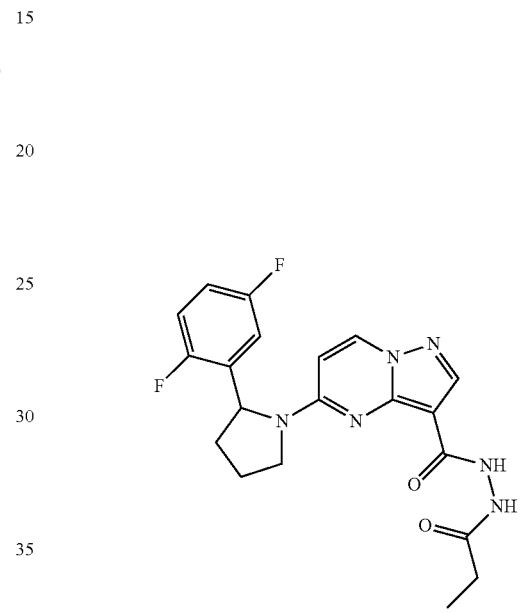

To a solution of 5-(2-(2,5-difluorophenyl)pyrrolidin-1-yl)pyrazolo[1,5-a]pyrimidine-3-carboxylic acid (Intermediate 8, 200 mg, 0.581 mmol) in DMF (4.0 mL) were added propionohydrazide hydrochloride (145 mg, 1.16 mmol), DIPEA (0.406 mL, 2.32 mmol), HATU (331 mg, 0.871 mmol) at room temperature. The reaction mixture was stirred at room temperature overnight and diluted with EtOAc. The mixture was washed with water and brine, dried over Na₂SO₄, filtered and concentrated in vacuo. The residue was purified by column chromatography on SiO₂ (EtOAc only to DCM:MeOH=20:1 to 10:1) to afford 5-(2-(2,5-difluorophenyl)pyrrolidin-1-yl)-N'-propionylpyrazolo[1,5-a]pyrimidine-3-carbohydrazide (177 mg, 73%) as a white solid. ¹H-NMR (CDCl₃, Varian, 400 MHz): δ 1.27 (3H, t, J=7.4 Hz), 2.04-2.28 (3H, m), 2.32-2.48 (2H, m), 2.48-2.51 (1H, m), 3.70-4.24 (2H, m), 5.22 (0.7H, d, J=7.2 Hz), 5.50-5.56 (0.3H, m), 5.92 (0.7H, d, J=7.2 Hz), 6.30-6.38 (0.3H, m), 6.72-7.09 (3H, m), 8.02-8.12 (0.3H, m), 8.16 (0.7H, d, J=7.2 Hz), 8.27-8.40 (1H, m), 9.13 (0.7H, d, J=6.8 Hz), 9.44-9.52 (0.3H, m), 10.9 (1H, d, J=6.8 Hz).

Step D: 2-(5-(2-(2,5-difluorophenyl)pyrrolidin-1-yl)pyrazolo[1,5-a]pyrimidin-3-yl)-5-ethyl-1,3,4-oxadiazole

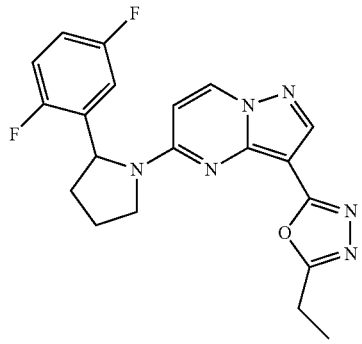

To a solution of 5-(2-(2,5-difluorophenyl)pyrrolidin-1-yl)-N'-propionylpyrazolo[1,5-a]pyrimidine-3-carbohydrazide (50.0 mg, 0.121 mmol) in DCM (1.0 mL) was added pyridine (0.0220 mL, 0.278 mmol) at 0° C. The mixture was cooled to −10° C., and then triflic anhydride (0.0430 mL, 0.253 mmol) was dropwise added to it. The reaction mixture was stirred at −10° C. for 1 hour and then at 0° C. for 1 hour. After quenched with water, the mixture was extracted with DCM twice. The combined organic layers were dried over Na$_2$SO$_4$, filtered and concentrate in vacuo. The residue was purified by column chromatography on SiO$_2$ (Hex: EtOAc=1:2 to 1:3) to afford 2-(5-(2-(2,5-difluorophenyl)pyrrolidin-1-yl)pyrazolo[1,5-a]pyrimidin-3-yl)-5-ethyl-1,3,4-oxadiazole (22.1 mg, 46%) as a white solid. $^1$H-NMR (CDCl$_3$, Varian, 400 MHz): δ 1.30-1.50 (3H, m), 2.00-2.18 (3H, m), 2.40-2.62 (1H, m), 2.80-3.04 (2H, m), 3.66-4.26 (2H, m), 5.21 and 5.74 (1H, s+s), 5.93 and 6.39 (1H, s+s), 6.72-7.6.80 (1H, m), 6.82-7.13 (2H, m), 8.10-8.40 (2H, m). MS: 397.3 [MH$^+$].

Example 12: Preparation of Chemical Compound 4: 2-(5-(2-(2,5-difluorophenyl)pyrrolidin-1-yl)pyrazolo[1,5-a]pyrimidin-3-yl)-5-ethyl-1,3,4-thiadiazole

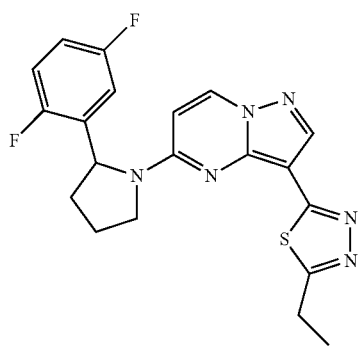

To a solution of 5-(2-(2,5-difluorophenyl)pyrrolidin-1-yl)-N'-propionylpyrazolo[1,5-a]pyrimidine-3-carbohydrazide (50.0 mg, 0.121 mmol) in toluene (2.5 mL) was added Lawesson's reagent (54.0 mg, 0.133 mmol) at room temperature. The reaction mixture was stirred at 110° C. for 2 hours, cooled to room temperature and partitioned between water and EtOAc. The separated organic layer was dried over Na$_2$SO$_4$, filtered and concentrated in vacuo. The residue was purified by column chromatography on SiO$_2$ (DCM only to DCM:MeOH=50:1) to afford 2-(5-(2-(2,5-difluorophenyl)pyrrolidin-1-yl)pyrazolo[1,5-a]pyrimidin-3-yl)-5-ethyl-1,3,4-thiadiazole (32.8 mg, 65%) as a white solid. $^1$H-NMR (CDCl$_3$, Varian, 400 MHz): δ 1.37-1.52 (3H, m), 2.00-2.21 (3H, m), 2.42-2.64 (1H, m), 3.31-3.22 (2H, m), 3.36-4.20 (2H, m), 5.21 and 5.69 (1H, s+s), 5.90 and 6.26 (1H, s+s), 6.65-6.70 (1H, m), 6.88-7.05 (2H, m), 8.20-8.38 (1H, m), 8.52-8.63 (1H, m). MS: 413.3 [MH$^+$].

Example 13: Preparation of Chemical Compound 5: 2-(5-(2-(2,5-difluorophenyl)pyrrolidin-1-yl)pyrazolo[1,5-a]pyrimidin-3-yl)-5-isopropyl-1,3,4-oxadiazole

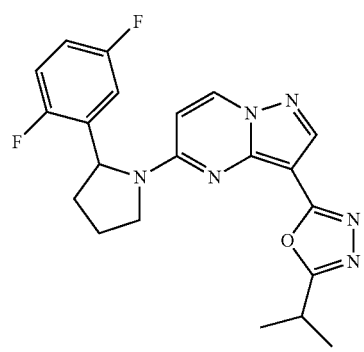

Step A: tert-butyl 2-isobutyryhydrazinecarboxylate

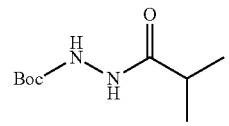

To a mixture of tert-butyl hydrazinecarboxylate (10.0 g, 76.0 mmol), TEA (21.1 mL, 151 mmol) in DCM (170 mL) was added a solution of isobutyryl chloride (12.1 g, 113 mmol) in DCM (34 mL) at 0° C. The reaction mixture was stirred at 0° C. for 1 hour and quenched with water. The mixture was extracted with DCM, washed with 1 N aq. HCl and brine, dried over Na$_2$SO$_4$, filtered and concentrated in vacuo. The residue was purified by column chromatography on SiO$_2$ (Hex:EtOAc=2:1 to 1:1) to afford tert-butyl 2-isobutyrylhydrazinecarboxylate (14.0 g, 91%) as a white solid. $^1$H-NMR (CDCl$_3$, Varian, 400 MHz): δ 1.20 (6H, d, J=6.8 Hz), 1.47 (9H, s), 2.41-2.47 (1H, m), 6.63 (1H, br. s), 7.57 (1H, br. s).

Step B: Isobutyrohydrazide Hydrochloride

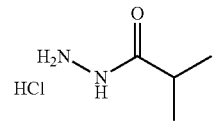

To a solution of tert-butyl 2-isobutyrylhydrazinecarboxylate (14.0 g, 69.2 mmol) in dioxane (230 mL) was added HCl (4 N in dioxane, 104 mL, 415 mmol) at room temperature. The reaction mixture was stirred at room temperature overnight and concentrated in vacuo. The residue was treated with ether. A precipitated solid was collected by filtration and dried under vacuum to afford isobutyrohydrazide hydrochloride (8.78 g, 92%) as a pale yellow solid. $^1$H-NMR (DMSO-$d_6$, Varian, 400 MHz): δ 1.06 (6H, d, J=6.8 Hz), 2.52-2.59 (1H, m), 10.4 (3H, br. s), 11.1 (1H, br. s).

Step C: 5-(2-(2,5-difluorophenyl)pyrrolidin-1-yl)-N'-isobutyrylpyrazolo[1,5-a]pyrimidine-3-carbohydrazide

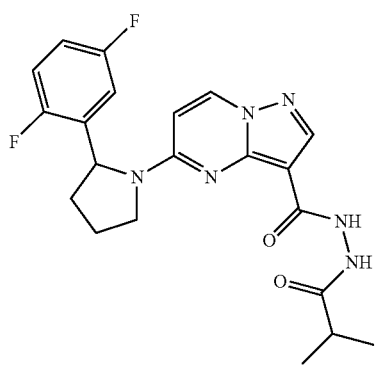 [SMILES: CC(C)C(=O)NNC(=O)c1cnn2ccc(N3CCCC3c3cc(F)ccc3F)nc12]

To a solution of 5-(2-(2,5-difluorophenyl)pyrrolidin-1-yl)pyrazolo[1,5-a]pyrimidine-3-carboxylic acid (Intermediate 8, 200 mg, 0.581 mmol) in DMF (4.0 mL) were added isobutyrohydrazide hydrochloride (161 mg, 1.16 mmol), DIPEA (0.406 mL, 2.32 mmol), HATU (331 mg, 0.871 mmol) at room temperature. The reaction mixture was stirred at room temperature overnight and diluted with EtOAc. The mixture was washed with water and brine, dried over $Na_2SO_4$, filtered and concentrated in vacuo. The residue was purified by column chromatography on $SiO_2$ (EtOAc only to DCM:MeOH=20:1 to 10:1) to afford 5-(2-(2,5-difluorophenyl)pyrrolidin-1-yl)-N'-isobutyrylpyrazolo[1,5-a]pyrimidine-3-carbohydrazide (186 mg, 75%) as a pale yellow solid. $^1$H-NMR (CDCl$_3$, Varian, 400 MHz): δ 1.28 (6H, d, J=6.0 Hz), 2.52-2.19 (3H, m), 2.50-2.61 (2H, m), 3.71-4.25 (2H, m), 5.22 (0.7H, d, J=7.6 Hz), 5.58-5.62 (0.3H, m), 5.92 (0.7H, d, J=7.2 Hz), 6.30-6.38 (0.3H, m), 6.72-7.09 (3H, m), 8.02-8.12 (0.3H, m), 8.19 (0.7H, d, J=7.6 Hz), 8.28-8.37 (1H, m), 9.02 (0.7H, d, J=6.0 Hz), 9.52-9.60 (0.3H, m), 10.9 (1H, d, J=7.2 Hz).

Step D: 2-(5-(2-(2,5-difluorophenyl)pyrrolidin-1-yl)pyrazolo[1,5-a]pyrimidin-3-yl)-5-isopropyl-1,3,4-oxadiazole

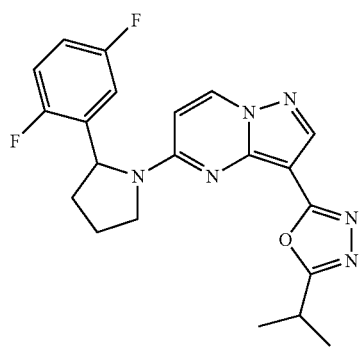

5

To a solution of 5-(2-(2,5-difluorophenyl)pyrrolidin-1-yl)-N'-isobutyrylpyrazolo[1,5-a]pyrimidine-3-carbohydrazide (70.0 mg, 0.163 mmol) in DCM (1.0 mL) was added pyridine (0.0300 mL, 0.376 mmol) at 0° C. The mixture was cooled to −10° C., and then triflic anhydride (0.0580 mL, 0.343 mmol) was dropwise added to it. The reaction mixture was stirred at −10° C. for 1 hour and then at 0° C. for 1 hour. After quenched with water, the mixture was extracted with DCM twice. The combined organic layers were dried over $Na_2SO_4$, filtered and concentrate in vacuo. The residue was purified by column chromatography on $SiO_2$ (Hex:EtOAc=1:2 to 1:3) to afford 2-(5-(2-(2,5-difluorophenyl)pyrrolidin-1-yl)pyrazolo[1,5-a]pyrimidin-3-yl)-5-isopropyl-1,3,4-oxadiazole (39.0 mg, 58%) as a white solid. $^1$H-NMR (CDCl$_3$, Varian, 400 MHz): δ 1.28-1.52 (6H, m), 2.00-2.21 (2H, m), 2.40-2.60 (1H, m), 3.10-3.30 (1H, m), 3.50-4.18 (3H, m), 5.22 and 5.80 (1H, s+s), 5.91 and 6.39 (1H, s+s), 6.69-6.80 (1H, m), 6.85-7.12 (2H, m), 8.12-8.42 (2H, m). MS: 411.3 [MH$^+$].

Example 14: Preparation of Chemical Compound 6: 2-(5-(2-(2,5-difluorophenyl)pyrrolidin-1-yl)pyrazolo[1,5-a]pyrimidin-3-yl)-5-isopropyl-1,3,4-thiadiazole

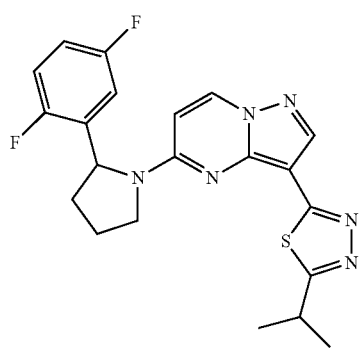

6

To a solution of 5-(2-(2,5-difluorophenyl)pyrrolidin-1-yl)-N'-isobutyrylpyrazolo[1,5-a]pyrimidine-3-carbohydrazide (100 mg, 0.233 mmol) in toluene (4.6 mL) was added Lawesson's Reagent (104 mg, 0.23 mmol) at room temperature. The reaction mixture was stirred at 110° C. for 2 hours, cooled to room temperature and partitioned between water and EtOAc. The separated organic layer was dried over Na₂SO₄, filtered and concentrated in vacuo. The residue was purified by column chromatography on SiO₂ (Hex: EtOAc=1:2 to EtOAc only) to afford 2-(5-(2-(2,5-difluorophenyl)pyrrolidin-1-yl)pyrazolo[1,5-a]pyrimidin-3-yl)-5-isopropyl-1,3,4-thiadiazole (61.0 mg, 61%) as a white solid. ¹H-NMR (CDCl₃, Varian, 400 MHz): δ 1.38-1.58 (6H, m), 2.01-2.28 (3H, m), 2.47-2.60 (1H, m), 3.42-3.75 (2H, m), 3.85-4.20 (2H, m), 5.22 and 5.72 (1H, s+s), 5.90 and 6.38 (1H, s+s), 6.62-6.80 (1H, m), 6.81-7.02 (2H, m), 8.20-8.37 (1H, m), 8.50-8.61 (1H, m). MS: 427.3 [MH⁺]

Example 15: Preparation of Chemical Compound 7: 2-cyclopropyl-5-(5-(2-(2,5-difluorophenyl)pyrrolidin-1-yl)pyrazolo[1,5-a]pyrimidin-3-yl)-1,3,4-oxadiazole

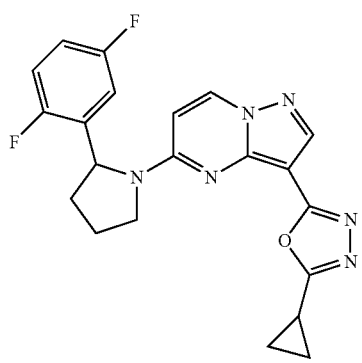

Step A: tert-butyl 2-(cyclopropanecarbonyl)hydrazinecarboxylate

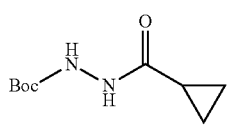

To a mixture of tert-butyl hydrazinecarboxylate (3.00 g, 22.7 mmol), TEA (6.33 mL, 45.4 mmol) in DCM (51 mL) was added a solution of cyclopropanecarbonyl chloride (3.10 mL, 34.0 mmol) in DCM (10 mL) at 0° C. The reaction mixture was stirred at 0° C. for 1 hour and quenched with water. The mixture was extracted with DCM, washed with 1 N aq. HCl and brine, dried over Na₂SO₄, filtered and concentrated in vacuo. The residue was purified by column chromatography on SiO₂ (Hex:EtOAc=2:1 to 1:1) to afford tert-butyl 2-(cyclopropanecarbonyl)hydrazinecarboxylate (2.16 g, 47%) as a white solid. ¹H-NMR (CDCl₃, Varian, 400 MHz): δ 0.81-0.84 (2H, m), 1.02-1.04 (2H, m), 1.45-1.52 (10H, m), 6.65 (1H, br. s), 7.95 (1H, br. s).

Step B: Cyclopropanecarbohydrazide Hydrochloride

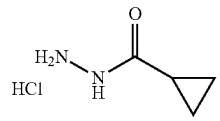

To a solution of tert-butyl 2-(cyclopropanecarbonyl)hydrazinecarboxylate (2.16 g, 10.8 mmol) in dioxane (36 mL) was added HCl (4 N in dioxane, 6.53 mL, 26.1 mmol) at room temperature. The reaction mixture was stirred at room temperature overnight and concentrated in vacuo. The residue was treated with ether. A precipitated solid was collected by filtration and dried under vacuum to afford cyclopropanecarbohydrazide hydrochloride (1.38 g, 94%) as a pale yellow solid. ¹H-NMR (DMSO-d₆, Varian, 400 MHz): δ 0.77-0.88 (4H, m), 1.73-1.79 (1H, m), 10.5 (3H, br. s), 11.3 (1H, br. s).

Step C: N'-(cyclopropanecarbonyl)-5-(2-(2,5-difluorophenyl)pyrrolidin-1-yl)pyrazolo[1,5-a]pyrimidine-3-carbohydrazide

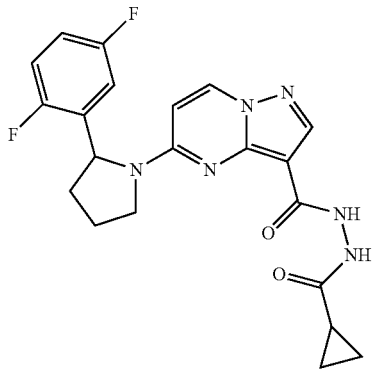 [SMILES: O=C(NNC(=O)C1CC1)c1cnn2ccc(N3CCCC3c3cc(F)ccc3F)nc12]

To a solution of 5-(2-(2,5-difluorophenyl)pyrrolidin-1-yl)pyrazolo[1,5-a]pyrimidine-3-carboxylic acid (Intermediate 8, 200 mg, 0.581 mmol) in DMF (4.0 mL) were added cyclopropanecarbohydrazide hydrochloride (159 mg, 1.16 mmol), DIPEA (0.406 mL, 2.32 mmol), and HATU (331 mg, 0.871 mmol) at room temperature. The reaction mixture was stirred at room temperature overnight and diluted with EtOAc. The mixture was washed with water and brine, dried over Na₂SO₄, filtered and concentrated in vacuo. The residue was purified by column chromatography on SiO₂ (DCM:MeOH=100:1 to 20:1) to afford N'-(cyclopropanecarbonyl)-5-(2-(2,5-difluorophenyl)pyrrolidin-1-yl)pyrazolo[1,5-a]pyrimidine-3-carbohydrazide (215 mg, 87%) as a white solid. ¹H-NMR (CDCl₃, Varian, 400 MHz): δ 0.84-0.90 (2H, m), 1.09-0.15 (2H, m), 2.00-2.25 (3H, m), 2.48-2.61 (1H, m), 3.71-4.17 (3H, m), 5.22 (0.7H, d, J=8.4 Hz), 5.50-5.58 (0.3H, m), 5.91 (0.7H, d, J=7.6 Hz), 6.30-6.38 (0.3H, m), 6.71-7.09 (2H, m), 8.18 (0.7H, d, J=7.2 Hz), 8.52-8.62 (0.3H, m), 8.25-8.37 (2H, m), 9.04-9.46 (1H, m), 10.65-10.75 (1H, m).

Step D: 2-cyclopropyl-5-(5-(2-(2,5-difluorophenyl)pyrrolidin-1-yl)pyrazolo[1,5-a]pyrimidin-3-yl)-1,3,4-oxadiazole

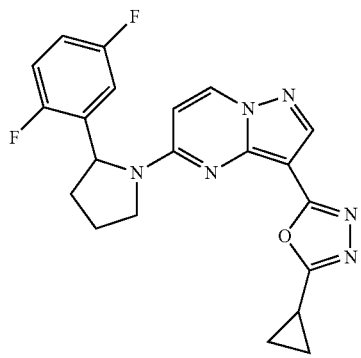

To a solution of N'-(cyclopropanecarbonyl)-5-(2-(2,5-difluorophenyl)pyrrolidin-1-yl)pyrazolo[1,5-a]pyrimidine-3-carbohydrazide (100 mg, 0.235 mmol) in DCM (1.5 mL) was added pyridine (0.0440 mL, 0.539 mmol) at 0° C. The mixture was cooled to −10° C., and then triflic anhydride (0.0830 mL, 0.492 mmol) was dropwise added to it. The reaction mixture was stirred at −10° C. for 1 hour and then at 0° C. for 1 hour. After quenched with water, the mixture was extracted with DCM twice. The combined organic layers were dried over Na$_2$SO$_4$, filtered and concentrate in vacuo. The residue was purified by column chromatography on SiO$_2$ (Hex:EtOAc=1:3 to 1:7) to afford 2-cyclopropyl-5-(5-(2-(2,5-difluorophenyl)pyrrolidin-1-yl)pyrazolo[1,5-a]pyrimidin-3-yl)-1,3,4-oxadiazole (49.0 mg, 51%) as a white solid. $^1$H-NMR (CDCl$_3$, Varian, 400 MHz): δ 1.00-1.18 (4H, m), 2.01-2.18 (4H, m), 2.32-2.61 (1H, m), 3.61-4.20 (2H, m), 5.20 and 5.77 (1H, s+s), 5.92 and 6.39 (1H, s+s), 6.70-6.80 (1H, m), 6.82-7.12 (2H, m), 8.12-8.37 (2H, m). MS: 409.3 [MH$^+$].

Example 16: Preparation of Chemical Compound 8: 2-cyclopropyl-5-(5-(2-(2,5-difluorophenyl)pyrrolidin-1-yl)pyrazolo[1,5-a]pyrimidin-3-yl)-1,3,4-thiadiazole

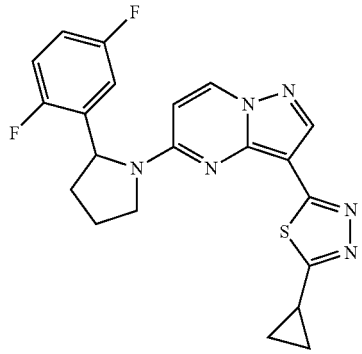

To a solution of N'-(cyclopropanecarbonyl)-5-(2-(2,5-difluorophenyl)pyrrolidin-1-yl)pyrazolo[1,5-a]pyrimidine-3-carbohydrazide (80.0 mg, 0.188 mmol) in toluene (3.5 mL) was added Lawesson's reagent (76.0 mg, 0.188 mmol) at room temperature. The reaction mixture was stirred at 110° C. for 2 hours, cooled to room temperature and partitioned between water and EtOAc. The separated organic layer was dried over Na$_2$SO$_4$, filtered and concentrated in vacuo. The residue was purified by column chromatography on SiO$_2$ (EtOAc only to DCM:MeOH=10:1) to afford 2-cyclopropyl-5-(5-(2-(2,5-difluorophenyl)pyrrolidin-1-yl)pyrazolo[1,5-a]pyrimidin-3-yl)-1,3,4-thiadiazole (23.0 mg, 29%) as a white solid. $^1$H-NMR (CDCl$_3$, Varian, 400 MHz): δ 0.88-0.95 (2H, m), 1.10-1.30 (2H, m), 2.01-2.25 (3H, m), 2.40-2.61 (2H, m), 3.61-3.67 (1H, m), 3.82-4.10 (1H, m), 5.21 and 5.68 (1H, s+s), 5.90 and 6.37 (1H, s+s), 6.62-6.80 (1H, m), 6.83-7.02 (1H, m), 7.04-7.12 (1H, m), 8.15-8.42 (1H, m), 8.50-8.61 (1H, m). MS: 425.3 [MH$^+$].

Example 17: Preparation of Chemical Compound 9: 2-tert-butyl-5-(5-(2-(2,5-difluorophenyl)pyrrolidin-1-yl)pyrazolo[1,5-a]pyrimidin-3-yl)-1,3,4-oxadiazole

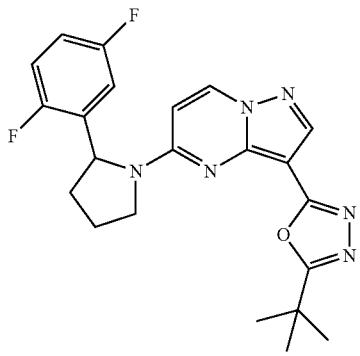

Step A: tert-butyl 2-pivaloylhydrazinecarboxylate

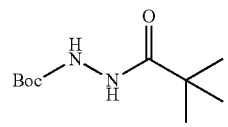

To a solution of tert-butyl hydrazinecarboxylate (5.00 g, 37.8 mmol), TEA (10.6 mL, 76.0 mmol) in DCM (85 mL) was added a solution of pivaloyl chloride (6.98 mL, 56.7 mmol) in DCM (85 mL) at 0° C. The reaction mixture was stirred at 0° C. for 1 hour and quenched with water. The mixture was extracted with DCM, washed with 1 N aq. HCl and brine, dried over Na$_2$SO$_4$, filtered and concentrated in vacuo. The residue was purified by column chromatography on SiO$_2$ (Hex:EtOAc=1:1) to afford tert-butyl 2-pivaloylhydrazinecarboxylate (7.65 g, 93%) as a white solid. $^1$H-NMR (CDCl$_3$, Varian, 400 MHz): δ 1.25 (9H, s), 1.47 (9H, s), 6.48 (1H, br. s), 7.39 (1H, br. s).

Step B: Pivalohydrazide Hydrochloride

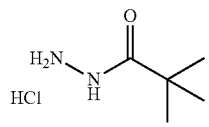

To a solution of tert-butyl 2-pivaloylhydrazinecarboxylate (7.65 g, 35.4 mmol) in dioxane (118 mL) was added HCl (4 N in dioxane, 70 mL, 283 mmol) at room temperature. The reaction mixture was stirred at room temperature overnight and concentrated in vacuo. The residue was treated with ether. A predipitated solid was collected by filtration and dried under vacuum to afford pivalohydrazide hydrochloride (5.06 g, 94%) as a pale yellow solid. $^1$H-NMR (DMSO-$d_6$, Varian, 400 MHz): δ 1.17 (9H, s), 10.3 (3H, br. s), 10.8 (1H, br. s).

Step C: 5-(2-(2,5-difluorophenyl)pyrrolidin-1-yl)-N'-pivaloylpyrazolo[1,5-a]pyrimidine-3-carbohydrazide

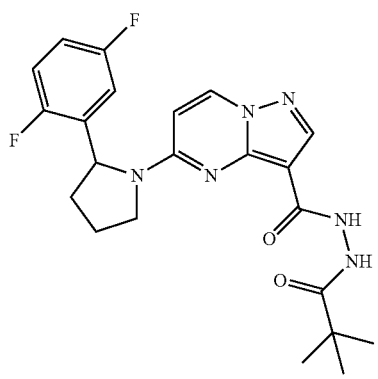 [SMILES: CC(C)(C)C(=O)NNC(=O)c1cnn2ccc(N3CCCC3c3cc(F)ccc3F)nc12]

To a solution of 5-(2-(2,5-difluorophenyl)pyrrolidin-1-yl)pyrazolo[1,5-a]pyrimidine-3-carboxylic acid (Intermediate 8, 441 mg, 1.28 mmol) in DMF (8.5 mL) were added pivalohydrazide hydrochloride (391 mg, 2.56 mmol), DIPEA (0.895 mL, 5.12 mmol), HATU (730 mg, 1.92 mmol) at room temperature. The reaction mixture was stirred at room temperature overnight, poured into water and stirred additional 30 min at room temperature. A precipitated solid was collected by filtration and dried under vacuum to afford 5-(2-(2,5-difluorophenyl)pyrrolidin-1-yl)-N'-pivaloylpyrazolo[1,5-a]pyrimidine-3-carbohydrazide (454 mg, 80%) as a pale yellow solid. $^1$H-NMR (DMSO-$d_6$, Varian, 400 MHz): δ 1.19 (9H, s), 1.81-2.15 (3H, m), 2.45-2.50 (1H, m), 3.65-3.72 (1H, m), 4.00-4.08 (1H, m), 5.36-5.42 (1H, m), 6.70 (1H, d, J=8.0 Hz), 6.95-7.11 (3H, m), 8.23 (1H, s), 8.55 (1H, s), 8.83 (1H, d, J=8.0 Hz), 9.53 (1H, s).

Step D: 2-tert-butyl-5-(5-(2-(2,5-difluorophenyl)pyrrolidin-1-yl)pyrazolo[1,5-a]pyrimidin-3-yl)-1,3,4-oxadiazole

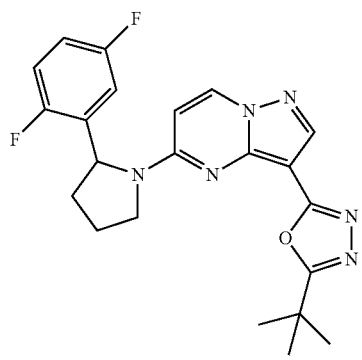

To a solution of 5-(2-(2,5-difluorophenyl)pyrrolidin-1-yl)-N'-pivaloylpyrazolo[1,5-a]pyrimidine-3-carbohydrazide (651 mg, 1.47 mmol) in DCM (10 mL) was added pyridine (0.274 mL, 3.38 mmol) at 0° C. The mixture was cooled to −10° C., and then triflic anhydride (0.522 mL, 3.09 mmol) was dropwise added to it. The reaction mixture was stirred at −10° C. for 1 hour and then at 0° C. for 1 hour. After quenched with water, the mixture was extracted with DCM twice. The combined organic layers were dried over Na$_2$SO$_4$, filtered and concentrate in vacuo. The residue was purified by column chromatography on SiO$_2$ (Hex:EtOAc=1:3 to 1:4) to afford 2-tert-butyl-5-(5-(2-(2,5-difluorophenyl)pyrrolidin-1-yl)pyrazolo[1,5-a]pyrimidin-3-yl)-1,3,4-oxadiazole (402 mg, 64%) as a white solid. $^1$H-NMR (DMSO-$d_6$, Varian, 400 MHz): δ 1.27 and 1.44 (9H, s+s), 1.82-2.18 (3H, m), 2.32-2.44 (1H, m), 3.54-3.90 (1H, m), 4.00-4.08 (1H, m), 5.32-5.38 (0.3H, m), 5.67 (0.7H, d, J=7.6 Hz), 6.06-6.12 (0.3H, m), 6.71 (0.7H, d, J=8.0 Hz), 6.88-7.38 (3H, m), 8.32-8.42 (1H, m), 8.58-8.65 (0.3H, m), 8.84 (0.7H, d, J=8.0 Hz). MS: 425.3 [MH$^+$].

Example 18: Preparation of Chemical Compound 10: 2-tert-butyl-5-(5-(2-(2,5-difluorophenyl)pyrrolidin-1-yl)pyrazolo[1,5-a]pyrimidin-3-yl)-1,3,4-thiadiazole

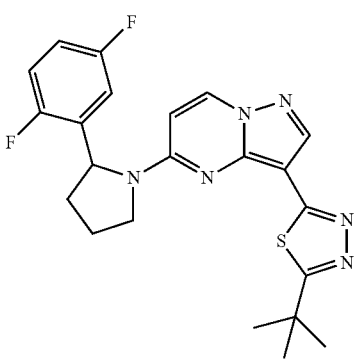

To a solution of 5-(2-(2,5-difluorophenyl)pyrrolidin-1-yl)-N'-pivaloylpyrazolo[1,5-a]pyrimidine-3-carbohydrazide (50.0 mg, 0.113 mmol) in diglyme (2.2 mL) were added P$_4$S$_{10}$ (100 mg, 0.226 mmol) and Na$_2$CO$_3$ (48.0 mg, 0.452 mmol) at room temperature. The reaction mixture was stirred at 90° C. for 2 hours, cooled to room temperature and partitioned between water and EtOAc. The separated organic layer was dried over Na$_2$SO$_4$, filtered and concentrated in vacuo. The residue was purified by column chromatography on SiO$_2$ (EtOAc only to DCM:MeOH=10:1) to afford 2-tert-butyl-5-(5-(2-(2,5-difluorophenyl)pyrrolidin-1-yl)pyrazolo[1,5-a]pyrimidin-3-yl)-1,3,4-thiadiazole (30.0 mg, 60%) as a white solid. MS: 441.4 [MH$^+$].

Preparation of Chemical Compounds 11-15

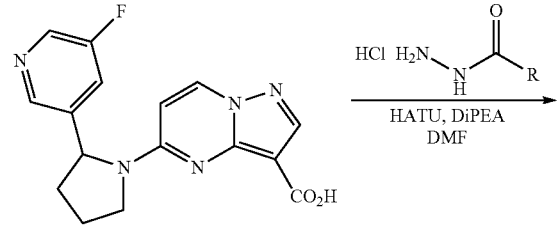

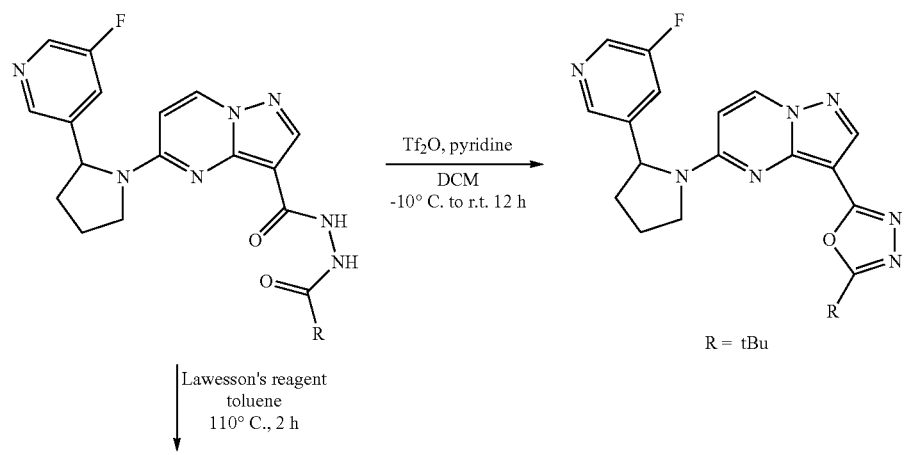

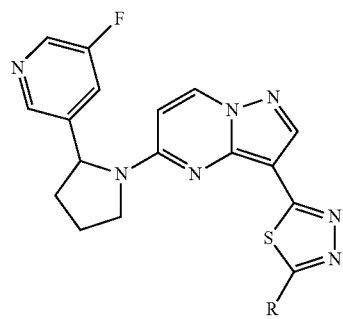

R = Me, Et, i-Pr, c-Pr, tBu

Example 19: Preparation of Chemical Compound 11: 2-(5-(2-(5-fluoropyridin-3-yl)pyrrolidin-1-yl)pyrazolo[1,5-a]pyrimidin-3-yl)-5-methyl-1,3,4-thiadiazole

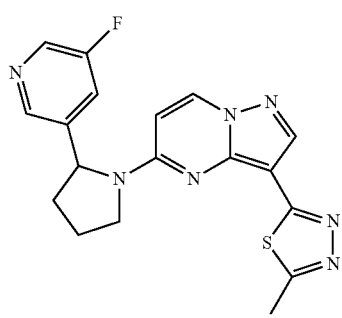

11

Step A: N'-acetyl-5-(2-(5-fluoropyridin-3-yl)pyrrolidin-1-yl)pyrazolo[1,5-a]pyrimidine-3-carbohydrazide

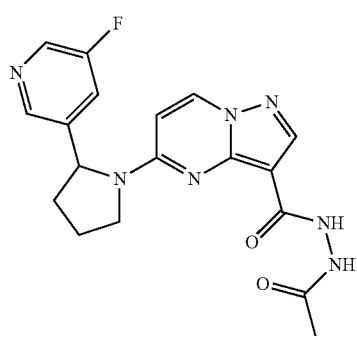 [SMILES: CC(=O)NNC(=O)c1cnn2ccc(N3CCCC3c3cncc(F)c3)nc12]

To a solution of 5-(2-(5-fluoropyridin-3-yl)pyrrolidin-1-yl)pyrazolo[1,5-a]pyrimidine-3-carboxylic acid (Intermediate 9, 200 mg, 0.611 mmol) in DMF (4.0 mL) were added acetohydrazide (91.0 mg, 1.22 mmol), DIPEA (0.320 mL, 283 mmol), and HATU (349 mg, 0.917 mmol) at room temperature. The reaction mixture was stirred at room temperature overnight and poured into water. The mixture was stirred for 30 min. A precipitated solid was collected by filtration and dried under vacuum to afford N'-acetyl-5-(2-(5-fluoropyridin-3-yl)pyrrolidin-1-yl)pyrazolo[1,5-a]pyrimidine-3-carbohydrazide (168 mg, 71%) as a white solid. $^1$H-NMR (CDCl$_3$, Varian, 400 MHz): δ 2.00-2.15 (5H, m), 2.50-2.63 (1H, m), 3.68-4.30 (2H, m), 5.06 and 5.30 (1H, s+s), 5.68 and 6.39 (1H, s+s), 7.10-7.40 (1H, m), 8.20-9.04 (4H, m), 9.84 and 10.8 (1H, s+s). * Two protons from NHNH were not observed.

Step B: 2-(5-(2-(5-fluoropyridin-3-yl)pyrrolidin-1-yl)pyrazolo[1,5-a]pyrimidin-3-yl)-5-methyl-1,3,4-thiadiazole

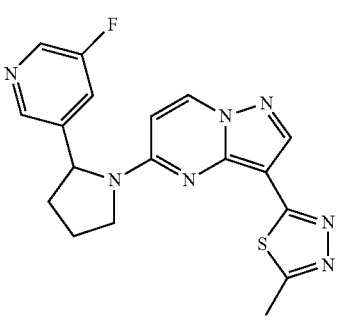

11

To a solution of N'-acetyl-5-(2-(5-fluoropyridin-3-yl)pyrrolidin-1-yl)pyrazolo[1,5-a]pyrimidine-3-carbohydrazide (50.0 mg, 0.130 mmol) in diglyme (2.6 mL) were added P$_4$S$_{10}$ (116 mg, 0.261 mmol) and Na$_2$CO$_3$ (55.0 mg, 0.522 mmol) at room temperature. The reaction mixture was stirred at 90° C. overnight, cooled to room temperature and partitioned between water and EtOAc. The separated organic layer was dried over Na$_2$SO$_4$, filtered and concentrated in vacuo. The residue was purified by column chromatography on SiO$_2$ (EtOAc:MeOH=100:1 to 10:1) to afford 2-(5-(2-(5-fluoropyridin-3-yl)pyrrolidin-1-yl)pyrazolo[1,5-a]pyrimidin-3-yl)-5-methyl-1,3,4-thiadiazole (36.0 mg, 72%) as a white solid. $^1$H-NMR (CDCl$_3$, Varian, 400 MHz): δ 2.00-2.30 (3H, m), 2.50-2.80 (4H, m), 3.62-4.12 (2H, m), 5.01 and 5.49 (1H, s+s), 5.90 and 6.68 (1H, s+s), 7.20-2.26 (1H, m), 8.29-8.62 (4H, m). MS: 382.3 [MH$^+$].

Example 20: Preparation of Chemical Compound 12: 2-ethyl-5-(5-(2-(5-fluoropyridin-3-yl)pyrrolidin-1-yl)pyrazolo[1,5-a]pyrimidin-3-yl)-1,3,4-thiadiazole

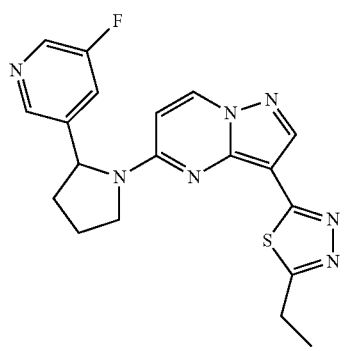

12

Step A: N'-acetyl-5-(2-(5-fluoropyridin-3-yl)pyrrolidin-1-yl)pyrazolo[1,5-a]pyrimidine-3-carbohydrazide

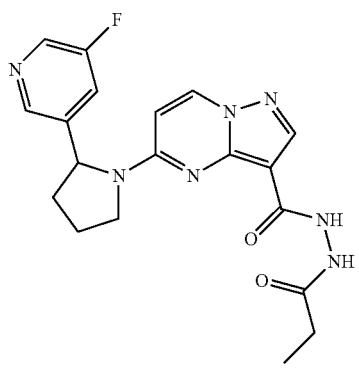 [SMILES: CCC(=O)NNC(=O)c1cnn2ccc(N3CCCC3c3cncc(F)c3)nc12]

To a solution of 5-(2-(5-fluoropyridin-3-yl)pyrrolidin-1-yl)pyrazolo[1,5-a]pyrimidine-3-carboxylic acid (Intermediate 9, 200 mg, 0.611 mmol) in DMF (4.0 mL) were added propionohydrazide hydrochloride (152 mg, 1.22 mmol), DIPEA (0.320 mL, 283 mmol) and HATU (349 mg, 0.917 mmol) at room temperature. The reaction mixture was stirred at room temperature overnight and poured into water. The mixture was stirred for 30 min. A precipitated solid was collected by filtration and dried under vacuum to afford N'-acetyl-5-(2-(5-fluoropyridin-3-yl)pyrrolidin-1-yl)pyrazolo[1,5-a]pyrimidine-3-carbohydrazide (168 mg, 71%) as a white solid. $^1$H-NMR (CDCl$_3$, Varian, 400 MHz): δ 1.27 (3H, t, J=7.4 Hz), 2.00-2.28 (3H, m), 2.32-2.45 (3H, m), 2.50-2.67 (1H, m), 3.73-4.26 (2H, m), 5.07 and 5.72 (1H, s+s), 5.71 and 5.90 (1H, s+s), 7.21-7.40 (1H, m), 8.19-9.04 (4H, m), 9.96 and 10.84 (1H, s+s).

Step B: 2-ethyl-5-(5-(2-(5-fluoropyridin-3-yl)pyrrolidin-1-yl)pyrazolo[1,5-a]pyrimidin-3-yl)-1,3,4-thiadiazole

12

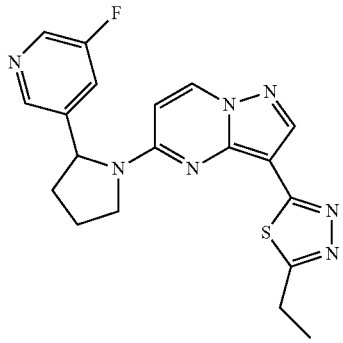

To a solution of 5-(2-(5-fluoropyridin-3-yl)pyrrolidin-1-yl)-N'-propionylpyrazolo[1,5-a]pyrimidine-3-carbohydrazide (50.0 mg, 0.126 mmol) in diglyme (2.6 mL) were added P$_4$S$_{10}$ (112 mg, 0.252 mmol) and Na$_2$CO$_3$ (53.0 mg, 0.503 mmol) at room temperature. The reaction mixture was stirred at 90° C. for 2 hours, cooled to room temperature and partitioned between water and EtOAc. The separated organic layer was dried over Na$_2$SO$_4$, filtered and concentrated in vacuo. The residue was purified by column chromatography on SiO$_2$ (EtOAc:MeOH=50:1 to 10:1) to afford 2-ethyl-5-(5-(2-(5-fluoropyridin-3-yl)pyrrolidin-1-yl)pyrazolo[1,5-a]pyrimidin-3-yl)-1,3,4-thiadiazole (36.0 mg, 72%) as a white solid. $^1$H-NMR (CDCl$_3$, Varian, 400 MHz): δ 1.40-1.52 (3H, m), 2.00-2.23 (3H, m), 2.52-2.65 (1H, m), 3.05-3.20 (2H, m), 3.60-3.80 (2H, m), 5.08 and 5.52 (1H, s+s), 5.88 and 6.38 (1H, s+s), 7.24-7.26 (1H, m), 8.30-8.60 (4H, m). MS: 396.3 [MH$^+$].

Example 21: Preparation of Chemical Compound 13: 2-(5-(2-(5-fluoropyridin-3-yl)pyrrolidin-1-yl)pyrazolo[1,5-a]pyrimidin-3-yl)-5-isopropyl-1,3,4-thiadiazole

13

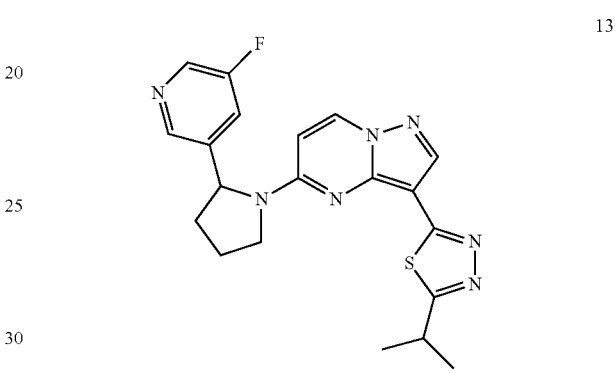

Step A: 5-(2-(5-fluoropyridin-3-yl)pyrrolidin-1-yl)-N'-isobutyrylpyrazolo[1,5-a]pyrimidine-3-carbohydrazide

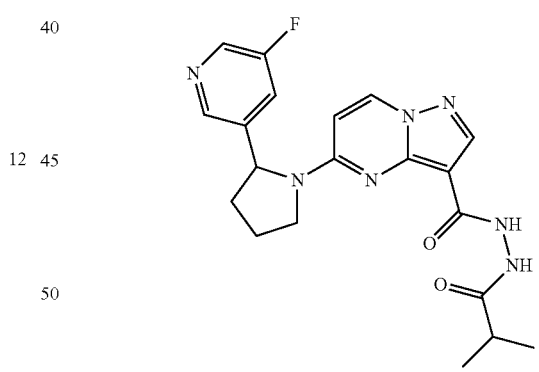

To a solution of 5-(2-(5-fluoropyridin-3-yl)pyrrolidin-1-yl)pyrazolo[1,5-a]pyrimidine-3-carboxylic acid (Intermediate 9, 200 mg, 0.611 mmol) in DMF (4.0 mL) were added isobutyrohydrazide hydrochloride (161 mg, 1.22 mmol), DIPEA (0.427 mL, 2.44 mmol) and HATU (349 mg, 0.917 mmol) at room temperature. The reaction mixture was stirred at room temperature overnight and poured into water. The mixture was stirred for 30 min. A precipitated solid was collected by filtration and dried under vacuum to afford 5-(2-(5-fluoropyridin-3-yl)pyrrolidin-1-yl)-N'-isobutyrylpyrazolo[1,5-a]pyrimidine-3-carbohydrazide (208 mg, 83%) as a pale yellow solid. $^1$H-NMR (CDCl$_3$, Varian, 400 MHz): δ 1.26-1.39 (6H, m), 2.00-2.26 (3H, m), 2.50-2.62

(2H, m), 3.70-4.26 (2H, m), 5.06 and 5.32 (1H, s+s), 5.76 (0.3H, s), 6.39 (0.7H, d, J=8.0 Hz), 7.26-7.52 (1H, m), 8.24-8.90 (5H, m), 10.06 and 10.85 (1H, s+s).

Step B: 2-(5-(2-(5-fluoropyridin-3-yl)pyrrolidin-1-yl)pyrazolo[1,5-a]pyrimidin-3-yl)-5-isopropyl-1,3,4-thiadiazole

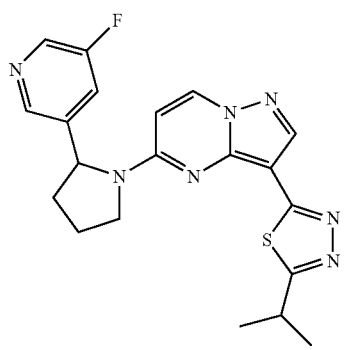

13

To a solution of 5-(2-(5-fluoropyridin-3-yl)pyrrolidin-1-yl)-N'-isobutyrylpyrazolo[1,5-a]pyrimidine-3-carbohydrazide (50.0 mg, 0.122 mmol) in diglyme (2.6 mL) were added P$_4$S$_{10}$ (108 mg, 0.243 mmol) and Na$_2$CO$_3$ (52.0 mg, 0.486 mmol) at room temperature. The reaction mixture was stirred at 90° C. overnight, cooled to room temperature and partitioned between water and EtOAc. The separated organic layer was dried over Na$_2$SO$_4$, filtered and concentrated in vacuo. The residue was purified by column chromatography on SiO$_2$ (EtOAc:MeOH=100:1 to 20:1) to afford 2-(5-(2-(5-fluoropyridin-3-yl)pyrrolidin-1-yl)pyrazolo[1,5-a]pyrimidin-3-yl)-5-isopropyl-1,3,4-thiadiazole (37.0 mg, 74%) as a white solid. $^1$H-NMR (CDCl$_3$, Varian, 400 MHz): δ 1.35-1.70 (7H, m), 2.00-2.28 (3H, m), 2.52-2.67 (1H, m), 3.38-3.57 (1H, m), 3.61-3.80 (1H, m), 3.87-4.17 (1H, m), 5.08 and 5.51 (1H, s+s), 5.84 and 6.38 (1H, s+s), 7.22-7.26 (1H, m), 8.29-8.40 (1H, m), 8.42 (1H, s), 8.55 (1H, s). MS: 410.3 [MH$^+$].

Example 22: Preparation of Chemical Compound 14: 2-cyclopropyl-5-(5-(2-(5-fluoropyridin-3-yl)pyrrolidin-1-yl)pyrazolo[1,5-a]pyrimidin-3-yl)-1,3,4-thiadiazole

14

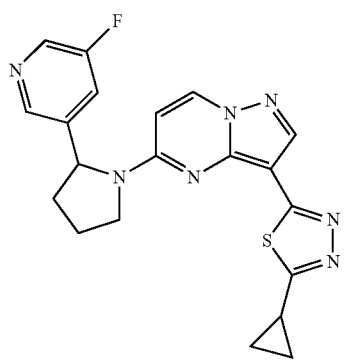

Step A: N'-(cyclopropanecarbonyl)-5-(2-(5-fluoropyridin-3-yl)pyrrolidin-1-yl)pyrazolo[1,5-a]pyrimidine-3-carbohydrazide

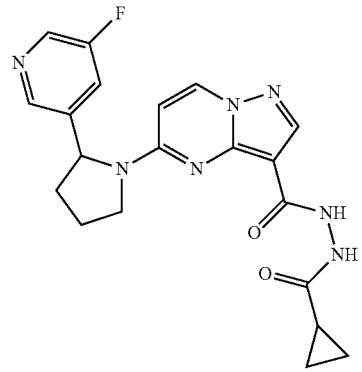 [SMILES: O=C(NNC(=O)C1CC1)c1cnn2ccc(N3CCCC3c3cncc(F)c3)nc12]

To a solution of 5-(2-(5-fluoropyridin-3-yl)pyrrolidin-1-yl)pyrazolo[1,5-a]pyrimidine-3-carboxylic acid (Intermediate 9, 200 mg, 0.611 mmol) in DMF (4.0 mL) were added cyclopropanecarbohydrazide hydrochloride (167 mg, 1.22 mmol), DIPEA (0.427 mL, 2.44 mmol) and HATU (349 mg, 0.917 mmol) at room temperature. The reaction mixture was stirred at room temperature overnight and poured into water. The mixture was stirred for 30 min. A precipitated solid was collected by filtration and dried under vacuum to afford N'-(cyclopropanecarbonyl)-5-(2-(5-fluoropyridin-3-yl)pyrrolidin-1-yl)pyrazolo[1,5-a]pyrimidine-3-carbohydrazide (196 mg, 78%) as a pale yellow solid. $^1$H-NMR (CDCl$_3$, Varian, 400 MHz): δ 0.80-0.98 (2H, m), 1.15-1.28 (2H, m), 1.50-1.55 (1H, m), 1.97-2.27 (3H, m), 2.47-2.61 (1H, m), 3.60-4.30 (2H, m), 5.06 and 5.66 (1H, s+s), 5.88 and 6.39 (1H, s+s), 7.02-7.33 (1H, m), 8.24-8.36 (4H, m), 8.74 and 9.21 (1H, s+s), 9.94 and 10.71 (1H, s+s).

Step B: 2-cyclopropyl-5-(5-(2-(5-fluoropyridin-3-yl)pyrrolidin-1-yl)pyrazolo[1,5-a]pyrimidin-3-yl)-1,3,4-thiadiazole

14

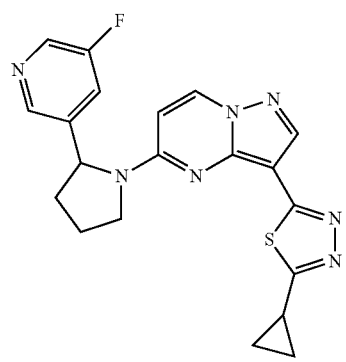

To a solution of N'-(cyclopropanecarbonyl)-5-(2-(5-fluoropyridin-3-yl)pyrrolidin-1-yl)pyrazolo[1,5-a]pyrimidine-3-carbohydrazide (50.0 mg, 0.122 mmol) in diglyme (2.6 mL) were added P$_4$S$_{10}$ (109 mg, 0.244 mmol) and Na$_2$CO$_3$ (52.0 mg, 0.488 mmol) at room temperature. The reaction mixture was stirred at 90° C. for 2 hours, cooled to room temperature and partitioned between water and EtOAc. The separated organic layer was dried over Na$_2$SO$_4$, filtered and concentrated in vacuo. The residue was purified by column chromatography on SiO$_2$ (EtOAc:MeOH=100:1 to 20:1) to afford 2-cyclopropyl-5-(5-(2-(5-fluoropyridin-3-yl)pyrrolidin-1-yl)pyrazolo[1,5-a]pyrimidin-3-yl)-1,3,4-thiadiazole (33.0 mg, 66%) as a white solid. $^1$H-NMR (CDCl$_3$, Varian, 400 MHz): δ 0.94-1.17 (2H, m), 1.17-1.31 (2H, m), 2.04-2.28 (3H, m), 2.37-2.48 (1H, m), 2.52-2.68 (1H, m), 3.50-4.17 (3H, m), 5.07 and 5.58 (1H, s+s), 5.90 and 6.37 (1H, s+s), 7.22 (1H, d, J=7.2 Hz), 8.30-8.40 (1H, m), 8.43 (1H, s), 8.48-5.56 (1H, m). MS: 408.3 [MH$^+$].

Example 23: Preparation of Chemical Compound 15: 2-tert-butyl-5-(5-(2-(5-fluoropyridin-3-yl)pyrrolidin-1-yl)pyrazolo[1,5-a]pyrimidin-3-yl)-1,3,4-thiadiazole

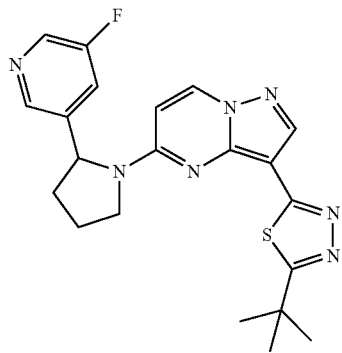

Step A: 5-(2-(5-fluoropyridin-3-yl)pyrrolidin-1-yl)-N'-pivaloylpyrazolo[1,5-a]pyrimidine-3-carbohydrazide

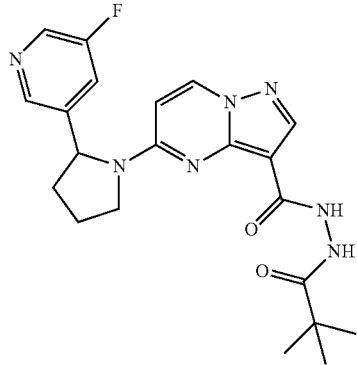 [SMILES: CC(C)(C)C(=O)NNC(=O)c1cnn2ccc(N3CCCC3c3cncc(F)c3)nc12]

To a solution of 5-(2-(2,5-difluorophenyl)pyrrolidin-1-yl)pyrazolo[1,5-a]pyrimidine-3-carboxylic acid (Intermediate 9, 316 mg, 0.965 mmol) in DMF (6.4 mL) were added pivalohydrazide hydrochloride (442 mg, 290 mmol), DIPEA (0.674 mL, 3.86 mmol) and HATU (551 mg, 1.45 mmol) at room temperature. The reaction mixture was stirred at room temperature overnight and poured into water. The mixture was stirred for 30 min. A precipitated solid was collected by filtration and dried under vacuum to afford 5-(2-(5-fluoropyridin-3-yl)pyrrolidin-1-yl)-N'-pivaloylpyrazolo[1,5-a]pyrimidine-3-carbohydrazide (362 mg, 88%) as a white solid. $^1$H-NMR (DMSO-d$_6$, Varian, 400 MHz): δ 1.20 (9H, s), 1.80-2.10 (3H, m), 2.40-2.50 (1H, m), 3.62-3.82 (1H, m), 4.00-4.10 (1H, m), 5.36 (0.7H, d, J=8.0 Hz), 6.17 (0.3H, d, J=8.4 Hz), 6.71 (0.7H, d, J=7.6 Hz), 7.65 (0.3H, d, J=8.0 Hz), 7.51 (1H, d, J=7.4 Hz), 8.13 and 8.22 (1H, s+s), 8.28 and 8.43 (1H, s+s), 8.36 and 8.50 (1H, s+s), 8.64 (0.3H, d, J=7.2 Hz), 8.83 (0.7H, d, J=7.6 Hz), 8.79 (1H, s), 9.55 and 9.80 (1H, s+s).

Step B: 2-tert-butyl-5-(5-(2-(5-fluoropyridin-3-yl)pyrrolidin-1-yl)pyrazolo[1,5-a]pyrimidin-3-yl)-1,3,4-thiadiazole

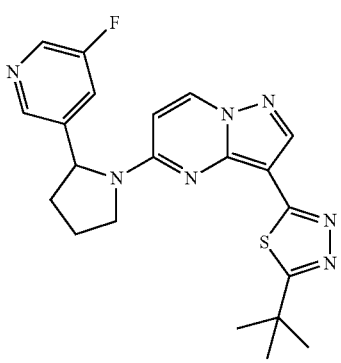

To a solution of 5-(2-(5-fluoropyridin-3-yl)pyrrolidin-1-yl)-N'-pivaloylpyrazolo[1,5-a]pyrimidine-3-carbohydrazide (100 mg, 0.235 mmol) in diglyme (4.7 mL) were added P$_4$S$_{10}$ (209 mg, 0.470 mmol) and Na$_2$CO$_3$ (100 mg, 0.940 mmol) at room temperature. The reaction mixture was stirred at 90° C. for 4 hours, cooled to room temperature and partitioned between water and EtOAc. The separated organic layer was dried over Na$_2$SO$_4$, filtered and concentrated in vacuo. The residue was purified by column chromatography on SiO$_2$ (EtOAc:MeOH=20:1) to afford 2-tert-butyl-5-(5-(2-(5-fluoropyridin-3-yl)pyrrolidin-1-yl)pyrazolo[1,5-a]pyrimidin-3-yl)-1,3,4-thiadiazole (34.0 mg, 34%) as a white solid. $^1$H-NMR (DMSO-d$_6$, Varian, 400 MHz): δ 1.42 and 1.48 (9H, s+s), 1.90-2.07 (3H, m), 2.40-2.50 (1H, m), 3.69 (1H, q, J=8.8 Hz), 4.00-4.18 (1H, m), 5.35 (0.2H, s), 5.46 (0.8H, d, J=8.4 Hz), 6.18 (0.2H, s), 6.71 (0.8H, d, J=8.0 Hz), 7.69 (1H, d, J=10.0 Hz), 8.38-8.40 (2H, m), 8.48 (1H, s), 8.83 (1H, d, J=7.6 Hz). MS: 424.4 [MH$^+$].

Example 24: Preparation of Chemical Compound 16: 2-tert-butyl-5-(5-(2-(5-fluoropyridin-3-yl)pyrrolidin-1-yl)pyrazolo[1,5-a]pyrimidin-3-yl)-1,3,4-oxadiazole

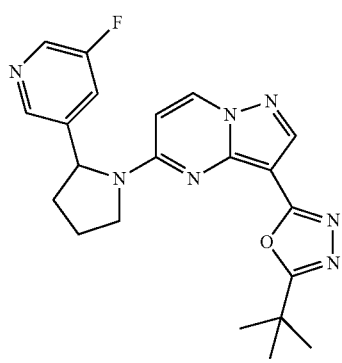

16

A mixture of 5-(2-(5-fluoropyridin-3-yl)pyrrolidin-1-yl)-N'-pivaloylpyrazolo[1,5-a]pyrimidine-3-carbohydrazide (60.0 mg, 0.141 mmol) and POCl₃ (0.394 mL, 4.23 mmol) was refluxed for 2 hours. After being cooled to room temperature, the reaction mixture was partitioned between water and DCM. The separated organic layer was washed with water and brine, dried over Na₂SO₄, filtered and concentrated in vacuo. The residue was purified by column chromatography on SiO₂ (DCM:MeOH=50:1 to 30:1) to afford 2-tert-butyl-5-(5-(2-(5-fluoropyridin-3-yl)pyrrolidin-1-yl)pyrazolo[1,5-a]pyrimidin-3-yl)-1,3,4-oxadiazole (38.0 mg, 66%) as a white solid. ¹H-NMR (DMSO-d₆, Varian, 400 MHz): δ 1.27 and 1.44 (9H, s+s), 1.89-2.21 (3H, m), 2.40-2.50 (1H, m), 3.61-3.88 (1H, m), 3.93-4.11 (1H, m), 5.32 (0.3H, s), 5.55 (0.7H, d, J=8.0 Hz), 6.18 (0.3H, s), 6.70 (0.7H, d, J=7.6 Hz), 7.65 (1H, d, J=9.2 Hz), 8.34-8.45 (3H, m), 8.64-8.83 (1H, m). MS: 408.4 [MH⁺].

Example 25: Preparation of Intermediate Compound 10

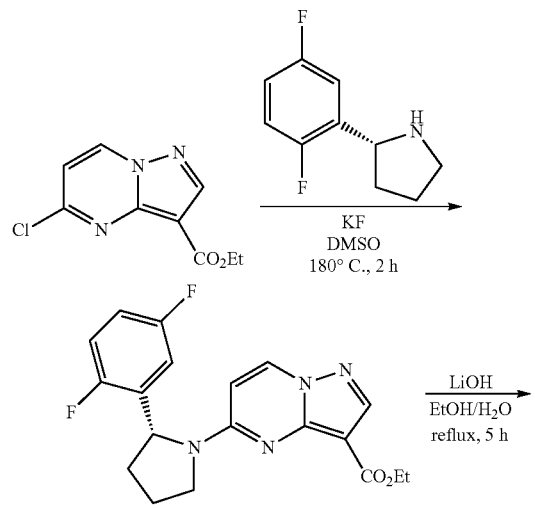

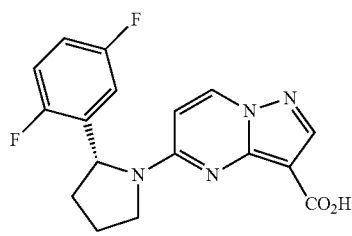

Intermediate Compound 10: (R)-5-(2-(2,5-difluorophenyl)pyrrolidin-1-yl)pyrazolo[1,5-a]pyrimidine-3-carboxylic acid

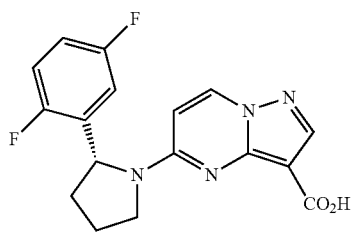

Step A: Ethyl (R)-5-(2-(2,5-difluorophenyl)pyrrolidin-1-yl)pyrazolo[1,5-a]pyrimidine-3-carboxylate

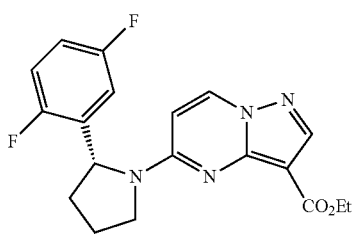

A mixture of ethyl 5-chloropyrazolo[1,5-a]pyrimidine-3-carboxylate (1.30 g, 5.76 mmol), (R)-2-(2,5-difluorophenyl)pyrrolidine (Intermediate 5, 1.13 g, 6.6 mmol) and KF (1.67 g, 28.8 mmol) in DMSO (19 mL) was stirred at 180° C. for 2 hours. After being cooled to room temperature, the reaction mixture was partitioned between water and EtOAc. The separated organic layer was washed with water and brine, dried over Na₂SO₄, filtered and concentrated in vacuo. The residue was purified by column chromatography on SiO₂ (Hex:EtOAc=1:1) to afford ethyl (R)-5-(2-(2,5-difluorophenyl)pyrrolidin-1-yl)pyrazolo[1,5-a]pyrimidine-3-carboxylate (2.11 g, 98%) as a yellow solid. MS: 372.90 [MH⁺]

Step B: (R)-5-(2-(2,5-difluorophenyl)pyrrolidin-1-yl)pyrazolo[1,5-a]pyrimidine-3-carboxylic acid

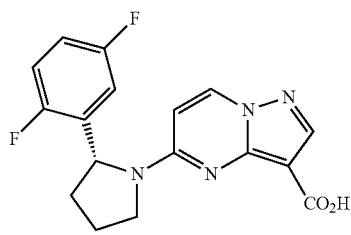

To a solution of (R)-5-(2-(2,5-difluorophenyl)pyrrolidin-1-yl)pyrazolo[1,5-a]pyrimidine-3-carboxylate (2.11 g, 5.68 mmol) in EtOH (42 mL) and water (14 mL) was added LiOH (408 mg, 17.0 mmol) at 0° C. The reaction mixture was heated at 90° C. for 5 hours and cooled to room temperature. After evaporation of EtOH, the residue was acidified with 2 N aq. HCl until pH 5-6, and then extracted with EtOAc twice. The combined organic layers were washed with brine, dried over $Na_2SO_4$, filtered and concentrated in vacuo to afford (R)-5-(2-(2,5-difluorophenyl)pyrrolidin-1-yl)pyrazolo[1,5-a]pyrimidine-3-carboxylic acid (1.92 g, 98%) as a pale yellow solid. $^1$H-NMR (DMSO-$d_6$, Varian, 400 MHz): δ 1.92-2.04 (3H, m), 2.33-2.60 (1H, br. s), 3.64 (0.5H, br. s), 3.77 (0.5H, br. s), 4.00 (1H, br. s), 5.32 (0.5H, s), 5.53 (0.5H, s), 6.07 (0.5H, s), 6.67 (0.5H, s), 6.99-7.33 (3H, m), 8.15-8.19 (1H, m), 8.59 and 8.77 (1H, s+s), 11.45 (1H, s).

Example 26: Preparation of Intermediate Compound 11

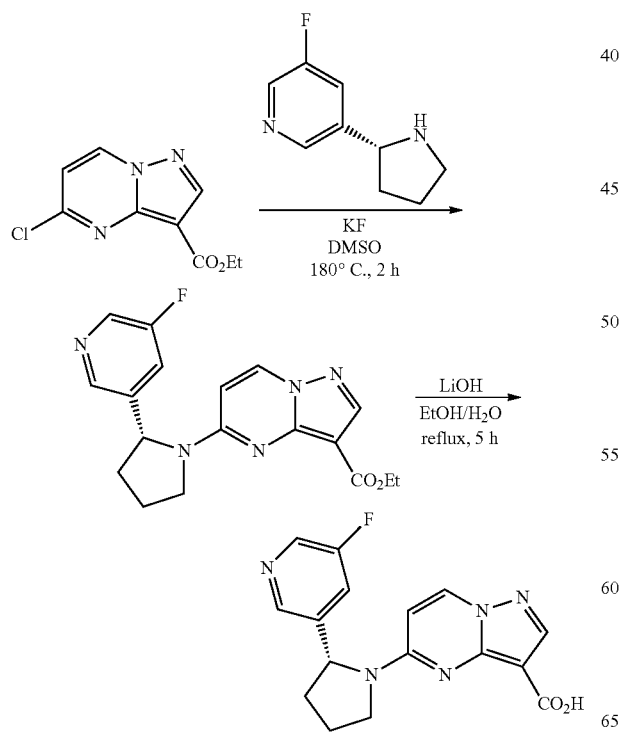

Intermediate Compound 11: (R)-5-(2-(5-fluoropyridin-3-yl)pyrrolidin-1-yl)pyrazolo[1,5-a]pyrimidine-3-carboxylic acid

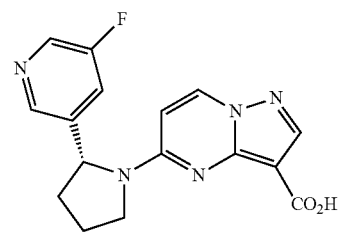 [SMILES: O=C(O)c1cnn2ccc(N3CCC[C@@H]3c3cncc(F)c3)nc12]

Step A: (R)-ethyl 5-(2-(5-fluoropyridin-3-yl)pyrrolidin-1-yl)pyrazolo[1,5-a]pyrimidine-3-carboxylate

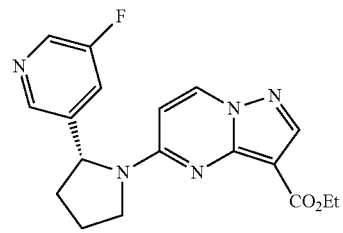 [SMILES: CCOC(=O)c1cnn2ccc(N3CCC[C@@H]3c3cncc(F)c3)nc12]

A mixture of ethyl 5-chloropyrazolo[1,5-a]pyrimidine-3-carboxylate (5.70 g, 25.3 mmol), (R)-3-fluoro-5-(pyrrolidin-2-yl)pyridine (Intermediate 4, 4.37 g, 26.3 mmol) and KF (7.34 g, 126 mmol) in DMSO (15 mL) was stirred at 180° C. for 2 hours. After being cooled to room temperature, the reaction mixture was partitioned between water and EtOAc. The separated organic layer was washed with water and brine, dried over $Na_2SO_4$, filtered and concentrated in vacuo. The residue was purified by column chromatography on $SiO_2$ (Hex:EtOAc=1:3 to 1:4) to afford (R)-ethyl 5-(2-(5-fluoropyridin-3-yl)pyrrolidin-1-yl)pyrazolo[1,5-a]pyrimidine-3-carboxylate (6.42 g, 71%) as a pale yellow solid. $^1$H-NMR (DMSO-$d_6$, Varian, 400 MHz: δ 1.17-1.30 (3H, m), 1.91-2.09 (3H, m), 2.40-2.50 (1H, m), 3.61-3.82 (1H, m), 3.94-4.08 (1H, m), 4.09-4.29 (2H, m), 5.24-5.34 (0.3H, m), 5.35-5.48 (0.7H, m), 6.10-6.19 (0.3H, m), 6.65-6.71 (0.7H, m), 7.60-7.74 (1H, m), 8.12-8.24 (1H, m), 8.36-8.54 (2H, m), 8.55-8.65 (0.3H, m), 8.70-8.81 (0.7H, m).

Step B: (R)-5-(2-(5-fluoropyridin-3-yl)pyrrolidin-1-yl)pyrazolo[1,5-a]pyrimidine-3-carboxylic acid

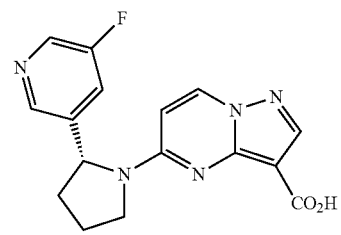 [SMILES: O=C(O)c1cnn2ccc(N3CCC[C@@H]3c3cncc(F)c3)nc12]

To a solution of (R)-ethyl 5-(2-(5-fluoropyridin-3-yl)pyr-rolidin-1-yl)pyrazolo[1,5-a]pyrimidine-3-carboxylate (6.56 g, 18.4 mmol) in EtOH (70 mL) and water (23 mL) was added LiOH (1.33 g, 55.4 mmol) at 0° C. The reaction mixture was heated at 90° C. for 5 hours and cooled to room temperature. After evaporation of EtOH, the residue was acidified with 2 N aq. HCl until pH 5-6, and then extracted with EtOAc twice. The combined organic layers were washed with brine, dried over $Na_2SO_4$, filtered and concentrated in vacuo to afford (R)-5-(2-(5-fluoropyridin-3-yl)pyrrolidin-1-yl)pyrazolo[1,5-a]pyrimidine-3-carboxylic acid (5.80 g, 96%) as a pale yellow solid. $^1$H-NMR (DMSO-$d_6$, Varian, 400 MHz): δ 1.89-2.20 (3H, m), 2.40-2.50 (1H, m), 3.61-3.82 (1H, m), 3.92-4.08 (1H, m), 5.24-5.48 (1H, m), 6.12 and 6.63 (1H, s+s), 7.56-7.78 (1H, m), 8.46 (1H, s), 8.32-8.78 (3H, m), 11.54 (1H, s).

Example 27: Preparation of Intermediate Compound 12

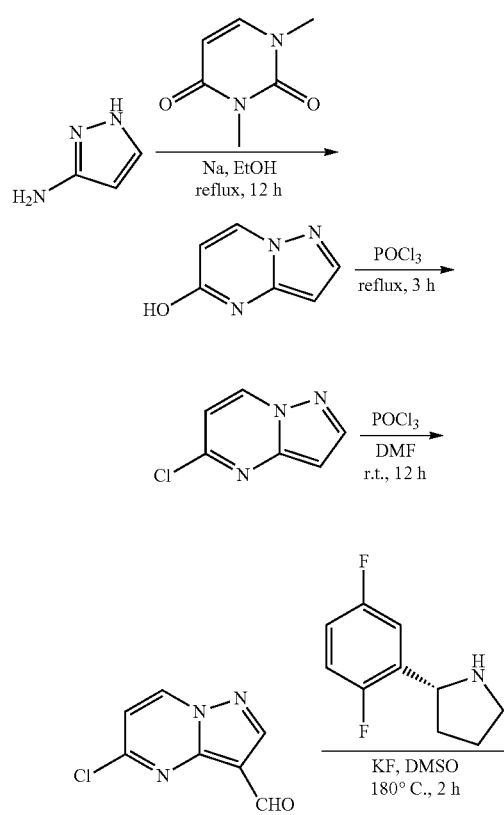

Intermediate Compound 12: (R)-5-(2-(2,5-difluoro-phenyl)pyrrolidin-1-yl)pyrazolo[1,5-a]pyrimidine-3-carbaldehyde

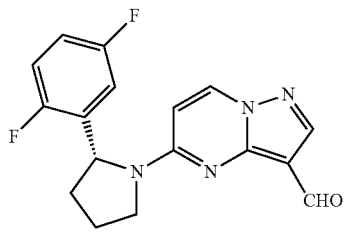

Step A: pyrazolo[1,5-a]pyrimidin-5-ol

A solution of sodium metal (11.1 g, 481 mmol) in EtOH (344 mL) was added 1H-pyrazol-3-amine (20.0 g, 241 mmol) and 1,3-dimethylpyrimidine-2,4(1H,3H)-dione (35.4 g, 253 mmol) at room temperature. The reaction mixture was refluxed overnight and cooled to room temperature. A precipitated solid was collected by filtration, washed with cold EtOH and dried under vacuum to afford pyrazolo[1,5-a]pyrimidin-5-ol (36.0 g, >99%) as a white solid. $^1$H-NMR (DMSO-$d_6$, Varian, 400 MHz): δ 5.35 (1H, d, J=1.6 Hz), 5.63 (1H, d, J=7.2 Hz), 7.43 (1H, d, J=1.6 Hz), 7.97 (1H, d, J=7.2 Hz). * A proton from OH was not observed.

Step B: 5-chloropyrazolo[1,5-a]pyrimidine

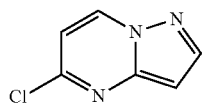

A mixture of pyrazolo[1,5-a]pyrimidin-5-ol (32.0 g, 237 mmol) and $POCl_3$ (177 mL, 1.89 mol) was refluxed for 3 hours. After being cooled to room temperature, the reaction mixture was concentrated in vacuo. The residue was diluted with DCM, washed with saturated aq. $NaHCO_3$, dried over $Na_2SO_4$, filtered and concentrated in vacuo. The residue was purified by column chromatography on $SiO_2$ (DCM: MeOH=20:1) to afford 5-chloropyrazolo[1,5-a]pyrimidine (14.1 g, 38%) as a yellow solid. $^1$H-NMR (DMSO-$d_6$, Varian, 400 MHz): δ 6.73 (1H, dd, J=2.0, 0.8 Hz), 7.14 (1H, d, J=7.2 Hz), 8.29 (1H, d, J=2.4 Hz), 9.19 (1H, dd, J=7.2, 0.8 Hz).

Step C: 5-chloropyrazolo[1,5-a]pyrimidine-3-carbaldehyde

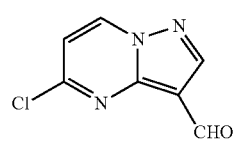 [SMILES: O=Cc1cnn2ccc(Cl)nc12]

To a solution of 5-chloropyrazolo[1,5-a]pyrimidine (14.1 g, 92.0 mmol) in DMF (184 mL) was added $POCl_3$ (21.4 mL, 230 mmol) at room temperature. The reaction mixture was stirred at room temperature overnight and then quenched with ice. The mixture was neutralized with 1 N aq. NaOH. A precipitated yellow solid was collected by filtration and dried under vacuum to afford 5-chloropyrazolo[1,5-a]pyrimidine-3-carbaldehyde (15.1 g, 90%) as a pale yellow solid. $^1$H-NMR (DMSO-$d_6$, Varian, 400 MHz): δ 7.50 (1H, d, J=7.2 Hz), 8.76 (1H, s), 9.40 (1H, d, J=7.2 Hz), 10.09 (1H, s).

Step D: (R)-5-(2-(2,5-difluorophenyl)pyrrolidin-1-yl)pyrazolo[1,5-a]pyrimidine-3-carbaldehyde

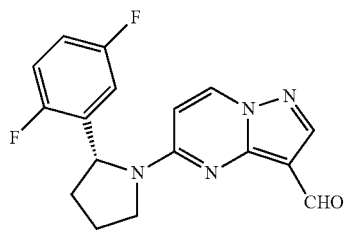 [SMILES: O=Cc1cnn2ccc(N3CCC[C@@H]3c3cc(F)ccc3F)nc12]

A mixture of 5-chloropyrazolo[1,5-a]pyrimidine-3-carbaldehyde (4.70 g, 25.9 mmol), (R)-2-(2,5-difluorophenyl)pyrrolidine (Intermediate 5, 5.07 g, 27.7 mmol) and KF (7.52 g, 129 mmol) in DMSO (86 mL) was heated at 180° C. for 2 hours. After being cooled to room temperature, the reaction mixture was poured into water. The mixture was extracted with EtOAc twice. The combined organic layers were washed with brine, dried over $Na_2SO_4$, filtered and concentrate in vacuo. The residue was purified by column chromatography on $SiO_2$ (EtOAc only to DCM:MeOH=20:1) to afford 5-(2-(2,5-difluorophenyl)pyrrolidin-1-yl)pyrazolo[1,5-a]pyrimidine-3-carbaldehyde (8.50 g, 100%) as a yellow solid. $^1$H-NMR (CDCl$_3$, Varian, 400 MHz): δ 1.90-2.28 (3H, m), 2.38-2.60 (1H, m), 3.60-4.18 (2H, m), 5.14-5.28 (0.6H, m), 5.54-5.72 (0.4H, m), 5.84-6.02 (0.6H, m), 6.35-6.46 (0.4H, m), 6.68-6.78 (1H, m), 6.82-7.20 (2H, m), 8.10-8.36 (2H, m), 9.77 and 10.11 (1H, s+s).

Example 28: Preparation of Chemical Compound 17

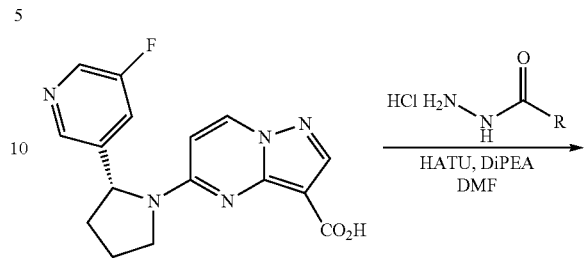

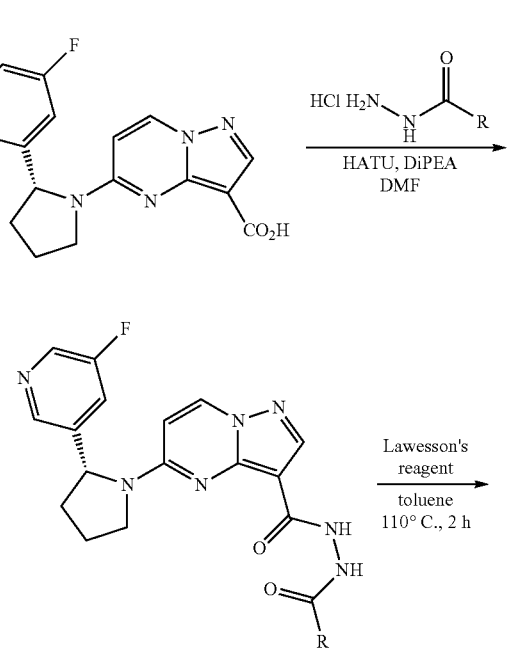

Chemical Compound 17: (R)-2-(5-(2-(5-fluoropyridin-3-yl)pyrrolidin-1-yl)pyrazolo[1,5-a]pyrimidin-3-yl)-5-isopropyl-1,3,4-thiadiazole

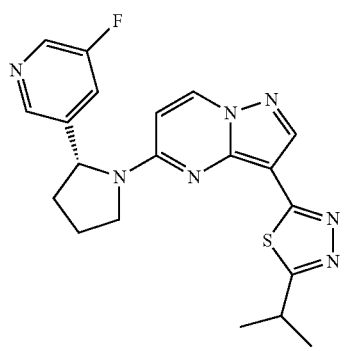

17

Step A: (R)-5-(2-(5-fluoropyridin-3-yl)pyrrolidin-1-yl)-N'-isobutyrylpyrazolo[1,5-a]pyrimidine-3-carbohydrazide

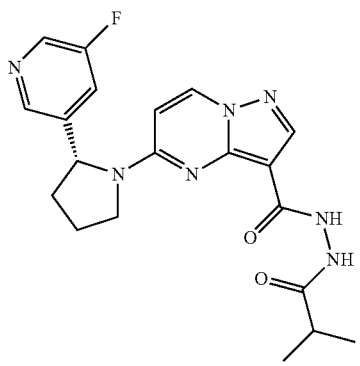 [SMILES: CC(C)C(=O)NNC(=O)c1cnn2ccc(N3CCC[C@@H]3c3cncc(F)c3)nc12]

To a solution of (R)-5-(2-(5-fluoropyridin-3-yl)pyrrolidin-1-yl)pyrazolo[1,5-a]pyrimidine-3-carboxylic acid (Intermediate 11, 5.65 g, 17.3 mmol) in DMF (115 mL) were added isobutyrohydrazide hydrochloride (4.78 g, 34.5 mmol), DIPEA (12.1 mL, 69.0 mmol) and HATU (13.1 mg, 34.5 mmol) at room temperature. The reaction mixture was stirred at room temperature overnight and partitioned between water and EtOAc. The separated organic layer was washed with water and brine, dried over $Na_2SO_4$, filtered and concentrated in vacuo. The residue was purified by column chromatography on $SiO_2$ (EtOAc:MeOH=20:1) to afford (R)-5-(2-(5-fluoropyridin-3-yl)pyrrolidin-1-yl)-N'-isobutyrylpyrazolo[1,5-a]pyrimidine-3-carbohydrazide (6.14 g, 86%) as a white solid. $^1$H-NMR (DMSO-$d_6$, Varian, 400 MHz): δ 1.03-1.42 (6H, m), 1.80-2.10 (3H, m), 3.66-3.81 (1H, m), 4.00-4.15 (1H, m), 5.36 (0.3H, d, J=7.2 Hz), 5.43 (0.7H, d, J=6.8 Hz), 6.17 (0.3H, d, J=7.6 Hz), 6.71 (0.7H, d, J=7.6 Hz), 7.53 (0.7H, d, J=9.6 Hz), 7.65 (0.3H, d, J=10.0 Hz), 8.14 and 8.23 (1H, s+s), 8.29 and 8.43 (1H, s+s), 8.36 and 8.50 (1H, s+s), 8.64 (0.3H, d, J=7.2 Hz), 8.83 (0.7H, d, J=8.0 Hz), 9.08 (0.7H, d, J=2.8 Hz), 9.92 (0.3H, s), 10.10 (0.7H, d, J=3.6 Hz), 10.44 (0.3H, s). * Two protons from NHNH were not observed.

Step B: (R)-2-(5-(2-(5-fluoropyridin-3-yl)pyrrolidin-1-yl)pyrazolo[1,5-a]pyrimidin-3-yl)-5-isopropyl-1,3,4-thiadiazole

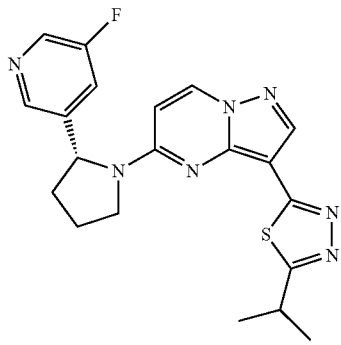

17

To a solution of (R)-5-(2-(5-fluoropyridin-3-yl)pyrrolidin-1-yl)-N'-isobutyrylpyrazolo[1,5-a]pyrimidine-3-carbohydrazide (5.20 g, 12.6 mmol) in THF (250 mL) were added Lawesson's reagent (10.2 g, 25.3 mmol) at room temperature. The reaction mixture was stirred at room temperature overnight and partitioned between water and EtOAc. The separated organic layer was washed with brine, dried over $Na_2SO_4$, filtered and concentrated in vacuo. The residue was purified by column chromatography on $SiO_2$ (DCM:MeOH=50:1) to afford (R)-2-(5-(2-(5-fluoropyridin-3-yl)pyrrolidin-1-yl)pyrazolo[1,5-a]pyrimidin-3-yl)-5-isopropyl-1,3,4-thiadiazole (1.88 g, 36%) as a white solid. $^1$H-NMR (DMSO-$d_6$, Varian, 400 MHz): δ 1.34-1.38 (6H, m), 1.87-2.10 (3H, m), 3.35-3.85 (1H, m), 3.66-3.75 (1H, m), 4.03-4.12 (1H, m), 5.35 (0.2H, d, J=6.4 Hz), 5.44 (0.8H, d, J=6.8 Hz), 6.17 (0.2H, s), 6.71 (0.8H, d, J=7.6 Hz), 7.70 (1H, d, J=9.2 Hz), 8.35-8.44 (2H, m), 8.45-5.57 (2H, m), 8.64 (0.2H, s), 8.83 (0.8H, d, J=8.0 Hz). MS: 410.4 [MH$^+$].

Example 29: Preparation of Chemical Compound 18

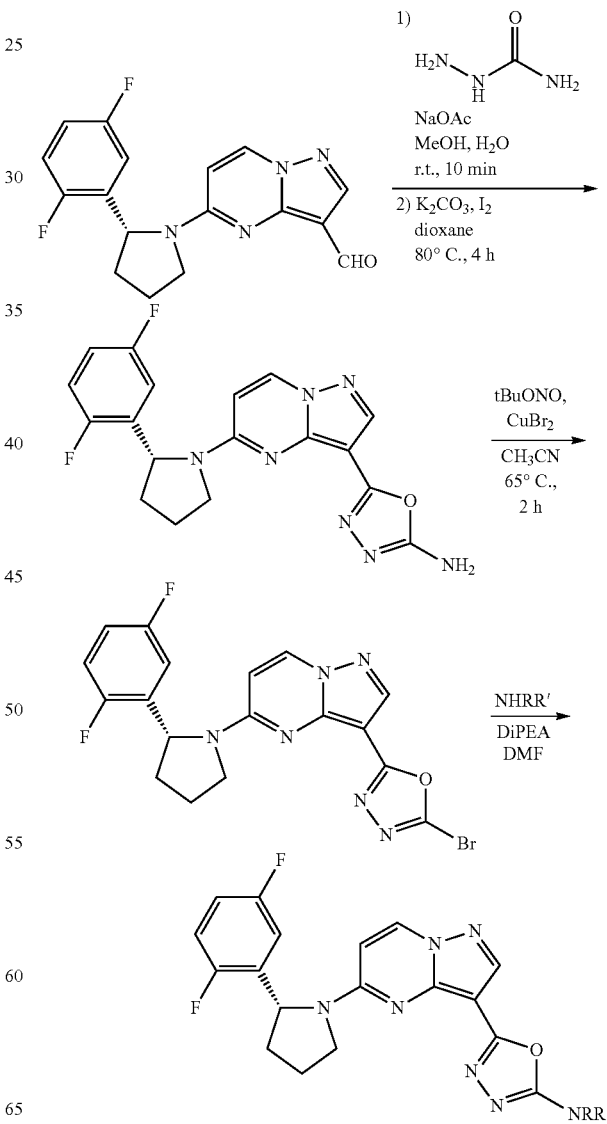

Chemical Compound 18: (R)-2-(5-(2-(2,5-difluorophenyl)pyrrolidin-1-yl)pyrazolo[1,5-a]pyrimidin-3-yl)-5-(piperazin-1-yl)-1,3,4-oxadiazole

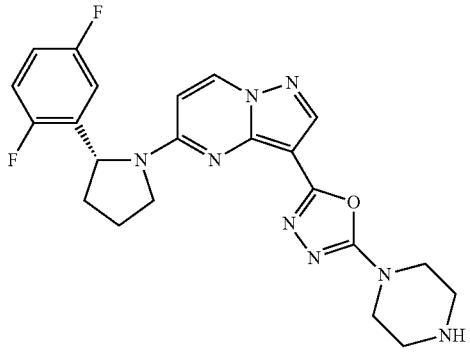

Step A: (R)-5-(5-(2-(2,5-difluorophenyl)pyrrolidin-1-yl)pyrazolo[1,5-a]pyrimidin-3-yl)-1,3,4-oxadiazol-2-amine

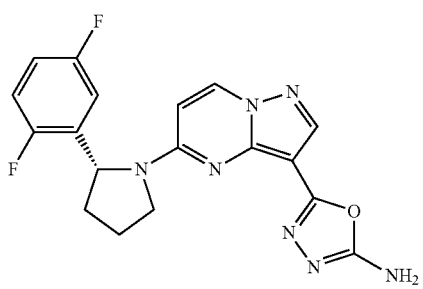 [SMILES: Nc1nnc(-c2cnn3ccc(N4CCC[C@@H]4c4cc(F)ccc4F)nc23)o1]

To a solution of hydrazinecarboxamide hydrochloride (85.0 mg, 0.761 mmol) and sodium acetate (62.0 mg, 0.761 mmol) in water (1.5 mL) was added a solution of (R)-5-(2-(2,5-difluorophenyl)pyrrolidin-1-yl)pyrazolo[1,5-a]pyrimidine-3-carbaldehyde (Intermediate 12, 250 mg, 0.761 mmol) in MeOH (1.5 mL) at room temperature. The reaction mixture was stirred at room temperature for 10 min and concentrated in vacuo. The resulting residue was dissolved in dioxan (7.7 mL). After addition of $K_2CO_3$ (316 mg, 2.28 mmol) followed by iodine (232 mg, 0.914 mmol), the reaction mixture was stirred at 80° C. for 4 hours, cooled to room temperature, and then quenched with 5% aq. $Na_2S_2O_3$. The mixture was extracted with DCM/MeOH (10:1, 10 mL×4). The combined organic layers were dried over $Na_2SO_4$, filtered and concentrated in vacuo. The residue was purified by column chromatography on $SiO_2$ (EtOAc:MeOH=50:1 to 25:1) to afford (R)-5-(5-(2-(2,5-difluorophenyl)pyrrolidin-1-yl)pyrazolo[1,5-a]pyrimidin-3-yl)-1,3,4-oxadiazol-2-amine (179 mg, 61%) as a yellow solid. $^1$H-NMR (DMSO-$d_6$, Varian, 400 MHz): δ 1.80-2.05 (3H, m), 2.35-2.55 (1H, m), 3.50-3.80 (1H, m), 3.90-4.05 (1H, m), 5.30 and 5.54 (1H, s+s), 6.05-6.67 (1H, m), 6.68-7.38 (4H, m), 8.00-8.18 (1H, m), 8.50-8.80 (1H, m).

Step B: (R)-2-bromo-5-(5-(2-(2,5-difluorophenyl)pyrrolidin-1-yl)pyrazolo[1,5-a]pyrimidin-3-yl)-1,3,4-oxadiazole

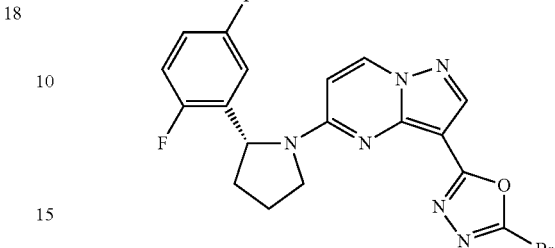

To a solution of copper(II) bromide (125 mg, 0.560 mmol) and tert-butyl nitrite (0.0670 mL, 0.560 mmol) in $CH_3CN$ (1.9 mL) was added a solution of (R)-5-(5-(2-(2,5-difluorophenyl)pyrrolidin-1-yl)pyrazolo[1,5-a]pyrimidin-3-yl)-1,3,4-oxadiazol-2-amine (179 mg, 0.467 mmol) in $CH_3CN$ (3.8 mL) at room temperature. The reaction mixture was stirred at 65° C. for 2 hours. After being cooled to room temperature, the reaction mixture was partitioned between water and EtOAc. The separated aqueous layer was extracted with EtOAc. The combined organic layers were washed with water and brine, dried over $Na_2SO_4$, filtered and concentrated in vacuo. The residue was purified by column chromatography on $SiO_2$ (Hex:EtOAc=2:1 to 1:1) to afford (R)-2-bromo-5-(5-(2-(2,5-difluorophenyl)pyrrolidin-1-yl)pyrazolo[1,5-a]pyrimidin-3-yl)-1,3,4-oxadiazole (72.0 mg, 34%) as pale yellow solid. $^1$H-NMR (DMSO-$d_6$, Varian, 400 MHz): δ 1.80-2.05 (3H, m), 2.35-2.50 (1H, m), 3.60-3.88 (1H, m), 3.96-4.08 (1H, m), 5.36 and 5.53 (1H, s+s), 6.12 and 6.69 (1H, s+s), 6.90-7.40 (3H, m), 8.33-8.40 (1H, m), 8.62-8.82 (1H, m).

Step C: (R)-tert-butyl 4-(5-(5-(2-(2,5-difluorophenyl)pyrrolidin-1-yl)pyrazolo[1,5-a]pyrimidin-3-yl)-1,3,4-oxadiazol-2-yl)piperazine-1-carboxylate

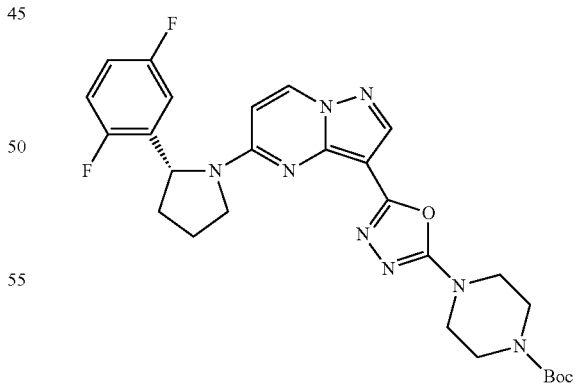

To a solution of (R)-2-bromo-5-(5-(2-(2,5-difluorophenyl)pyrrolidin-1-yl)pyrazolo[1,5-a]pyrimidin-3-yl)-1,3,4-oxadiazole (72.0 mg, 0.161 mmol) and tert-butyl piperazine-1-carboxylate (60.0 mg, 0.322 mmol) in DMF (2.0 mL) were added DIPEA (0.0840 mL, 0.483 mmol) and DMAP (20.0 mg, 0.161 mmol) at room temperature. The reaction mixture was stirred at 80° C. for 7 hours and poured into H₂O. The mixture was extracted with EtOAc twice. The combined organic layers were washed with brine, dried and concentrated in vacuo. The residue was purified by column chromatography on SiO₂ (Hex:EtOAc=1:3 to 1:9) to afford (R)-tert-butyl 4-(5-(5-(2-(2,5-difluorophenyl)pyrrolidin-1-yl)pyrazolo[1,5-a]pyrimidin-3-yl)-1,3,4-oxadiazol-2-yl)piperazine-1-carboxylate (58.0 mg, 65%) as a pale yellow solid. ¹H-NMR (DMSO-d₆, Varian, 400 MHz): δ 1.45 (9H, s), 1.80-2.10 (3H, m), 2.30-2.45 (1H, m), 2.95-3.08 (1H, m), 3.20-3.63 (4H, m), 3.40-3.51 (3H, m), 3.52-3.88 (1H, m), 3.98-4.08 (1H, m), 5.39 and 5.69 (1H, s+s), 6.14 and 6.66 (1H, s+s), 6.82-7.40 (3H, m), 8.20-8.30 (1H, m), 8.55-5.88 (1H, m).

Step D: (R)-2-(5-(2-(2,5-difluorophenyl)pyrrolidin-1-yl)pyrazolo[1,5-a]pyrimidin-3-yl)-5-(piperazin-1-yl)-1,3,4-oxadiazole To a solution of (R)-tert-butyl 4-(5-(5-(2-(2,5-difluorophenyl)pyrrolidin-1-yl)pyrazolo[1,5-a]pyrimidin-3-yl)-1,3,4-oxadiazol-2-yl)piperazine-1-carboxylate (58.0 mg, 0.105 mmol) in DCM (0.70 mL) was added TFA (0.162 mL, 2.10 mmol) at room temperature. The reaction mixture was stirred for 2 hours at room temperature. After concentration in vacuo, the residue was diluted with DCM, basified with saturated aq. NaHCO₃, washed with brine, dried over Na₂SO₄, filtered and concentrated in vacuo. The residue was purified by column chromatography in SiO₂ (DCM:MeOH=30:1 to 4:1) to afford the (R)-2-(5-(2-(2,5-difluorophenyl)pyrrolidin-1-yl)pyrazolo[1,5-a]pyrimidin-3-yl)-5-(piperazin-1-yl)-1,3,4-oxadiazole (29.0 mg, 61%) as a pale yellow solid. ¹H-NMR (DMSO-d₆, Varian, 400 MHz): δ 1.82-2.08 (4H, m), 2.30-2.45 (1H, m), 2.74-2.90 (4H, m), 3.10-3.28 (3H, m), 3.36-3.45 (1H, m), 3.52-3.84 (1H, m), 3.96-4.06 (1H, m), 5.29 and 5.61 (1H, s+s), 6.06 and 6.66 (1H, s+s), 6.90-7.40 (3H, m), 8.20-8.30 (1H, m), 8.55-8.80 (1H, m). MS: 453.2 [MH⁺].

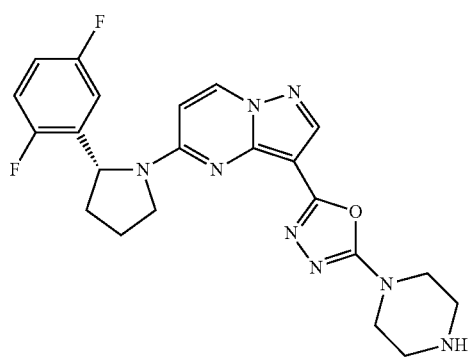

Example 30: Preparation of Chemical Compound 19

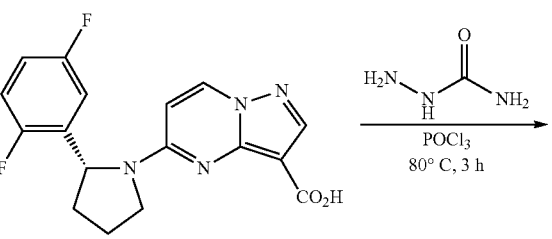

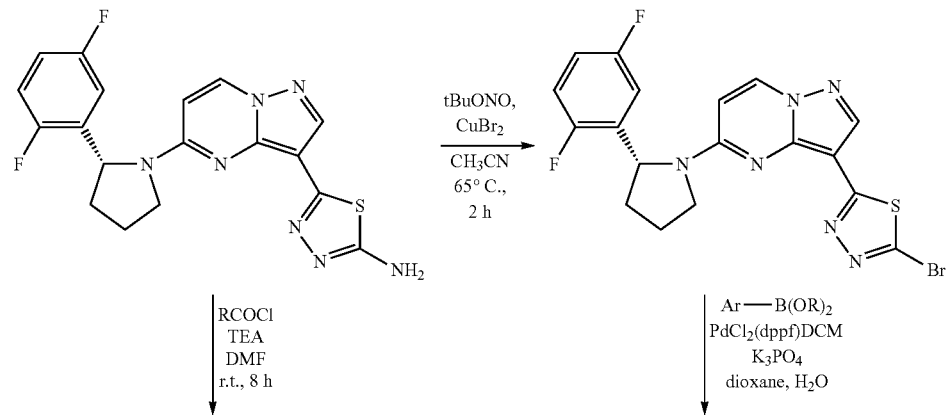

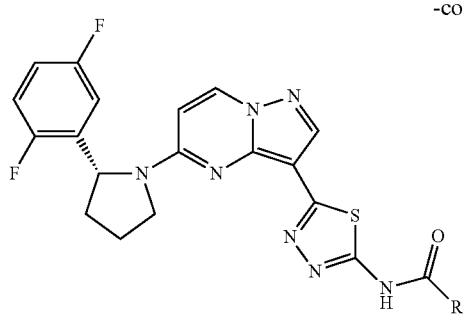
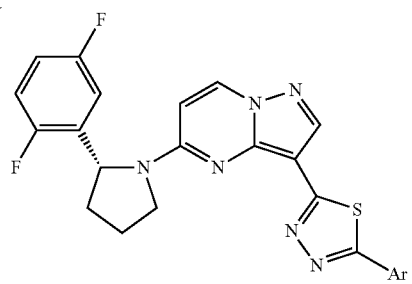

Chemical Compound 19: (R)-2-(5-(2-(2,5-difluorophenyl)pyrrolidin-1-yl)pyrazolo[1,5-a]pyrimidin-3-yl)-5-(1H-pyrazol-4-yl)-1,3,4-thiadiazole

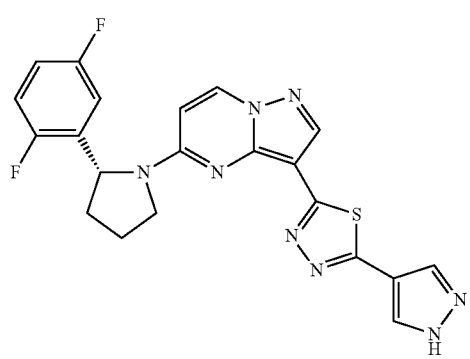

Step A: (R)-5-(5-(2-(2,5-difluorophenyl)pyrrolidin-1-yl)pyrazolo[1,5-a]pyrimidin-3-yl)-1,3,4-thiadiazol-2-amine

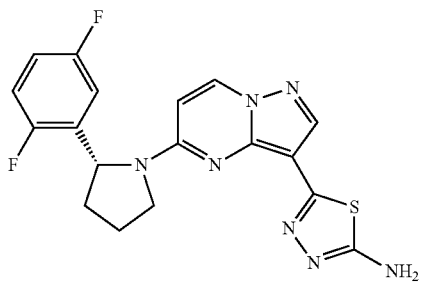 [SMILES: Nc1nnc(-c2cnn3ccc(N4CCC[C@@H]4c4cc(F)ccc4F)nc23)s1]

To a mixture of (R)-5-(2-(2,5-difluorophenyl)pyrrolidin-1-yl)pyrazolo[1,5-a]pyrimidine-3-carboxylic acid (Intermediate 10, 1.00 g, 2.90 mmol) and hydrazinecarbothioamide (265 mg, 2.90 mmol) was added POCl₃ (1.08 mL, 11.6 mmol) at 0° C. The reaction mixture was stirred at 80° C. for 3 hours in sealed tube while built up pressure was released every hour. After being cooled to 0° C., the reaction mixture was poured into water. The mixture was stirred vigorously for 30 min. A precipitated solid was collected by filtration, washed with water and dried over vacuum afford to (R)-5-(5-(2-(2,5-difluorophenyl)pyrrolidin-1-yl)pyrazolo[1,5-a]pyrimidin-3-yl)-1,3,4-thiadiazol-2-amine (1.16 g, >99%) as a pale yellow solid, which was used for the next reaction without further purification. $^1$H-NMR (DMSO-$d_6$, Varian, 400 MHz): δ 1.85-2.20 (3H, m), 2.45-2.55 (1H, m), 3.50-3.75 (4H, m), 5.38 (0.5H, d, J=8.0 Hz), 5.50 (0.5H, d, J=7.6 Hz), 6.15 (0.5H, d, J=7.6 Hz), 6.73 (0.5H, d, J=7.6 Hz), 6.95-7.30 (2H, m), 7.33-7.39 (1H, m), 8.37 and 8.49 (1H, s+s), 8.72 (0.5H, d, J=6.0 Hz), 8.92 (0.5H, d, J=7.6 Hz). 9.36 (1H, br. s).

Step B: (R)-2-bromo-5-(5-(2-(2,5-difluorophenyl)pyrrolidin-1-yl)pyrazolo[1,5-a]pyrimidin-3-yl)-1,3,4-oxadiazole

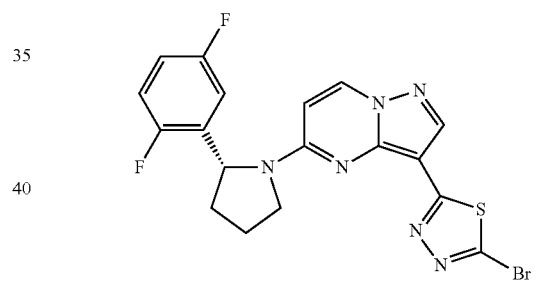

To a solution of CuBr₂ (777 mg, 3.48 mmol) and tert-butyl nitrite (4.14 mL, 3.48 mmol) in CH₃CN (9.6 mL) was added a solution of (R)-5-(5-(2-(2,5-difluorophenyl)pyrrolidin-1-yl)pyrazolo[1,5-a]pyrimidin-3-yl)-1,3,4-thiadiazol-2-amine (1.15 g, 2.90 mmol) in CH₃CN (19 mL) at room temperature. The reaction mixture was stirred at 65° C. for 2 hours. After being cooled to room temperature, the reaction mixture was partitioned between water and EtOAc. The separated aqueous layer was extracted with EtOAc. The combined organic layers were washed with water and brine, dried over Na₂SO₄, filtered and concentrated in vacuo. The residue was purified by column chromatography on SiO₂ (Hex:EtOAc=2:1 to 1:2) to afford (R)-2-bromo-5-(5-(2-(2,5-difluorophenyl)pyrrolidin-1-yl)pyrazolo[1,5-a]pyrimidin-3-yl)-1,3,4-thiadiazole (586 mg, 43%) as a pale yellow solid. $^1$H-NMR (CDCl₃, Varian, 400 MHz): δ 1.14-2.18 (3H, m), 2.46-2.56 (1H, m), 3.63-3.82 (1H, m), 4.03-4.07 (1H, m), 5.36 (0.3H, d, J=8.4H), 5.46 (0.7H, d. J=8.4), 6.37 (0.3H, d. J=7.2 Hz), 6.72 (0.7H, d, J=8.0 Hz), 6.95-7.40 (3H, m), 8.40 and 8.50 (1H, s+s), 8.66 (0.3H, d, J=7.2 Hz), 8.85 (0.7H, d, J=7.6 Hz).

Step C: (R)-2-(5-(2-(2,5-difluorophenyl)pyrrolidin-1-yl)pyrazolo[1,5-a]pyrimidin-3-yl)-5-(1H-pyrazol-4-yl)-1,3,4-thiadiazole

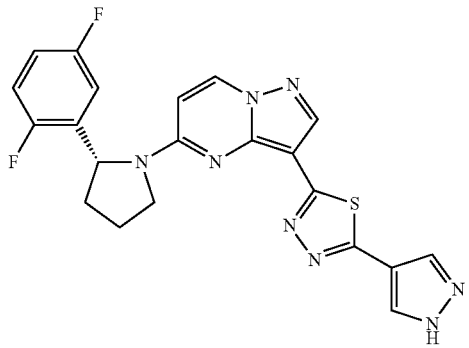

19

A mixture of (R)-2-bromo-5-(5-(2-(2,5-difluorophenyl)pyrrolidin-1-yl)pyrazolo[1,5-a]pyrimidin-3-yl)-1,3,4-thiadiazole (100 mg, 0.216 mmol), tert-butyl 4-(4,4,5,5-tetramethyl-1,3,2-dioxaborolan-2-yl)-1H-pyrazole-1-carboxylate (127 mg, 0.432 mmol), $K_3PO_4$ (137 mg, 0.648 mmol) and $PdCl_2(dppf)$-$CH_2Cl_2$ adduct (35.0 mg, 0.043 mmol) in dioxane (1.9 mL) and water (0.21 mL) was degassed with $N_2$ gas. The reaction mixture was stirred at 100° C. for 15 hours in a sealed tube. After concentration in vacuo, the residue was diluted with EtOAc and filtered through a silica gel pad. The filtrate was concentrated in vacuo. The residue was purified by column chromatography on $SiO_2$ (DCM:MeOH=50:1 to 15:1) to afford the (R)-2-(5-(2-(2,5-difluorophenyl)pyrrolidin-1-yl)pyrazolo[1,5-a]pyrimidin-3-yl)-5-(1H-pyrazol-4-yl)-1,3,4-thiadiazole (14.0 mg, 14%) as a white solid. MS: 451.2 [MH+].

Example 31: Preparation of Chemical Compound 20: (R)-5-(2-(2,5-difluorophenyl)pyrrolidin-1-yl)-3-(1-(piperidin-4-yl)-1H-1,2,3-triazol-4-yl)pyrazolo[1,5-a]pyrimidine

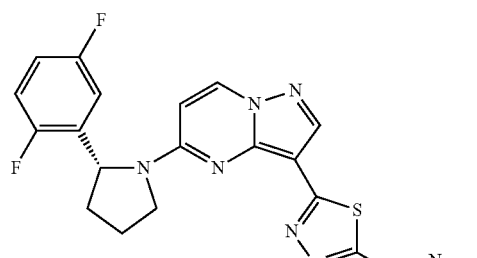

20

A mixture of (R)-2-bromo-5-(5-(2-(2,5-difluorophenyl)pyrrolidin-1-yl)pyrazolo[1,5-a]pyrimidin-3-yl)-1,3,4-thiadiazole (100 mg, 0.216 mmol), 1H-pyrazol-3-ylboronic acid (48.0 mg, 0.432 mmol), $K_3PO_4$ (137 mg, 0.648 mmol) and $PdCl_2(dppf)$-$CH_2Cl_2$ adduct (35.0 mg, 0.043 mmol) in dioxane (1.9 mL) and water (0.21 mL) was degassed with $N_2$ gas. The reaction mixture was stirred at 100° C. for 15 hours in a sealed tube. After concentration in vacuo, the residue was diluted with EtOAc and filtered through a silica gel pad. The filtrate was concentrated in vacuo. The residue was purified by column chromatography on $SiO_2$ (DCM:MeOH=50:1 to 15:1) to afford the (R)-2-(5-(2-(2,5-difluorophenyl)pyrrolidin-1-yl)pyrazolo[1,5-a]pyrimidin-3-yl)-5-(1H-pyrazol-3-yl)-1,3,4-thiadiazole (16.0 mg, 16%) as a white solid. MS: 451.2 [MH+].

Example 32: Preparation of Chemical Compound 21: (R)—N-(5-(5-(2-(2,5-difluorophenyl)pyrrolidin-1-yl)pyrazolo[1,5-a]pyrimidin-3-yl)-1,3,4-thiadiazol-2-yl)benzamide

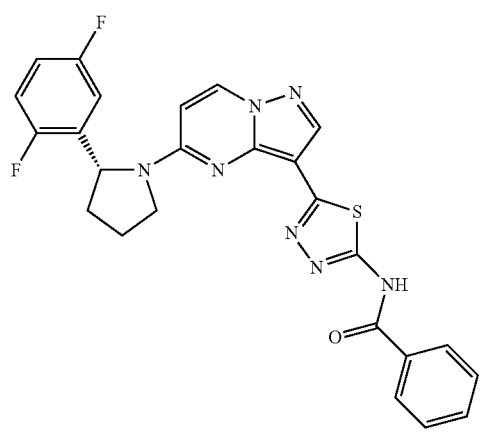

21

To a solution of (R)-5-(5-(2-(2,5-difluorophenyl)pyrrolidin-1-yl)pyrazolo[1,5-a]pyrimidin-3-yl)-1,3,4-thiadiazol-2-amine (50.0 mg, 0.125 mmol) in DMF (0.20 mL) were added TEA (0.0130 mL) followed by benzoly chloride (0.0150 mL, 0.125 mmol) at room temperature. The reaction mixture was stirred for 8 hours at room temperature and then treated with water. A precipitated solid was collected by filtration, washed with water and dried under vacuum. The solid was purified by column chromatography in $SiO_2$ (Hex:EtOAc=1:4 to 1:5) to afford (R)—N-(5-(5-(2-(2,5-difluorophenyl)pyrrolidin-1-yl)pyrazolo[1,5-a]pyrimidin-3-yl)-1,3,4-thiadiazol-2-yl)benzamide (23.0 mg, 36%) as a pale yellow solid. MS: 504.3 [MH+].

Example 33: Preparation of Chemical Compound 22

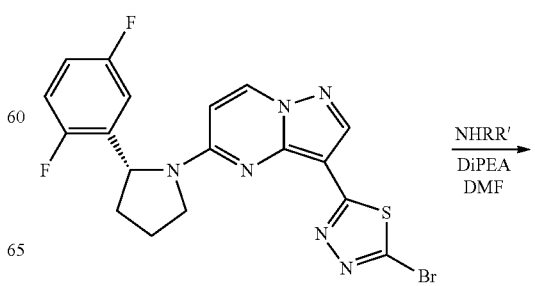

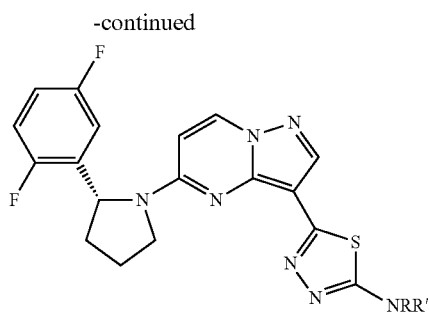

Chemical Compound 22: (R)-5-(2-(2,5-difluorophenyl)pyrrolidin-1-yl)-3-(1-(piperidin-4-yl)-1H-1,2,3-triazol-4-yl)pyrazolo[1,5-a]pyrimidine

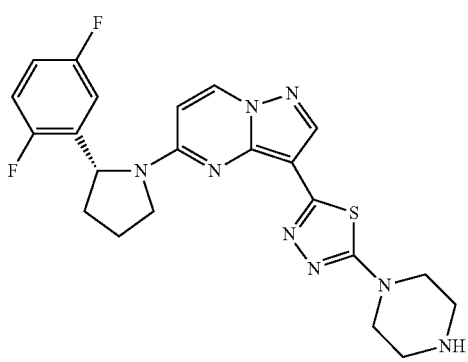

To a solution of (R)-2-bromo-5-(5-(2-(2,5-difluorophenyl)pyrrolidin-1-yl)pyrazolo[1,5-a]pyrimidin-3-yl)-1,3,4-thiadiazole (89.0 mg, 0.192 mmol) and piperazine (41.0 mg, 0.480 mmol) in DMF (2.4 mL) was added DIPEA (0.0840 mL, 0.480 mmol) at room temperature. The reaction mixture was stirred at 70° C. for 16 hours, cooled to room temperature and poured into water. The mixture was extracted with EtOAc twice. The combined organic layers were washed with brine, dried under Na$_2$SO$_4$, filtered and concentrated in vacuo. The residue was purified by column chromatography on SiO$_2$ (DCM:MeOH=20:1 to MeOH only) to afford (R)-2-(5-(2-(2,5-difluorophenyl)pyrrolidin-1-yl)pyrazolo[1,5-a]pyrimidin-3-yl)-5-(piperazin-1-yl)-1,3,4-thiadiazole (12.0 mg, 13%) as a yellow solid. MS: 469.3 [MH$^+$].

Example 34: Preparation of Chemical Compound 23: (R)-2-(1,4-diazepan-1-yl)-5-(5-(2-(2,5-difluorophenyl)pyrrolidin-1-yl)pyrazolo[1,5-a]pyrimidin-3-yl)-1,3,4-thiadiazole

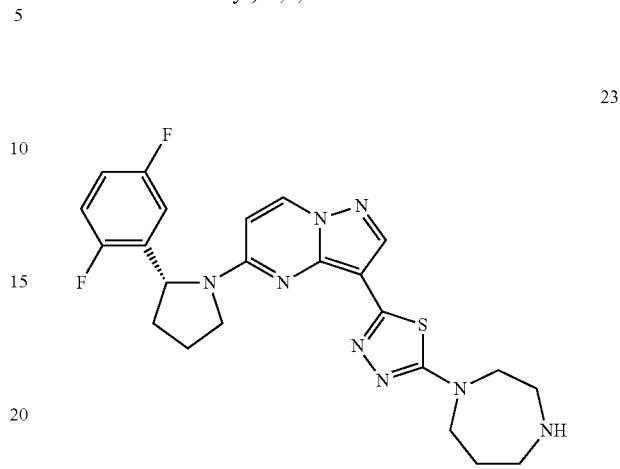

To a solution of (R)-2-bromo-5-(5-(2-(2,5-difluorophenyl)pyrrolidin-1-yl)pyrazolo[1,5-a]pyrimidin-3-yl)-1,3,4-thiadiazole (100 mg, 0.216 mmol) and 1,4-diazepane (43.0 mg, 0.432 mmol) in DMF (2.7 mL) was added DIPEA (0.113 mL, 0.648 mmol) at room temperature. The reaction mixture was stirred at 70° C. for 16 hours, cooled to room temperature and poured into water. The mixture was extracted with EtOAc twice. The combined organic layers were washed with brine, dried under Na$_2$SO$_4$, filtered and concentrated in vacuo. The residue was purified by column chromatography on SiO$_2$ (DCM:MeOH=20:1 to MeOH only) to afford (R)-2-(1,4-diazepan-1-yl)-5-(5-(2-(2,5-difluorophenyl)pyrrolidin-1-yl)pyrazolo[1,5-a]pyrimidin-3-yl)-1,3,4-thiadiazole (16.0 mg, 15%) as a yellow solid. MS: 483.3 [MH$^+$].

Example 35: Preparation of Chemical Compound 24

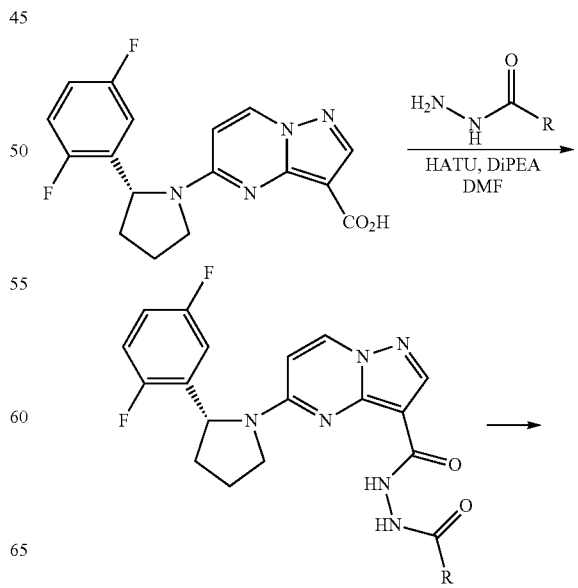

123

-continued

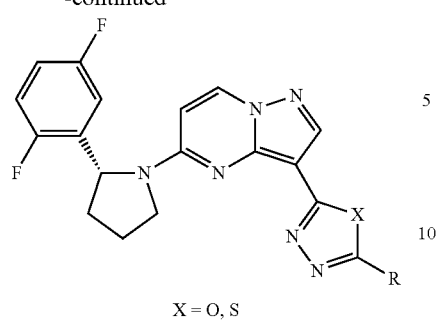

X = O, S

Chemical Compound 24: (R)-2-(5-(2-(2,5-difluorophenyl)pyrrolidin-1-yl)pyrazolo[1,5-a]pyrimidin-3-yl)-5-(piperidin-4-yl)-1,3,4-oxadiazole

24

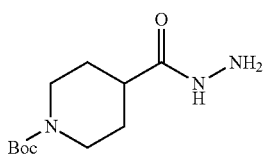 [SMILES: CC(C)(C)OC(=O)N1CCC(C(=O)NN)CC1]

Step A: tert-butyl 4-(hydrazinecarbonyl)piperidine-1-carboxylate

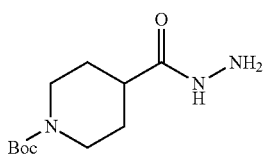 [SMILES: CC(C)(C)OC(=O)N1CCC(C(=O)NN)CC1]

To a solution of 1-tert-butyl 4-ethyl piperidine-1,4-dicarboxylate (2.00 g, 7.77 mmol) in EtOH (26 mL) was added hydrazine hydrate (5.84 g, 117 mmol) at room temperature. The reaction mixture was refluxed overnight, cooled to room temperature and concentrated in vacuo. The residue was dissolved in DCM, washed with water 3 times and brine, dried over Na$_2$SO$_4$, filtered and concentrated in vacuo to afford tert-butyl 4-(hydrazinecarbonyl)piperidine-1-carboxylate (985 mg, 52%) as a white solid. $^1$H-NMR (CDCl$_3$, Varian, 400 MHz): δ 1.46 (9H, s), 1.58-1.70 (2H, m), 1.73-1.85 (2H, m), 2.19-2.26 (1H, m), 2.27 (2H, br. s), 3.90 (2H, s), 4.15 (2H, br. s), 6.99 (1H, s).

124

Step B: (R)-tert-butyl 4-(2-(5-(2-(2,5-difluorophenyl)pyrrolidin-1-yl)pyrazolo[1,5-a]pyrimidine-3-carbonyl)hydrazinecarbonyl)piperidine-1-carboxylate

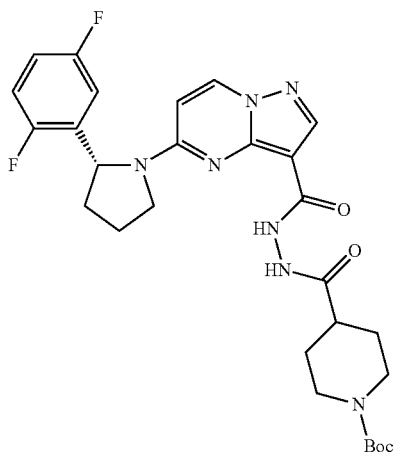 [SMILES: CC(C)(C)OC(=O)N1CCC(C(=O)NNC(=O)c2cnn3ccc(N4CCC[C@@H]4c4cc(F)ccc4F)nc23)CC1]

To a solution of (R)-5-(2-(2,5-difluorophenyl)pyrrolidin-1-yl)pyrazolo[1,5-a]pyrimidine-3-carboxylic acid (Intermediate 10, 200 mg, 0.581 mmol) in DMF (3.8 mL) were added tert-butyl 4-(hydrazinecarbonyl)piperidine-1-carboxylate (212 mg, 0.871 mmol), DIPEA (0.304 mL, 1.74 mmol), HATU (331 mg, 0.871 mmol) at room temperature, The reaction mixture was stirred at room temperature for 18 hours and diluted with EtOAc. The mixture was washed with saturated aq. NH$_4$Cl and brine, dried over Na$_2$SO$_4$, filtered and concentrate in vacuo. The residue was purified by column chromatography on SiO$_2$ (EtOAc only to DCM:MeOH=20:1 to 10:1) to give the (R)-tert-butyl 4-(2-(5-(2-(2,5-difluorophenyl)pyrrolidin-1-yl)pyrazolo[1,5-a]pyrimidine-3-carbonyl)hydrazinecarbonyl)piperidine-1-carboxylate (265 mg, 80%) as a white solid. MS: 569.90 [MH$^+$].

(R)-2-(5-(2-(2,5-difluorophenyl)pyrrolidin-1-yl)pyrazolo[1,5-a]pyrimidin-3-yl)-5-(piperidin-4-yl)-1,3,4-oxadiazole

24

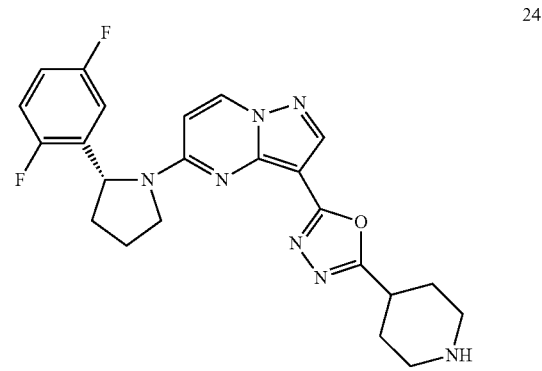 [SMILES: Fc1ccc(F)c([C@H]2CCCN2c2ccn3ncc(-c4nnc(C5CCNCC5)o4)c3n2)c1]

To a solution of (R)-tert-butyl 4-(2-(5-(2-(2,5-difluorophenyl)pyrrolidin-1-yl)pyrazolo[1,5-a]pyrimidine-3-carbonyl)hydrazinecarbonyl)piperidine-1-carboxylate (90.0 mg, 0.158 mmol) in DCM (1.0 mL) was added pyridine (0.0290 mL, 0.363 mmol) at 0° C. The mixture was cooled to −10° C., and triflic anhydride (0.0560 mL, 0.332 mmol) was dropwise added to it. The reaction mixture was stirred at −10° C. for 1 hour and then at 0° C. for 1 hour. After quenched with water, the mixture was extracted with DCM twice. The combined organic layers were dried over $Na_2SO_4$, filtered and concentrate in vacuo. The residue was purified by column chromatography on $SiO_2$ (DCM:MeOH=20:1 to 5:1) to afford (R)-2-(5-(2-(2,5-difluorophenyl)pyrrolidin-1-yl)pyrazolo[1,5-a]pyrimidin-3-yl)-5-(piperidin-4-yl)-1,3,4-oxadiazole (31.0 mg, 43%) as a yellow solid. $^1$H-NMR (CDCl$_3$, Varian, 400 MHz): δ 1.80-2.28 (4H, m), 2.30-2.62 (4H, m), 3.13-3.33 (2H, m), 3.35-3.74 (4H, m), 3.82-4.22 (2H, m), 5.21 and 5.76 (1H, s+s), 5.93 and 6.42 (1H, s+s), 6.65-6.80 (1H, m), 6.58-7.15 (2H, m), 8.19-8.38 (2H, m).

Example 36: Preparation of Chemical Compound 25: (R)-2-(5-(2-(2,5-difluorophenyl)pyrrolidin-1-yl)pyrazolo[1,5-a]pyrimidin-3-yl)-5-(piperidin-4-yl)-1,3,4-thiadiazole

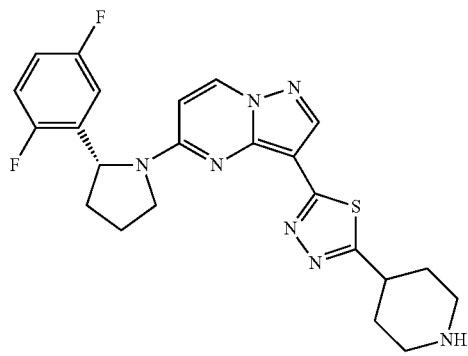

25

To a solution of (R)-tert-butyl 4-(2-(5-(2-(2,5-difluorophenyl)pyrrolidin-1-yl)pyrazolo[1,5-a]pyrimidine-3-carbonyl)hydrazinecarbonyl)piperidine-1-carboxylate (90.0 mg, 0.158 mmol) in diglyme (3.1 mL) were added $P_4S_{10}$ (140 mg, 0.316 mmol) and $Na_2CO_3$ (67.0 mg, 0.632 mmol) at room temperature. The reaction mixture was stirred at 90° C. for 2 hours, cooled to room temperature and partitioned between water and EtOAc. The separated organic layer was dried over $Na_2SO_4$ and concentrated in vacuo. The residue was purified by column chromatography on $SiO_2$ (EtOAc only to DCM:MeOH=10:1) to afford (R)-2-(5-(2-(2,5-difluorophenyl)pyrrolidin-1-yl)pyrazolo[1,5-a]pyrimidin-3-yl)-5-(piperidin-4-yl)-1,3,4-thiadiazole (49.0 mg, 66%) as a yellow solid. MS: 468.2 [MH$^+$].

Example 37: Preparation of Chemical Compound 26

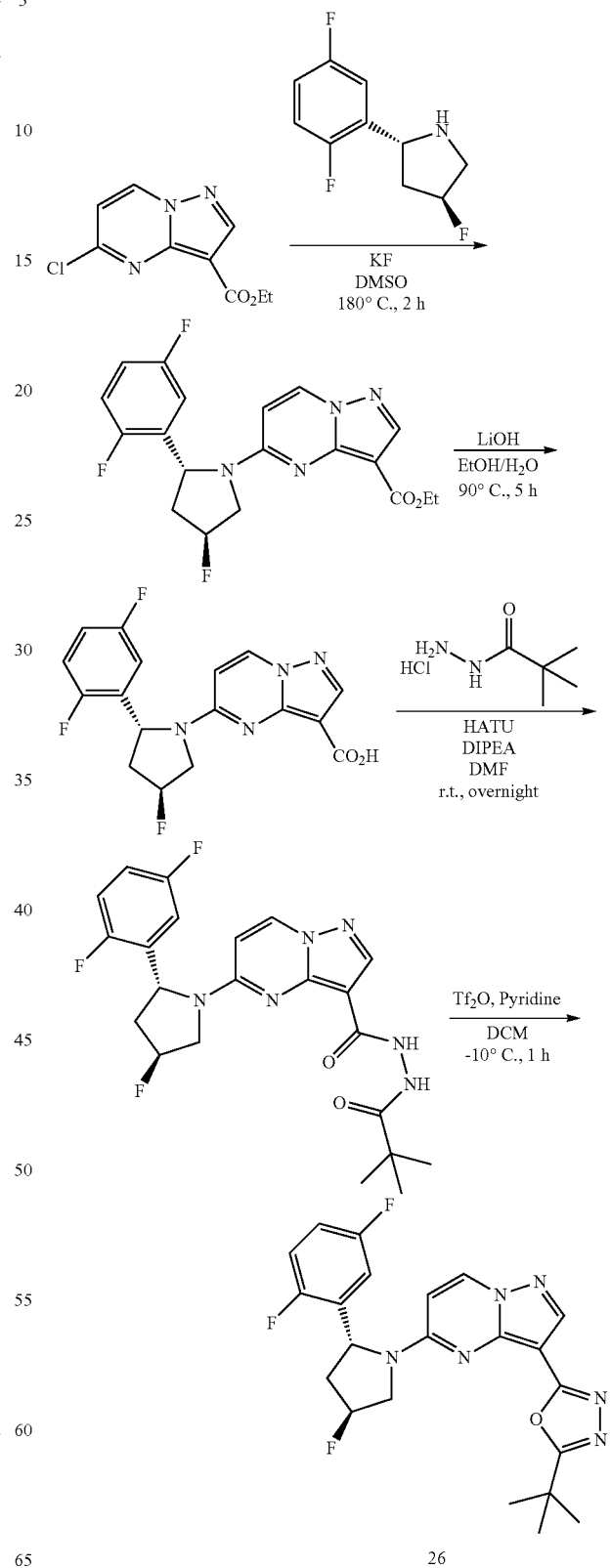

26

Chemical Compound 26: 2-tert-butyl-5-(5-((2R,4S)-2-(2,5-difluorophenyl)-4-fluoropyrrolidin-1-yl)pyrazolo[1,5-a]pyrimidin-3-yl)-1,3,4-oxadiazole

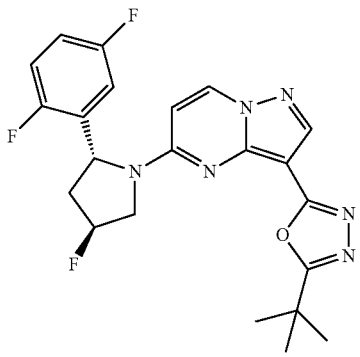

Step A: (R)-ethyl 5-((2R,4S)-2-(2,5-difluorophenyl)-4-fluoropyrrolidin-1-yl)pyrazolo[1,5-a]pyrimidine-3-carboxylate

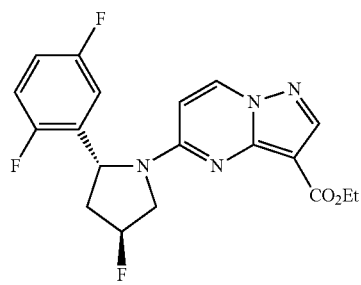 [SMILES: CCOC(=O)c1cnn2ccc(N3C[C@@H](F)C[C@@H]3c3cc(F)ccc3F)nc12]

A mixture of ethyl 5-chloropyrazolo[1,5-a]pyrimidine-3-carboxylate (100 mg, 0.443 mmol), (2R,4S)-2-(2,5-difluorophenyl)-4-fluoropyrrolidine (Intermediate 6, 94.0 mg, 0.465 mmol) and KF (129 mg, 2.21 mmol) in DMSO (1.5 mL) was stirred at 180° C. for 2 hours. After being cooled to room temperature, the reaction mixture was partitioned between water and EtOAc. The separated organic layer was washed with water and brine, dried over Na$_2$SO$_4$, filtered and concentrated in vacuo. The residue was purified by column chromatography on SiO$_2$ (Hex:EtOAc=1:1) to afford (R)-ethyl 5-((2R,4S)-2-(2,5-difluorophenyl)-4-fluoropyrrolidin-1-yl)pyrazolo[1,5-a]pyrimidine-3-carboxylate (161 mg, 93%) as a pale yellow foam. $^1$H-NMR (DMSO-d$_6$, Varian, 400 MHz): δ 1.16-1.30 (3H, m), 2.10-2.34 (1H, m), 2.73-2.95 (1H, m), 4.00-4.30 (3H, m), 4.52 and 5.47 (1H, s+s), 5.49-5.67 (2H, m), 6.11 and 6.74 (1H, s+s), 7.12-7.40 (3H, m), 8.15-8.30 (1H, m), 8.60-8.82 (1H, m).

Step B: 5-((2R,4S)-2-(2,5-difluorophenyl)-4-fluoropyrrolidin-1-yl)pyrazolo[1,5-a]pyrimidine-3-carboxylic acid

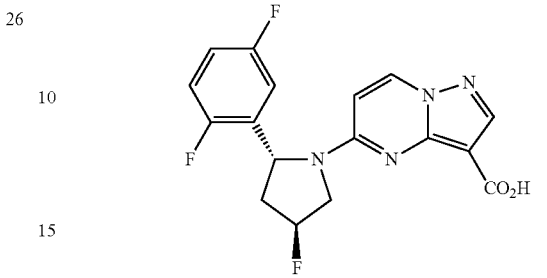

To a solution of ethyl 5-((2R,4S)-2-(2,5-difluorophenyl)-4-fluoropyrrolidin-1-yl)pyrazolo[1,5-a]pyrimidine-3-carboxylate (161 mg, 0.412 mmol) in EtOH (3.0 mL) and water (1.0 mL) was added LiOH (30.0 mg, 1.24 mmol) at 0° C. The reaction mixture was heated at 90° C. for 5 hours and cooled to room temperature. After evaporation of EtOH, the residue was acidified with 2 N aq. HCl until pH 5-6, and then extracted with EtOAc twice. The combined organic layers were washed with brine, dried over Na$_2$SO$_4$, filtered and concentrated in vacuo to afford 5-((2R,4S)-2-(2,5-difluorophenyl)-4-fluoropyrrolidin-1-yl)pyrazolo[1,5-a]pyrimidine-3-carboxylic acid (107 mg, 72%) as a white solid. $^1$H-NMR (DMSO-d$_6$, Varian, 400 MHz): δ 2.93-2.37 (1H, m), 2.70-2.95 (1H, m), 3.94-4.60 (2H, m), 5.35-5.68 (2H, m), 6.11 and 6.71 (1H, s+s), 7.00-7.40 (3H, m), 8.17 (1H, s), 8.60-6.82 (1H, m), 11.60 (1H, br. s).

Step C: 5-((2R,4S)-2-(2,5-difluorophenyl)-4-fluoropyrrolidin-1-yl)-N'-pivaloylpyrazolo[1,5-a]pyrimidine-3-carbohydrazide

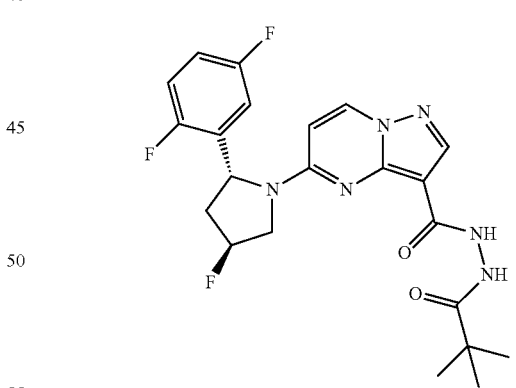

To a solution of 5-((2R,4S)-2-(2,5-difluorophenyl)-4-fluoropyrrolidin-1-yl)pyrazolo[1,5-a]pyrimidine-3-carboxylic acid (107 mg, 0.295 mmol) in DMF (2.0 mL) were added pivalohydrazide hydrochloride (135 mg, 0.886 mmol), DIPEA (0.206 mL, 1.18 mmol) and HATU (168 mg, 0.443 mmol) at room temperature. The reaction mixture was stirred at room temperature overnight and poured into water. The mixture was stirred for 30 min. A precipitated solid was collected by filtration and dried under vacuum to afford 5-((2R,4S)-2-(2,5-difluorophenyl)-4-fluoropyrrolidin-1-yl)-N'-pivaloylpyrazolo[1,5-a]pyrimidine-3-carbohydrazide (101 mg, 74%) as a white solid. $^1$H-NMR (DMSO-$d_6$, Varian, 400 MHz): δ 1.17-1.26 (9H, m), 2.10-2.30 (1H, m), 2.78-2.95 (1H, m), 4.10-4.38 (2H, m), 5.35-5.67 (2H, m), 6.14 (0.3H, s), 6.76 (0.7H, d, J=7.6 Hz), 7.02-7.40 (3H, m), 8.15 and 8.24 (1H, s+s), 8.39 and 8.71 (1H, s+s), 8.86 (1H, d, J=7.2 Hz), 9.48 and 9.83 (1H, s+s).

Step D: 2-tert-butyl-5-(5-((2R,4S)-2-(2,5-difluorophenyl)-4-fluoropyrrolidin-1-yl)pyrazolo[1,5-a]pyrimidin-3-yl)-1,3,4-oxadiazole

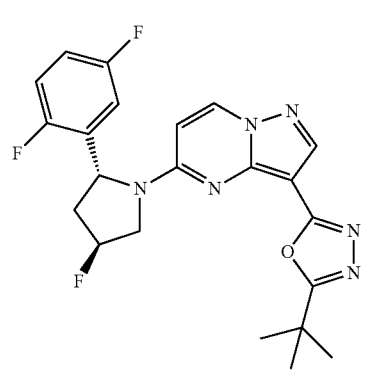

26

To a solution of 5-((2R,4S)-2-(2,5-difluorophenyl)-4-fluoropyrrolidin-1-yl)-N'-pivaloylpyrazolo[1,5-a]pyrimidine-3-carbohydrazide (101 mg, 0.219 mmol) in DCM (1.5 mL) was added pyridine (0.0410 mL, 0.505 mmol) at 0° C. The mixture was cooled to −10° C., and then triflic anhydride (0.0780 mL, 0.461 mmol) was dropwise added to it. The reaction mixture was stirred at −10° C. for 1 hour and then at 0° C. for 1 hour. After quenched with water, the mixture was extracted with DCM twice. The combined organic layers were dried over Na$_2$SO$_4$, filtered and concentrate in vacuo. The residue was purified by column chromatography on SiO$_2$ (Hex:EtOAC=1:1) to afford 2-tert-butyl-5-(5-((2R,4S)-2-(2,5-difluorophenyl)-4-fluoropyrrolidin-1-yl)pyrazolo[1,5-a]pyrimidin-3-yl)-1,3,4-oxadiazole (68.0 mg, 70%) as a white solid. $^1$H-NMR (DMSO-$d_6$, Varian, 400 MHz): δ 1.23-1.44 (9H, m), 2.10-2.38 (1H, m), 2.80-3.00 (1H, m), 4.00-4.60 (2H, m), 5.35-5.51 (1H, m), 5.52-5.71 (1H, m), 6.14 and 6.81 (1H, s+s), 7.02-7.40 (3H, m), 8.38 (1H, s), 8.71-8.87 (1H, m). MS: 443.4 [MH$^+$].

Example 38: Preparation of Chemical Compound 27

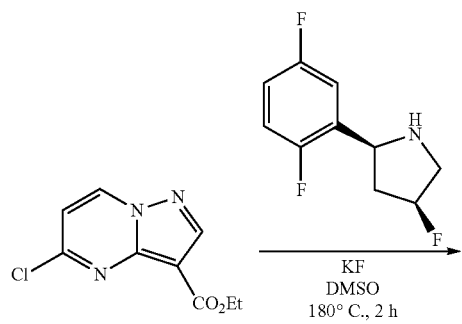

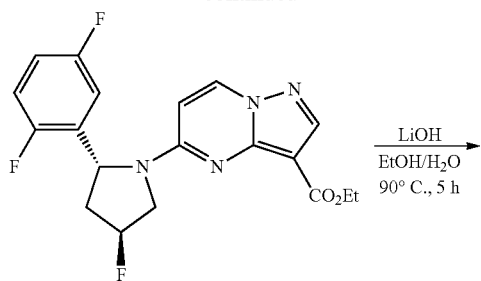

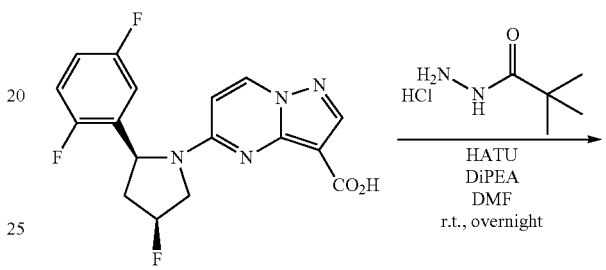

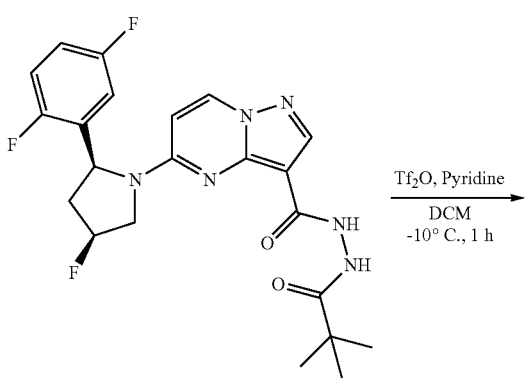

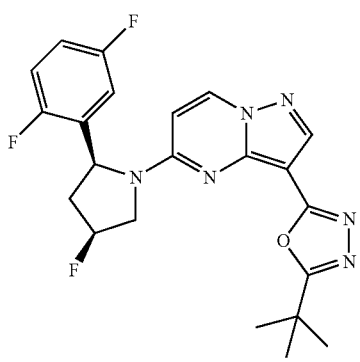

27

131

Chemical Compound 27: 5-((2S,4S)-2-(2,5-difluorophenyl)-4-fluoropyrrolidin-1-yl)-N'-pivaloylpyrazolo[1,5-a]pyrimidine-3-carbohydrazide

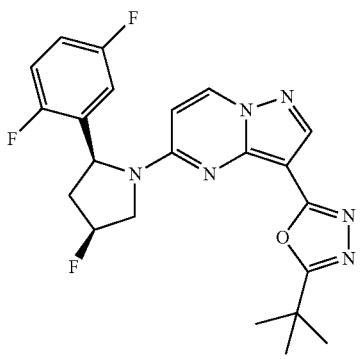

Step A: 5-((2S,4S)-2-(2,5-difluorophenyl)-4-fluoropyrrolidin-1-yl)pyrazolo[1,5-a]pyrimidine-3-carboxylate

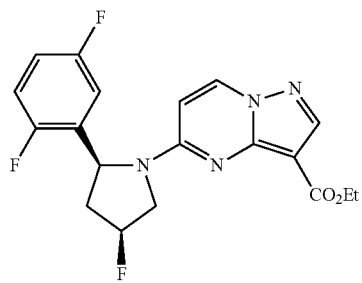 [SMILES: CCOC(=O)c1cnn2ccc(N3C[C@@H](F)C[C@H]3c3cc(F)ccc3F)nc12]

A mixture of ethyl 5-chloropyrazolo[1,5-a]pyrimidine-3-carboxylate (112 mg, 0.496 mmol), (2S,4S)-2-(2,5-difluorophenyl)-4-fluoropyrrolidine (Intermediate 7, 105 mg, 0.521 mmol) and KF (114 mg, 2.48 mmol) in DMSO (1.6 mL) was stirred at 180° C. for 2 hours. After being cooled to room temperature, the reaction mixture was poured into water. The mixture was stirred for 30 min. A precipitated solid was collected by filtration and dried under vacuum to afford ethyl 5-((2S,4S)-2-(2,5-difluorophenyl)-4-fluoropyrrolidin-1-yl)pyrazolo[1,5-a]pyrimidine-3-carboxylate (171 mg, 88%) as a pale yellow solid. $^1$H-NMR (DMSO-$d_6$, Varian, 400 MHz): δ 1.04-1.38 (3H, m), 2.17-2.40 (1H, m), 2.62-2.98 (1H, m), 3.85-4.39 (4H, m), 5.45-5.53 (1H, m), 5.61 and 5.75 (1H, s+s), 6.17 and 6.71 (1H, s+s), 6.87-6.95 (1H, m), 7.05-7.40 (2H, m), 8.18-8.29 (1H, m), 8.60-8.90 (1H, m).

132

Step B: 5-((2S,4S)-2-(2,5-difluorophenyl)-4-fluoropyrrolidin-1-yl)pyrazolo[1,5-a]pyrimidine-3-carboxylic acid

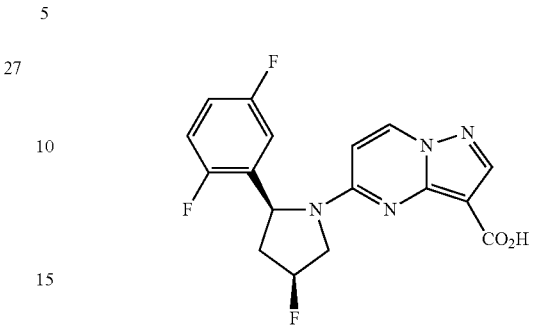

To a solution of ethyl 5-((2S,4S)-2-(2,5-difluorophenyl)-4-fluoropyrrolidin-1-yl)pyrazolo[1,5-a]pyrimidine-3-carboxylate (171 mg, 0.438 mmol) in EtOH (3.3 mL) and water (1.1 mL) was added LiOH (31.0 mg, 1.31 mmol) at 0° C. The reaction mixture was heated at 90° C. for 5 hours and cooled to room temperature. After evaporation of EtOH, the residue was acidified with 2 N aq. HCl until pH 5-6, and then extracted with EtOAc twice. The combined organic layers were washed with brine, dried over $Na_2SO_4$, filtered and concentrated in vacuo to afford 5-((2S,4S)-2-(2,5-difluorophenyl)-4-fluoropyrrolidin-1-yl)pyrazolo[1,5-a]pyrimidine-3-carboxylic acid (150 mg, 95%) as a yellow solid. $^1$H-NMR (DMSO-$d_6$, Varian, 400 MHz): δ 2.26-2.34 (1H, m), 2.70-2.95 (1H, m), 3.92-4.18 (1H, m), 4.20-4.38 (1H, m), 5.46-6.17 (3H, m), 6.84-6.92 (1H, m), 7.09-7.19 (1H, m), 7.25-7.28 (1H, m), 8.18 (1H, s), 8.60-8.75 (1H, m). * A proton from $CO_2H$ was not observed.

Step C: 5-((2S,4S)-2-(2,5-difluorophenyl)-4-fluoropyrrolidin-1-yl)-N'-pivaloylpyrazolo[1,5-a]pyrimidine-3-carbohydrazide

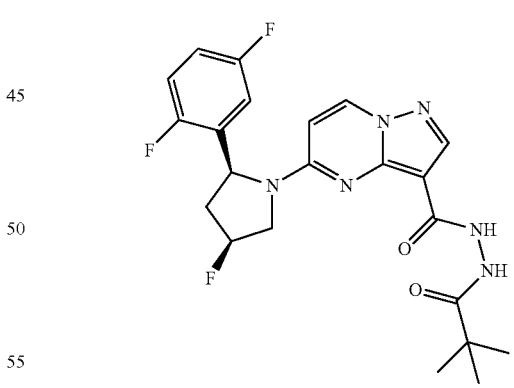

To a solution of 5-((2S,4S)-2-(2,5-difluorophenyl)-4-fluoropyrrolidin-1-yl)pyrazolo[1,5-a]pyrimidine-3-carboxylic acid (150 mg, 0.414 mmol) in DMF (2.7 mL) were added pivalohydrazide hydrochloride (190 mg, 1.24 mmol), DIPEA (0.289 mL, 1.65 mmol) and HATU (236 mg, 0.621 mmol) at room temperature. The reaction mixture was stirred at room temperature overnight and poured into water. The mixture was stirred for 30 min. A precipitated solid was collected by filtration and dried under vacuum to afford 5-((2S,4S)-2-(2,5-difluorophenyl)-4-fluoropyrrolidin-1-yl)-

N'-pivaloylpyrazolo[1,5-a]pyrimidine-3-carbohydrazide (102 mg, 53%) as a pale yellow solid. $^1$H-NMR (DMSO-$d_6$, Varian, 400 MHz): δ 1.47 (9H, s), 2.15-2.40 (1H, m), 2.70-2.98 (1H, m), 3.88-4.18 (1H, m), 4.20-4.45 (1H, m), 5.40-5.60 (2H, m), 6.75 (1H, d, J=7.6 Hz), 6.85-7.40 (3H, m), 8.17 and 8.27 (1H, s+s), 8.53 and 8.71 (1H, s+s), 8.91 (1H, d, J=7.6 Hz), 9.39 and 9.55 (1H, s+s).

Step D: 2-tert-butyl-5-(5-((2S,4S)-2-(2,5-difluorophenyl)-4-fluoropyrrolidin-1-yl)pyrazolo[1,5-a]pyrimidin-3-yl)-1,3,4-oxadiazole

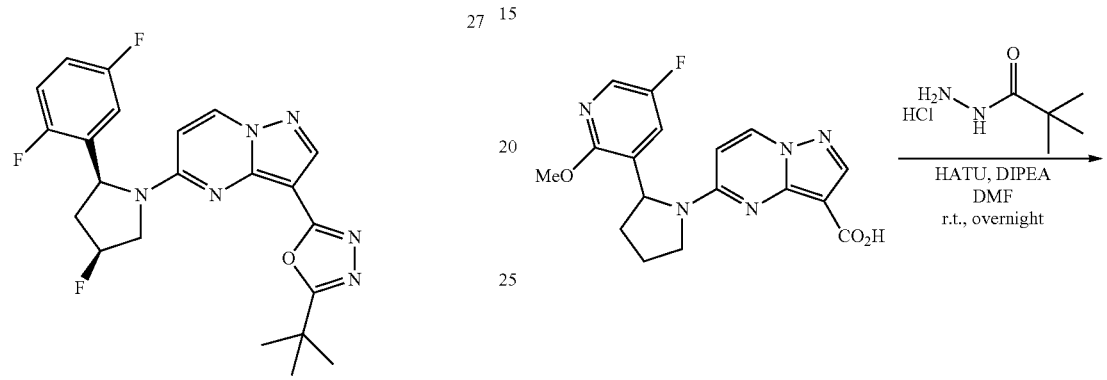

To a solution of 5-((2S,4S)-2-(2,5-difluorophenyl)-4-fluoropyrrolidin-1-yl)-N'-pivaloylpyrazolo[1,5-a]pyrimidine-3-carbohydrazide (102 mg, 0.222 mmol) in DCM (1.5 mL) was added pyridine (0.0410 mL, 0.509 mmol) at 0° C. The mixture was cooled to −10° C., and then triflic anhydride (0.0790 mL, 0.465 mmol) was dropwise added to it. The reaction mixture was stirred at −10° C. for 1 hour and then at 0° C. for 1 hour. After quenched with water, the mixture was extracted with DCM twice. The combined organic layers were dried over $Na_2SO_4$, filtered and concentrate in vacuo. The residue was purified by column chromatography on $SiO_2$ (Hex:EtOAc=1:3) to afford 2-tert-butyl-5-(5-((2S,4S)-2-(2,5-difluorophenyl)-4-fluoropyrrolidin-1-yl)pyrazolo[1,5-a]pyrimidin-3-yl)-1,3,4-oxadiazole (28.0 mg, 26%) as a white solid. $^1$H-NMR (DMSO-$d_6$, Varian, 400 MHz): δ 1.15-1.52 (9H, m), 2.20-2.40 (1H, m), 2.65-2.81 (1H, m), 3.88-4.38 (2H, m), 5.40-5.85 (2H, m), 6.19-6.75 (1H, m), 6.85-7.40 (3H, m), 8.34 (1H, s), 8.70-8.70 (1H, m). MS: 443.4 [MH$^+$].

Example 39: Preparation of Chemical Compound 28

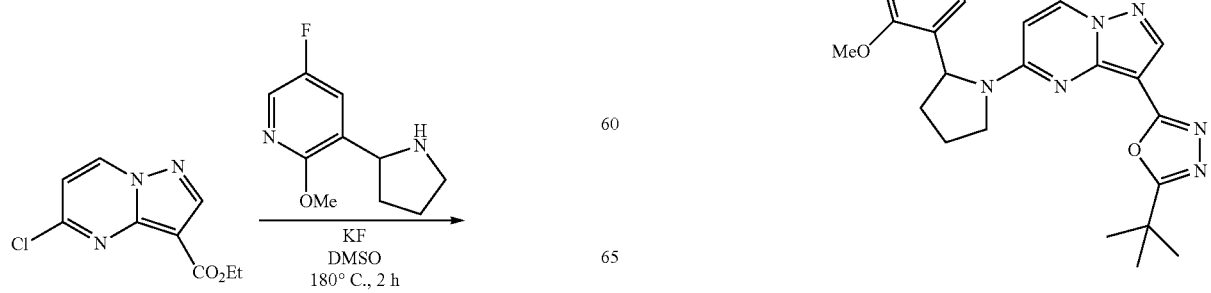

Chemical Compound 28: 2-tert-butyl-5-(5-(2-(5-fluoro-2-methoxypyridin-3-yl)pyrrolidin-1-yl)pyrazolo[1,5-a]pyrimidin-3-yl)-1,3,4-oxadiazole

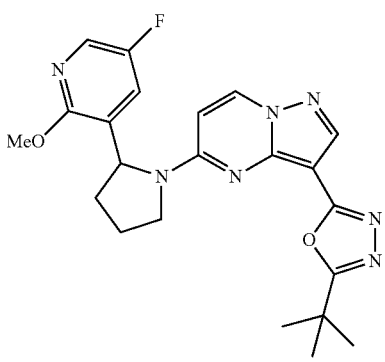

Step A: Ethyl 5-(2-(5-fluoro-2-methoxypyridin-3-yl)pyrrolidin-1-yl)pyrazolo[1,5-a]pyrimidine-3-carboxylate

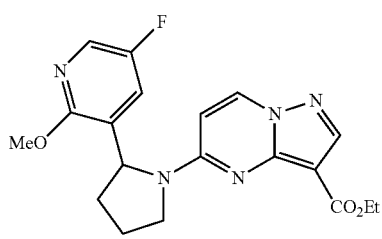 [SMILES: CCOC(=O)c1cnn2ccc(N3CCCC3c3cc(F)cnc3OC)nc12]

A mixture of ethyl 5-chloropyrazolo[1,5-a]pyrimidine-3-carboxylate (200 mg, 0.886 mmol), 5-fluoro-2-methoxy-3-(pyrrolidin-2-yl)pyridine (Intermediate 3, 186 mg, 0.948 mmol) and KF (257 mg, 4.43 mmol) in DMSO (3.0 mL) was stirred at 180° C. for 2 hours. After being cooled to room temperature, the reaction mixture was partitioned between water and EtOAc. The separated organic layer was washed with water and brine, dried over $Na_2SO_4$, filtered and concentrated in vacuo. The residue was purified by column chromatography on $SiO_2$ (Hex:EtOAc=1:1) to afford ethyl 5-(2-(5-fluoro-2-methoxypyridin-3-yl)pyrrolidin-1-yl)pyrazolo[1,5-a]pyrimidine-3-carboxylate (225 mg, 74%) as a white foam. $^1$H-NMR (DMSO-$d_6$, Varian, 400 MHz): δ 1.25-1.30 (3H, m), 1.88-2.08 (3H, m), 2.23-2.37 (1H, m), 3.48-3.85 (1H, m), 3.90-4.09 (5H, m), 4.15-4.30 (1H, m), 5.14 (0.3H, m), 5.48 (0.7H, d, J=7.6 Hz), 5.98 (0.3H, m), 6.65 (0.7H, d, J=6.8 Hz), 7.22-7.41 (1H, m), 7.93-8.11 (1H, m), 8.12-8.30 (1H, m), 8.53 (0.3H, s), 8.76 (0.7H, d, J=7.2 Hz).

Step B: 5-(2-(5-fluoro-2-methoxypyridin-3-yl)pyrrolidin-1-yl)pyrazolo[1,5-a]pyrimidine-3-carboxylic acid

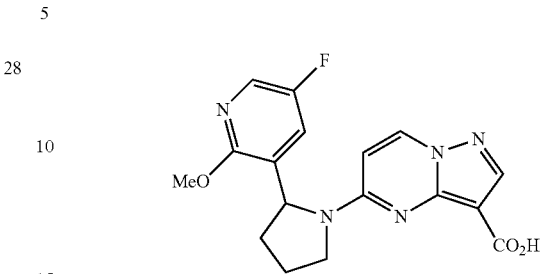

To a solution of ethyl 5-(2-(5-fluoro-2-methoxypyridin-3-yl)cyclopentyl)pyrazolo[1,5-a]pyrimidine-3-carboxylate (255 mg, 0.663 mmol) in EtOH (5.0 mL) and water (1.6 mL) was added LiOH (48.0 mg, 1.99 mmol) at 0° C. The reaction mixture was heated at 90° C. for 5 hours and cooled to room temperature. After evaporation of EtOH, the residue was acidified with 2 N aq. HCl until pH 5-6, and then extracted with EtOAc twice. The combined organic layers were washed with brine, dried over $Na_2SO_4$, filtered and concentrated in vacuo to afford 5-(2-(5-fluoro-2-methoxypyridin-3-yl)pyrrolidin-1-yl)pyrazolo[1,5-a]pyrimidine-3-carboxylic acid (170 mg, 72%) as a white solid. $^1$H-NMR (DMSO-$d_6$, Varian, 400 MHz): δ 1.82-2.08 (3H, m), 2.26-2.48 (1H, m), 3.45-3.80 (2H, m), 3.88-4.08 (3H, m), 5.15 and 5.46 (1H, s+s), 6.64 and 7.34 (1H, s+s), 7.34 (1H, s), 7.92-8.18 (2H, m), 8.42-8.85 (1H, m). * A proton from $CO_2H$ was not observed.

Step C: 5-(2-(5-fluoro-2-methoxypyridin-3-yl)pyrrolidin-1-yl)-N'-pivaloylpyrazolo[1,5-a]pyrimidine-3-carbohydrazide

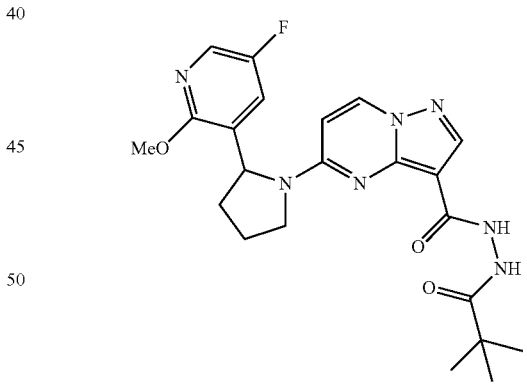

To a solution of 5-(2-(5-fluoro-2-methoxypyridin-3-yl)pyrrolidin-1-yl)pyrazolo[1,5-a]pyrimidine-3-carboxylic acid (170 mg, 0.476 mmol) in DMF (3.1 mL) were added pivalohydrazide hydrochloride (218 mg, 0.1.43 mmol), DIPEA (0.332 mL, 1.90 mmol) and HATU (271 mg, 0.714 mmol) at room temperature. The reaction mixture was stirred at room temperature overnight and poured into water. The mixture was stirred for 30 min. A precipitated solid was collected by filtration and dried under vacuum to afford 5-(2-(5-fluoro-2-methoxypyridin-3-yl)pyrrolidin-1-yl)-N'-pivaloylpyrazolo[1,5-a]pyrimidine-3-carbohydrazide (164 mg, 76%) as a white solid. $^1$H-NMR (DMSO-$d_6$, Varian, 400

MHz): δ 1.10-1.23 (9H, m), 1.77-2.10 (3H, m), 2.20-2.48 (1H, m), 3.57-3.78 (1H, m), 3.88-3.99 (3H, m), 4.00-4.10 (1H, m), 5.19 (0.3H, d, J=7.2 Hz), 5.31 (0.7H, d, J=8.8 Hz), 6.01 (0.3H, d, J=8.4 Hz), 6.69 (0.7H, d, J=7.6 Hz), 7.3-7.42 (1H, m), 7.89-7.98 (1H, m), 8.05-8.18 (1H, m), 8.19-8.32 (1H, m), 8.60 (0.3H, d, J=8.0 Hz), 8.83 (0.7H, d, J=7.6 Hz), 9.29 and 9.54 (1H, s+s).

Step D: 2-tert-butyl-5-(5-(2-(5-fluoro-2-methoxy-pyridin-3-yl)pyrrolidin-1-yl)pyrazolo[1,5-a]pyrimidin-3-yl)-1,3,4-oxadiazole

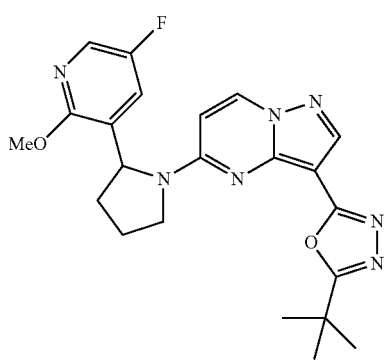

A mixture of 5-(2-(5-fluoro-2-methoxypyridin-3-yl)pyrrolidin-1-yl)-N'-pivaloylpyrazolo[1,5-a]pyrimidine-3-carbohydrazide (110 mg, 242 mmol) and POCl₃ (0.675 mL, 7.25 mmol) was refluxed for 2 hours. After being cooled to room temperature, the reaction mixture was partitioned between water and DCM. The separated organic layer was washed with water and brine, dried over Na₂SO₄, filtered and concentrated in vacuo. The residue was purified by column chromatography on SiO₂ (Hex:EtOAc=1:1 to 1:4) to afford 2-tert-butyl-5-(5-(2-(5-fluoro-2-methoxypyridin-3-yl)pyrrolidin-1-yl)pyrazolo[1,5-a]pyrimidin-3-yl)-1,3,4-oxadiazole (61.0 mg, 58%) as a white solid. ¹H-NMR (DMSO-d₆, Varian, 400 MHz): δ 1.22 and 1.44 (9H, s+s), 1.70-2.10 (3H, m), 2.20-2.40 (1H, m), 3.52-3.85 (1H, m), 3.95-4.12 (4H, m), 5.15 (0.3H, d, J=7.6 Hz), 5.50 (0.7H, d, J=7.6 Hz), 6.00 (0.3H, d, J=7.2 Hz), 6.70 (0.7H, d, J=8.0 Hz), 7.23-7.42 (1H, m), 7.95-8.15 (1H, m), 8.30-8.42 (1H, m), 8.60 (0.3H, d, J=7.2 Hz), 8.83 (0.7H, d, J=7.2 Hz). MS: 438.4 [MH⁺].

Example 40: Preparation of Chemical Compound 29

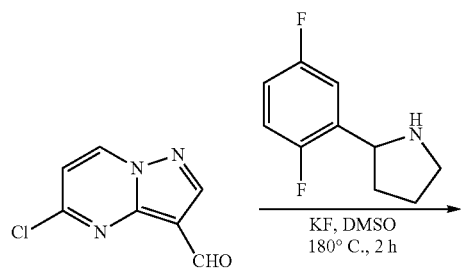

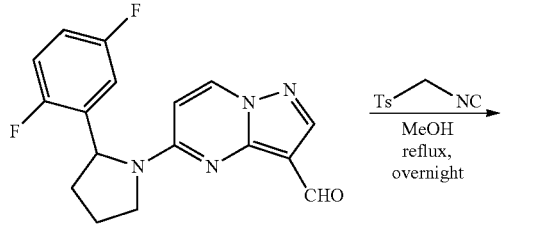

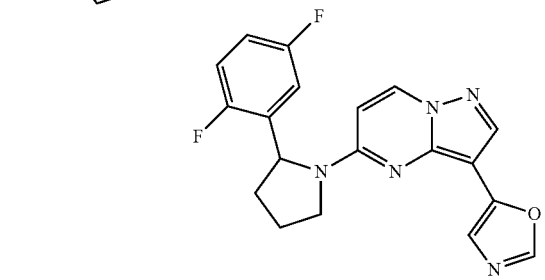

Chemical Compound 29: 5-(5-(2-(2,5-difluorophenyl)pyrrolidin-1-yl)pyrazolo[1,5-a]pyrimidin-3-yl)oxazole

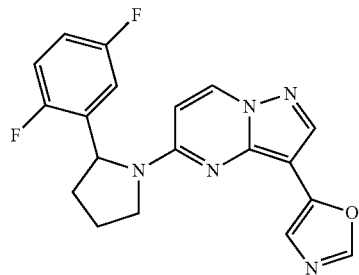

Step A: 5-(2-(2,5-difluorophenyl)pyrrolidin-1-yl)pyrazolo[1,5-a]pyrimidine-3-carbaldehyde

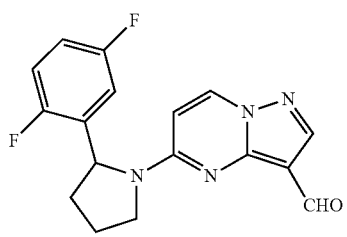

A mixture of 5-chloropyrazolo[1,5-a]pyrimidine-3-carbaldehyde (300 mg, 1.65 mmol), 2-(2,5-difluorophenyl)pyrrolidine (Intermediate 2, 324 mg, 1.77 mmol) and KF (480 mg, 8.26 mmol) in DMSO (5.5 mL) was heated at 180° C. for 2 hours. After being cooled to room temperature, the reaction mixture was poured into water. The mixture was extracted with EtOAc twice. The combined organic layers were washed with brine, dried over Na₂SO₄, filtered and concentrate in vacuo. The residue was purified by column chromatography on SiO₂ (EtOAc only to DCM:MeOH=20:

1) to afford 5-(2-(2,5-difluorophenyl)pyrrolidin-1-yl)pyrazolo[1,5-a]pyrimidine-3-carbaldehyde (540 mg, 100%) as a yellow solid. $^1$H-NMR (CDCl$_3$, Varian, 400 MHz): δ 1.90-2.28 (3H, m), 2.38-2.60 (1H, m), 3.60-4.18 (2H, m), 5.14-5.28 (0.6H, m), 5.54-5.72 (0.4H, m), 5.84-6.02 (0.6H, m), 6.35-6.46 (0.4H, m), 6.68-6.78 (1H, m), 6.82-7.20 (2H, m), 8.10-8.36 (2H, m), 9.77 and 10.11 (1H, s+s).

Step B: 5-(5-(2-(2,5-difluorophenyl)pyrrolidin-1-yl)pyrazolo[1,5-a]pyrimidin-3-yl)oxazole

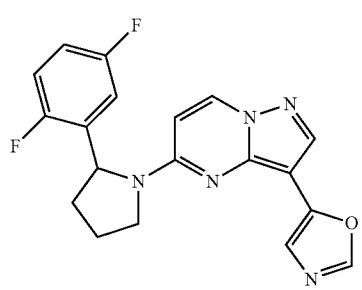

29

To a solution of 5-(2-(2,5-difluorophenyl)pyrrolidin-1-yl)pyrazolo[1,5-a]pyrimidine-3-carbaldehyde (300 mg, 0.914 mmol) in MeOH (9.2 mL) were added 1-(isocyanomethylsulfonyl)-4-methylbenzene (178 mg, 0.914 mmol) and K$_2$CO$_3$ (126 mg, 0.914 mmol) at room temperature. The reaction mixture was refluxed for 4 hours and cooled to room temperature. After evaporation of MeOH, the residue was partitioned between DCM and water. The organic layer was washed with brine, dried over Na$_2$SO$_4$, filtered and concentrated in vacuo. The residue was purified by column chromatography on SiO$_2$ (Hex:EtOAc=1:1) to afford 5-(5-(2-(2,5-difluorophenyl)pyrrolidin-1-yl)pyrazolo[1,5-a]pyrimidin-3-yl)oxazole (46.0 mg, 13%) as a yellow solid. $^1$H-NMR (MeOH-d$_4$, Varian, 400 MHz): δ 1.95-2.25 (3H, m), 2.40-2.50 (1H, m), 3.50-3.88 (2H, m), 3.89-4.10 (1H, m), 5.20-5.70 (1H, m), 6.56-6.77 (1H, m), 6.80-7.20 (3H, m), 7.07-7.20 (1H, m), 7.92-8.20 (1H, m), 8.22-8.55 (1H, m). MS: 368.2 [MH$^+$].

Example 41: Preparation of Chemical Compound 30

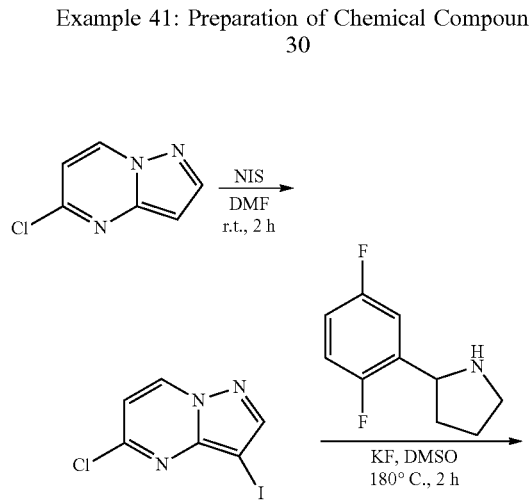

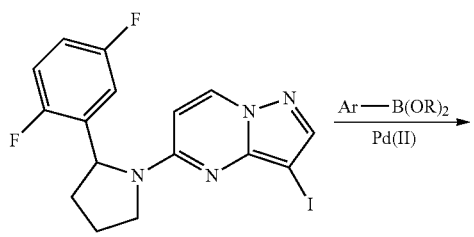

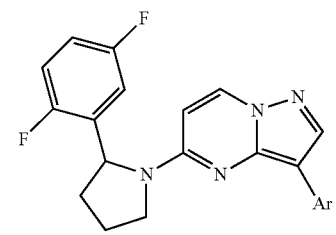

Chemical Compound 30: 4-(5-(2-(2,5-difluorophenyl)pyrrolidin-1-yl)pyrazolo[1,5-a]pyrimidin-3-yl)isoxazole

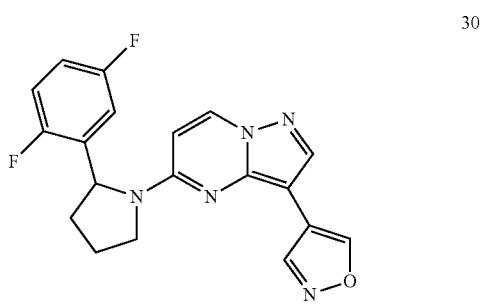 [SMILES: Fc1ccc(F)c(C2CCCN2c2ccn3ncc(-c4cnoc4)c3n2)c1]

30

Step A: 5-chloro-3-iodopyrazolo[1,5-a]pyrimidine

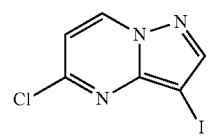 [SMILES: Clc1ccn2ncc(I)c2n1]

To a solution of 5-chloropyrazolo[1,5-a]pyrimidine (1.00 g, 6.51 mmol) in DMF (13 mL) was added portionwise N-iodosuccinamide (1.61 g, 7.16 mmol) at room temperature. The reaction mixture was stirred for 2 hours at room temperature. After addition of water, the mixture was stirred for further 30 min at room temperature. A precipitated solid was collected by filtration and dried under vacuum to afford 5-chloro-3-iodopyrazolo[1,5-a]pyrimidine (1.74 g, 96%) as a pale yellow solid. $^1$H-NMR (DMSO-d$_6$, Varian, 400 MHz): δ 7.15 (1H, d, J=7.2 Hz), 8.34 (1H, s), 9.17 (1H, d, J=7.2 Hz).

Step B: 5-(2-(2,5-difluorophenyl)pyrrolidin-1-yl)-3-iodopyrazolo[1,5-a]pyrimidine

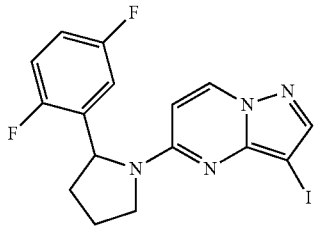 [SMILES: Fc1ccc(F)c(C2CCCN2c2ccn3ncc(I)c3n2)c1]

A solution of 5-chloro-3-iodopyrazolo[1,5-a]pyrimidine (621 mg, 2.22 mmol), 2-(2,5-difluorophenyl)pyrrolidine (Intermediate 2, 407 mg, 2.22 mmol) and KF (645 mg, 11.1 mmol) in DMSO (7.4 mL) was stirred at 180° C. for 2 hours. After being cooled to room temperature, the reaction mixture was diluted with water. The mixture was extracted with EtOAc twice. The combined organic layers were washed with brine, dried over $Na_2SO_4$, filtered and concentrate in vacuo. The residue was purified by column chromatography on $SiO_2$ (Hex:EtOAc=5:1 to 3:1 to 2:1) to afford 5-(2-(2,5-difluorophenyl)pyrrolidin-1-yl)-3-iodopyrazolo[1,5-a]pyrimidine (819 mg, 86%) a pale yellow solid. $^1$H-NMR (DMSO-$d_6$, Varian, 400 MHz): δ 1.80-2.15 (3H, m), 2.38-2.50 (1H, m), 3.50-3.80 (1H, m), 3.95-3.99 (1H, m), 5.21-5.51 (1H, m), 5.99 and 6.53 (1H, s+s), 6.97 (1H, s), 7.11-7.26 (1H, m), 7.95 (1H, m), 8.44-8.64 (1H, m).

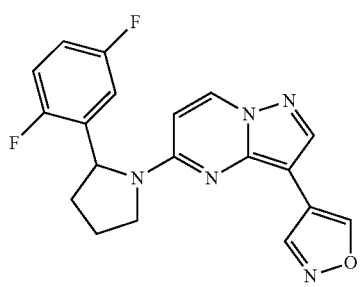

Step C: 4-(5-(2-(2,5-difluorophenyl)pyrrolidin-1-yl)pyrazolo[1,5-a]pyrimidin-3-yl)isoxazole A mixture of 5-(2-(2,5-difluorophenyl)pyrrolidin-1-yl)-3-iodopyrazolo[1,5-a]pyrimidine (40.0 mg, 0.0940 mmol), $K_3PO_4$ (60.0 mg, 0.282 mmol), $PdCl_2(dppf)$-$CH_2Cl_2$ adduct (7.66 mg, 9.39 μmol) and isoxazol-4-ylboronic acid (21.0 mg, 0.188 mmol) in dioxane (0.90 mL) and water (0.10 mL) was degassed with $N_2$ gas. The reaction mixture was heated at 100° C. for 15 hours in a sealed bottle and cooled to room temperature. After concentration in vacuo, the residue was diluted with EtOAc, filtered through a silica gel pad. The filtrate was concentrated in vacuo. The residue was purified by column chromatography on $SiO_2$ (Hex:EtOAc=1:3 to 1:4) to afford 4-(5-(2-(2,5-difluorophenyl)pyrrolidin-1-yl)pyrazolo[1,5-a]pyrimidin-3-yl)isoxazole (5.90 mg, 17%) as a brown oil. $^1$H-NMR (MeOH-$d_4$, Varian, 400 MHz): δ 1.95-2.20 (3H, m), 2.40-2.60 (1H, m), 3.50-4.12 (3H, m), 5.12-5.70 (1H, m), 5.80-6.40 (1H, m), 6.74 (1H, s), 6.92 (1H, s), 7.00-7.18 (1H, m), 8.00 (1H, s), 8.10-8.50 (2H, m). MS: 368.2 [MH$^+$].

Example 42: Preparation of Chemical Compound 31: 4-(5-(2-(2,5-difluorophenyl)pyrrolidin-1-yl)pyrazolo[1,5-a]pyrimidin-3-yl)-3,5-dimethylisoxazole

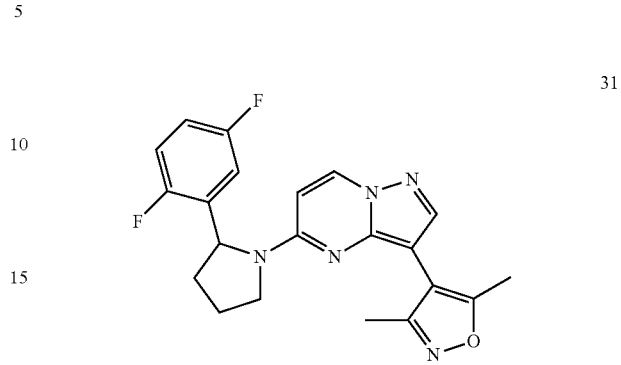

31

A mixture of 5-(2-(2,5-difluorophenyl)pyrrolidin-1-yl)-3-iodopyrazolo[1,5-a]pyrimidine (90.0 mg, 0.211 mmol), $K_3PO_4$ (134 mg, 0.634 mmol), $PdCl_2(dppf)$-$CH_2Cl_2$ adduct (17.0 mg, 0.0210 mmol) and 3,5-dimethylisoxazol-4-ylboronic acid (60.0 mg, 0.422 mmol) in dioxane (1.9 mL) and water (0.21 mL) was degassed with $N_2$ gas. The reaction mixture was heated at about 100° C. for 15 hours in a sealed tube, cooled to room temperature and partitioned between EtOAc and water. The separated organic layer was washed with brine, dried over $Na_2SO_4$, filtered and concentrated in vacuo. The residue was purified by column chromatography on $SiO_2$ (Hex:EtOAc=1:3 to 1:4) to afford 4-(5-(2-(2,5-difluorophenyl)pyrrolidin-1-yl)pyrazolo[1,5-a]pyrimidin-3-yl)-3,5-dimethylisoxazole (13.0 mg, 15%) as a yellow solid. $^1$H-NMR (CDCl$_3$, Varian, 400 MHz): δ 1.95-2.63 (10H, m), 3.70 (1H, s), 3.91 (1H, s), 5.08-5.55 (1H, m), 5.70-6.38 (1H, m), 6.84 (1H, m), 6.91 (1H, m), 7.00-7.10 (1H, m), 7.84 (1H, s), 8.27 (1H, m). MS: 369.2 [MH$^+$].

Example 43: Preparation of Chemical Compound 32

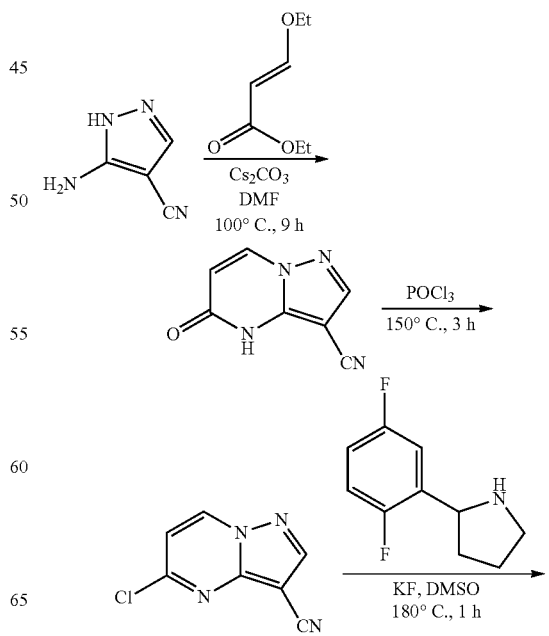

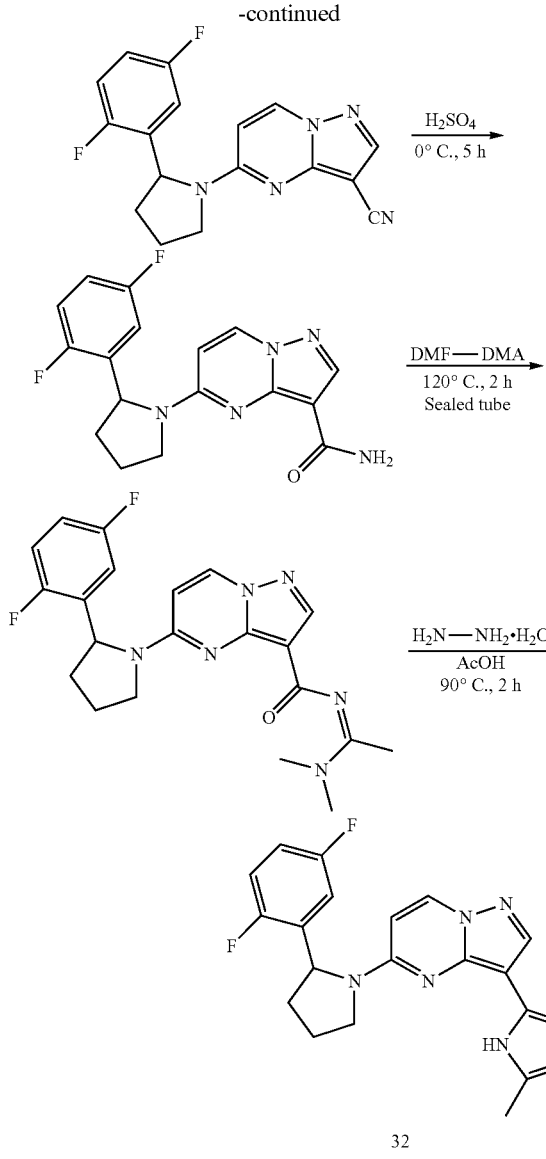

Chemical Compound 32: 5-(2-(2,5-difluorophenyl)pyrrolidin-1-yl)-3-(5-methyl-1H-1,2,4-triazol-3-yl)pyrazolo[1,5-a]pyrimidine Step A: 5-oxo-4,5-dihydropyrazolo[1,5-a]pyrimidine-3-carbonitrile

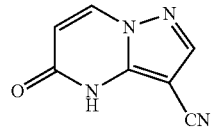 [SMILES: N#Cc1cnn2ccc(=O)[nH]c12]

A mixture of 5-amino-1H-pyrazole-4-carbonitrile (1.00 g, 9.25 mmol), ethyl 3-ethoxyacrylate (2.00 mL, 13.8 mmol) and $Cs_2CO_3$ (4.52 g, 13.88 mmol) in DMF (18 mL) was heated at 100° C. for 9 hours. The reaction mixture was cooled to 0° C. and acidified with 2 N aq. HCl until pH=2-3. A precipitated solid was collected by filtration, washed with water followed by EtOAc and dried under vacuum to afford 5-oxo-4,5-dihydropyrazolo[1,5-a]pyrimidine-3-carbonitrile (1.33 g, 90%) as a white solid. $^1$H-NMR (DMSO-$d_6$, Varian, 400 MHz): δ 6.24 (1H, d, J=8.0 Hz), 8.31 (1H, s), 8.63 (1H, d, J=7.6 Hz), 13.24 (1H, br. s).

Step B: 5-chloropyrazolo[1,5-a]pyrimidine-3-carbonitrile

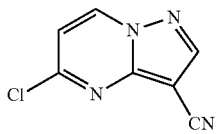 [SMILES: N#Cc1cnn2ccc(Cl)nc12]

A mixture of 5-oxo-4,5-dihydropyrazolo[1,5-a]pyrimidine-3-carbonitrile (1.33 g, 8.31 mmol) and $POCl_3$ (7.74 mL, 83 mmol) was heated at 150° C. for 3 hours and cooled to room temperature. After concentration in vacuo, the residue was purified by column chromatography on $SiO_2$ (Hex:EtOAc=2:1) to afford 5-chloropyrazolo[1,5-a]pyrimidine-3-carbonitrile (343 mg, 23%) as a white solid. $^1$H-NMR ($CDCl_3$, Varian, 400 MHz): δ 7.09 (1H, d, J=7.6 Hz), 8.39 (1H, s), 8.68 (1H, d, J=7.2 Hz).

Step C: 5-(2-(2,5-difluorophenyl)pyrrolidin-1-yl)pyrazolo[1,5-a]pyrimidine-3-carbonitrile

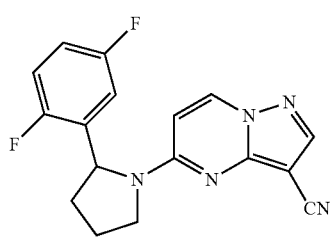 [SMILES: N#Cc1cnn2ccc(N3CCCC3c3cc(F)ccc3F)nc12]

A mixture of 5-chloropyrazolo[1,5-a]pyrimidine-3-carbonitrile (343 mg, 1.92 mmol) and 2-(2,5-difluorophenyl)pyrrolidine (Intermediate 2, 343 mg, 1.87 mmol) in DMSO (10 mL) was heated at 180° C. for 1 hour and cooled to room temperature. The reaction mixture was diluted with water and extracted with EtOAc twice. The combined organic layers were washed with brine, dried over $Na_2SO_4$, filtered and concentrated in vacuo. The residue was purified by column chromatography on SiO₂ (Hex:EtOAc=2:1 to 1:1) to afford 5-(2-(2,5-difluorophenyl)pyrrolidin-1-yl)pyrazolo[1,5-a]pyrimidine-3-carbonitrile (611 mg, 98%) as a ivory solid. ¹H-NMR (CDCl₃, Varian, 400 MHz): δ 2.05-2.11 (3H, m), 2.47-2.55 (1H, m), 3.67-4.10 (2H, m), 5.20 (0.7H, s), 5.65 (0.3H, s), 5.96 (0.7H, s), 6.43 (0.3H, s), 6.69-6.73 (1H, m), 6.96-7.09 (2H, m), 8.01-8.31 (3H, m).

Step D: 5-(2-(2,5-difluorophenyl)pyrrolidin-1-yl)pyrazolo[1,5-a]pyrimidine-3-carboxamide

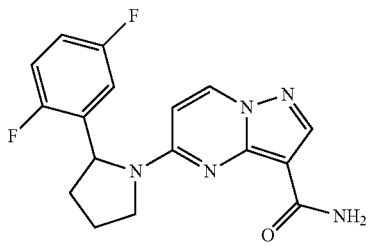 [SMILES: NC(=O)c1cnn2ccc(N3CCCC3c3cc(F)ccc3F)nc12]

A mixture of of 5-(2-(2,5-difluorophenyl)pyrrolidin-1-yl)pyrazolo[1,5-a]pyrimidine-3-carbonitrile (230 mg, 0.707 mmol) and conc. H₂SO₄ (1.13 mL, 21.2 mmol) was stirred at 0° C. for 5 hours. After addition of ice-water, the mixture was extracted with EtOAc twice. The combined organic layers were washed with brine, dried over Na₂SO₄, filtered and concentrated in vacuo to afford 5-(2-(2,5-difluorophenyl)pyrrolidin-1-yl)pyrazolo[1,5-a]pyrimidine-3-carboxamide (172 mg, 71%) as a white solid. ¹H-NMR (CDCl₃, Varian, 400 MHz): δ 2.05-1.11 (2H, m), 2.47-2.55 (1H, m), 3.67-4.10 (2H, m), 5.12-5.32 (1H, m), 5.52 (0.6H, s), 5.74 (0.4H, s), 5.90 (0.4H, s), 6.32 (0.6H, s), 6.69-6.74 (1H, m), 6.96-7.09 (2H, m), 7.80 (0.5H, s), 8.20 (0.5H, s), 8.25-8.40 (1H, m). * Two protons from NH₂NH₂ were not observed.

Step E: (Z)-5-(2-(2,5-difluorophenyl)pyrrolidin-1-yl)-N-(1-(dimethylamino)ethylidene)-pyrazolo[1,5-a]pyrimidine-3-carboxamide

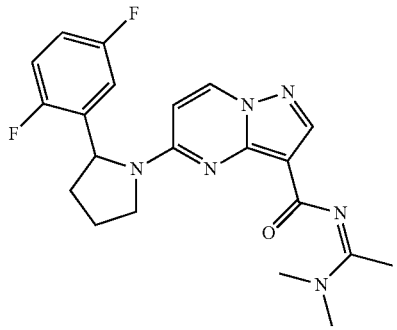 [SMILES: C/C(=N/C(=O)c1cnn2ccc(N3CCCC3c3cc(F)ccc3F)nc12)N(C)C]

A mixture of 5-(2-(2,5-difluorophenyl)pyrrolidin-1-yl)pyrazolo[1,5-a]pyrimidine-3-carboxamide (100 mg, 0.291 mmol) and 1,1-dimethoxy-N,N-dimethylethanamine (1.06 mL, 7.28 mmol) was heated 120° C. for 2 hours in a sealed tube. The reaction mixture was cooled to room temperature and concentrated in vacuo to afford crude (Z)-5-(2-(2,5-difluorophenyl)pyrrolidin-1-yl)-N-(1-(dimethylamino)eth-ylidene)pyrazolo[1,5-a]pyrimidine-3-carboxamide (160 mg, 99%), which was used for the next reaction without further purification.

Step F: 5-(2-(2,5-difluorophenyl)pyrrolidin-1-yl)-3-(5-methyl-1H-1,2,4-triazol-3-yl)pyrazolo[1,5-a]pyrimidine

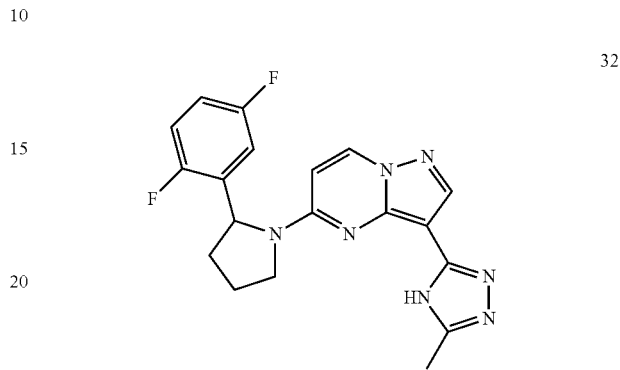

32

To a solution of the crude (Z)-5-(2-(2,5-difluorophenyl)pyrrolidin-1-yl)-N-(1-(dimethylamino)ethylidene)pyrazolo[1,5-a]pyrimidine-3-carboxamide (160 mg, 0.291 mmol) in AcOH (1.0 mL) was added hydrazine hydrate (22.0 mg, 0.437 mmol). The reaction mixture was heated at 90° C. for 2 hours and then concentrated in vacuo. The residue was treated with water, while a solid was precipitated. The solid was collected by filtration, washed with water and hexanes, and dried under vacuum to afford 5-(2-(2,5-difluorophenyl)pyrrolidin-1-yl)-3-(5-methyl-1H-1,2,4-triazol-3-yl)pyrazolo[1,5-a]pyrimidine (58.0 mg, 52%) as a white solid. ¹H-NMR (MeOH-d₄, Varian, 400 MHz): δ 1.92-2.26 (3H, m), 2.34 (3H, m), 2.44-2.60 (2H, m), 3.67-4.22 (2H, m), 5.17 (0.4H, s), 5.68 (0.6H, s), 6.11 (0.4H, s), 6.65 (0.6H, s), 6.80-7.20 (2H, m), 7.20-7.43 (1H, m), 8.20-8.60 (2H, m). MS: 382.3 [MH⁺].

Example 44: Preparation of Intermediate Compound 13

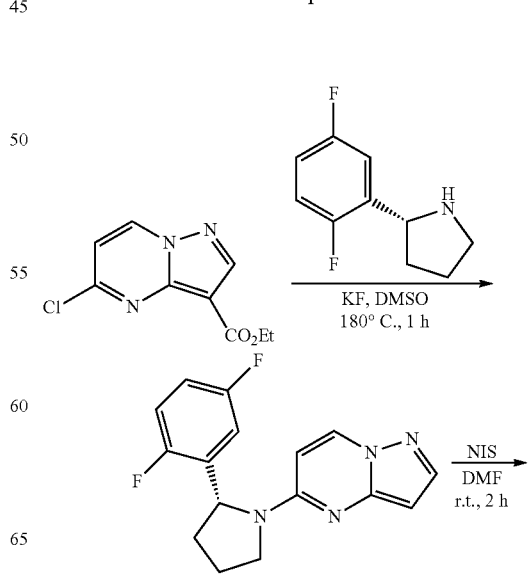

-continued

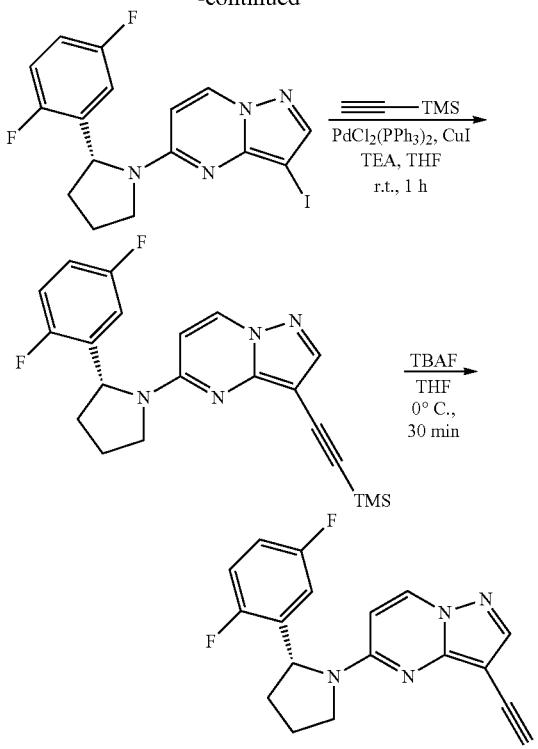

Intermediate Compound 13: tert-butyl 3-(4-(5-((R)-2-(2,5-difluorophenyl)pyrrolidin-1-yl)pyrazolo[1,5-a]pyrimidin-3-yl)-1H-1,2,3-triazol-1-yl)piperidine-1-carboxylate

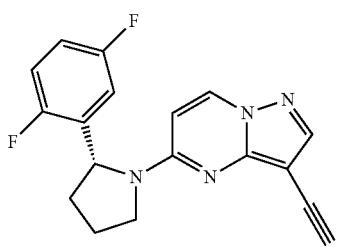 [SMILES: C#Cc1cnn2ccc(N3CCC[C@@H]3c3cc(F)ccc3F)nc12]

Step A: (R)-5-(2-(2,5-difluorophenyl)pyrrolidin-1-yl)pyrazolo[1,5-a]pyrimidine

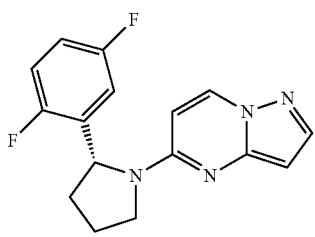 [SMILES: Fc1ccc(F)c([C@H]2CCCN2c2ccn3nccc3n2)c1]

A mixture of 5-chloropyrazolo[1,5-a]pyrimidine (1.18 g, 7.68 mmol), (R)-2-(2,5-difluorophenyl)pyrrolidine (1.51 g, 8.22 mmol) and KF (2.32 g, 39.1 mmol) in DMSO (26 mL) was heated at 180° C. for 2 hours. The reaction mixture was cooled to room temperature and poured into water. The mixture was stirred for additional 30 min at room temperature. A precipitated solid was collected by filtration and dried under vacuum to afford (R)-5-(2-(2,5-difluorophenyl)pyrrolidin-1-yl)pyrazolo[1,5-a]pyrimidine (1.70 g, 74%) as a yellow solid. ¹H-NMR (DMSO-d₆, Varian, 400 MHz): δ 1.88-2.06 (3H, m), 2.33-2.45 (1H, m), 3.56-3.70 (1H, m), 3.90-4.00 (1H, m), 5.38 (1H, s), 5.98 (1H, s), 6.10-6.50 (1H, m), 6.85-6.91 (1H, m), 7.10-7.15 (1H, m), 7.26-7.32 (1H, m), 7.81 (1H, d, J=1.6 Hz), 8.60 (1H, s).

Step B: (R)-5-(2-(2,5-difluorophenyl)pyrrolidin-1-yl)-3-iodopyrazolo[1,5-a]pyrimidine

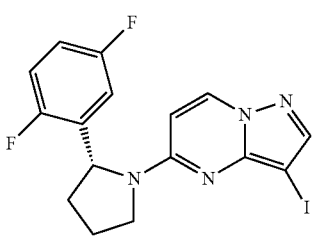 [SMILES: Fc1ccc(F)c([C@H]2CCCN2c2ccn3ncc(I)c3n2)c1]

To a solution of (R)-5-(2-(2,5-difluorophenyl)pyrrolidin-1-yl)pyrazolo[1,5-a]pyrimidine (975 mg, 3.25 mmol) in DMF (6.5 mL) was added portionwise NIS (804 mg, 3.57 mmol) at room temperature. The reaction mixture was stirred for 2 hours and poured into water. The mixture was stirred for further 30 min. A precipitated solid was collected by filtration and dried under vacuum to afford (R)-5-(2-(2,5-difluorophenyl)pyrrolidin-1-yl)-3-iodopyrazolo[1,5-a]pyrimidine (1.19 g, 86%) as a pale yellow solid. ¹H-NMR (DMSO-d₆, Varian, 400 MHz): δ 1.80-2.15 (3H, m), 2.38-2.50 (1H, m), 3.50-3.80 (1H, m), 3.95-3.99 (1H, m), 5.21-5.51 (1H, m), 5.99 and 6.53 (1H, s+s), 6.97 (1H, s), 7.11-7.26 (1H, m), 7.95 (1H, m), 8.44-8.64 (1H, m).

Step C: (R)-5-(2-(2,5-difluorophenyl)pyrrolidin-1-yl)-3-((trimethylsilyl)ethynyl)pyrazolo-[1,5-a]pyrimidine

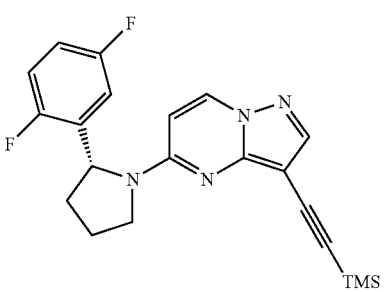 [SMILES: C[Si](C)(C)C#Cc1cnn2ccc(N3CCC[C@@H]3c3cc(F)ccc3F)nc12]

To a solution of (R)-5-(2-(2,5-difluorophenyl)pyrrolidin-1-yl)-3-iodopyrazolo[1,5-a]-pyrimidine (1.19 g, 2.79 mmol) in THF (10 mL) and TEA (10 mL) were added CuI (53.0 mg, 0.279 mmol), PdCl₂(PPh₃)₂ (196 mg, 0.279 mmol) and ethynyltrimethylsilane (0.596 mL, 4.19 mmol). The reaction mixture was stirred at room temperature for 1 hour. After filtration through on Celite pad while washing with EtOAc, the filtrate was concentrated in vacuo. The residue was diluted with EtOAc, washed with brine, dried over Na₂SO₄, filtered and concentrated in vacuo. The residue was purified by column chromatography on SiO$_2$ (Hex:EtOAc=2:1 to 1:1) to afford (R)-5-(2-(2,5-difluorophenyl)pyrrolidin-1-yl)-3-((trimethylsilyl)ethynyl)pyrazolo[1,5-a]pyrimidine (832 mg, 75%) as a viscous yellow oil. $^1$H-NMR (CDCl$_3$, Varian, 400 MHz): δ 0.260 (9H, s), 2.03-2.20 (3H, m), 2.49 (1H, br. s), 3.63-4.15 (2H, m), 5.17 and 6.25 (1H, br. s+br. s), 5.83 (1H, br. s), 6.73-6.77 (1H, m), 6.91 (1H, br. s), 7.04 (1H, br. s), 7.93 (1H, s), 8.11 (1H, br. s).

Step D: (R)-5-(2-(2,5-difluorophenyl)pyrrolidin-1-yl)-3-ethynylpyrazolo[1,5-a]pyrimidine

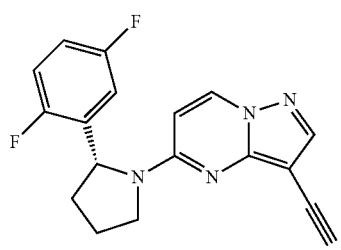 [SMILES: C#Cc1cnn2ccc(N3CCC[C@@H]3c3cc(F)ccc3F)nc12]

To a solution of (R)-5-(2-(2,5-difluorophenyl)pyrrolidin-1-yl)-3-((trimethylsilyl)ethynyl)-pyrazolo[1,5-a]pyrimidine (832 mg, 2.10 mmol) in THF (10 mL) was added TBAF (1 M solution in THF, 2.52 mL, 2.52 mmol) at 0° C. The reaction mixture was stirred at 0° C. for 30 min. After quenched with saturated aq. NH$_4$Cl, the mixture was extracted with EtOAc twice. The combined organic layers were washed with brined, dried over Na$_2$SO$_4$, filtered and concentrated in vacuo. The residue was purified by column chromatography on SiO$_2$ (Hex:EtOAc=3:2 to 1:1) to afford (R)-5-(2-(2,5-difluorophenyl)pyrrolidin-1-yl)-3-ethynylpyrazolo[1,5-a]pyrimidine (659 mg, 97%) as a viscous yellow oil. $^1$H-NMR (CDCl$_3$, Varian, 400 MHz): δ 1.98-2.18 (3H, m), 2.50 (1H, br. s), 3.24 (1H, s), 3.93 (1H, br. s), 4.06 (1H, br. s), 5.19 (1H, br. s), 5.87 (1H, br. s), 6.75 (1H, br. s), 6.92 (1H, br. s), 7.05 (1H, br. s), 7.96 (1H, s), 8.14 (1H, br. s).

Example 45: Preparation of Chemical Compound 33

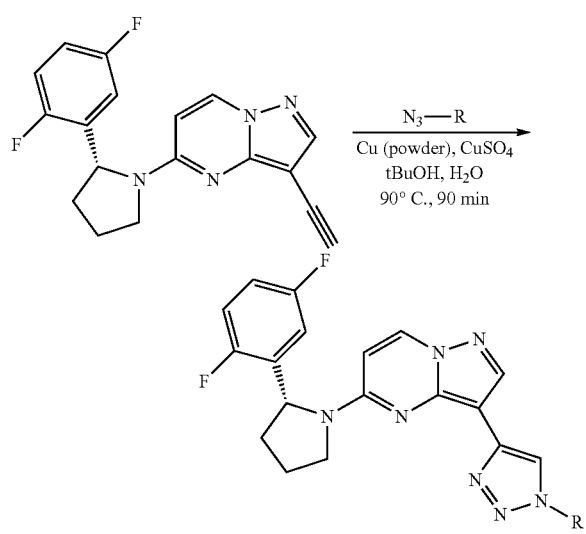

Chemical Compound 33: (R)-5-(2-(2,5-difluorophenyl)pyrrolidin-1-yl)-3-(1-(piperidin-4-yl)-1H-1,2,3-triazol-4-yl)pyrazolo[1,5-a]pyrimidine

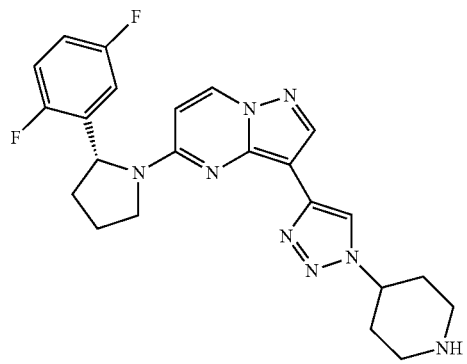

Step A: tert-butyl 4-hydroxypiperidine-1-carboxylate

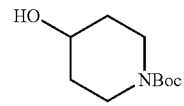

To a solution of tert-butyl 4-oxopiperidine-1-carboxylate (1.00 g, 5.02 mmol) in MeOH (16 mL) was added NaBH$_4$ (285 mg, 7.53 mmol) at 0° C. The reaction mixture was stirred at 0° C. for 1 hour. After concentration in vacuo, the residue was partitioned between EtOAc and water. The separated aqueous layer was extracted with EtOAc. The combined organic layers were dried over Na$_2$SO$_4$, filtered and concentrated in vacuo to afford tert-butyl 4-hydroxypiperidine-1-carboxylate (1.01 g, 100%) as a viscous pale yellow oil, which was used for the next reaction without further purification. $^1$H-NMR (CDCl$_3$, Varian, 400 MHz): δ 1.46 (9H, s), 1.48-1.50 (2H, m), 1.84-1.87 (2H, m), 2.99-3.06 (2H, m), 3.81-3.87 (3H, m). * OH was not observed.

Step B: tert-butyl 4-(methylsulfonyloxy)piperidine-1-carboxylate

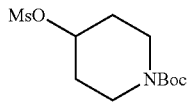 [SMILES: CC(C)(C)OC(=O)N1CCC(OS(C)(=O)=O)CC1]

To a solution of tert-butyl 4-hydroxypiperidine-1-carboxylate (1.01 g, 5.02 mmol) in DCM (16 mL) was added TEA (0.909 mL, 6.52 mmol) and DMAP (61.0 mg, 0.502 mmol) followed by MsCl (0.469 mL, 6.02 mmol) at 0° C. The reaction mixture was stirred at room temperature for 3 hours. The reaction mixture was diluted with DCM, washed with water, 2 N aq. HCl, saturated aq. NaHCO$_3$, and brine successively, dried over Na$_2$SO$_4$, filtered and concentrated in vacuo to afford tert-butyl 4-(methylsulfonyloxy)piperidine-1-carboxylate (1.40 g, 100%) as a white solid, which was used for the next reaction without further purification. ¹H-NMR (CDCl₃, Varian, 400 MHz): δ 1.46 (9H, s), 1.78-1.86 (2H, m), 1.94-1.99 (2H, m), 3.04 (3H, s), 3.27-3.34 (2H, m), 3.68-3.72 (2H, m), 4.86-4.91 (1H, m).

Step C: tert-butyl 4-azidopiperidine-1-carboxylate

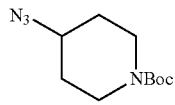

To a solution of tert-butyl 4-(methylsulfonyloxy)piperidine-1-carboxylate (1.40 g, 5.02 mmol) in DMF (25 mL) was added sodium azide (979 mg, 15.0 mmol). The reaction mixture was heated at 100° C. for 12 hours with stirring, while a white solid was formed. After concentration in vacuo, the residue was partitioned between EtOAc and water. The aqueous layer was extracted with EtOAc. The combined organic layers were washed with brine, dried over Na₂SO₄, filtered and concentrated in vacuo. The residue was purified by column chromatography on SiO₂ (Hex:EtOAc=5:1) to afford tert-butyl 4-azidopiperidine-1-carboxylate (948 mg, 83%) as a colorless oil. ¹H-NMR (CDCl₃, Varian, 400 MHz): δ 1.46 (9H, s), 1.53-1.57 (2H, m), 1.85-1.88 (2H, m), 3.05-3.12 (2H, m), 3.54-3.60 (1H, m), 3.81-3.84 (1H, m).

Step D: (R)-tert-butyl 4-(4-(5-(2-(2,5-difluorophenyl)pyrrolidin-1-yl)pyrazolo[1,5-a]pyrimidin-3-yl)-1H-1,2,3-triazol-1-yl)piperidine-1-carboxylate

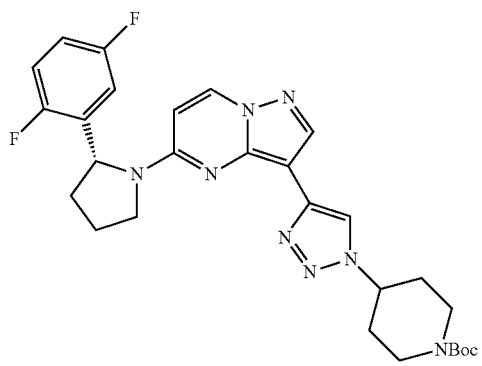 [SMILES: CC(C)(C)OC(=O)N1CCC(n2cc(-c3cnn4ccc(N5CCC[C@@H]5c5cc(F)ccc5F)nc34)nn2)CC1]

To a solution of (R)-5-(2-(2,5-difluorophenyl)pyrrolidin-1-yl)-3-ethynylpyrazolo[1,5-a]pyrimidine (Intermediate 13, 144 mg, 0.444 mmol) and tert-butyl 4-azidopiperidine-1-carboxylate (111 mg, 0.488 mmol) in tBuOH (2.0 mL) was added copper powder (23.0 mg, 0.355 mmol) followed by water (1.0 mL) and 1 M aq. solution of copper sulfate (0.089 mL, 0.089 mmol). The reaction mixture was heated at 90° C. for 90 min. The reaction mixture was cooled to room temperature and diluted with EtOAc. After addition of conc. NH₄OH (2.0 mL) followed by water (2.0 mL), the mixture was vigorously stirred for 30 min and extracted with EtOAc twice. The combined organic layers were washed with brine, dried over Na₂SO4, filtered and concentrated in vacuo. The residue was purified by column chromatography on SiO₂ (EtOAc only to DCM:MeOH=30:1) to afford (R)-tert-butyl-4-(4-(5-(2-(2,5-difluorophenyl)pyrrolidin-1-yl)pyrazolo[1,5-a]pyrimidin-3-yl)-1H-1,2,3-triazol-1-yl)piperidine-1-carboxylate (177 mg, 72%) as a yellow foam. ¹H-NMR (CDCl₃, Varian, 400 MHz): δ 1.49 (9H, s), 1.83-2.22 (7H, m), 2.48 (1H, br. s), 2.97 (2H, s), 3.66 (1H, br. s), 3.91 (1H, br. s), 4.35 (2H, br. s), 4.67 (1H, br. s), 5.70 (1H, br. s), 6.34 (1H, br. s), 6.75 (1H, br. s), 6.91 (1H, br. s), 7.13 (1H, br. s), 7.52 (1H, s), 8.35 (1H, br. s), 8.48 (1H, s).

Step E: (R)-5-(2-(2,5-difluorophenyl)pyrrolidin-1-yl)-3-(1-(piperidin-4-yl)-1H-1,2,3-triazol-4-yl)pyrazolo[1,5-a]pyrimidine

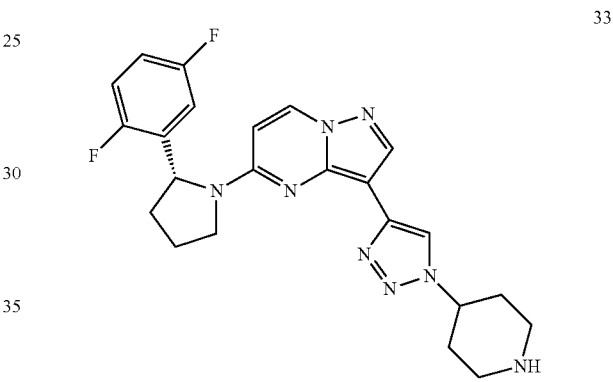

33

To a solution of (R)-tert-butyl-4-(4-(5-(2-(2,5-difluorophenyl)pyrrolidin-1-yl)pyrazolo[1,5-a]pyrimidin-3-yl)-1H-1,2,3-triazol-11-yl)piperidine-1-carboxylate (177 mg, 0.321 mmol) in DCM (1.6 mL) was added TFA (0.867 mL, 11.2 mmol) at 0° C. The reaction mixture was stirred at room temperature for 2 hours. After concentration in vacuo, the residue was diluted with DCM, washed with saturated aq. NaHCO₃ and brined, dried over Na₂SO₄, filtered and concentrated in vacuo. The residue was purified by column chromatography on SiO₂ (DCM:MeOH=10:1 to 3:1 to 2:1) to afford (R)-5-(2-(2,5-difluorophenyl)pyrrolidin-1-yl)-3-(1-(piperidin-4-yl)-1H-1,2,3-triazol-4-yl)pyrazolo[1,5-a]pyrimidine (100 mg, 69%) as a yellow foam. ¹H-NMR (CDCl₃, Varian, 400 MHz): δ 1.83-2.30 (8H, m), 2.50 (1H, br. s), 2.85 (2H, t, J=11.2 Hz), 3.30-3.33 (2H, m), 3.69 (1H, br. s), 3.93 (1H, br. s), 4.58 (1H, br. s), 5.24 and 5.68 (1H, br. s+br. s), 5.87 and 6.30 (1H, br. s+br. s), 6.75 (1H, br. s), 6.90 (1H, br. s), 7.12 (1H, br. s), 7.57 (1H, s), 8.30 (1H, br. s), 8.48 (1H, s). MS: 451.1 [MH⁺].

Example 46: Preparation of Chemical Compound 34: 5-((R)-2-(2,5-difluorophenyl)pyrrolidin-1-yl)-3-(1-(piperidin-3-yl)-1H-1,2,3-triazol-4-yl)pyrazolo[1,5-a]pyrimidine

34

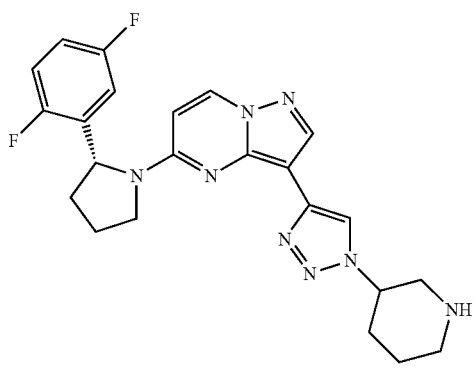

Step A: tert-butyl 3-(methylsulfonyloxy)piperidine-1-carboxylate

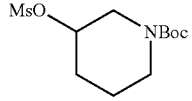

To a solution of tert-butyl 3-hydroxypiperidine-1-carboxylate (1.00 g, 4.97 mmol) in DCM (16 mL) was added TEA (0.895 mL, 6.46 mmol) followed by MsCl (0.465 mL, 5.96 mmol) at 0° C. The reaction mixture was stirred at room temperature for 2 hours. The reaction mixture was diluted with DCM, washed with water, 2 N aq. HCl, saturated aq. NaHCO₃, and brine successively, dried over Na₂SO₄, filtered and concentrated in vacuo to afford tert-butyl 3-(methylsulfonyloxy)piperidine-1-carboxylate (1.39 g, 100%) as a colorless oil, which was used for the next reaction without further purification. ¹H-NMR (CDCl₃, Varian, 400 MHz): δ 1.47 (9H, s), 1.55 (1H, br. s), 1.78-2.01 (3H, m), 3.06 (3H, s), 3.28-3.38 (1H, m), 3.42-3.48 (1H, m), 3.54-3.68 (2H, m), 4.72 (1H, br. s).

Step B: tert-butyl 3-azidopiperidine-1-carboxylate

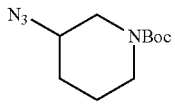

To a solution of tert-butyl 3-(methylsulfonyloxy)piperidine-1-carboxylate (1.39 g, 4.98 mmol) in DMF (24 mL) was added sodium azide (970 mg, 14.9 mmol). The reaction mixture was heated at 100° C. for 4 hours with stirring, while a white solid was formed. After concentration in vacuo, the residue was partitioned between EtOAc and water. The aqueous layer was extracted with EtOAc. The combined organic layers were washed with brine, dried over Na₂SO₄, filtered and concentrated in vacuo. The residue was purified by column chromatography on SiO₂ (Hex: EtOAc=20:1 to 10:1 to 5:1) to afford tert-butyl 3-azidopiperidine-1-carboxylate (840 mg, 74%) as a colorless oil. ¹H-NMR (CDCl₃, Varian, 400 MHz): δ 1.47 (9H, s), 1.49-1.62 (2H, m), 1.77 (1H, br. s), 1.96 (1H, br. s), 2.90-3.30 (2H, m), 3.44-3.50 (1H, m), 3.52-3.90 (2H, m).

Step C: tert-butyl 3-(4-(5-((R)-2-(2,5-difluorophenyl)pyrrolidin-1-yl)pyrazolo[1,5-a]pyrimidin-3-yl)-1H-1,2,3-triazol-1-yl)piperidine-1-carboxylate

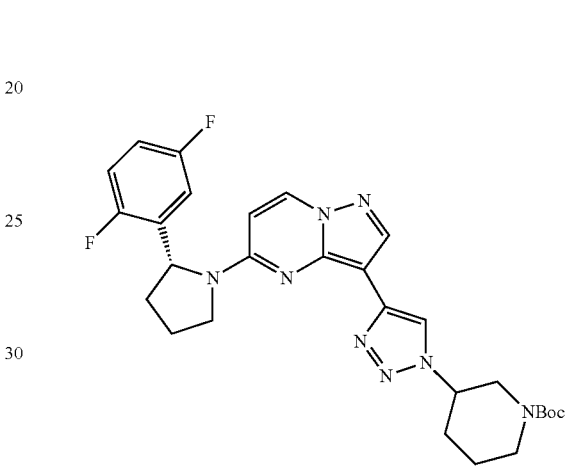

To a solution of (R)-5-(2-(2,5-difluorophenyl)pyrrolidin-1-yl)-3-ethynylpyrazolo[1,5-a]pyrimidine (Intermediate 13, 92.0 mg, 0.284 mmol) and tert-butyl 3-azidopiperidine-1-carboxylate (71.0 mg, 0.312 mmol) in tBuOH (1.4 mL) were added copper powder (14.0 mg, 0.227 mmol) followed by water (1.0 mL) and 1 M aq. solution of copper sulfate (0.057 mL, 0.057 mmol). The reaction mixture was heated at 90° C. for 90 min. The reaction mixture was cooled to room temperature and then diluted with EtOAc. After addition of conc. NH₄OH (2.0 mL) followed by water (2.0 mL), the mixture was vigorously stirred for 30 min and extracted with EtOAc twice. The combined organic layers were washed with brine, dried over Na₂SO₄, filtered and concentrated in vacuo. The residue was purified by column chromatography on SiO₂ (EtOAc only to DCM:MeOH=30:1) to afford tert-butyl 3-(4-(5-((R)-2-(2,5-difluorophenyl)pyrrolidin-1-yl)pyrazolo[1,5-a]pyrimidin-3-yl)-1H-1,2,3-triazol-1-yl)piperidine-1-carboxylate (123 mg, 79%) as a yellow oil. ¹H-NMR (CDCl₃, Varian, 400 MHz): δ 1.48 (9H, s), 1.63-1.76 (2H, m), 1.90-1.94 (1H, m), 2.04 (1H, br. s), 2.16 (2H, br. s), 2.29 (1H, br. s), 2.40-2.58 (1H, m), 2.80-3.50 (2H, m), 3.68 (1H, br. s), 3.92 (1H, br. s), 4.18 (1H, br. s), 4.30-4.60 (2H, m), 5.23 and 5.66 (1H, br. s+br. s), 5.86 and 6.31 (1H, br. s+br. s), 6.75-6.77 (1H, m), 6.91 (1H, br. s), 7.04 (1H, br. s), 7.56 (1H, s), 8.31 (1H, br. s), 8.47 (1H, s).

Step D: 5-((R)-2-(2,5-difluorophenyl)pyrrolidin-1-yl)-3-(1-(piperidin-3-yl)-1H-1,2,3-triazol-4-yl)pyrazolo[1,5-a]pyrimidine

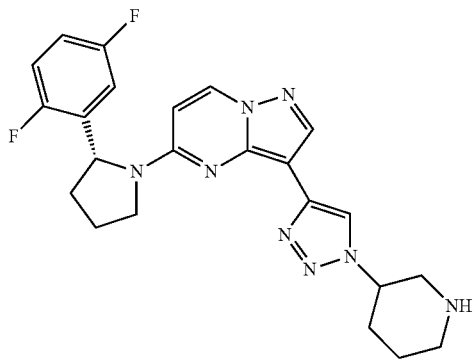

To a solution of tert-butyl 3-(4-(5-((R)-2-(2,5-difluorophenyl)pyrrolidin-1-yl)pyrazolo[1,5-a]pyrimidin-3-yl)-1H-1,2,3-triazol-1-yl)piperidine-1-carboxylate (123 mg, 0.223 mmol) in DCM (1.1 mL) was added TFA (0.602 mL, 7.82 mmol) at 0° C. The reaction mixture was stirred at room temperature for 2 hours. After concentration in vacuo, the residue was diluted with DCM, washed with saturated aq. NaHCO₃ and brined, dried over Na₂SO₄, filtered and concentrated in vacuo. The residue was purified by column chromatography on SiO₂ (DCM:MeOH=10:1 to 3:1) to afford 5-((R)-2-(2,5-difluorophenyl)pyrrolidin-1-yl)-3-(1-(piperidin-3-yl)-1H-1,2,3-triazol-4-yl)pyrazolo[1,5-a]pyrimidine (70.0 mg, 69%) as a yellow foam. ¹H-NMR (CDCl₃, Varian, 400 MHz): δ 1.92-1.95 (1H, m), 1.89-2.14 (8H, m), 2.28 (1H, br. s), 2.49 (1H, br. s), 2.77 (1H, t, J=10.8 Hz) 2.85-3.18 (2H, m), 3.40 (1H, br. s), 3.66 (1H, br. s), 3.91 (1H, br. s), 4.50 (1H, br. s), 5.30 and 5.67 (1H, br. s+br. s), 5.85 and 6.29 (1H, br. s+br. s), 6.75 (1H, s), 6.90 (1H, s), 7.00-7.10 (1H, m), 7.57 (1H, s), 8.31 (1H, br. s), 8.47 (1H, s). MS: 451.1 [MH⁺].

Example 47: Preparation of Chemical Compound 35: 5-((R)-2-(2,5-difluorophenyl)pyrrolidin-1-yl)-3-(1-(pyrrolidin-3-yl)-1H-1,2,3-triazol-4-yl)pyrazolo[1,5-a]pyrimidine

Step A: tert-butyl 3-(methylsulfonyloxy)pyrrolidine-1-carboxylate

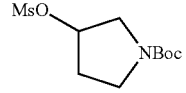

To a solution of tert-butyl 3-hydroxypyrrolidine-1-carboxylate (1.00 g, 5.34 mmol) in DCM (17 mL) was added TEA (0.962 mL, 6.94 mmol) followed by MsCl (0.499 mL, 6.41 mmol) at 0° C. The reaction mixture was stirred at room temperature for 2 hours. The reaction mixture was diluted with DCM, washed with water, 2 N aq. HCl, saturated aq. NaHCO₃, and brine successively, dried over Na₂SO₄, filtered and concentrated in vacuo to afford tert-butyl 3-(methylsulfonyloxy)pyrrolidine-1-carboxylate (1.42 g, 100%) as a colorless oil, which was used for the next reaction without further purification. ¹H-NMR (CDCl₃, Varian, 400 MHz): δ 1.47 (9H, s), 2.06-2.20 (1H, m), 2.21-2.36 (1H, m), 3.05 (3H, s), 3.44-3.54 (1H, m), 3.54-3.72 (3H, m), 5.27 (1H, br. s).

Step B: tert-butyl 3-azidopyrrolidine-1-carboxylate

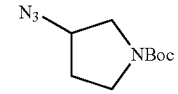

To a solution of tert-butyl 3-(methylsulfonyloxy)pyrrolidine-1-carboxylate (1.42 g, 5.35 mmol) in DMF (26 mL) was added sodium azide (1.04 g, 16.0 mmol). The reaction mixture was heated at 100° C. for 4 hours with stirring, while a white solid was formed. After concentration in vacuo, the residue was partitioned between EtOAc and water. The aqueous layer was extracted with EtOAc. The combined organic layers were washed with brine, dried over Na₂SO₄, filtered and concentrated in vacuo. The residue was purified by column chromatography on SiO₂ (Hex:EtOAc=10:1 to 5:1) to afford tert-butyl 3-azidopyrrolidine-1-carboxylate (1.07 g, 94%) as a colorless oil. ¹H-NMR (CDCl₃, Varian, 400 MHz): δ 1.47 (9H, s), 2.02-2.08 (2H, m), 3.35-3.54 (4H, m), 4.14-4.16 (1H, m).

Step C: tert-butyl 3-(4-(5-((R)-2-(2,5-difluorophenyl)pyrrolidin-1-yl)pyrazolo[1,5-a]pyrimidin-3-yl)-1H-1,2,3-triazol-1-yl)pyrrolidine-1-carboxylate

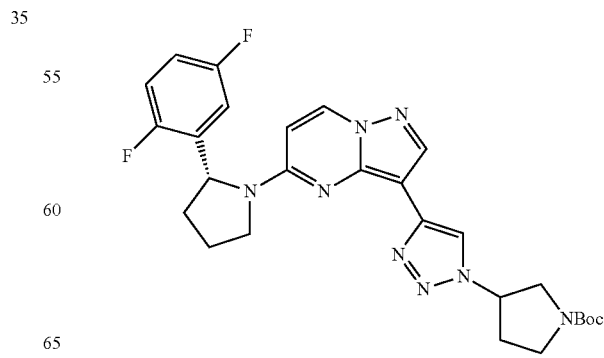

To a solution of (R)-5-(2-(2,5-difluorophenyl)pyrrolidin-1-yl)-3-ethynylpyrazolo[1,5-a]pyrimidine (Intermediate 13, 92.0 mg, 0.284 mmol) and tert-butyl 3-azidopyrrolidine-1-carboxylate (66.0 mg, 0.312 mmol) in tBuOH (1.4 mL) were added copper powder (14.0 mg, 0.227 mmol) followed by water (1.0 mL) and 1 M aq. solution of copper sulfate (0.057 mL, 0.057 mmol). The reaction mixture was heated at 90° C. for 90 min. The reaction mixture was cooled to room temperature and then diluted with EtOAc. After addition of conc. NH₄OH (2.0 mL) followed by water (2.0 mL), the mixture was vigorously stirred for 30 min and extracted with EtOAc twice. The combined organic layers were washed with brine, dried over Na₂SO₄, filtered and concentrated in vacuo. The residue was purified by column chromatography on SiO₂ (EtOAc only to DCM:MeOH=30:1) to afford tert-butyl 3-(4-(5-((R)-2-(2,5-difluorophenyl)pyrrolidin-1-yl)pyrazolo[1,5-a]pyrimidin-3-yl)-1H-1,2,3-triazol-1-yl)pyrrolidine-1-carboxylate (127 mg, 83%) as a yellow foam. ¹H-NMR (CDCl₃, Varian, 400 MHz): δ 1.50 (9H, s), 1.98-2.20 (3H, m), 2.22-2.63 (3H, m), 3.50-3.83 (4H, m), 3.83-4.20 (2H, m), 5.15 (1H, br. s), 5.30 and 5.66 (1H, br. s+br. s), 5.84 and 6.31 (1H, br. s+br. s), 6.75 (1H, br. s), 6.91 (1H, br. s), 7.00-7.18 (1H, m), 7.52 (1H, s), 8.32 (1H, br. s), 8.48 (1H, s).

Step D: 5-((R)-2-(2,5-difluorophenyl)pyrrolidin-1-yl)-3-(1-(pyrrolidin-3-yl)-1H-1,2,3-triazol-4-yl)pyrazolo[1,5-a]pyrimidine To a solution of tert-butyl 3-(4-(5-((R)-2-(2,5-difluorophenyl)pyrrolidin-1-yl)pyrazolo[1,5-a]pyrimidin-3-yl)-1H-1,2,3-triazol-1-yl)pyrrolidine-1-carboxylate (127 mg, 0.237 mmol) in DCM (1.2 mL) was added TFA (0.638 mL, 8.28 mmol) at 0° C. The reaction mixture was stirred at room temperature for 2 hours. After concentration in vacuo, the residue was diluted with DCM, washed with saturated aq. NaHCO₃ and brined, dried over Na₂SO₄, filtered and concentrated in vacuo. The residue was purified by column chromatography on SiO₂ (DCM:MeOH=10:1 to 3:1 to 2:1) to afford 5-((R)-2-(2,5-difluorophenyl)pyrrolidin-1-yl)-3-(1-(pyrrolidin-3-yl)-1H-1,2,3-triazol-4-yl)pyrazolo[1,5-a]pyrimidine (78.0 mg, 76%) as a yellow foam. ¹H-NMR (CDCl₃, Varian, 400 MHz): δ 2.00-2.20 (4H, m), 2.26-2.60 (3H, m), 3.11 (1H, br. s), 3.24-3.46 (3H, m), 3.68 (1H, br. s), 3.91 (1H, br. s), 5.02 (1H, br. s), 5.39 and 5.64 (1H, br. s+br. s), 5.84 and 6.30 (1H, br. s+br. s), 6.75 (1H, s), 6.90 (1H, br. s), 7.06 (1H, br. s), 7.56 (1H, s), 8.31 (1H, br. s), 8.46 (1H, s).

Example 48: Preparation of Chemical Compound 36: (R)-5-(2-(2,5-difluorophenyl)pyrrolidin-1-yl)-3-(1-(tetrahydro-2H-pyran-4-yl)-1H-1,2,3-triazol-4-yl)pyrazolo[1,5-a]pyrimidine Step A: tetrahydro-2H-pyran-4-yl methanesulfonate To a solution of tetrahydro-2H-pyran-4-ol (500 mg, 4.90 mmol) in DCM (16 mL) was added TEA (0.882 mL, 6.36 mmol) followed by MsCl (0.458 mL, 5.87 mmol) at 0° C. The reaction mixture was stirred at room temperature for 2 hours. The reaction mixture was diluted with DCM, washed with water, 2 N aq. HCl, saturated aq. NaHCO₃, and brine successively, dried over Na₂SO₄, filtered and concentrated in vacuo to afford tetrahydro-2H-pyran-4-yl methanesulfonate (882 mg, 100%) as a colorless oil, which was used for the next reaction without further purification. ¹H-NMR (CDCl₃, Varian, 400 MHz): δ 1.84-1.92 (2H, m), 2.03-2.07 (2H, m), 3.04 (3H, s), 3.52-3.58 (2H, m), 3.92-3.97 (2H, m), 4.87-4.93 (1H, m).

Step B: 4-azidotetrahydro-2H-pyran

To a solution of tetrahydro-2H-pyran-4-yl methanesulfonate (0.882 g, 4.89 mmol) in DMF (16 mL) was added sodium azide (954 mg, 14.68 mmol). The reaction mixture was heated at 100° C. for 2 hours. After concentration in vacuo, the residue was partitioned between EtOAc and water. The aqueous layer was extracted with EtOAc. The combined organic layers were washed with brine, dried over Na₂SO₄, filtered and concentrated in vacuo. The residue was purified by column chromatography on SiO₂ (Hex:EtOAc=3:1) to afford 4-azidotetrahydro-2H-pyran (110 mg, 17%) as a colorless oil. ¹H-NMR (CDCl₃, Varian, 400

MHz): δ 1.60-1.70 (2H, m), 1.88-1.92 (2H, m), 3.44-3.50 (2H, m), 3.56-3.63 (1H, m), 3.92-3.97 (2H, m).

Step C: (R)-5-(2-(2,5-difluorophenyl)pyrrolidin-1-yl)-3-(1-(tetrahydro-2H-pyran-4-yl)-1H-1,2,3-triazol-4-yl)pyrazolo[1,5-a]pyrimidine To a solution of (R)-5-(2-(2,5-difluorophenyl)pyrrolidin-1-yl)-3-ethynylpyrazolo[1,5-a]pyrimidine (96.0 mg, 0.296 mmol) and 4-azidotetrahydro-2H-pyran (41.0 mg, 0.326 mmol) in tBuOH (1.5 mL) were added copper powder (15.0 mg, 0.237 mmol) followed by water (1.0 mL) and 1 M aq. solution of copper sulfate (0.059 mL, 0.059 mmol). The reaction mixture was heated at 90° C. for 90 min, cooled to room temperature and then diluted with EtOAc. After addition of conc. NH$_4$OH (2.0 mL) followed by water (2.0 mL), the mixture was vigorously stirred for 30 min and extracted with EtOAc twice. The combined organic layers were washed with brine, dried over Na$_2$SO$_4$, filtered and concentrated in vacuo. The residue was purified by column chromatography on SiO$_2$ (EtOAc only to DCM:MeOH=30:1) to afford (R)-5-(2-(2,5-difluorophenyl)pyrrolidin-1-yl)-3-(1-(tetrahydro-2H-pyran-4-yl)-1H-1,2,3-triazol-4-yl)pyrazolo[1,5-a]pyrimidine (84.0 mg, 63%) as a yellow oil. $^1$H-NMR (CDCl$_3$, Varian, 400 MHz): δ 2.04-2.30 (7H, m), 2.49 (1H, br. s), 3.61 (2H, t, J=11.6 Hz), 3.92 (1H, br. s), 4.18 (2H, t, J=11.6 Hz), 4.73 (1H, br. s), 5.19 and 5.66 (1H, br. s+br. s), 5.88 and 6.31 (1H, br. s+br. s), 6.73-6.78 (1H, m), 6.91 (1H, br. s), 7.01-7.16 (1H, m), 7.52 (1H, s), 8.32 (1H, br. s), 8.47 (1H, s). MS: 452.2 [MH$^+$].

Example 49: Preparation of Chemical Compound 37: (R)-2-(4-(5-(2-(2,5-difluorophenyl)pyrrolidin-1-yl)pyrazolo[1,5-a]pyrimidin-3-yl)-1H-1,2,3-triazol-1-yl)-1-(piperazin-1-yl)ethan-1-one

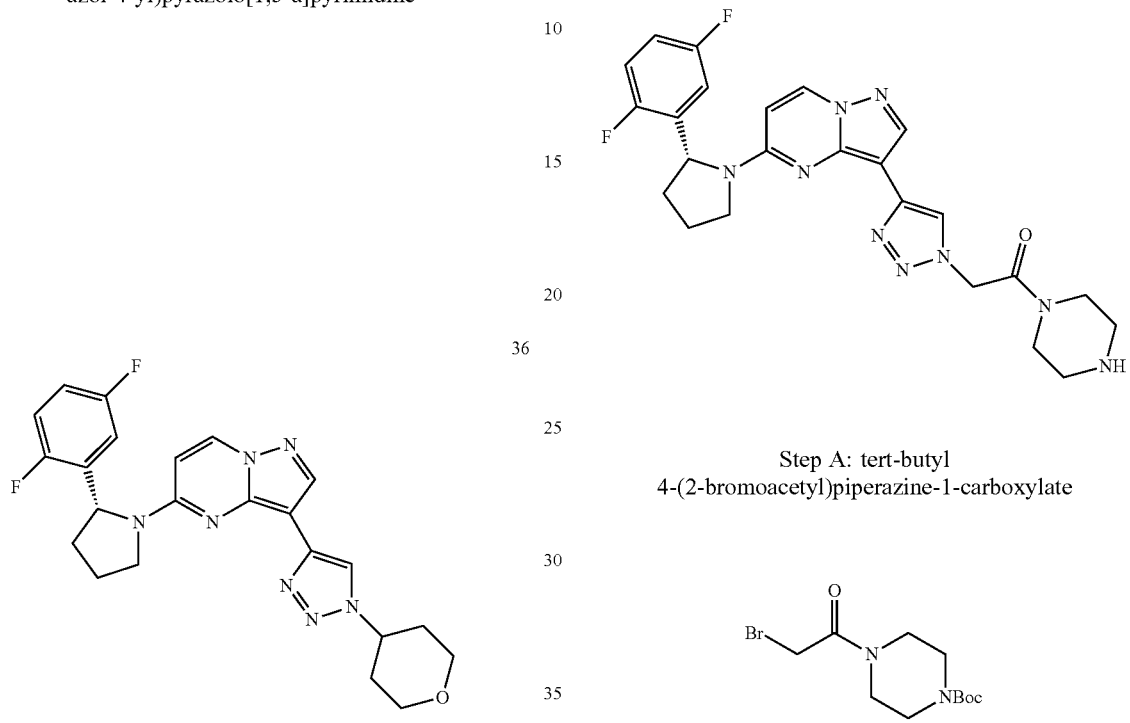

Step A: tert-butyl 4-(2-bromoacetyl)piperazine-1-carboxylate

To a solution of tert-butyl piperazine-1-carboxylate (2.00 g, 10.7 mmol) in 5 wt % aq NaHCO$_3$ (36 mL) and DCM (36 mL) was added 2-bromoacetyl bromide (1.40 mL, 16.1 mmol) at 0° C. The reaction mixture was stirred at 0° C. and then at room temperature for 2 hours. After separation of phase, the organic layer was washed with water, 2 N aq. HCl, water and brine, dried over Na$_2$SO$_4$, filtered and concentrated in vacuo. The residual solid was purified by recrystallization from EtOAc and hexanes to afford tert-butyl 4-(2-azidoacetyl)piperazine-1-carboxylate (2.92 g, 89%) as a white solid. $^1$H-NMR (CDCl$_3$, Varian, 400 MHz): δ 1.47 (9H, s), 3.42-3.44 (2H, m), 3.46-3.54 (4H, m), 3.58-3.60 (2H, m), 3.86 (2H, s).

Step B: tert-butyl 4-(2-azidoacetyl)piperazine-1-carboxylate

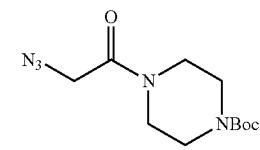 [SMILES: CC(C)(C)OC(=O)N1CCN(C(=O)CN=[N+]=[N-])CC1]

A suspension of tert-butyl 4-(2-azidoacetyl)piperazine-1-carboxylate (2.92 g, 9.51 mmol) and sodium azide (1.54 g, 23.7 mmol) in CH$_3$CN (47 mL) was refluxed for 1 hour and cooled to room temperature. The reaction mixture was diluted with EtOAc, washed with water and brine, dried over Na₂SO₄, filtered and concentrated in vacuo. The residue was purified by recrystallization from EtOAc and hexanes to afford tert-butyl 4-(2-azidoacetyl)piperazine-1-carboxylate (2.28 g, 89%) as a white solid. ¹H-NMR (CDCl₃, Varian, 400 MHz): δ 1.47 (9H, s), 3.33-3.38 (2H, m), 3.42-3.50 (4H, m), 3.58-3.66 (2H, m), 3.95 (2H, s).

Step C: tert-butyl (R)-4-(2-(4-(5-(2-(2,5-difluorophenyl)pyrrolidin-1-yl)pyrazolo[1,5-a]pyrimidin-3-yl)-1H-1,2,3-triazol-1-yl)acetyl)piperazine-1-carboxylate

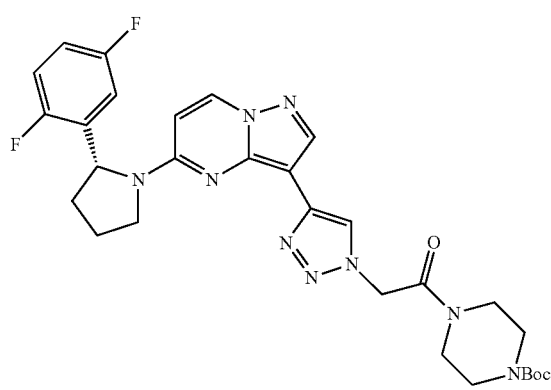 [SMILES: CC(C)(C)OC(=O)N1CCN(C(=O)Cn2cc(-c3cnn4ccc(N5CCC[C@@H]5c5cc(F)ccc5F)nc34)nn2)CC1]

To a solution of (R)-5-(2-(2,5-difluorophenyl)pyrrolidin-1-yl)-3-ethynylpyrazolo[1,5-a]pyrimidine (Intermediate 13, 100 mg, 0.308 mmol) and tert-butyl 4-(2-azidoacetyl)piperazine-1-carboxylate (91.0 mg, 0.339 mmol) in tBuOH (1.5 mL) was added copper powder (16.0 mg, 0.247 mmol) followed by water (0.70 mL) and 1 M aq. solution of copper sulfate (0.0620 mL, 0.0620 mmol). The reaction mixture was heated at 90° C. for 90 min, cooled to room temperature and then diluted with EtOAc. After addition of conc. NH₄OH (2.0 mL) followed by water (2.0 mL), the resulting mixture was vigorously stirred for 30 min and extracted with EtOAc twice. The combined organic layers were washed with brine, dried over Na₂SO₄, filtered and concentrated in vacuo. The residue was purified by column chromatography on SiO₂ (EtOAc only to DCM:MeOH=30:1) to afford (R)-tert-butyl 4-(2-(4-(5-(2-(2,5-difluorophenyl)pyrrolidin-1-yl)pyrazolo[1,5-a]pyrimidin-3-yl)-1H-1,2,3-triazol-1-yl)acetyl)piperazine-1-carboxylate (108 mg, 59%) as a yellow foam. ¹H-NMR (CDCl₃, Varian, 400 MHz): δ 1.47 (9H, s), 2.00-2.25 (3H, m), 2.42-2.58 (1H, m), 3.34 (4H, br. s), 3.59 (2H, br. s), 3.65 (2H, br. s), 3.92 (1H, br. s), 5.20 and 5.52 (1H, br. s+br. s), 5.28-5.32 (2H, m), 5.85 and 6.27 (1H, br. s+br. s), 6.78 (1H, br. s), 6.90 (1H, br. s), 7.04-7.10 (1H, m), 7.63 (1H, s), 8.25 (1H, br. s), 8.47 (1H, s).

Step D: (R)-2-(4-(5-(2-(2,5-difluorophenyl)pyrrolidin-1-yl)pyrazolo[1,5-a]pyrimidin-3-yl)-1H-1,2,3-triazol-1-yl)-1-(piperazin-1-yl)ethan-1-one

37

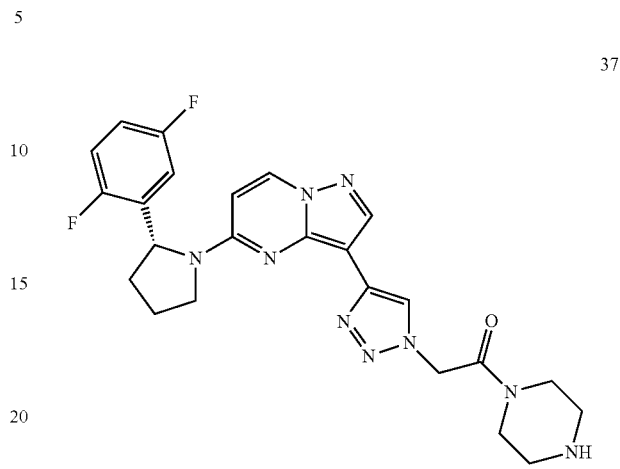

To a solution of (R)-tert-butyl 4-(2-(4-(5-(2-(2,5-difluorophenyl)pyrrolidin-1-yl)pyrazolo[1,5-a]pyrimidin-3-yl)-1H-1,2,3-triazol-1-yl)acetyl)piperazine-1-carboxylate (108 mg, 0.182 mmol) in DCM (1.0 mL) was added TFA (0.500 mL, 6.49 mmol) at room temperature. The reaction mixture was stirred at room temperature for 2 hours. After concentration in vacuo, the residue was diluted with DCM, washed with saturated aq. NaHCO₃ and brine, dried over Na₂SO₄, filtered and concentrated in vacuo. The residue was purified by column chromatography on SiO₂ (DCM:MeOH=10:1 to 3:1 to 2:1) to afford (R)-2-(4-(5-(2-(2,5-difluorophenyl)pyrrolidin-1-yl)pyrazolo[1,5-a]pyrimidin-3-yl)-1H-1,2,3-triazol-1-yl)-1-(piperazin-1-yl)ethanone (78.0 mg, 87%) as a pale yellow foam. ¹H-NMR (CDCl₃, Varian, 400 MHz): δ 1.47 (9H, s), 2.00-2.25 (3H, m), 2.50 (1H, br. s), 2.85 (4H, br. s), 3.57 (2H, br. s), 3.64 (2H, br. s), 3.90 (1H, br. s), 5.26 and 5.52 (1H, br. s+br. s), 5.26-5.30 (2H, m), 5.85 and 6.26 (1H, br. s+br. s), 6.77 (1H, br. s), 6.88 (1H, br. s), 7.00-7.12 (1H, m), 7.62 (1H, s), 8.24 (1H, br. s), 8.46 (1H, s). MS: 494.2 [MH⁺].

Example 50: Preparation of Chemical Compound 38

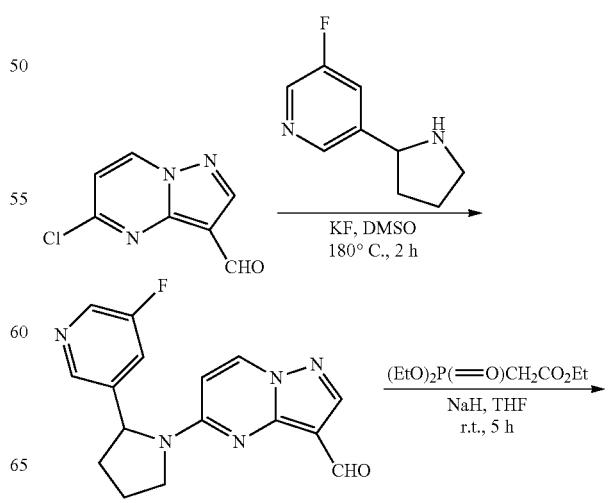

163
-continued

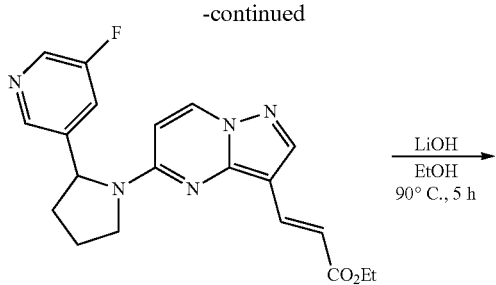

LiOH
EtOH
90° C., 5 h

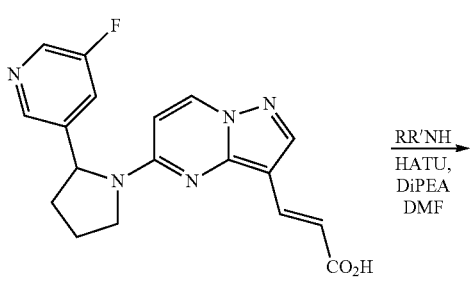

RR'NH
HATU,
DiPEA
DMF

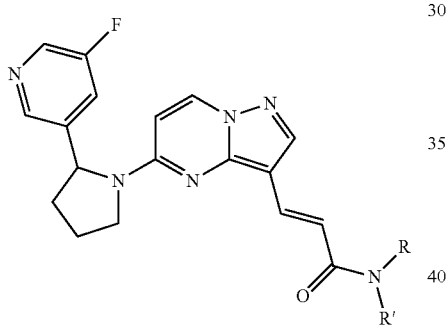

R = Et, R' = H
R = c-Pr, R' = H
R, R' = Me

Chemical Compound 38: (E)-N-ethyl-3-(5-(2-(5-fluoropyridin-3-yl)pyrrolidin-1-yl)pyrazolo[1,5-a]pyrimidin-3-yl)acrylamide

38

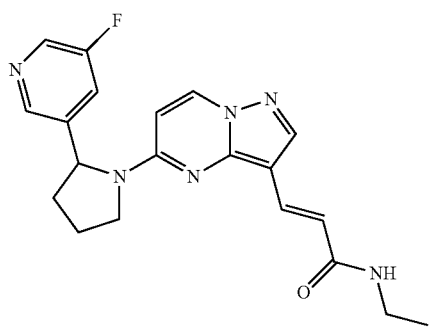

164

Step A: 5-(2-(5-fluoropyridin-3-yl)pyrrolidin-1-yl)pyrazolo[1,5-a]pyrimidine-3-carbaldehyde

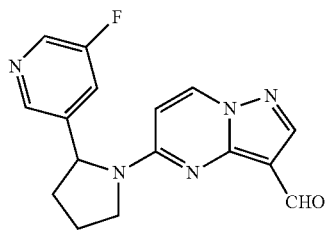 [SMILES: O=Cc1cnn2ccc(N3CCCC3c3cncc(F)c3)nc12]

A mixture of 5-chloropyrazolo[1,5-a]pyrimidine-3-carbaldehyde (500 mg, 2.75 mmol), 3-fluoro-5-(pyrrolidin-2-yl)pyridine (Intermediate 1, 490 mg, 2.95 mmol) and KF (800 mg, 13.8 mmol) in DMSO (9.2 mL) was stirred at 180° C. for 2 hours. After being cooled to room temperature, the reaction mixture was poured into water. The mixture was extracted with EtOAc twice. The combined organic layers were washed with brine, dried over $Na_2SO_4$, filtered and concentrated in vacuo. The residue was purified by column chromatography on $SiO_2$ (EtOAc only to DCM:MeOH=20:1) to afford 5-(2-(5-fluoropyridin-3-yl)pyrrolidin-1-yl)pyrazolo[1,5-a]pyrimidine-3-carbaldehyde (779 mg, 91%) as a yellow solid. $^1$H-NMR (DMSO-$d_6$, Varian, 400 MHz): δ 1.92-2.20 (3H, m), 2.40-2.50 (1H, m), 3.62-3.88 (1H, m), 3.98-4.15 (1H, m), 5.30-5.45 (1H, m), 6.22 (0.3H, m), 6.72 (0.7H, d, J=6.8 Hz), 7.60-7.75 (1H, m), 8.18-8.36 (1H, m), 8.38-8.56 (2H, m), 8.65 (0.3H, m), 8.80 (0.7H, d, J=6.0 Hz), 9.60 and 9.94 (1H, s+s).

Step B: (E)-ethyl-3-(5-(2-(5-fluoropyridin-3-yl)pyrrolidin-1-yl)pyrazolo[1,5-a]pyrimidin-3-yl)acrylate

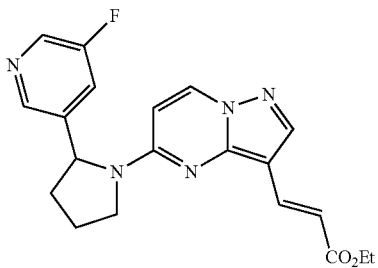 [SMILES: CCOC(=O)/C=C/c1cnn2ccc(N3CCCC3c3cncc(F)c3)nc12]

To a suspension NaH (55 wt %, 328 mg, 7.51 mmol) in dry THF (8.0 mL) was added a solution of ethyl 2-(diethoxyphosphoryl)acetate (841 mg, 3.75 mmol) in dry THF at 0° C. The mixture was stirred room temperature for 30 min. After addition of a solution of 5-(2-(5-fluoropyridin-3-yl)pyrrolidin-1-yl)pyrazolo[1,5-a]pyrimidine-3-carbaldehyde (0.779 g, 2.50 mmol) in dry THF, the reaction mixture was stirred for 5 hours at room temperature, quenched with saturated aq. $NH_4Cl$, and extracted with EtOAc twice. The combined organic layers were washed with brine, dried over $Na_2SO_4$, filtered and concentrated in vacuo. The residue was purified by column chromatography on $SiO_2$ (Hex:EtOAc=1:1) to afford (E)-ethyl-3-(5-(2-(5-fluoropyridin-3-yl)pyrrolidin-1-yl)pyrazolo[1,5-a]pyrimidin-3-yl)acrylate (511 mg, 54%) as a yellow solid. $^1$H-NMR (DMSO-$d_6$, Varian, 400 MHz): δ 1.20-1.32 (4H, m), 1.85-2.13 (3H, m), 3.60-3.90 (1H, m), 3.96-4.22 (3H, m), 5.28-5.42 (1H, m), 6.05-6.32 (1H, m), 6.54-6.70 (1H, m), 7.40-7.77 (2H, m), 8.09-8.12 (1H, m), 8.15-8.80 (3H, m).

Step C: (E)-3-(5-(2-(5-fluoropyridin-3-yl)pyrrolidin-1-yl)pyrazolo[1,5-a]pyrimidin-3-yl)acrylic acid

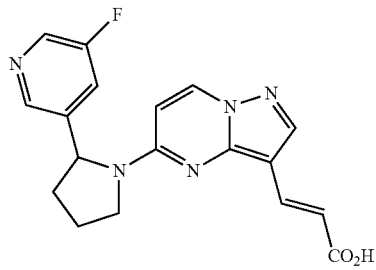 [SMILES: O=C(O)/C=C/c1cnn2ccc(N3CCCC3c3cncc(F)c3)nc12]

To a solution of (E)-ethyl-3-(5-(2-(5-fluoropyridin-3-yl)pyrrolidin-1-yl)pyrazolo[1,5-a]pyrimidin-3-yl)acrylate (511 mg, 1.340 mmol) in EtOH (5.0 mL) and water (1.7 mL) was added LiOH (96.0 mg, 4.02 mmol) at 0° C. The reaction mixture was heated at 90° C. for 5 hours and cooled to room temperature. After evaporation of EtOH, the residue was acidified with 2 N aq. HCl until pH 5-6 and then extracted with EtOAc twice. The combined organic layers were washed with brine, dried over $Na_2SO_4$, filtered and concentrated in vacuo to afford (E)-3-(5-(2-(5-fluoropyridin-3-yl)pyrrolidin-1-yl)pyrazolo[1,5-a]pyrimidin-3-yl)acrylic acid (373 mg, 79%) as a white solid. $^1$H-NMR (DMSO-$d_6$, Varian, 400 MHz): δ 1.92-2.13 (3H, m), 2.40-2.50 (1H, m), 3.60-3.92 (1H, m), 3.93-4.12 (1H, m), 5.28-5.42 (1H, m), 6.05-6.32 (1H, m), 6.54-6.70 (1H, m), 7.40-7.77 (2H, m), 8.09-8.29 (1H, m), 8.32-8.80 (3H, m), 11.73 (1H, br. s).

Step D: (E)-N-ethyl-3-(5-(2-(5-fluoropyridin-3-yl)pyrrolidin-1-yl)pyrazolo[1,5-a]pyrimidin-3-yl)acrylamide

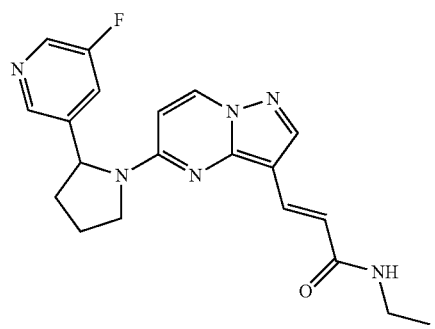

To a solution of (E)-3-(5-(2-(5-fluoropyridin-3-yl)pyrrolidin-1-yl)pyrazolo[1,5-a]pyrimidin-3-yl)acrylic acid (50.0 mg, 0.142 mmol) in DMF (1.0 mL) were added ethylamine (2.0 M in THF, 0.142 mL, 0.283 mmol), DIPEA (0.0740 mL, 0.425 mmol), and HATU (81.0 mg, 0.212 mmol) at room temperature. The reaction mixture was stirred at room temperature for 18 hours and diluted with EtOAc. The mixture was washed with saturated aq. $NH_4Cl$ and brine, dried over $Na_2SO_4$, filtered and concentrated in vacuo. The residue was purified by column chromatography on $SiO_2$ (EtOAc only to DCM:MeOH=20:1 to 10:1) to afford (E)-N-ethyl-3-(5-(2-(5-fluoropyridin-3-yl)pyrrolidin-1-yl)pyrazolo[1,5-a]pyrimidin-3-yl)acrylamide (48.0 mg, 89%) as a white solid. $^1$H-NMR (DMSO-$d_6$, Varian, 400 MHz): δ 1.10 (3H, t, J=6.6 Hz), 1.92-2.20 (3H, m), 2.43-2.50 (1H, m), 3.10-3.30 (2H, m), 3.60-3.92 (1H, m), 4.00-4.15 (1H, m), 5.28-5.58 (1H, m), 6.05-6.42 (1H, m), 6.54-6.80 (1H, m), 7.18-8.10 (4H, m), 8.32-8.75 (3H, m). MS: 381.1 [MH$^+$].

Example 51: Preparation of Chemical Compound 39: (E)-N-cyclopropyl-3-(5-(2-(5-fluoropyridin-3-yl)pyrrolidin-1-yl)pyrazolo[1,5-a]pyrimidin-3-yl)acrylamide

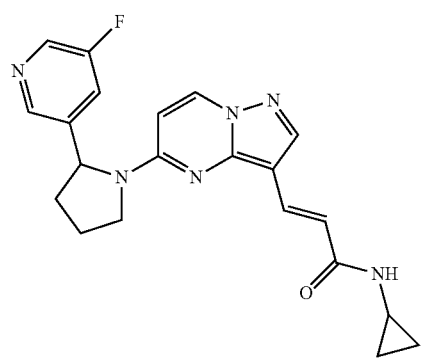

To a solution of (E)-3-(5-(2-(5-fluoropyridin-3-yl)pyrrolidin-1-yl)pyrazolo[1,5-a]pyrimidin-3-yl)acrylic acid (50.0 mg, 0.142 mmol) in DMF (1.0 mL) were added cyclopropanamine (0.0200 mL, 0.283 mmol), DIPEA (0.0740 mL, 0.425 mmol), and HATU (81.0 mg, 0.212 mmol) at room temperature. The reaction mixture was stirred at room temperature for 18 hours and diluted with EtOAc. The mixture was washed with saturated aq. $NH_4Cl$ and brine, dried over $Na_2SO_4$, filtered and concentrated in vacuo. The residue was purified by column chromatography on $SiO_2$ (EtOAc only to DCM:MeOH=20:1 to 10:1) to afford (E)-N-cyclopropyl-3-(5-(2-(5-fluoropyridin-3-yl)pyrrolidin-1-yl)pyrazolo[1,5-a]pyrimidin-3-yl)acrylamide (21.0 mg, 38%) as a white solid. $^1$H-NMR (DMSO-$d_6$, Varian, 400 MHz): δ 0.40-0.60 (2H, m), 0.61-0.75 (2H, m), 1.86-2.17 (3H, m), 2.43-2.50 (1H, m), 2.72-2.80 (1H, m), 3.60-3.92 (1H, m), 4.00-4.15 (1H, m), 5.25-5.52 (1H, m), 6.05-6.38 (1H, m), 6.54-6.70 (1H, m), 7.28-8.12 (4H, m), 8.32-8.75 (3H, m). MS: 393.1 [MH$^+$].

Example 52: Preparation of Chemical Compound 40: (E)-3-(5-(2-(5-fluoropyridin-3-yl)pyrrolidin-1-yl)pyrazolo[1,5-a]pyrimidin-3-yl)-N,N-dimethyl-acryl-amide

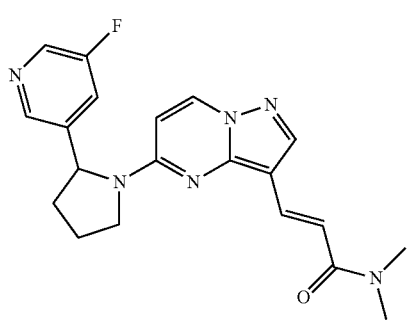

40

To a solution of (E)-3-(5-(2-(5-fluoropyridin-3-yl)pyrrolidin-1-yl)pyrazolo[1,5-a]pyrimidin-3-yl)acrylic acid (50.0 mg, 0.142 mmol) in DMF (1.0 mL) were added dimethylamine hydrochloride (23.0 mg, 0.283 mmol), DIPEA (0.0740 mL, 0.425 mmol), and HATU (81.0 mg, 0.212 mmol) at room temperature. The reaction mixture was stirred at room temperature for 18 hours and diluted with EtOAc. The mixture was washed with saturated aq. $NH_4Cl$ and brine, dried over $Na_2SO_4$, filtered and concentrated in vacuo. The residue was purified by column chromatography on $SiO_2$ (EtOAc only to DCM:MeOH=20:1 to 10:1) to afford (E)-3-(5-(2-(5-fluoropyridin-3-yl)pyrrolidin-1-yl)pyrazolo[1,5-a]pyrimidin-3-yl)-N,N-dimethylacryl-amide (39.0 mg, 72%) as a white solid. $^1$H-NMR (DMSO-$d_6$, Varian, 400 MHz): δ 1.86-2.10 (3H, m), 2.38-2.50 (1H, m), 2.80-3.00 (6H, m), 3.54-3.88 (1H, m), 3.92-4.15 (1H, m), 5.25-5.50 (1H, m), 6.05-6.12 (0.3H, m), 6.48-6.70 (0.7H, m), 6.73-7.70 (3H, m), 8.00-8.70 (4H, m). MS: 381.1 [MH$^+$].

Example 53: Preparation of Chemical Compound 41

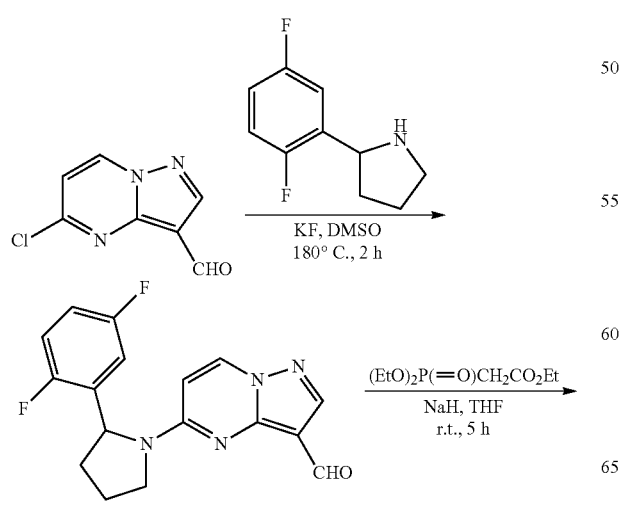

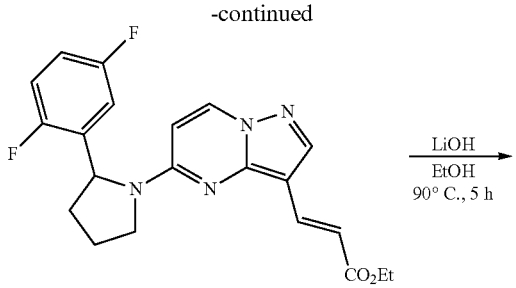

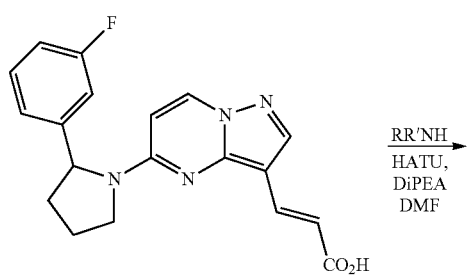

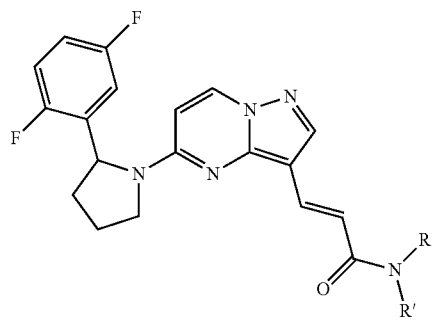

Chemical Compound 41: (E)-3-(5-(2-(2,5-difluorophenyl)pyrrolidin-1-yl)pyrazolo[1,5-a]pyrimidin-3-yl)-N-ethylacrylamide

41

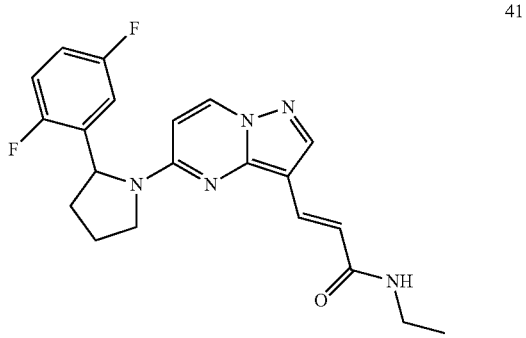 [SMILES: CCNC(=O)/C=C/c1cnn2ccc(N3CCCC3c3cc(F)ccc3F)nc12]

Step A: 5-(2-(2,5-difluorophenyl)pyrrolidin-1-yl)pyrazolo[1,5-a]pyrimidine-3-carbaldehyde

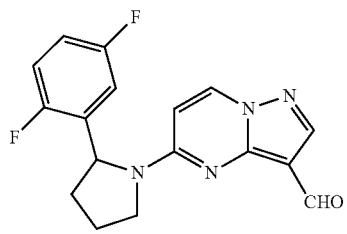 [SMILES: O=Cc1cnn2ccc(N3CCCC3c3cc(F)ccc3F)nc12]

A mixture of 5-chloropyrazolo[1,5-a]pyrimidine-3-carbaldehyde (300 mg, 1.65 mmol), 2-(2,5-difluorophenyl)pyrrolidine (Intermediate 2, 324 mg, 1.77 mmol) and KF (480 mg, 8.26 mmol) in DMSO (5.5 mL) was heated at 180° C. for 2 hours. After being cooled to room temperature, the reaction mixture was poured into water. The mixture was extracted with EtOAc twice. The combined organic layers were washed with brine, dried over $Na_2SO_4$, filtered and concentrate in vacuo. The residue was purified by column chromatography on $SiO_2$ (EtOAc only to DCM:MeOH=20: 1) to afford 5-(2-(2,5-difluorophenyl)pyrrolidin-1-yl)pyrazolo[1,5-a]pyrimidine-3-carbaldehyde (540 mg, 100%) as a yellow solid. $^1$H-NMR ($CDCl_3$, Varian, 400 MHz): δ 1.90-2.28 (3H, m), 2.38-2.60 (1H, m), 3.60-4.18 (2H, m), 5.14-5.28 (0.6H, m), 5.54-5.72 (0.4H, m), 5.84-6.02 (0.6H, m), 6.35-6.46 (0.4H, m), 6.68-6.78 (1H, m), 6.82-7.20 (2H, m), 8.10-8.36 (2H, m), 9.77 and 10.11 (1H, s+s).

Step B: (E)-ethyl-3-(5-(2-(2,5-difluorophenyl)pyrrolidin-1-yl)pyrazolo[1,5-a]pyrimidin-3-yl)acrylate

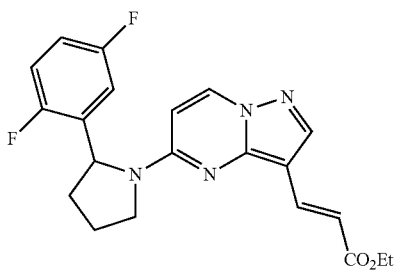 [SMILES: CCOC(=O)/C=C/c1cnn2ccc(N3CCCC3c3cc(F)ccc3F)nc12]

To a suspension NaH (55 wt %, 349 mg, 8.00 mmol) in dry THF (8.9 mL) was added a solution of ethyl 2-(diethoxyphosphoryl)acetate (896 mg, 4.00 mmol) in dry THF at 0° C. The mixture was stirred room temperature for 30 min. After addition of a solution of 5-(2-(2,5-difluorophenyl)pyrrolidin-1-yl)pyrazolo[1,5-a]pyrimidine-3-carbaldehyde (875 mg, 2.67 mmol) in dry THF, the reaction mixture was stirred for 5 hours and then quenched with saturated aq. $NH_4Cl$. The mixture was extracted with EtOAc twice. The combined organic layers were washed with brine, dried over $Na_2SO_4$, filtered and concentrated in vacuo. The residue was purified by column chromatography on $SiO_2$ (Hex:EtOAc=1:1) to afford (E)-ethyl-3-(5-(2-(2,5-difluorophenyl)pyrrolidin-1-yl)pyrazolo[1,5-a]pyrimidin-3-yl)acrylate (609 mg, 57%) as a yellow solid. $^1$H-NMR ($CDCl_3$, Varian, 400 MHz): δ 1.36 (3H, t, J=7.0 Hz), 1.95-2.20 (3H, m), 2.45-2.60 (1H, m), 3.60-4.18 (2H, m), 4.20-4.43 (2H, m), 5.14-5.28 (0.6H, m), 5.54-5.70 (0.4H, m), 5.84-5.96 (0.4H, m), 6.25-6.46 (0.6H, m), 6.65-6.78 (2H, m), 6.82-7.00 (1H, m), 7.10-4.15 (1H, m), 7.50-7.85 (1H, m), 7.80-8.05 (1H, m), 8.12-8.35 (1H, m).

Step C: (E)-3-(5-(2-(2,5-difluorophenyl)pyrrolidin-1-yl)pyrazolo[1,5-a]pyrimidin-3-yl)acrylic acid

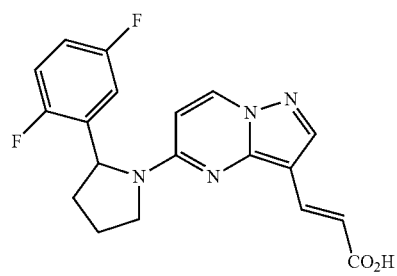

To a solution of (E)-ethyl-3-(5-(2-(2,5-difluorophenyl)pyrrolidin-1-yl)pyrazolo[1,5-a]pyrimidin-3-yl)acrylate (345 mg, 0.866 mmol) in EtOH (3.3 mL) and water (1.1 mL) was added LiOH (62.0 mg, 2.60 mmol) at 0° C. The reaction mixture was heated at 90° C. for 5 hours and cooled to room temperature. After evaporation of EtOH, the residue was acidified by 2 N aq. HCl until pH 5~6. The mixture was extracted with EtOAc twice. The combined organic layers were washed with brine, dried over $Na_2SO_4$, filtered and concentrated in vacuo to afford (E)-3-(5-(2-(2,5-difluorophenyl)pyrrolidin-1-yl)pyrazolo[1,5-a]pyrimidin-3-yl)acrylic acid (297 mg, 93%) as a white solid. $^1$H-NMR (DMSO-$d_6$, Varian, 400 MHz): δ 1.80-2.14 (3H, m), 2.38-2.50 (1H, m), 3.35-3.88 (1H, m), 3.98-4.18 (1H, m), 5.28-5.53 (1H, m), 6.00-3.20 (1H, m), 6.50-6.70 (1H, m), 6.90-7.00 (1H, m), 7.01-7.70 (3H, m), 8.05-8.20 (1H, m), 8.50-8.78 (1H, m), 11.95 (1H, s).

Step D: (E)-3-(5-(2-(2,5-difluorophenyl)pyrrolidin-1-yl)pyrazolo[1,5-a]pyrimidin-3-yl)-N-ethylacrylamide

41

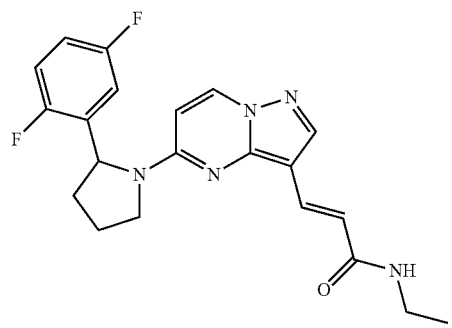

To a solution of (E)-3-(5-(2-(2,5-difluorophenyl)pyrrolidin-1-yl)pyrazolo[1,5-a]pyrimidin-3-yl)acrylic acid (75.0 mg, 0.203 mmol) in DCM (2.0 mL) were added 2 drops of DMF followed by oxalyl chloride (0.0355 mL, 0.405 mmol). The reaction mixture was stirred at room temperature for 30 min and then concentrated under reduced pressure to afford the corresponding acyl chloride compound. The residual crude acyl chloride compound was dissolved in DCM (2.0 mL), and then ethylamine hydrochloride (18.2 mg, 0.405 mmol) was added thereto. The reaction mixture was stirred at room temperature for 5 hours and quenched with 1 N aq. HCl. The mixture was washed with water and brine, dried over Na₂SO₄, filtered and concentrated in vacuo. The residue was purified by column chromatography on SiO₂ (Hex:EtOAc=1:10 to EtOAc only) to afford (E)-3-(5-(2-(2,5-difluorophenyl)pyrrolidin-1-yl)pyrazolo[1,5-a]pyrimidin-3-yl)-N-ethylacrylamide (13.0 mg, 16%) as a yellow solid. ¹H-NMR (CDCl₃, Varian, 400 MHz): δ 1.15-1.32 (6H, m), 1.98-2.32 (3H, m), 2.42-2.60 (1H, m), 3.38-3.50 (2H, m), 3.61-4.05 (2H, m), 5.38-5.50 (1H, m), 6.23-6.60 (1H, m), 6.70-6.78 (1H, m), 6.86-7.13 (2H, m), 7.80-9.00 (1H, m), 8.10-8.36 (1H, m). MS: 398.1 [MH⁺].

Example 54: Preparation of Chemical Compound 42: (E)-3-(5-(2-(2,5-difluorophenyl)-pyrrolidin-1-yl)pyrazolo[1,5-a]pyrimidin-3-yl)-N-isopropylacrylamide

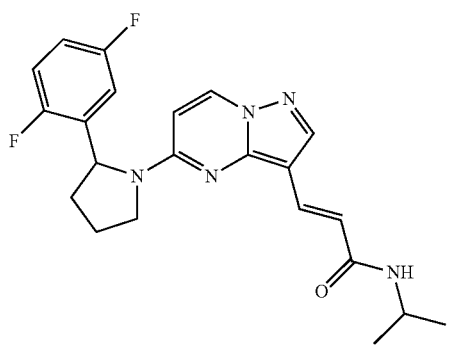

42

To a solution of (E)-3-(5-(2-(2,5-difluorophenyl)pyrrolidin-1-yl)pyrazolo[1,5-a]pyrimidin-3-yl)acrylic acid (55.0 mg, 0.149 mmol) in DMF (1.5 mL) was added HATU (73.4 mg, 0.193 mmol), DIPEA (78.0 μL, 0.446 mmol) and isopropylamine (9.66 mg, 0.163 mmol) at room temperature. The reaction mixture was stirred at room temperature for 1 hour and diluted with EtOAc. The mixture was washed with saturated aq. NH₄Cl and brine, dried over Na₂SO₄, filtered and concentrated in vacuo. The residue was purified by column chromatography on SiO₂ (Hex:EtOAc=1:10 to EtOAc only) to afford (E)-3-(5-(2-(2,5-difluorophenyl)-pyrrolidin-1-yl)pyrazolo[1,5-a]pyrimidin-3-yl)-N-isopropylacrylamide (30.0 mg, 49%) as a yellow solid. ¹H-NMR (CDCl₃, Varian, 400 MHz): δ 1.13-1.32 (6H, m), 2.00-2.29 (3H, m), 2.42-2.60 (1H, m), 3.60-4.00 (2H, m), 4.20-4.30 (1H, m), 5.25-5.38 (1H, m), 5.62-5.95 (1H, m), 6.20-6.60 (2H, m), 6.70-6.77 (1H, m), 6.82-6.98 (1H, m), 7.00-7.10 (1H, m), 7.45-7.55 (1H, m), 7.82-7.99 (1H, m), 8.10-8.40 (1H, m). MS: 412.1 [MH⁺].

Example 55: Preparation of Chemical Compound 43: (E)-N-cyclopropyl-3-(5-(2-(2,5-difluorophenyl)pyrrolidin-1-yl)pyrazolo[1,5-a]pyrimidin-3-yl)acrylamide

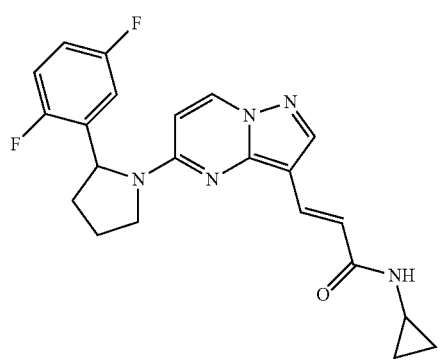

43

To a solution of (E)-3-(5-(2-(2,5-difluorophenyl)pyrrolidin-1-yl)pyrazolo[1,5-a]pyrimidin-3-yl)acrylic acid (50.0 mg, 0.135 mmol) in DMF (1.4 mL) were added HATU (66.7 mg, 0.176 mmol), DIPEA (70.7 μl, 0.405 mmol) and cyclopropylamine (10.5 μl, 0.149 mmol) at room temperature. The reaction mixture was stirred at room temperature for 1 hour and diluted with EtOAc. The mixture was washed with saturated aq. NH₄Cl and brine, dried over Na₂SO₄, filtered and concentrated in vacuo. The residue was purified by column chromatography on SiO₂ (Hex:EtOAc=10:1 to EtOAc only) to afford (E)-N-cyclopropyl-3-(5-(2-(2,5-difluorophenyl)pyrrolidin-1-yl)pyrazolo[1,5-a]pyrimidin-3-yl)acrylamide (30.0 mg, 54%) as a yellow solid. ¹H-NMR (CDCl₃, Varian, 400 MHz): δ 0.50-0.65 (2H, m), 0.78-0.92 (2H, m), 1.92-2.30 (4H, m), 2.39-2.59 (1H, m), 2.82-2.85 (1H, m), 3.58-3.80 (1H, m), 3.86-4.12 (1H, m), 5.50-5.70 (2H, m), 6.23-6.48 (1H, m), 6.69-6.78 (1H, m), 6.82-7.08 (2H, m), 7.45-7.62 (1H, m), 7.82-8.00 (1H, m), 8.12-8.40 (1H, m). MS: 410.1 [MH⁺].

Example 56: Preparation of Chemical Compound 44: (E)-N-tert-butyl-3-(5-(2-(2-(2,5-difluorophenyl)pyrrolidin-1-yl)pyrazolo-[1,5-a]pyrimidin-3-yl)acrylamide

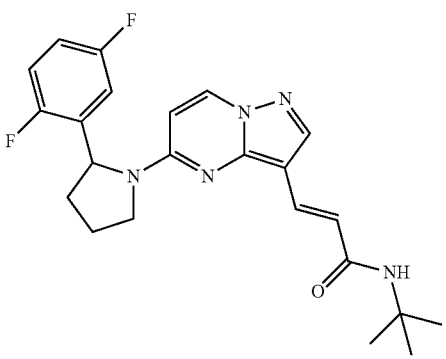

44

To a solution of (E)-3-(5-(2-(2,5-difluorophenyl)pyrrolidin-1-yl)pyrazolo[1,5-a]pyrimidin-3-yl)acrylic acid (50.0 mg, 0.135 mmol) in DMF (0.90 mL) was added tert-butylamine (20.0 mg, 0.270 mmol), DIPEA (0.0710 mL, 0.405 mmol), and HATU (77.0 mg, 0.203 mmol) at room temperature. The reaction mixture was stirred at room temperature for 18 hours and diluted with EtOAc. The mixture was washed with saturated aq. NH₄Cl and brine, dried over Na₂SO₄, filtered and concentrated in vacuo. The residue was purified by column chromatography on SiO₂ (EtOAc only to DCM:MeOH=20:1 to 10:1) to afford (E)-N-tert-butyl-3-(5-(2-(2,5-difluorophenyl)pyrrolidin-1-yl)pyrazolo-[1,5-a]pyrimidin-3-yl)acrylamide (38.0 mg, 66%) as a white solid. $^1$H-NMR (DMSO-d$_6$, Varian, 400 MHz): δ 1.31 (9H, s), 1.80-2.10 (3H, m), 2.38-2.50 (1H, m), 3.58-3.90 (1H, m), 3.95-4.12 (1H, m), 5.25-5.40 (0.4H, m), 5.50-5.62 (0.6H, m), 5.97-6.10 (0.4H, m), 6.30-6.54 (0.6H, m), 6.52-6.68 (1H, m), 6.70-7.00 (1H, m), 7.01-7.52 (4H, m), 7.95-8.10 (1H, m), 8.43-8.72 (1H, m). MS: 426.2 [MH$^+$].

Example 57: Preparation of Chemical Compound 45: (E)-3-(5-(2-(2,5-difluorophenyl)pyrrolidin-1-yl)pyrazolo[1,5-a]pyrimidin-3-yl)-N,N-dimethylacrylamide

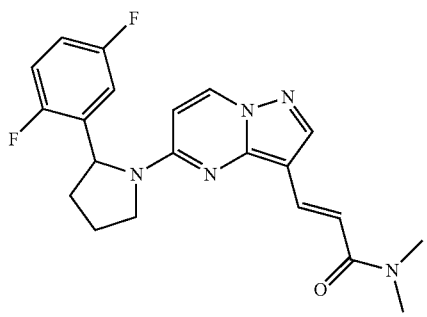

45

To a solution of (E)-3-(5-(2-(2,5-difluorophenyl)pyrrolidin-1-yl)pyrazolo[1,5-a]pyrimidin-3-yl)acrylic acid (55.0 mg, 0.149 mmol) in DMF (1.5 mL) were added HATU (73.4 mg, 0.193 mmol), DIPEA (78.0 μl, 0.446 mmol) and dimethyl amine hydrochloride (7.36 mg, 0.163 mmol). The reaction mixture was stirred at room temperature for 1 hour and diluted with EtOAc. The mixture was washed with saturated aq. NH₄Cl and brine, dried over Na₂SO₄, filtered and concentrated in vacuo. The residue was purified by column chromatography on SiO₂ (Hex:EtOAc=1:10 to EtOAc only) to afford (E)-3-(5-(2-(2,5-difluorophenyl)pyrrolidin-1-yl)pyrazolo[1,5-a]pyrimidin-3-yl)-N,N-dimethyl-acrylamide (38.0 mg, 64%) as a yellow solid. $^1$H-NMR (CDCl₃, Varian, 400 MHz): δ 1.98-2.15 (3H, m), 2.35-2.60 (1H, m), 2.82-3.30 (6H, m), 3.50-3.78 (1H, m), 3.80-4.15 (2H, m), 5.64-6.01 (1H, m), 6.18-6.44 (1H, m), 6.60-6.78 (1H, m), 6.83-7.13 (2H, m), 7.55-7.86 (1H, m), 7.90-8.05 (1H, m), 8.10-8.43 (1H, m). MS: 398.1 [MH$^+$].

Example 58: Preparation of Chemical Compound 46: (E)-3-(5-(2-(2,5-difluorophenyl)pyrrolidin-1-yl)pyrazolo[1,5-a]pyrimidin-3-yl)-N-(2-methoxyethyl)-acrylamide

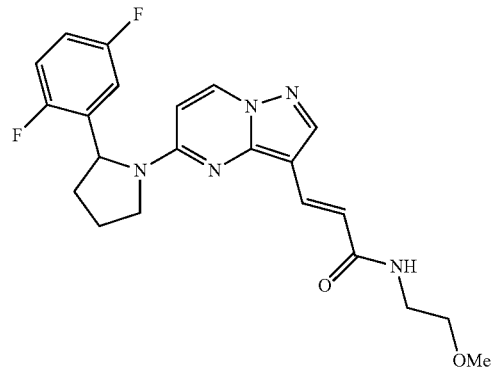

46

To a solution of (E)-3-(5-(2-(2,5-difluorophenyl)pyrrolidin-1-yl)pyrazolo[1,5-a]pyrimidin-3-yl)acrylic acid (60.0 mg, 0.162 mmol) in DMF (1.1 mL) was added 2-methoxyethanamine (37.0 mg, 0.486 mmol), DIPEA (0.0850 mL, 0.486 mmol), and HATU (185 mg, 0.486 mmol) at room temperature. The reaction mixture was stirred at room temperature for 3 hours and diluted with water. After being stirred for an additional 30 min, a precipitated white solid was collected by filtration and dried under vacuum to afford (E)-3-(5-(2-(2,5-difluorophenyl)pyrrolidin-1-yl)pyrazolo[1,5-a]pyrimidin-3-yl)-N-(2-methoxyethyl)-acrylamide (43.4 mg, 63%) as a white solid. $^1$H-NMR (DMSO-d$_6$, Varian, 400 MHz): δ 1.80-2.10 (3H, m), 2.38-2.50 (1H, m), 3.20-3.30 (3H, m), 3.33-3.45 (2H, m), 3.46-3.88 (2H, m), 3.90-4.15 (1H, m), 5.20-5.60 (1H, m), 5.88-6.38 (1H, m), 6.40-6.80 (1H, m), 6.81-7.55 (4H, m), 7.90-8.15 (2H, m), 8.40-8.80 (1H, m). * A proton from NH was not observed. MS: 428.2 [MH$^+$].

Example 59: Preparation of Chemical Compound 47: (E)-3-(5-(2-(2,5-difluorophenyl)pyrrolidin-1-yl)pyrazolo[1,5-a]pyrimidin-3-yl)-1-(3-hydroxyazetidin-1-yl)prop-2-en-1-one

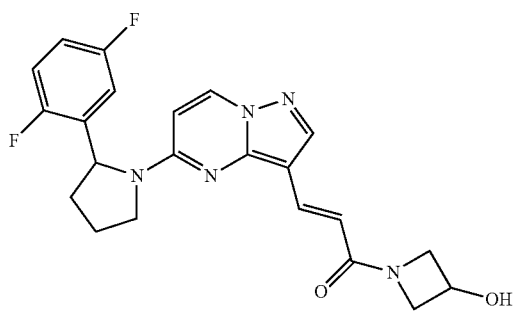

47

To a solution of (E)-3-(5-(2-(2,5-difluorophenyl)pyrrolidin-1-yl)pyrazolo[1,5-a]pyrimidin-3-yl)acrylic acid (50.0 mg, 0.135 mmol) in DMF (0.90 mL) were added azetidin- 3-ol hydrochloride (44.0 mg, 0.405 mmol), DIPEA (0.141 mL, 0.810 mmol), and HATU (0.103 g, 0.270 mmol) at room temperature. The reaction mixture was stirred at room temperature for 18 hours and diluted with EtOAc. The mixture was washed with saturated aq. NH$_4$Cl and brine, dried over Na$_2$SO$_4$, filtered and concentrated in vacuo. The residue was purified by column chromatography on SiO$_2$ (EtOAc only to DCM:MeOH=20:1 to 10:1) to afford (E)-3-(5-(2-(2,5-difluorophenyl)pyrrolidin-1-yl)pyrazolo[1,5-a]pyrimidin-3-yl)-1-(3-hydroxyazetidin-1-yl)prop-2-en-1-one (21.0 mg, 36%) as a white solid. $^1$H-NMR (DMSO-d$_6$, Varian, 400 MHz): δ 1.86-2.10 (3H, m), 2.38-2.50 (1H, m), 3.56-3.90 (2H, m), 3.92-4.19 (3H, m), 4.20-4.58 (2H, m), 5.30-5.40 (0.4H, m), 5.50-5.62 (0.6H, m), 5.74 (1H, d, J=5.6 Hz), 5.97-6.10 (0.4H, m), 6.28-6.40 (0.6H, m), 6.52-7.70 (2H, m), 7.05-7.52 (3H, m), 8.09-8.20 (1H, m), 8.50-8.78 (1H, m). MS: 426.2 [MH$^+$].

Example 60: Preparation of Chemical Compound 48

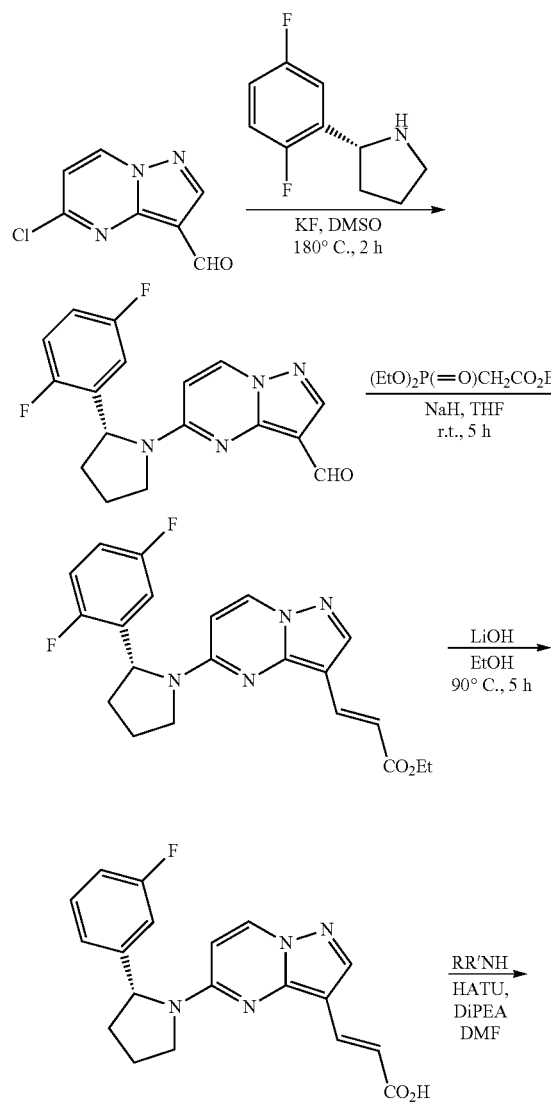

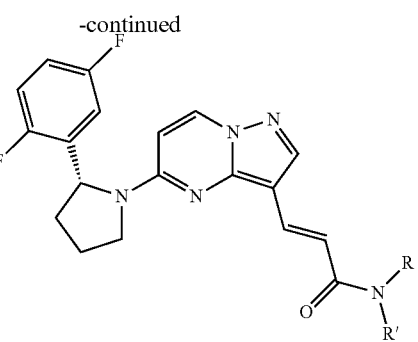

Chemical Compound 48: (R,E)-3-(5-(2-(2,5-difluorophenyl)pyrrolidin-1-yl)pyrazolo[1,5-a]pyrimidin-3-yl)-N-(2-hydroxyethyl)-acrylamide

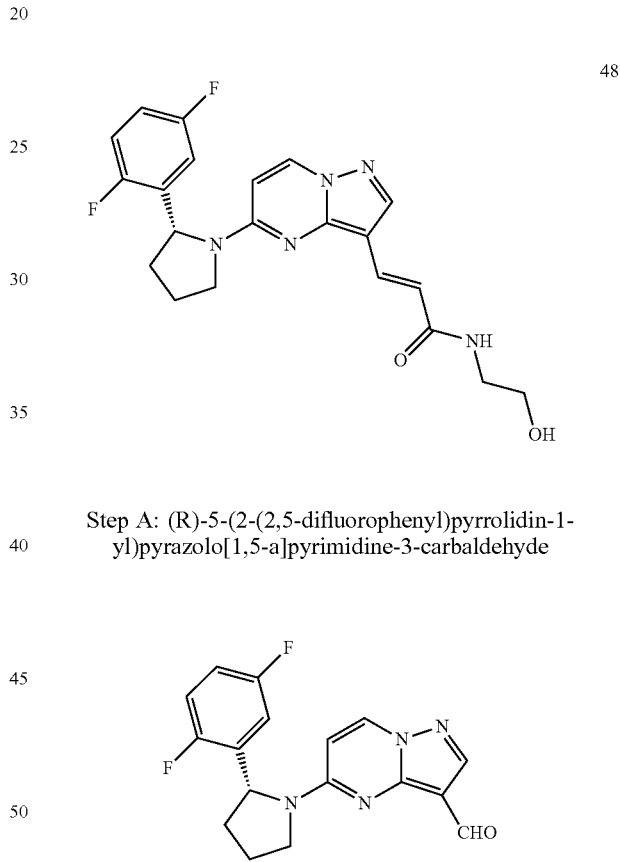

Step A: (R)-5-(2-(2,5-difluorophenyl)pyrrolidin-1-yl)pyrazolo[1,5-a]pyrimidine-3-carbaldehyde A mixture of 5-chloropyrazolo[1,5-a]pyrimidine-3-carbaldehyde (Intermediate 10, 4.70 g, 25.9 mmol), (R)-2-(2,5-difluorophenyl)pyrrolidine (Intermediate 5, 5.07 g, 27.7 mmol) and KF (7.52 g, 129 mmol) in DMSO (86 mL) was stirred at 180° C. for 2 hours. After being cooled to room temperature, the reaction mixture was diluted with water. The mixture was extracted with EtOAc twice. The combined organic layers were washed with brine, dried over Na$_2$SO$_4$, filtered and concentrated in vacuo. The residue was purified by column chromatography on SiO$_2$ (EtOAc only to DCM: MeOH=20:1) to afford (R)-5-(2-(2,5-difluorophenyl)pyrrolidin-1-yl)pyrazolo[1,5-a]pyrimidine-3-carbaldehyde (8.50 g, 100%) as a yellow oil. $^1$H-NMR (CDCl$_3$, Varian, 400 MHz): δ 1.90-2.28 (3H, m), 2.38-2.60 (1H, m), 3.60-4.18

(2H, m), 5.14-5.28 (0.6H, m), 5.54-5.72 (0.4H, m), 5.84-6.02 (0.6H, m), 6.35-6.46 (0.4H, m), 6.68-6.78 (1H, m), 6.82-7.20 (2H, m), 8.10-8.36 (2H, m), 9.77 and 10.11 (1H, s+s).

Step B: (R,E)-ethyl-3-(5-(2-(2,5-difluorophenyl)pyrrolidin-1-yl)pyrazolo[1,5-a]pyrimidin-3-yl)acrylate

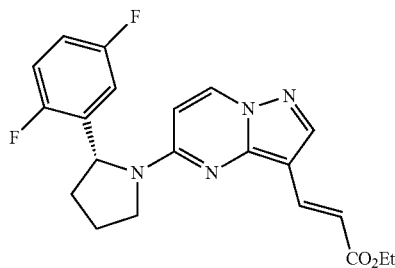

To a suspension NaH (55 wt %, 3.30 g, 76 mmol) in dry THF (80 mL) was added a solution of ethyl 2-(diethoxyphosphoryl)acetate (8.47 g, 37.8 mmol) in dry THF at 0° C. The mixture was stirred room temperature for 1 hour. After addition of a solution of (R)-5-(2-(2,5-difluorophenyl)pyrrolidin-1-yl)pyrazolo[1,5-a]pyrimidine-3-carbaldehyde (8.27 g, 25.2 mmol) in dry THF (40 mL), the reaction mixture was stirred for 5 hours at room temperature and then quenched with saturated aq. NH$_4$Cl. The mixture was extracted with EtOAc, washed with water and brine, dried over Na$_2$SO$_4$, filtered and concentrated in vacuo. The residue was purified by column chromatography on SiO$_2$ (Hex: EtOAc=1:1) to afford (R,E)-ethyl-3-(5-(2-(2,5-difluorophenyl)pyrrolidin-1-yl)pyrazolo[1,5-a]pyrimidin-3-yl)acrylate (6.00 g, 60%) as a reddish solid. $^1$H-NMR (CDCl$_3$, Varian, 400 MHz): δ 1.36 (3H, t, J=7.0 Hz), 1.95-2.20 (3H, m), 2.45-2.60 (1H, m), 3.60-4.18 (2H, m), 4.20-4.43 (2H, m), 5.14-5.28 (0.6H, m), 5.54-5.70 (0.4H, m), 5.84-5.96 (0.4H, m), 6.25-6.46 (0.6H, m), 6.65-6.78 (2H, m), 6.82-7.00 (1H, m), 7.10-4.15 (1H, m), 7.50-7.85 (1H, m), 7.80-8.05 (1H, m), 8.12-8.35 (1H, m).

Step C: (R,E)-3-(5-(2-(2,5-difluorophenyl)pyrrolidin-1-yl)pyrazolo[1,5-a]pyrimidin-3-yl)acrylic acid

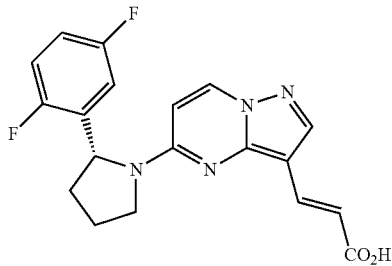

To a solution of (R,E)-ethyl-3-(5-(2-(2,5-difluorophenyl)pyrrolidin-1-yl)pyrazolo[1,5-a]pyrimidin-3-yl)acrylate (6.00 g, 15.1 mmol) in EtOH (56 mL) and water (19 mL) was added lithium hydroxide hydrate (1.90 g, 45.2 mmol) at room temperature. The reaction mixture was heated at 90° C. for 5 hours and cooled to room temperature. After evaporation of EtOH, the residue was acidified with 2 N aq. HCl and diluted with EtOAc. A precipitated yellow solid was collected by filtration and washed with EtOAc, dried under vacuum to afford (R,E)-3-(5-(2-(2,5-difluorophenyl)pyrrolidin-1-yl)pyrazolo[1,5-a]pyrimidin-3-yl)acrylic acid (5.58 g, >99%) as a pale yellow solid. $^1$H-NMR (DMSO-d$_6$, Varian, 400 MHz): δ 1.80-2.14 (3H, m), 2.38-2.50 (1H, m), 3.35-3.88 (1H, m), 3.98-4.18 (1H, m), 5.28-5.53 (1H, m), 6.00-6.20 (1H, m), 6.50-6.70 (1H, m), 6.90-7.00 (1H, m), 7.01-7.70 (3H, m), 8.05-8.20 (1H, m), 8.50-8.78 (1H, m), 11.95 (1H, s). MS: 371.03 [MH$^+$].

Step D: (R,E)-3-(5-(2-(2,5-difluorophenyl)pyrrolidin-1-yl)pyrazolo[1,5-a]pyrimidin-3-yl)-N-(2-hydroxyethyl)-acrylamide

48

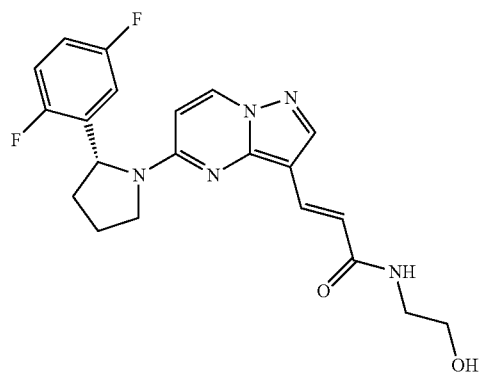

To a solution of (R,E)-3-(5-(2-(2,5-difluorophenyl)pyrrolidin-1-yl)pyrazolo[1,5-a]pyrimidin-3-yl)acrylic acid (400 mg, 1.080 mmol) in DMF (2.1 mL) were added HATU (616 mg, 1.62 mmol) and DIPEA (0.472 mL, 2.70 mmol) at room temperature. The mixture was stirred for 1 hour at room temperature. After addition of 2-aminoethanol (66.0 mg, 1.08 mmol) at room temperature, the reaction mixture was stirred at room temperature overnight. The mixture was diluted with DCM, washed with water twice and 1 N aq. NaOH, dried over Na$_2$SO$_4$, filtered and concentrated in vacuo. The residue was purified by column chromatography on SiO$_2$ (EtOAc:MeOH=20:1 to 10:1) to afford (R,E)-3-(5-(2-(2,5-difluorophenyl)pyrrolidin-1-yl)pyrazolo[1,5-a]pyrimidin-3-yl)-N-(2-hydroxyethyl)-acrylamide (279 mg, 62%) as a yellow solid. $^1$H-NMR (DMSO-d$_6$, Varian, 400 MHz): δ 1.82-2.12 (3H, m), 2.40-2.50 (1H, m), 3.20-3.30 (3H, m), 3.33-3.52 (2H, m), 3.56-3.92 (2H, m), 3.95-4.15 (1H, m), 5.23-5.62 (1H, m), 5.92-6.43 (1H, m), 6.53-6.83 (1H, m), 6.90-7.55 (4H, m), 7.90-8.20 (1H, m), 8.50-8.80 (1H, m). MS: 414.1 [MH$^+$].

Example 61: Preparation of Chemical Compound 49: (R,E)-3-(5-(2-(2,5-difluorophenyl)pyrrolidin-1-yl)pyrazolo[1,5-a]pyrimidin-3-yl)-1-morpholinoprop-2-en-1-one

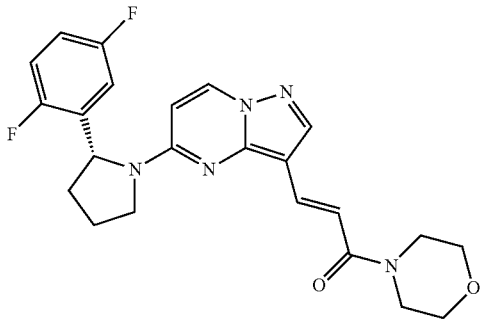

49

To a solution of (R,E)-3-(5-(2-(2,5-difluorophenyl)pyrrolidin-1-yl)pyrazolo[1,5-a]pyrimidin-3-yl)acrylic acid (3.00 g, 8.10 mmol) in DMF (16 mL) was added HATU (4.62 g, 12.1 mmol) and DIPEA (3.54 mL, 20.2 mmol) at room temperature. The mixture was stirred for 30 min at room temperature. After addition of morpholine (1.05 mL, 12.1 mmol) at room temperature, the reaction mixture was stirred at room temperature overnight. After concentration in vacuo, the residue was diluted with EtOAc, washed with water twice, 1 N aq. NaOH and brine successively, dried over $Na_2SO_4$, filtered and concentrated in vacuo. The residue was purified by column chromatography on $SiO_2$ (EtOAc only to EtOAc:MeOH=10:1) to afford (R,E)-3-(5-(2-(2,5-difluorophenyl)pyrrolidin-1-yl)pyrazolo[1,5-a]pyrimidin-3-yl)-1-morpholinoprop-2-en-1-one (2.13 g, 60%) as a pink solid. $^1$H-NMR (DMSO-$d_6$, Varian, 400 MHz): δ 1.86-2.40 (5H, m), 2.38-2.50 (1H, m), 3.40-3.70 (6H, m), 3.95-4.10 (1H, m), 5.24-5.40 (0.4H, m), 5.50-5.62 (0.6H, m), 5.95-6.18 (0.4H, m), 6.58-6.70 (0.6H, m), 6.71-6.85 (1H, m), 6.86-7.50 (5H, m), 8.05-8.30 (1H, m), 8.50-8.83 (1H, m). MS: 440.2 [MH$^+$].

Example 62: Preparation of Chemical Compound 50: (R,E)-3-(5-(2-(2,5-difluorophenyl)pyrrolidin-1-yl)pyrazolo[1,5-a]pyrimidin-3-yl)-1-(piperazin-1-yl)prop-2-en-1-one

50

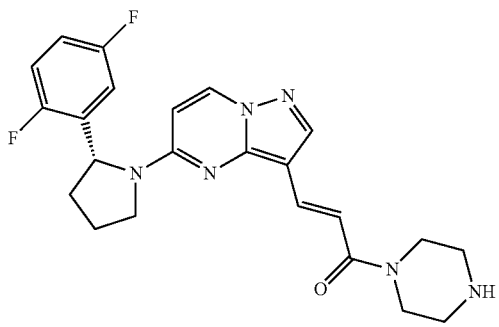

Step A: (R,E)-tert-butyl 4-(3-(5-(2-(2,5-difluorophenyl)pyrrolidin-1-yl)pyrazolo[1,5-a]pyrimidin-3-yl)acryloyl)-piperazine-1-carboxylate

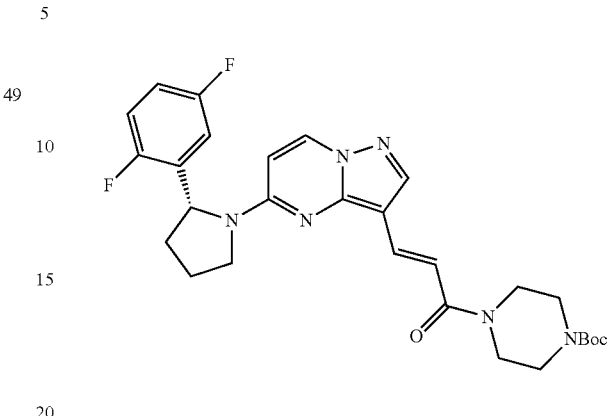

To a solution of (R,E)-3-(5-(2-(2,5-difluorophenyl)pyrrolidin-1-yl)pyrazolo[1,5-a]pyrimidin-3-yl)acrylic acid (400 mg, 1.08 mmol) in DMF (2.2 mL) were added HATU (616 mg, 1.62 mmol) and DIPEA (0.472 mL, 2.70 mmol) at room temperature. The mixture was stirred for 1 hour at room temperature. After addition of tert-butyl piperazine-1-carboxylate (201 mg, 1.08 mmol) at room temperature, the reaction mixture was stirred at room temperature overnight, while a yellow solid was formed. The mixture was diluted with DCM, washed with water twice and 1 N aq. NaOH, dried over $Na_2SO_4$, filtered and concentrated in vacuo. The residue was purified by column chromatography on $SiO_2$ (Hex:EtOAc=1:1 to DCM:EtOAc=1:10) to afford (R,E)-tert-butyl 4-(3-(5-(2-(2,5-difluorophenyl)pyrrolidin-1-yl)pyrazolo[1,5-a]pyrimidin-3-yl)acryloyl)-piperazine-1-carboxylate (413 mg, 71%) as a yellow solid. $^1$H-NMR (CDCl$_3$, Varian, 400 MHz): δ 1.48 (9H, s), 1.95-2.09 (3H, m), 2.43-2.78 (1H, m), 3.20-4.00 (10H, m), 5.17 and 5.75 (1H, s+s), 5.85 and 6.34 (1H, s+s), 6.67 (1H, s), 6.91 (1H, s), 7.05 (1H, s), 7.32 (1H, s), 7.50-8.32 (3H, m).

Step B: (R,E)-3-(5-(2-(2,5-difluorophenyl)pyrrolidin-1-yl)pyrazolo[1,5-a]pyrimidin-3-yl)-1-(piperazin-1-yl)prop-2-en-1-one

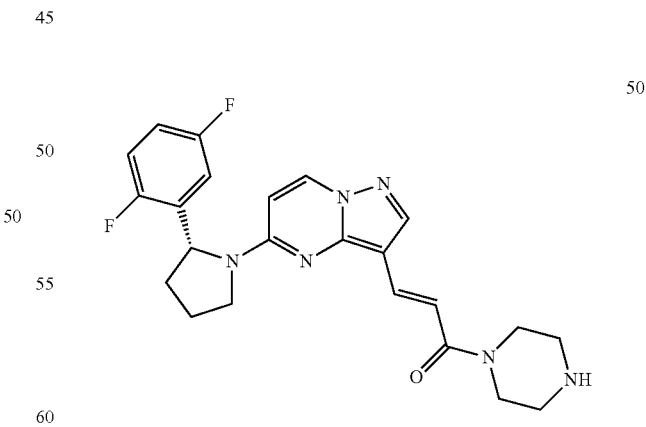

To a solution of (R,E)-tert-butyl 4-(3-(5-(2-(2,5-difluorophenyl)pyrrolidin-1-yl)pyrazolo[1,5-a]pyrimidin-3-yl)acryloyl)-piperazine-1-carboxylate (413 mg, 0.767 mmol) in DCM (3.8 mL) was added TFA (2.00 mL, 26.0 mmol) at room temperature. The reaction mixture was stirred for 1 hour at room temperature. After concentration in vacuo, the residue was diluted with DCM, basified with saturated aq. NaHCO₃, washed with brine, dried over Na₂SO₄, filtered and concentrated in vacuo. The residue was purified by column chromatography on SiO₂ (DCM:MeOH=10:1 to 5:1) to afford (R,E)-3-(5-(2-(2,5-difluorophenyl)pyrrolidin-1-yl)pyrazolo[1,5-a]pyrimidin-3-yl)-1-(piperazin-1-yl)prop-2-en-1-one (220 mg, 65%) as a pale yellow solid. ¹H-NMR (DMSO-d₆, Varian, 400 MHz): δ 1.86-2.40 (3H, m), 2.38-2.50 (1H, m), 2.64-2.80 (3H, m), 3.40-3.82 (7H, m), 3.95-4.10 (1H, m), 5.24-5.40 (0.4H, m), 5.50-5.62 (0.6H, m), 5.95-6.18 (0.4H, m), 6.58-6.70 (0.6H, m), 6.71-6.85 (1H, m), 6.86-7.00 (1H, m), 7.05-7.50 (3H, m), 8.05-8.25 (1H, m), 8.46-8.80 (1H, m). MS: 439.2 [MH⁺].

Example 63: Preparation of Chemical Compound 51: (R,E)-4-(3-(5-(2-(2,5-difluorophenyl)pyrrolidin-1-yl)pyrazolo[1,5-a]pyrimidin-3-yl)acryloyl)piperazin-2-one

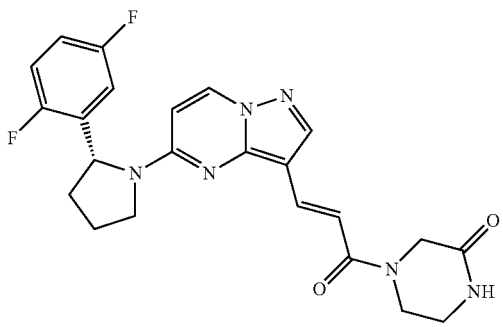

51

To a solution of (R,E)-3-(5-(2-(2,5-difluorophenyl)pyrrolidin-1-yl)pyrazolo[1,5-a]pyrimidin-3-yl)acrylic acid (50.0 mg, 0.162 mmol) in DMF (0.68 mL) were added HATU (62.0 mg, 0.162 mmol) and DIPEA (0.0570 mL, 0.324 mmol) at room temperature. The mixture was stirred for 1 hour at room temperature. After addition of piperazine-2-one (16.0 mg, 0.162 mmol) at room temperature, the reaction mixture was stirred at room temperature overnight, while a yellow solid was formed. The mixture was diluted with DCM, washed with water twice and 1 N aq. NaOH, dried over Na₂SO₄, filtered and concentrated in vacuo. The residue was purified by column chromatography on SiO₂ (Hex:EtOAc=1:1 to DCM:EtOAc=1:10) to afford (R,E)-4-(3-(5-(2-(2,5-difluorophenyl)pyrrolidin-1-yl)pyrazolo[1,5-a]pyrimidin-3-yl)acryloyl)piperazin-2-one (52.0 mg, 85%) as a yellow solid.

MS: 453.1 [MH⁺].

Example 64: Preparation of Chemical Compound 52: (E)-3-(5-((R)-2-(2,5-difluorophenyl)pyrrolidin-1-yl)pyrazolo[1,5-a]pyrimidin-3-yl)-1-(3-(2-hydroxypropan-2-yl)piperazin-1-yl)prop-2-en-1-one

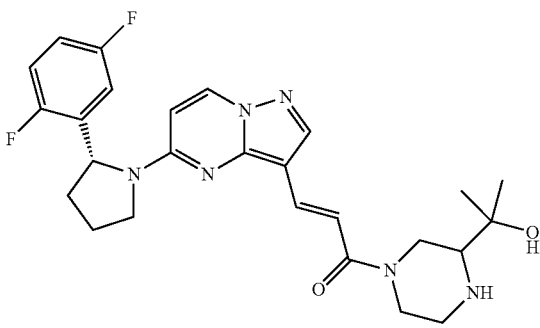

52

Step A: 1,4-bis(tert-butoxycarbonyl)piperazine-2-carboxylic acid

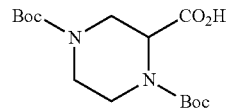

To a solution of 1,4-bis(tert-butoxycarbonyl)piperazine-2-carboxylic acid (5.00 g, 15.1 mmol) and Na₂CO₃ (5.79 g, 54.7 mmol) in water (49 mL) was added a solution of (t-Boc)₂O (7.20 mL, 31.0 mmol) in THF (31 mL) at room temperature. The reaction mixture was stirred at room temperature for 18 hours. The reaction mixture was carefully acidified with 5 N aq. HCl until pH=1 and then extracted with EtOAc twice. The combined organic layers were washed with brine, dried over Na₂SO₄, filtered and concentrated in vacuo to afford 1,4-bis(tert-butoxycarbonyl)piperazine-2-carboxylic acid (5.00 g, 100%) as a white solid, which was used for the next reaction without further purification. ¹H-NMR (CDCl₃, Varian, 400 MHz): δ 1.44 and 1.48 (18H, s and s), 2.83 (1H, br. s), 3.08-3.23 (2H, m), 3.84 (1H, dd, J=17.2, 13.2 Hz), 4.01 (1H, br. s), 4.52-4.60 (1H, m), 4.75 (1H, s), 9.56 (1H, br. s).

Step B: 1,4-di-tert-butyl 2-methyl piperazine-1,2,4-tricarboxylate

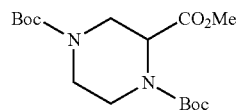

To a solution of 1,4-bis(tert-butoxycarbonyl)piperazine-2-carboxylic acid (4.88 g, 14.7 mmol) in DMF (49 mL) was added K₂CO₃ (2.65 g, 19.2 mmol), and the mixture cooled to 0° C. To the mixture was then slowly added methyl iodide (1.38 mL, 22.1 mmol). The reaction stirred was stirred at room temperature for 18 hours and quenched with saturated aqueous NH₄Cl (100 mL). The mixture was diluted with water and extracted with EtOAc twice. The combined organic layers were washed with water and brine, dried over Na₂SO₄, filtered and concentrated in vacuo. The residue was purified by column chromatography on SiO₂ (Hex: EtOAc=7:1 to 5:1 to 3:1) to afford 1,4-di-tert-butyl 2-methyl piperazine-1,2,4-tricarboxylate (5.09 g, 100%) as a pale brown viscous oil. ¹H-NMR (CDCl₃, Varian, 400 MHz): δ 1.44 (18H, s), 2.80 (1H, br. s), 3.12-3.24 (1H, m), 3.21 (1H, br. s), 3.74 (3H, s), 3.80-4.10 (2H, m), 4.48-4.73 (2H, m).

Step C: di-tert-butyl 2-(2-hydroxypropan-2-yl)piperazine-1,4-dicarboxylate

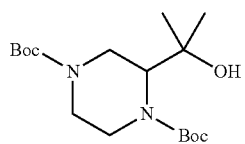 [SMILES: CC(C)(C)OC(=O)N1CCN(C(=O)OC(C)(C)C)C(C(C)(C)O)C1]

To a solution of 1,4-di-tert-butyl 2-methyl piperazine-1,2,4-tricarboxylate (5.09 g, 14.7 mmol) in dry THF (49 mL) was added methylmagnesium bromide (3.0 M in THF and tol, 31.7 mL, 44.3 mmol) at 0° C. The reaction mixture was stirred at room temperature for 18 hours. After quenched with saturated aq. NH₄Cl, the mixture was diluted with water and extracted with EtOAc twice. The combined organic layers were washed with brine, dried over Na₂SO₄, filtered and concentrated in vacuo. The residue was purified by column chromatography on SiO₂ (Hex:EtOAc=5:1 to 3:1 to 2:1) to afford di-tert-butyl 2-(2-hydroxypropan-2-yl)piperazine-1,4-dicarboxylate (2.47 g, 48%) as a colorless viscous oil. ¹H-NMR (CDCl₃, Varian, 400 MHz): δ 1.21 (3H, s), 1.31 (3H, s), 1.46 (18H, s), 3.01-3.38 (4H, m), 3.79-4.21 (4H, m).

Step D: 2-(piperazin-2-yl)propan-2-ol 2HCl

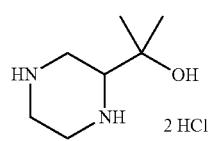

To a solution of di-tert-butyl 2-(2-hydroxypropan-2-yl) piperazine-1,4-dicarboxylate (2.47 g, 7.17 mmol) in MeOH (23 mL) was added HCl (4 M solution in dioxane, 8.96 mL, 35.9 mmol) at 0° C. The reaction mixture was stirred at room temperature for 5 hours, while a solid was precipitated. After concentration in vacuo, the residual solid was dried under vacuum to afford 2-(piperazin-2-yl)propan-2-ol 2HCl (1.17 g, 75%) as a pale brown solid, which was used for the next reaction without further purification. ¹H-NMR (DMSO-d₆, Varian, 400 MHz): δ 1.19 (3H, s), 1.25 (3H, s), 2.97 (1H, t, J=13.6 Hz), 3.20-3.34 (3H, m), 3.34-3.48 (2H, m), 3.53-3.56 (2H, m), 9.14 (1H, br. s), 9.60 (1H, br. s), 9.89 (2H, br. s).

Step E: (E)-3-(5-((R)-2-(2,5-difluorophenyl)pyrrolidin-1-yl)pyrazolo[1,5-a]pyrimidin-3-yl)-1-(3-(2-hydroxypropan-2-yl)piperazin-1-yl)prop-2-en-1-one

52

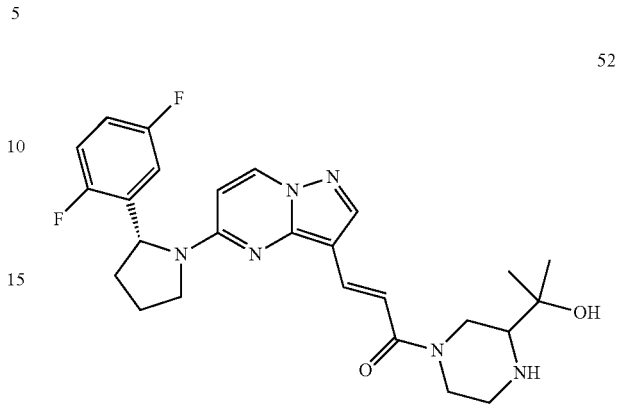

To a solution of (R,E)-3-(5-(2-(2,5-difluorophenyl)pyrrolidin-1-yl)pyrazolo[1,5-a]pyrimidin-3-yl)acrylic acid (67.0 mg, 0.181 mmol) in DMF (1.2 mL) was added HATU (89.0 mg, 0.235 mmol) and DIPEA (0.142 mL, 0.814 mmol) at 0° C. The mixture was stirred for 1 hour at room temperature and cooled to 0° C. After addition of 2-(piperazin-2-yl) propan-2-ol 2HCl (47.0 mg, 0.217 mmol) at 0° C., the reaction mixture was stirred at room temperature for 2 hours. After concentration in vacuo, the residue was diluted with DCM, washed with water and brine, dried over Na₂SO₄, filtered and concentrated in vacuo. The residue was purified by column chromatography on SiO₂ (DCM:MeOH=20:1 to 10:1) to afford (E)-3-(5-((R)-2-(2,5-difluorophenyl)pyrrolidin-1-yl)pyrazolo[1,5-a]pyrimidin-3-yl)-1-(3-(2-hydroxypropan-2-yl)piperazin-1-yl)prop-2-en-1-one (64.0 mg, 71%) as a pale yellow solid. MS: 468.1 [MH⁺]

Example 65: Preparation of Chemical Compound 53: (R,E)-3-(5-(2-(2,5-difluorophenyl)pyrrolidin-1-yl)pyrazolo[1,5-a]pyrimidin-3-yl)-1-(4-methylpiperazin-1-yl)prop-2-en-1-one

53

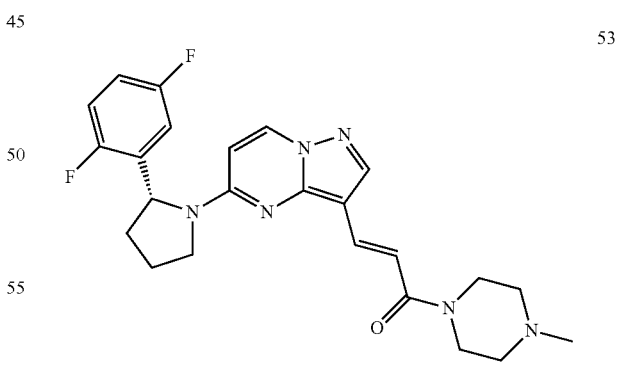

A mixture of (R,E)-3-(5-(2-(2,5-difluorophenyl)pyrrolidin-1-yl)pyrazolo[1,5-a]pyrimidin-3-yl)-1-(piperazin-1-yl) prop-2-en-1-one (50.0 mg, 0.114 mmol) and formaldehyde (water solution 37%, 0.011 mL, 0.148 mmol) in MeOH (1.1 mL) was stirred at room temperature for 10 min. After addition sodium cyanoborohydride (10.7 mg, 0.171 mmol) in a one portion, the reaction mixture was stirred for 1 hour at room temperature and then quenched with 2 N aq. NaOH (1.42 mL, 2.85 mmol). The mixture was stirred for 30 min at room temperature and extracted with DCM twice. The combined organic layers was dried over Na$_2$SO$_4$, filtered and concentrated in vacuo. The residue was purified by column chromatography on SiO$_2$ (DCM:MeOH=20:1 to 10:1) to afford (R,E)-3-(5-(2-(2,5-difluorophenyl)pyrrolidin-1-yl)pyrazolo[1,5-a]pyrimidin-3-yl)-1-(4-methylpiperazin-1-yl)prop-2-en-1-one (44.0 mg, 85%) as a yellow solid. $^1$H-NMR (CDCl$_3$, Varian, 400 MHz): δ 1.65-1.85 (4H, m), 2.34 (3H, s), 2.40-2.52 (5H, m), 3.40-4.20 (6H, m), 5.20 (0.5H, s), 5.70-5.92 (1H, m), 6.38 (0.5H, s), 6.69 (1H, s), 6.82-7.16 (2H, m), 7.60-7.82 (1H, m), 7.95 (1H, s), 8.10-8.40 (1H, m). MS: 453.1 [MH$^+$].

Example 66: Preparation of Chemical Compound 54: (R,E)-3-(5-(2-(2,5-difluorophenyl)pyrrolidin-1-yl)pyrazolo[1,5-a]pyrimidin-3-yl)-1-(4-ethylpiperazin-1-yl)prop-2-en-1-one

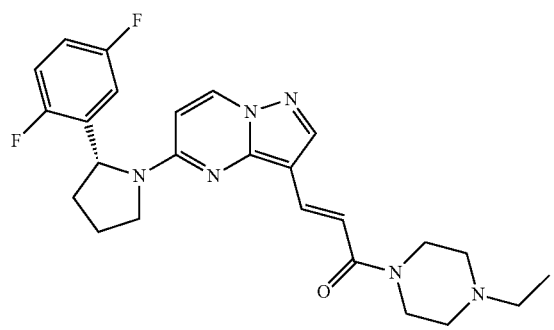

54

A mixture of (R,E)-3-(5-(2-(2,5-difluorophenyl)pyrrolidin-1-yl)pyrazolo[1,5-a]pyrimidin-3-yl)-1-(piperazin-1-yl)prop-2-en-1-one (100 mg, 0.228 mmol) and acetaldehyde (129 μL, 0.228 mmol) in MeOH (1.1 mL) was stirred at room temperature for 10 min. After addition of sodium triacetoxyhydroborate (73.0 mg, 0.342 mmol) followed by acetic acid (261 μL, 4.56 mmol), the reaction mixture was stirred for 1 hour at room temperature and then quenched with 2 N aq. NaOH (1.42 mL, 2.85 mmol). The mixture was stirred for 30 min at room temperature and extracted with DCM twice. The combined organic layers was dried over Na$_2$SO$_4$, filtered and concentrated in vacuo. The residue was purified by column chromatography on SiO$_2$ (DCM:MeOH=20:1 to 15:1) to afford (R,E)-3-(5-(2-(2,5-difluorophenyl)pyrrolidin-1-yl)pyrazolo[1,5-a]pyrimidin-3-yl)-1-(4-ethylpiperazin-1-yl)prop-2-en-1-one (69.5 mg, 63%) as a yellow solid. $^1$H-NMR (DMSO-d$_6$, Varian, 400 MHz): δ 1.03 (3H, t, J=7.2 Hz), 1.83-2.00 (2H, m), 2.02-2.10 (1H, m), 2.30-2.48 (6H, m), 3.40-3.70 (4H, m). 4.03 (2H, q, J=7.2 Hz), 5.35 and 5.59 (1H, s+s), 6.01 and 6.64 (1H, s+s), 6.76-6.79 (1H, m), 7.05-7.21 (1H, m), 7.23-7.48 (2H, m), 8.13-8.23 (1H, m), 8.54 and 8.74 (1H, s+s). MS: 467.1 [MH$^+$].

Example 67: Preparation of Chemical Compound 55: (R,E)-3-(5-(2-(2,5-difluorophenyl)pyrrolidin-1-yl)pyrazolo[1,5-a]pyrimidin-3-yl)-1-(4-isopropylpiperazin-1-yl)prop-2-en-1-one

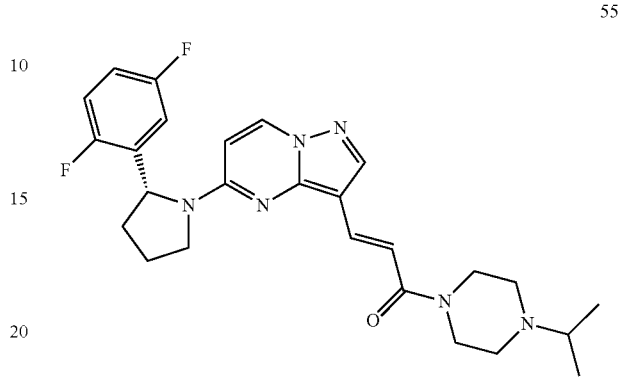

55

A mixture of (R,E)-3-(5-(2-(2,5-difluorophenyl)pyrrolidin-1-yl)pyrazolo[1,5-a]pyrimidin-3-yl)-1-(piperazin-1-yl)prop-2-en-1-one (50.0 mg, 0.114 mmol) and acetone (0.025 mL, 0.342 mmol) in MeOH (1.1 mL) was stirred at room temperature for 10 min. After addition of sodium cyanoborohydride (10.7 mg, 0.171 mmol) in a one portion, the reaction mixture was stirred for 30 hours and quenched with 2 N aq. NaOH (1.4 mL, 2.85 mmol). The mixture was stirred for 30 min at room temperature and extracted with DCM twice. The combined organic layers was dried over Na$_2$SO$_4$, filtered and concentrated in vacuo. The residue was purified by column chromatography on SiO$_2$ (DCM:MeOH=20:1 to 10:1) to afford (R,E)-3-(5-(2-(2,5-difluorophenyl)pyrrolidin-1-yl)pyrazolo[1,5-a]pyrimidin-3-yl)-1-(4-isopropylpiperazin-1-yl)prop-2-en-1-one (46.3 mg, 84%) as a yellow solid. $^1$H-NMR (CDCl$_3$, Varian, 400 MHz): δ 1.08 (6H, d, J=6.8 Hz), 1.95-2.36 (4H, m), 2.40-2.50 (5H, m), 2.70-2.78 (1H, m), 3.40-4.20 (6H, m), 5.18 (0.5H, s), 5.65-5.92 (1H, m), 6.34 (0.5H, s), 6.69 (1H, s), 6.82-7.20 (2H, m), 7.60-7.82 (1H, m), 7.95 (1H, s), 8.10-8.40 (1H, m). MS: 481.1 [MH$^+$].

Example 68: Preparation of Chemical Compound 56: (R,E)-1-(1,4-diazepan-1-yl)-3-(5-(2-(2,5-difluorophenyl)pyrrolidin-1-yl)pyrazolo[1,5-a]pyrimidin-3-yl)prop-2-en-1-one

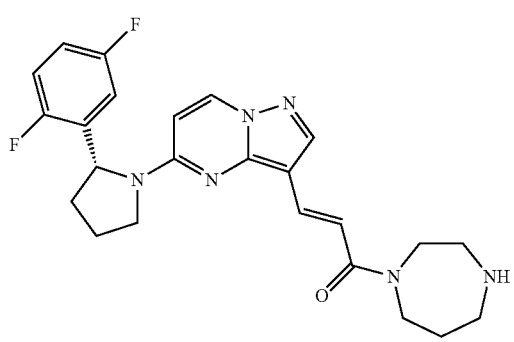

56

Step A: tert-butyl 1,4-diazepane-1-carboxylate

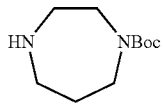

To a solution of 1,4-diazepane (1.00 g, 9.98 mmol) in DCM (22 mL) was added a solution of (t-Boc)$_2$O (1.08 g, 4.99 mmol) in DCM (11 mL) at room temperature. The reaction mixture was stirred at room temperature overnight and concentrated in vacuo. The residue was dissolved in Et$_2$O and extracted with 10% aq. citric acid solution. The aqueous layer was basified with solid K$_2$CO$_3$ until pH 11 and then extracted with EtOAc twice. The combined organic layers were dried over Na$_2$SO$_4$, filtered and concentrated in vacuo to afford tert-butyl 1,4-diazepane-1-carboxylate (795 mg, 88%) as a yellow oil, which was used for the next reaction without further purification. $^1$H-NMR (CDCl$_3$, Varian, 400 MHz): δ 1.47 (9H, s) 1.59 (1H, br. s), 1.74-1.80 (2H, m), 2.84-2.93 (4H, m), 3.39-3.51 (4H, m).

Step B: (R,E)-tert-butyl 4-(3-(5-(2-(2,5-difluorophenyl)pyrrolidin-1-yl)pyrazolo[1,5-a]pyrimidin-3-yl)acryloyl)-1,4-diazepane-1-carboxylate

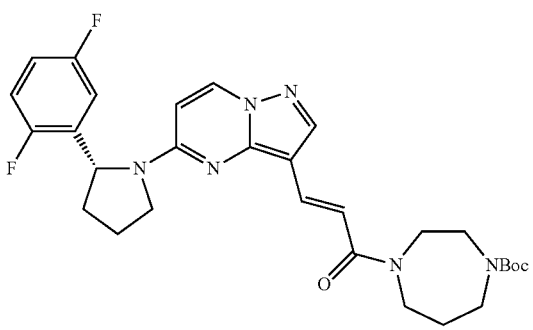 [SMILES: CC(C)(C)OC(=O)N1CCCN(C(=O)/C=C/c2cnn3ccc(N4CCC[C@@H]4c4cc(F)ccc4F)nc23)CC1]

To a solution of (R,E)-3-(5-(2-(2,5-difluorophenyl)pyrrolidin-1-yl)pyrazolo[1,5-a]pyrimidin-3-yl)acrylic acid (100 mg, 0.270 mmol) in DMF (1.8 mL) were added HATU (154 mg, 0.405 mmol), DIPEA (118 µl, 0.675 mmol) and tert-butyl 1,4-diazepane-1-carboxylate (65.0 mg, 0.324 mmol) at room temperature. The reaction mixture was stirred at room temperature overnight and diluted with EtOAc. The mixture was washed with saturated aq. NH$_4$Cl and brine, dried over Na$_2$SO$_4$, filtered and concentrated in vacuo. The residue was purified by column chromatography on SiO$_2$ (Hex:EtOAc=1:4 to 1:5) to afford (R,E)-tert-butyl 4-(3-(5-(2-(2,5-difluorophenyl)pyrrolidin-1-yl)pyrazolo[1,5-a]pyrimidin-3-yl)acryloyl)-1,4-diazepane-1-carboxylate (137 mg, 92%) as a yellow solid. $^1$H-NMR (DMSO-d$_6$, Varian, 400 MHz): δ 1.12-1.43 (9H, m), 1.55-1.80 (2H, m), 1.81-2.00 (3H, m), 2.32-2.50 (1H, m), 2.19-3.30 (3H, m), 3.38-3.88 (7H, m), 4.00-4.10 (1H, m), 5.32 and 5.95 (1H, s+s), 6.11 and 3.64 (1H, s+s), 6.67 (1H, s), 6.91 (1H, s), 7.05 (1H, s), 7.32 (1H, s), 7.50-8.32 (3H, m).

Step C: (R,E)-1-(1,4-diazepan-1-yl)-3-(5-(2-(2,5-difluorophenyl)pyrrolidin-1-yl)pyrazolo[1,5-a]pyrimidin-3-yl)prop-2-en-1-one

56

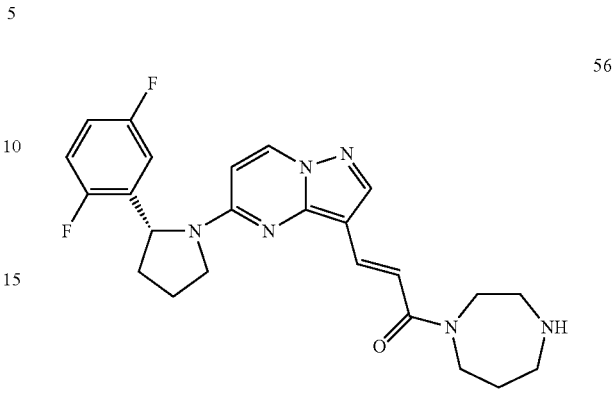

To a solution of (R,E)-tert-butyl 4-(3-(5-(2-(2,5-difluorophenyl)pyrrolidin-1-yl)pyrazolo[1,5-a]pyrimidin-3-yl)acryloyl)-1,4-diazepane-1-carboxylate (137 mg, 0.283 mmol) in DCM (2.5 mL) was added TFA (382 µl g, 4.96 mmol) at 0° C. The reaction mixture was stirred for 2 hours at room temperature and concentrated in vacuo. The residue was dissolved in water, neutralized with saturated aq. NaHCO$_3$ and washed with EtOAc. The separated aqueous layer was extracted with DCM twice. The combined organic layers (only DCM) were dried over Na$_2$SO$_4$, filtered and concentrated in vacuo to afford (R,E)-1-(1,4-diazepan-1-yl)-3-(5-(2-(2,5-difluorophenyl)pyrrolidin-1-yl)pyrazolo[1,5-a]pyrimidin-3-yl)prop-2-en-1-one (48.1 mg, 42%) as a pale yellow solid. MS: 453.1 [MH$^+$].

Example 69: Preparation of Chemical Compound 57: (R,E)-3-(5-(2-(2,5-difluorophenyl)pyrrolidin-1-yl)pyrazolo[1,5-a]pyrimidin-3-yl)-1-(4-hydroxypiperidin-1-yl)prop-2-en-1-one

57

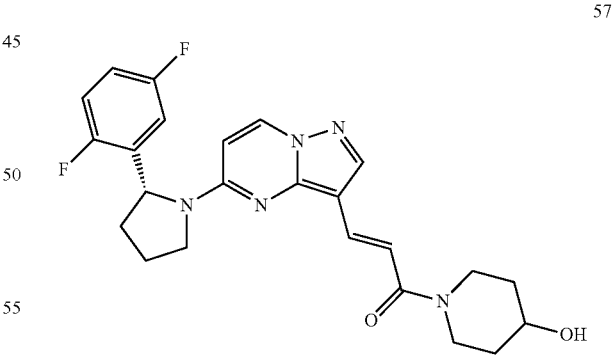

To a solution of (R,E)-3-(5-(2-(2,5-difluorophenyl)pyrrolidin-1-yl)pyrazolo[1,5-a]pyrimidin-3-yl)acrylic acid (100 mg, 0.270 mmol) in DMF (1.35 mL) was added HATU (0.133 g, 0.351 mmol) and DIPEA (0.118 mL, 0.675 mmol) at 0° C. The mixture was stirred for 1 hour at room temperature and cooled to 0° C. After addition of piperidin-4-ol (0.0330 g, 0.324 mmol) at room temperature, the reaction mixture was stirred at room temperature for 2 hours. After concentration in vacuo, the residue was diluted with DCM, washed with water and saturated aq. NaHCO₃, dried over Na₂SO₄, filtered and concentrated in vacuo. The residue was purified by column chromatography on SiO₂ (EtOAc only to DCM:MeOH 20:1 to 10:1) to afford (R,E)-3-(5-(2-(2,5-difluorophenyl)pyrrolidin-1-yl)pyrazolo[1,5-a]pyrimidin-3-yl)-1-(4-hydroxypiperidin-1-yl)prop-2-en-1-one (120 mg, 98%) as a yellow foam. MS: 454.1 [MH⁺]

Example 70: Preparation of Chemical Compound 58: (R,E)-3-(5-(2-(2,5-difluorophenyl)pyrrolidin-1-yl)pyrazolo[1,5-a]pyrimidin-3-yl)-1-(4-hydroxy-4-methylpiperidin-1-yl)prop-2-en-1-one

58

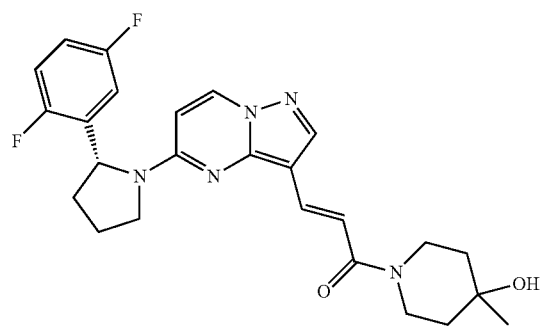

Step A: tert-butyl 4-hydroxy-4-methylpiperidine-1-carboxylate

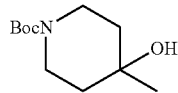

To a solution of tert-butyl 4-oxopiperidine-1-carboxylate (1.00 g, 5.02 mmol) in dry THF (25 mL) was added methylmagnesium chloride (2.17 mL, 6.52 mmol) at −78° C. The reaction mixture was slowly warmed to 0° C. with stirring for 2 hours and quenched with saturated aq. NH₄Cl. The mixture was extracted with EtOAc twice, and the combined organic layers were dried over Na₂SO₄, filtered and concentrated in vacuo to afford tert-butyl 4-hydroxy-4-methylpiperidine-1-carboxylate (1.08 g, >99%) as a colorless oil, which was used for the next reaction without further purification. ¹H-NMR (CDCl₃, Varian, 400 MHz): δ 1.27 (3H, s), 1.46 (9H, s), 1.50-1.58 (4H, m), 3.20-3.27 (2H, m), 3.64-3.76 (2H, m).

Step B: 4-methylpiperidin-4-ol

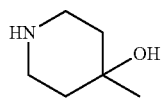

To a solution of tert-butyl 4-hydroxy-4-methylpiperidine-1-carboxylate (1.08 g, 5.02 mmol) in DCM was added TFA (1.93 mL, 25.1 mmol) at 0° C. The reaction mixture was stirred at room temperature for 12 hours. After basified with saturated aq. NaHCO₃, the separated aqueous layer was concentrated in vacuo (The compound was dissolved in aqueous layer). The residue was diluted with MeOH and then filtered through a SiO₂ pad while washing with MeOH. The filtrate was concentrated in vacuo to afford 4-methylpiperidin-4-ol (235 mg, 40%) as a viscous oil, which was used for the next reaction without further purification.

Step C: (R,E)-3-(5-(2-(2,5-difluorophenyl)pyrrolidin-1-yl)pyrazolo[1,5-a]pyrimidin-3-yl)-1-(4-hydroxy-4-methylpiperidin-1-yl)prop-2-en-1-one

58

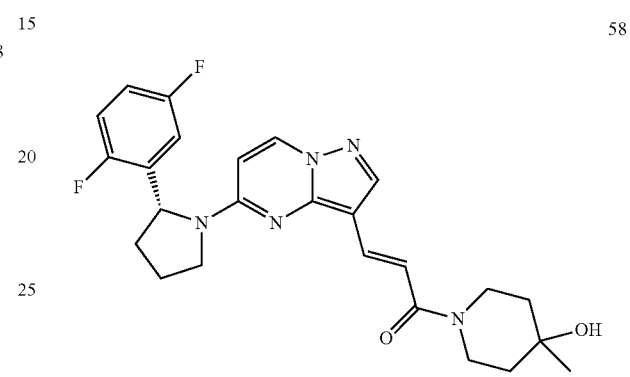

To a solution of (R,E)-3-(5-(2-(2,5-difluorophenyl)pyrrolidin-1-yl)pyrazolo[1,5-a]pyrimidin-3-yl)acrylic acid (100 mg, 0.270 mmol) in DMF (1.35 mL) was added HATU (133 mg, 0.351 mmol) and DIPEA (0.165 mL, 0.945 mmol) at 0° C. The mixture was stirred for 1 hour at room temperature and cooled to 0° C. After addition of crude 4-methylpiperidin-4-ol (0.155 g, 1.35 mmol) at room temperature, the reaction mixture was stirred at room temperature for 4 hours. After concentration in vacuo, the residue was diluted with DCM, washed with water and saturated aq. NaHCO₃, dried over Na₂SO₄, filtered and concentrated in vacuo. The residue was purified by column chromatography on SiO₂ (EtOAc only to DCM:MeOH 20:1) to afford (R,E)-3-(5-(2-(2,5-difluorophenyl)pyrrolidin-1-yl)pyrazolo[1,5-a]pyrimidin-3-yl)-1-(4-hydroxy-4-methylpiperidin-1-yl)prop-2-en-1-one (126 mg, 100%) as a pale yellow foam. MS: 468.1 [MH⁺].

Example 71: Preparation of Chemical Compound 59: (E)-3-(5-((R)-2-(2,5-difluorophenyl)pyrrolidin-1-yl)pyrazolo[1,5-a]pyrimidin-3-yl)-1-((R)-3-hydroxypyrrolidin-1-yl)prop-2-en-1-one

59

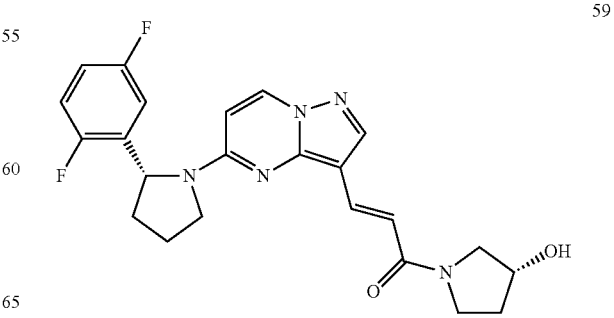

To a solution of (R,E)-3-(5-(2-(2,5-difluorophenyl)pyrrolidin-1-yl)pyrazolo[1,5-a]pyrimidin-3-yl)acrylic acid (70.0 mg, 0.189 mmol) in DMF (1.5 mL) were added HATU (108 mg, 0.284 mmol), DIPEA (99.0 μl, 0.567 mmol) and (R)-pyrrolidin-3-ol (49.0 mg, 0.567 mmol).

The reaction mixture was stirred at room temperature overnight and diluted with EtOAc. The mixture was washed with saturated aq. NH₄Cl and brine, dried over Na₂SO₄, filtered and concentrated in vacuo. The residue was purified by column chromatography on SiO₂ (EtOAc:MeOH=30:1 to 10:1) to afford (E)-3-(5-((R)-2-(2,5-difluorophenyl)pyrrolidin-1-yl)pyrazolo[1,5-a]pyrimidin-3-yl)-1-((R)-3-hydroxypyrrolidin-1-yl)prop-2-en-1-one (15.0 mg, 18%) as a yellow solid. MS: 440.2 [MH⁺].

Example 72: Preparation of Chemical Compound 60: (E)-3-(5-((R)-2-(2,5-difluorophenyl)pyrrolidin-1-yl)pyrazolo[1,5-a]pyrimidin-3-yl)-1-((S)-3-hydroxypyrrolidin-1-yl)prop-2-en-1-one

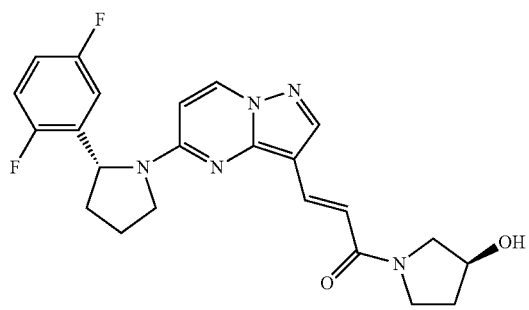

To a solution of (R,E)-3-(5-(2-(2,5-difluorophenyl)pyrrolidin-1-yl)pyrazolo[1,5-a]pyrimidin-3-yl)acrylic acid (70.0 mg, 0.189 mmol) in DMF (1.5 mL) were added HATU (108 mg, 0.284 mmol), DIPEA (99.0 μl, 0.567 mmol) and (S)-pyrrolidin-3-ol (49.0 mg, 0.567 mmol). The reaction mixture was stirred at room temperature overnight and diluted with EtOAc. The mixture was washed with saturated aq. NH₄Cl and brine, dried over Na₂SO₄, filtered and concentrated in vacuo. The residue was purified by column chromatography on SiO₂ (EtOAc:MeOH=30:1 to 10:1) to afford (E)-3-(5-((R)-2-(2,5-difluorophenyl)pyrrolidin-1-yl)pyrazolo[1,5-a]pyrimidin-3-yl)-1-((S)-3-hydroxypyrrolidin-1-yl)prop-2-en-1-one (15.0 mg, 18%) as a yellow solid. MS: 440.2 [MH⁺].

Example 73: Preparation of Chemical Compound 61: 3-(5-(2-(2,5-difluorophenyl)pyrrolidin-1-yl)pyrazolo[1,5-a]pyrimidin-3-yl)-1-morpholinoprop-2-yn-1-one

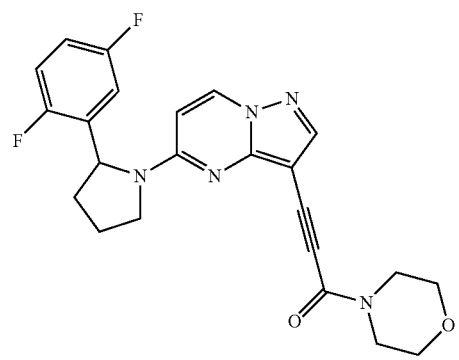

A solution of 5-(2-(2,5-difluorophenyl)pyrrolidin-1-yl)-3-iodopyrazolo[1,5-a]pyrimidine (456 mg, 1.070 mmol), 1-morpholinoprop-2-yn-1-one (223 mg, 1.60 mmol) and PdCl₂(PPh₃)₂ (75.0 mg, 0.107 mmol) and copper(I) iodide (20.0 mg, 0.107 mmol) in TEA (5.0 mL) and THF (5.0 mL) was stirred at 70° C. for 12 hours. After concentration in vacuo, the residue was purified by column chromatography on SiO₂ (Hex:EtOAc=1:1 to EtOAc only) to afford 3-(5-(2-(2,5-difluorophenyl)pyrrolidin-1-yl)pyrazolo[1,5-a]pyrimidin-3-yl)-1-morpholinoprop-2-yn-1-one (45.7 mg, 9.7%) as an orange solid. ¹H-NMR (CDCl₃, Varian, 400 MHz): δ 2.05-2.20 (3H, m), 2.24-2.60 (1H, m), 3.58-4.20 (10H, m), 5.18 and 5.73 (1H, s+s), 5.88 and 6.36 (1H, s+s), 6.69 (1H, br. s), 6.94 (1H, br. s), 7.13 (1H, br. s), 7.44-7.77 (1H, m), 8.15-8.50 (1H, m). MS: 438.3 [MH⁺].

Example 74: TRK A, B & C Kinase Assay

ADP-Glo assay kit was purchased from Promega. poly (Glu, Tyr), Magnesium sulfate, Bovine serum albumin (BSA) and dimethylsulfoxide(DMSO) were purchased from Sigma-Aldrich. Tris-HCl buffer was purchased from BD Gentest. HTRF KinEASE-TK kit was purchased from cisbio. TRK A, B & C kinase was purchased from Carna bioscience.

Kinase assay was performed for Chemical Compounds 1-61 using two methods using luminescent ADP-Glo assay kit (Promega) and HTRF KinEASE-TK assay kit (cisbio). The luminescent ADP-Glo assay kit (Promega) measures ADP formed from a kinase reaction. ADP converted into ATP, which is then converted into light by Ultra-Glo luciferase. The HTRF KinEASE-TK assay kit (cisbio) measures tyrosine kinase activities using one substrate and a universal detection system.

ADP-Glo Assay Kit (Promega)

The protein kinase assay was performed for Chemical Compounds 1-61 at 30hemical Compounds 1-61 using one substrate and a universal detection system.tion. ADP converted into ATP, which ich. cl concentrations are 0.4 ng/ul of TrKA, 0.5 ng/ul of TrKB and 3 ng/ul of TrKC, respectively), 5 μL of 1 ug/ul stock solution of poly(glu, Tyr), 5 μL of compounds or assay buffer, 5 μL of ATP (125 μM stock solution).

The assay was started by incubating the reaction mixture in a 96-well plate at 30° C. for 1 hr. After the incubation, the assay was terminated by the addition of 25 plate at 30° C. for 1 hr. verted into ATP, which ich. cl concentrations are 0.4 ng/ul of TrKA, 0.5 ng/ul Then 50 e incuKinase Detection Reagent was added, and the 96-well plate was shaken and then incubated for additional 30 min at ambient temperature. The 96-well reaction plate was then read on an Enspire plate reader. The IC50 values were derived through a curve fitting using SigmaPlot.

HTRF KinEASE-TK Assay Kit (Cisbio)

The HTRF KinEASE-TK assay was performed for Chemical Compounds 1-61 in 384-well low volume microplate (Greiner). The HTRF KinEASE-TK assay format involves the two steps. The first step is kinase reaction step. This kinase reaction step was performed at RT (room temperature) in final volume of 10 ul according to the following assay reaction recipe: 10 ul of kinase mixture (Kinase (2 ul)+ATP (2 ul)+Substrate (2 ul)+Compound (4 ul)). Kinase final concentrations were 0.3 ng/ul of TRKA, 0.1 ng/ul of TRKB, 0.03 ng/ul of TRKC, respectively. ATP final concentrations were 14.7 uM (TRKA), 4.77 uM (TRKB), 25.6 uM (TRKC) respectively. TK-substrate final concentration was 0.3 ng/ul. The mixtures exposed to Dose response concentration (DRC) compound from 0 to 100 nM for 40 min. During the kinase reaction step, the kinase reaction was started by the addition of ATP. Kinase phosphorylates the substrate.

The second is detection step. 10 ul of detection reagents (5 ul Sa-XL 665 in EDTA+5 ul TK Antibody-Eu in EDTA) was added to kinase mixture. This step was performed at room temperature for 1 hr. The detection reagent detects phosphorylated substrates.

Finally 384-well reaction plate was then read on FlexStation 3 machine. The fluorescence was measured at 620 nm (Cryptate) and 665 nm (XL665). A ratio is calculated $(655/620) \times 10^4$ for each well. The IC50 value was derived through a curve fitting using GraphPad Prism. Table 1 below includes the results of the assays.

Example 74: Cell Proliferation Assays

Doxorubicin was purchased from Sigma Aldrich (D1515). All compounds were diluted in DMSO (Sigma Aldrich, D2650). AlamarBlue® cell viability reagent was purchased from Thermo Scientific (88952). CellTiter 96® AQueous One Solution Cell proliferation assay was purchased from Promega. KM12-luc cells were obtained from JCRB (National Institute of Health Sciences, Tokyo, Japan). They were maintained in DMEM medium (GIB-11965-118) supplemented with 10% fetal bovine serum (Gibco, 16000-044) and MEM Non-Essential Amino Acids Solution (Thermo Scientific, 11140-050). TF-1 cells were obtained from ATCC. They were maintained in RPMI medium (GIB-A10491) supplemented with 10% fetal bovine serum (Gibco, 16000-044), GM-CSF (Thermo Scientific, 11140-050), and β-NGF (R&D systems). Trypsin/EDTA was purchased from Gibco (GIB-25300-054, 0.05%). 96-well plates were purchased from Corning Inc.

Cell Proliferation Assay

The proliferation assay was performed for Chemical Compounds 1-61 s in media supplemented with 10% FBS, using AlamarBlue® cell viability reagent or CellTiter 96® AQueous One Solution Cell proliferation assay kit. Cells were cultured in humidified 37° C. incubator with 5% CO2. To evaluate the antiproliferation activity of compounds, TF-1 cells were adjusted to GM-CSF free media (RPMI, 10% FBS, and 1% penicillin-streptomycin) for 16 hr and were seeded in 96-well plates at 30,000 cells/well with medium (RPMI, 10% FBS, 1% penicillin-streptomycin and 10 ng/ml human β-NGF). KM12-luc were seeded at 10,000 cells per well into 96-well plates. After overnight incubation, serial dilutions of compounds were added to triplicate wells, and cells were exposed for 72 hours. The final concentration of DMSO was adjusted to 0.5% in media. Quantitation of cell growth was assessed using two kinds of reagent. 20 ul of AlamarBlue® reagent in an amount equal to 10% of the culture volume was added to each well and were incubated in humidified 37° C. incubator with 5% CO2 for 2 hr. Otherwise, 20 ul of CellTiter 96® reagent was added to each well and were incubated in the same conditions as previously described. Data were plotted, and GI50 values were calculated using GraphPad software. Table 1 below includes the results of the assays.

TABLE 1

| Chemical Compound No. | Structure | IC$_{50}$ (nM) | | |
| --- | --- | --- | --- | --- |
| | | Enzymatic assay | Cell-based assay (TF-1) | Cell-based assay (KM12) |
| 1 | 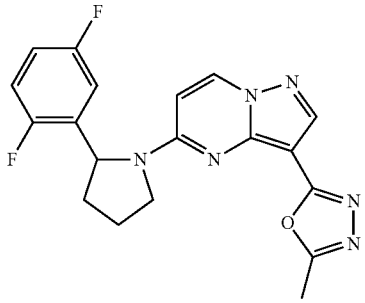 [SMILES: Cc1nnc(-c2cnn3ccc(N4CCCC4c4cc(F)ccc4F)nc23)o1] | <10 | <100 | <100 |

TABLE 1-continued

| Chemical Compound No. | Structure | IC$_{50}$ (nM) | | |
|---|---|---|---|---|
| | | Enzymatic assay | Cell-based assay (TF-1) | Cell-based assay (KM12) |
| 2 | 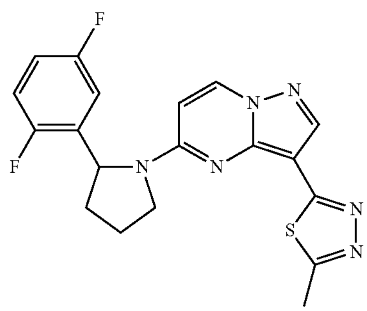 [SMILES: Cc1nnc(-c2cnn3ccc(N4CCCC4c4cc(F)ccc4F)nc23)s1] | <10 | <10 | <100 |
| 3 | 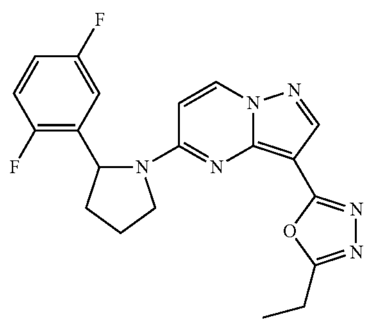 [SMILES: CCc1nnc(-c2cnn3ccc(N4CCCC4c4cc(F)ccc4F)nc23)o1] | <10 | <10 | <100 |
| 4 | 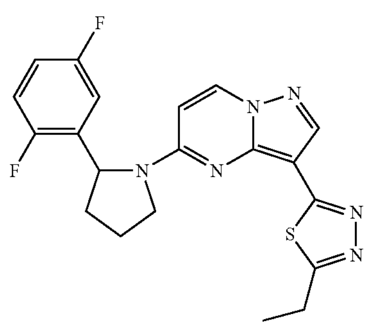 [SMILES: CCc1nnc(-c2cnn3ccc(N4CCCC4c4cc(F)ccc4F)nc23)s1] | <10 | <10 | <100 |
| 5 | 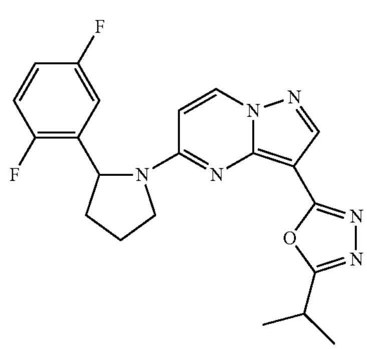 [SMILES: CC(C)c1nnc(-c2cnn3ccc(N4CCCC4c4cc(F)ccc4F)nc23)o1] | <10 | <10 | <10 |

TABLE 1-continued
| Chemical Compound No. | Structure | IC$_{50}$ (nM) | | |
|---|---|---|---|---|
| | | Enzymatic assay | Cell-based assay (TF-1) | Cell-based assay (KM12) |
| 6 | 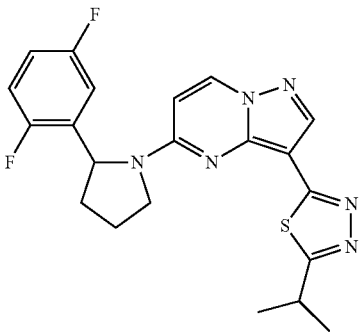 [SMILES: CC(C)c1nnc(-c2cnn3ccc(N4CCCC4c4cc(F)ccc4F)nc23)s1] | <10 | <10 | <10 |
| 7 | 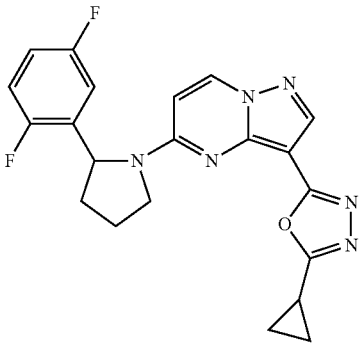 [SMILES: Fc1ccc(F)c(C2CCCN2c2ccn3ncc(-c4nnc(C5CC5)o4)c3n2)c1] | <10 | <10 | <100 |
| 8 | 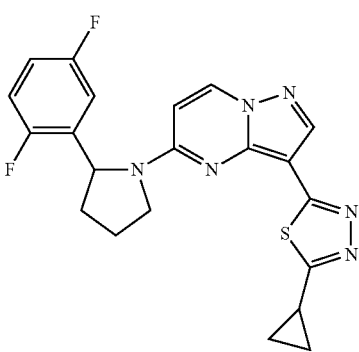 [SMILES: Fc1ccc(F)c(C2CCCN2c2ccn3ncc(-c4nnc(C5CC5)s4)c3n2)c1] | <10 | <10 | <100 |
| 9 | 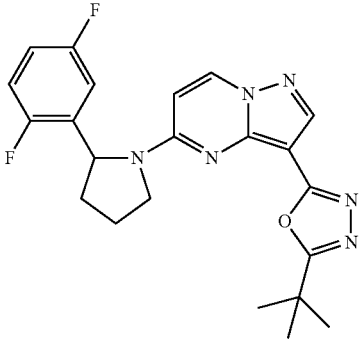 [SMILES: CC(C)(C)c1nnc(-c2cnn3ccc(N4CCCC4c4cc(F)ccc4F)nc23)o1] | <10 | <10 | <10 |

TABLE 1-continued

| Chemical Compound No. | Structure | IC$_{50}$ (nM) | | |
|---|---|---|---|---|
| | | Enzymatic assay | Cell-based assay (TF-1) | Cell-based assay (KM12) |
| 10 | 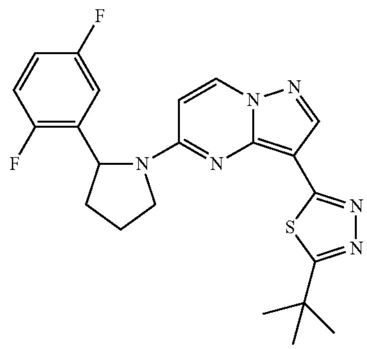 [SMILES: CC(C)(C)c1nnc(-c2cnn3ccc(N4CCCC4c4cc(F)ccc4F)nc23)s1] | <10 | <10 | <10 |
| 11 | 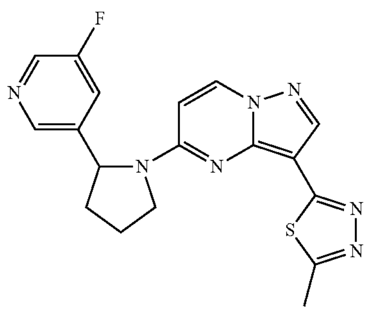 [SMILES: Cc1nnc(-c2cnn3ccc(N4CCCC4c4cncc(F)c4)nc23)s1] | <10 | <100 | <100 |
| 12 | 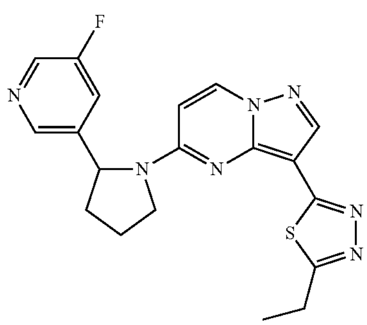 [SMILES: CCc1nnc(-c2cnn3ccc(N4CCCC4c4cncc(F)c4)nc23)s1] | <10 | <100 | <100 |
| 13 | 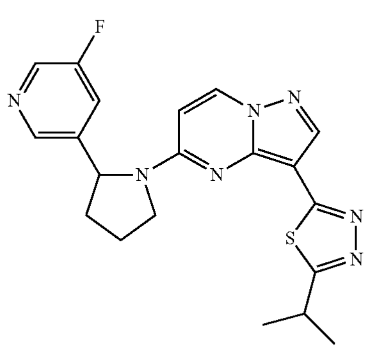 [SMILES: CC(C)c1nnc(-c2cnn3ccc(N4CCCC4c4cncc(F)c4)nc23)s1] | <10 | <100 | <100 |

TABLE 1-continued

| Chemical Compound No. | Structure | IC$_{50}$ (nM) Enzymatic assay | Cell-based assay (TF-1) | Cell-based assay (KM12) |
|---|---|---|---|---|
| 14 | 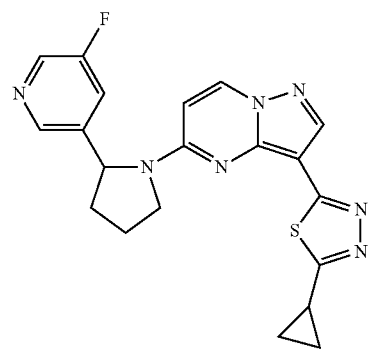 [SMILES: Fc1cncc(C2CCCN2c2ccn3ncc(-c4nnc(C5CC5)s4)c3n2)c1] | <10 | <100 | <100 |
| 15 | 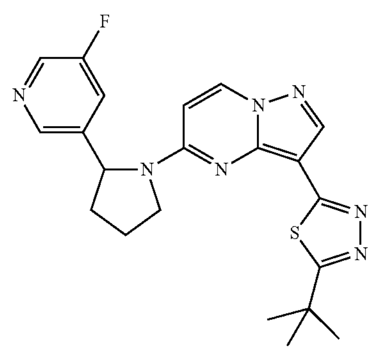 [SMILES: CC(C)(C)c1nnc(-c2cnn3ccc(N4CCCC4c4cncc(F)c4)nc23)s1] | <10 | <100 | <100 |
| 16 | 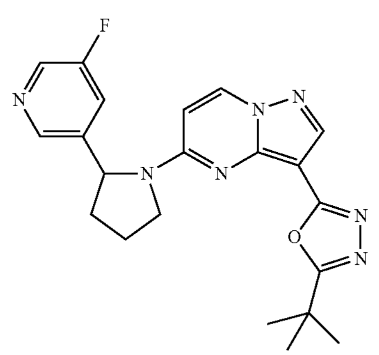 [SMILES: CC(C)(C)c1nnc(-c2cnn3ccc(N4CCCC4c4cncc(F)c4)nc23)o1] | <10 | <100 | <100 |
| 17 | 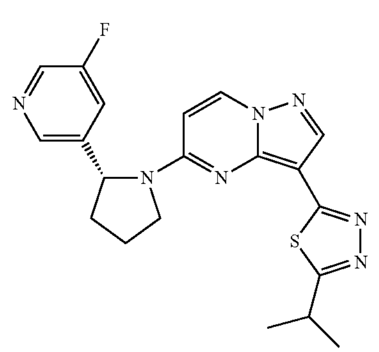 [SMILES: CC(C)c1nnc(-c2cnn3ccc(N4CCC[C@@H]4c4cncc(F)c4)nc23)s1] | <10 | <10 | <10 |

TABLE 1-continued
| Chemical Compound No. | Structure | IC$_{50}$ (nM) Enzymatic assay | Cell-based assay (TF-1) | Cell-based assay (KM12) |
|---|---|---|---|---|
| 18 | 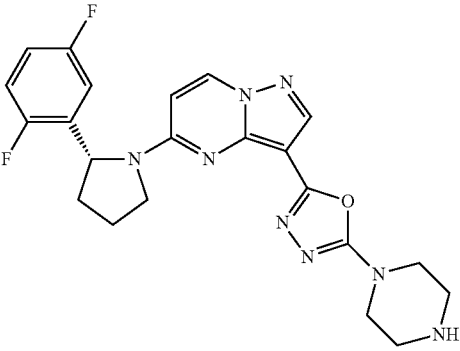 [SMILES: Fc1ccc(F)c([C@H]2CCCN2c2ccn3ncc(-c4nnc(N5CCNCC5)o4)c3n2)c1] | >100 | | |
| 19 | 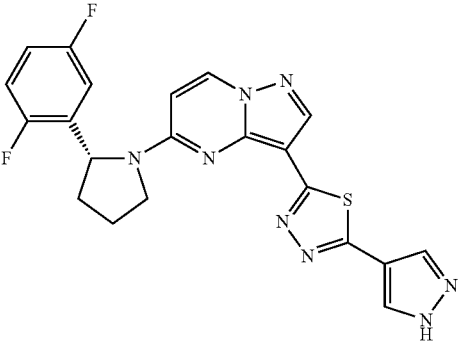 [SMILES: Fc1ccc(F)c([C@H]2CCCN2c2ccn3ncc(-c4nnc(-c5cn[nH]c5)s4)c3n2)c1] | <10 | | |
| 20 | 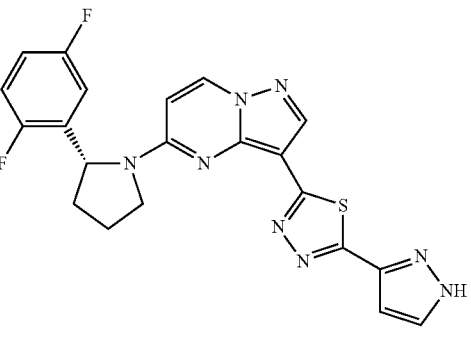 | >100 | | |
| 21 | 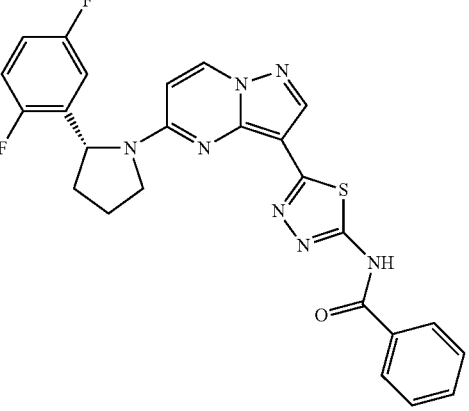 | >100 | | |

TABLE 1-continued

| Chemical Compound No. | Structure | IC$_{50}$ (nM) Enzymatic assay | Cell-based assay (TF-1) | Cell-based assay (KM12) |
|---|---|---|---|---|
| 22 | 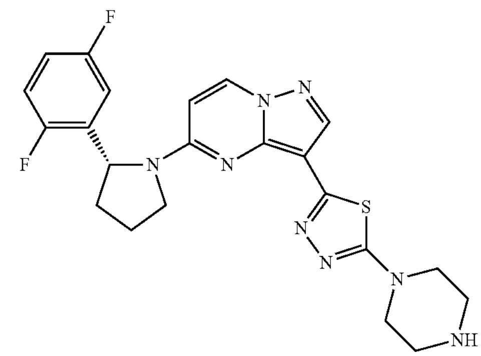 | <10 | | |
| 23 | 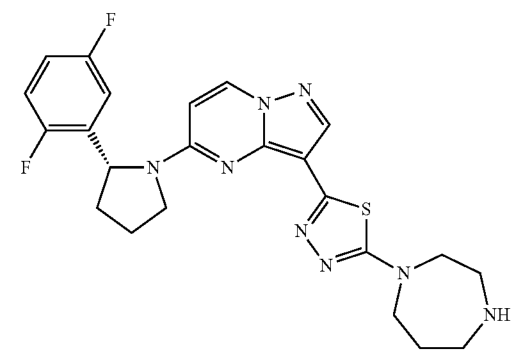 [SMILES: Fc1ccc(F)c([C@H]2CCCN2c2ccn3ncc(-c4nnc(N5CCCNCC5)s4)c3n2)c1] | <10 | | |
| 24 | 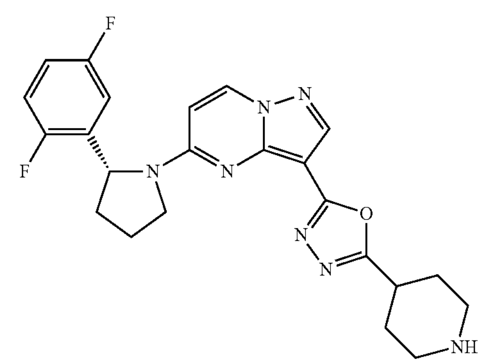 [SMILES: Fc1ccc(F)c([C@H]2CCCN2c2ccn3ncc(-c4nnc(C5CCNCC5)o4)c3n2)c1] | <10 | | |
| 25 | 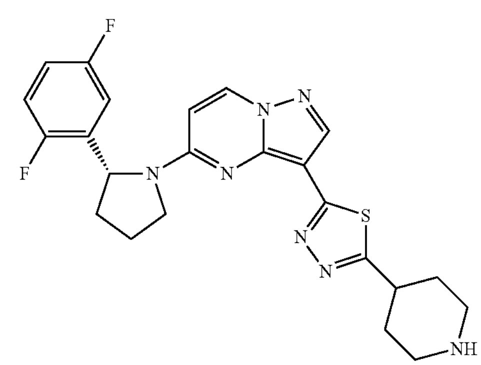 | — | — | — |

TABLE 1-continued

| Chemical Compound No. | Structure | IC$_{50}$ (nM) Enzymatic assay | Cell-based assay (TF-1) | Cell-based assay (KM12) |
|---|---|---|---|---|
| 26 | 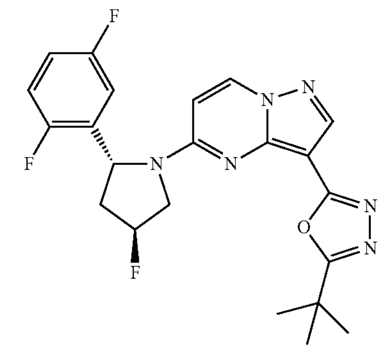 [SMILES: CC(C)(C)c1nnc(-c2cnn3ccc(N4C[C@@H](F)C[C@@H]4c4cc(F)ccc4F)nc23)o1] | <10 | <10 | <10 |
| 27 | 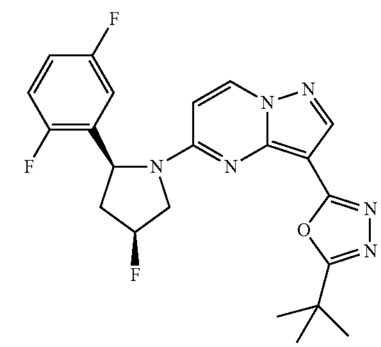 [SMILES: CC(C)(C)c1nnc(-c2cnn3ccc(N4C[C@@H](F)C[C@H]4c4cc(F)ccc4F)nc23)o1] | >100 | >1000 | >1000 |
| 28 | 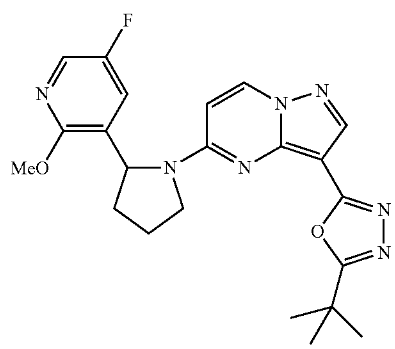 [SMILES: COc1ncc(F)cc1C1CCCN1c1ccn2ncc(-c3nnc(C(C)(C)C)o3)c2n1] | <10 | <10 | <10 |
| 29 | 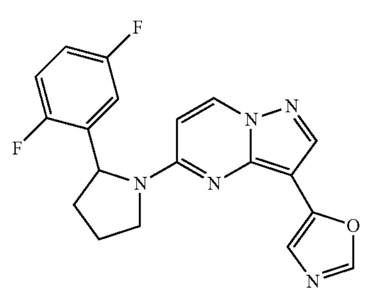 [SMILES: Fc1ccc(F)c(C2CCCN2c2ccn3ncc(-c4cnco4)c3n2)c1] | <10 | <100 | <100 |

TABLE 1-continued

| Chemical Compound No. | Structure | IC$_{50}$ (nM) | | |
|---|---|---|---|---|
| | | Enzymatic assay | Cell-based assay (TF-1) | Cell-based assay (KM12) |
| 30 | 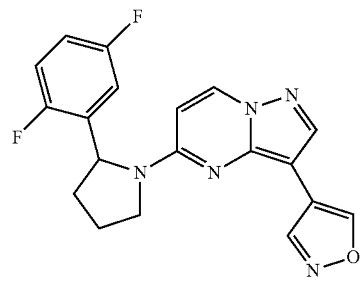 [SMILES: Fc1ccc(F)c(C2CCCN2c2ccn3ncc(-c4cnoc4)c3n2)c1] | <10 | <100 | <100 |
| 31 | 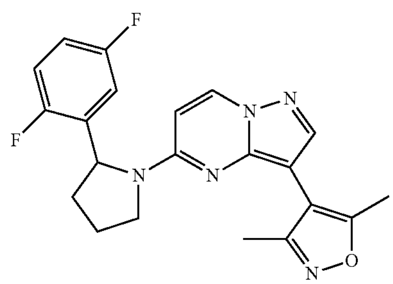 [SMILES: Cc1noc(C)c1-c1cnn2ccc(N3CCCC3c3cc(F)ccc3F)nc12] | <100 | <1000 | <1000 |
| 32 | 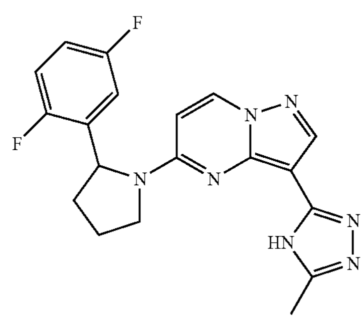 [SMILES: Cc1nnc(-c2cnn3ccc(N4CCCC4c4cc(F)ccc4F)nc23)[nH]1] | <10 | <100 | <100 |
| 33 | 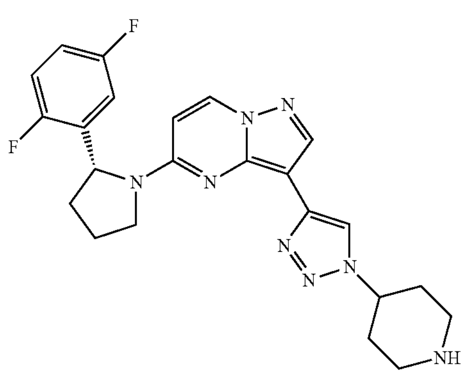 [SMILES: Fc1ccc(F)c([C@H]2CCCN2c2ccn3ncc(-c4cn(C5CCNCC5)nn4)c3n2)c1] | <10 | | |

TABLE 1-continued

| Chemical Compound No. | Structure | IC$_{50}$ (nM) Enzymatic assay | Cell-based assay (TF-1) | Cell-based assay (KM12) |
|---|---|---|---|---|
| 34 | 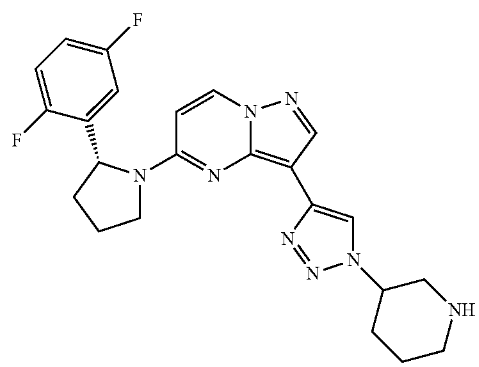 [SMILES: Fc1ccc(F)c([C@H]2CCCN2c2ccn3ncc(-c4cn(C5CCCNC5)nn4)c3n2)c1] | <10 | | |
| 35 | 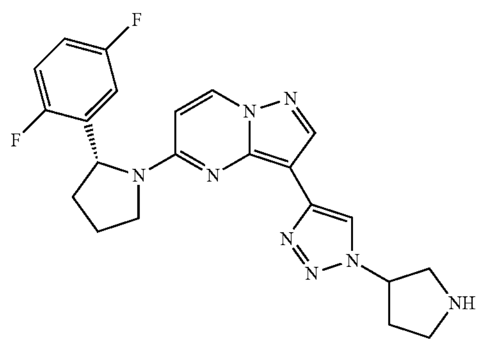 [SMILES: Fc1ccc(F)c([C@H]2CCCN2c2ccn3ncc(-c4cn(C5CCNC5)nn4)c3n2)c1] | <10 | | |
| 36 | 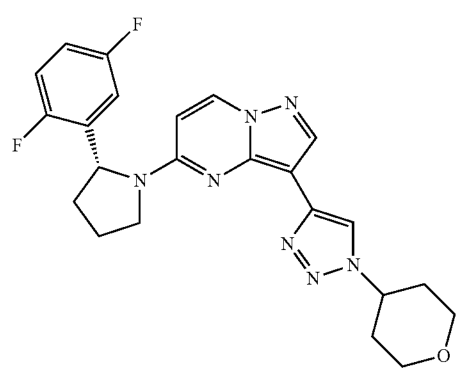 [SMILES: Fc1ccc(F)c([C@H]2CCCN2c2ccn3ncc(-c4cn(C5CCOCC5)nn4)c3n2)c1] | — | — | — |
| 37 | 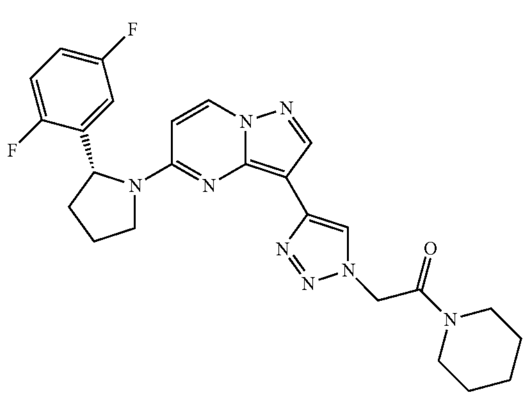 [SMILES: O=C(Cn1cc(-c2cnn3ccc(N4CCC[C@@H]4c4cc(F)ccc4F)nc23)nn1)N1CCCCC1] | <10 | | |

TABLE 1-continued

| Chemical Compound No. | Structure | IC$_{50}$ (nM) | | |
|---|---|---|---|---|
| | | Enzymatic assay | Cell-based assay (TF-1) | Cell-based assay (KM12) |
| 38 | 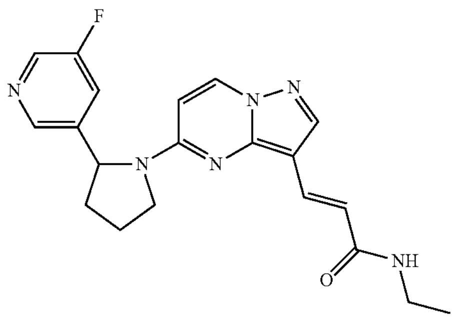 [SMILES: CCNC(=O)/C=C/c1cnn2ccc(N3CCCC3c3cncc(F)c3)nc12] | <10 | <1000 | <1000 |
| 39 | 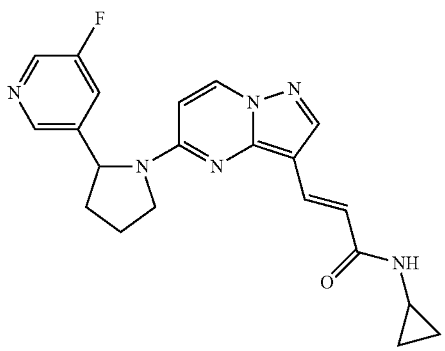 [SMILES: O=C(/C=C/c1cnn2ccc(N3CCCC3c3cncc(F)c3)nc12)NC1CC1] | <10 | <1000 | <1000 |
| 40 | 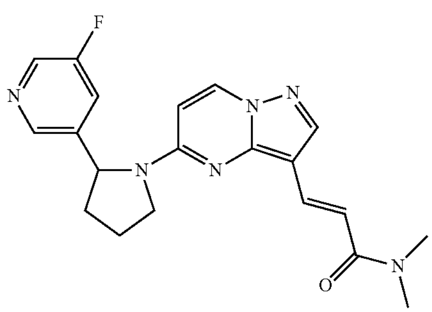 [SMILES: CN(C)C(=O)/C=C/c1cnn2ccc(N3CCCC3c3cncc(F)c3)nc12] | <10 | <100 | <1000 |
| 41 | 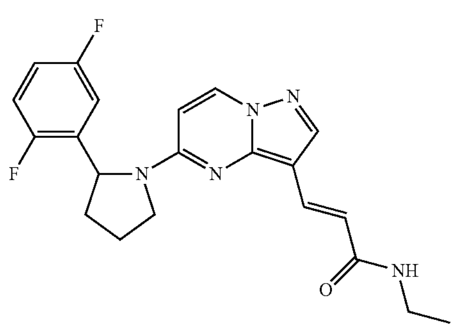 [SMILES: CCNC(=O)/C=C/c1cnn2ccc(N3CCCC3c3cc(F)ccc3F)nc12] | <10 | <100 | <100 |

TABLE 1-continued
| Chemical Compound No. | Structure | IC$_{50}$ (nM) | | |
|---|---|---|---|---|
| | | Enzymatic assay | Cell-based assay (TF-1) | Cell-based assay (KM12) |
| 42 | 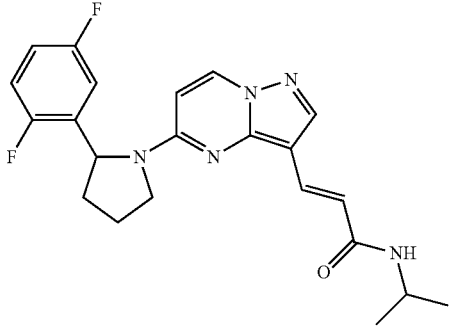 [SMILES: CC(C)NC(=O)/C=C/c1cnn2ccc(N3CCCC3c3cc(F)ccc3F)nc12] | <10 | <100 | <100 |
| 43 | 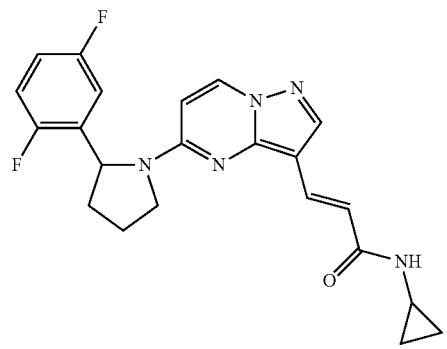 [SMILES: O=C(/C=C/c1cnn2ccc(N3CCCC3c3cc(F)ccc3F)nc12)NC1CC1] | <10 | <100 | <100 |
| 44 | 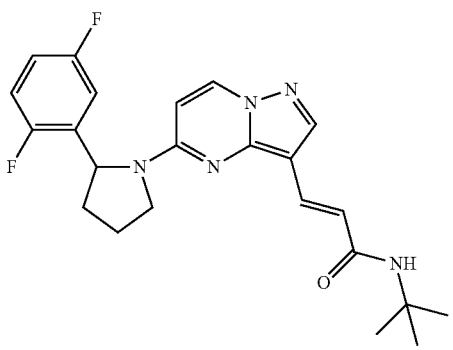 [SMILES: CC(C)(C)NC(=O)/C=C/c1cnn2ccc(N3CCCC3c3cc(F)ccc3F)nc12] | <10 | <100 | <100 |
| 45 | 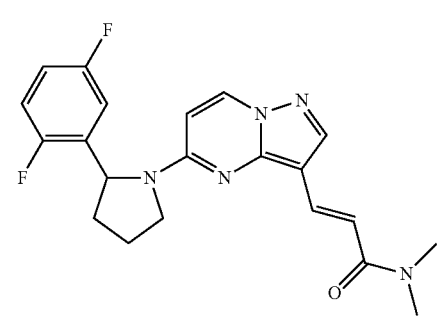 [SMILES: CN(C)C(=O)/C=C/c1cnn2ccc(N3CCCC3c3cc(F)ccc3F)nc12] | <10 | <100 | <100 |

TABLE 1-continued

| Chemical Compound No. | Structure | IC$_{50}$ (nM) | | |
|---|---|---|---|---|
| | | Enzymatic assay | Cell-based assay (TF-1) | Cell-based assay (KM12) |
| 46 | 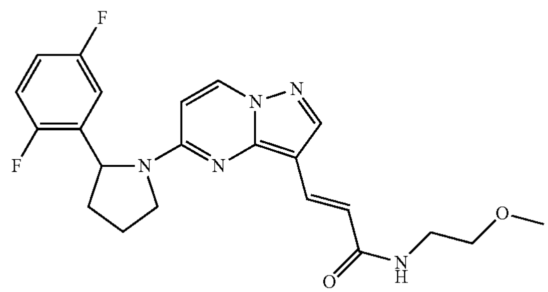 [SMILES: COCCNC(=O)/C=C/c1cnn2ccc(N3CCCC3c3cc(F)ccc3F)nc12] | <10 | <100 | <100 |
| 47 | 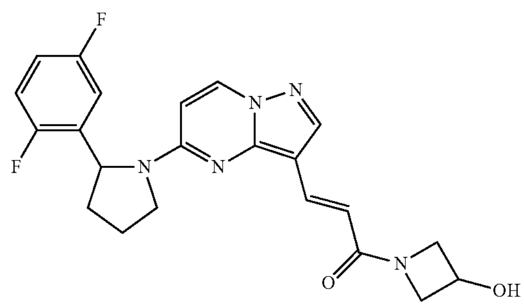 [SMILES: O=C(/C=C/c1cnn2ccc(N3CCCC3c3cc(F)ccc3F)nc12)N1CC(O)C1] | <10 | <100 | <100 |
| 48 | 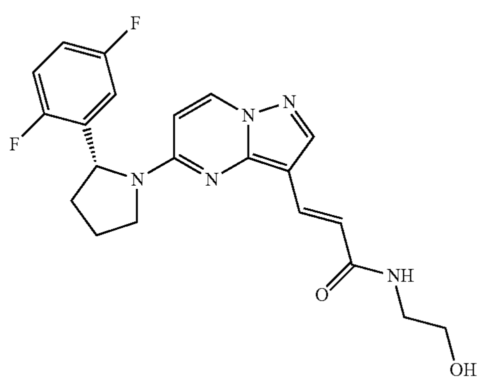 [SMILES: O=C(/C=C/c1cnn2ccc(N3CCC[C@@H]3c3cc(F)ccc3F)nc12)NCCO] | <10 | <100 | <100 |
| 49 | 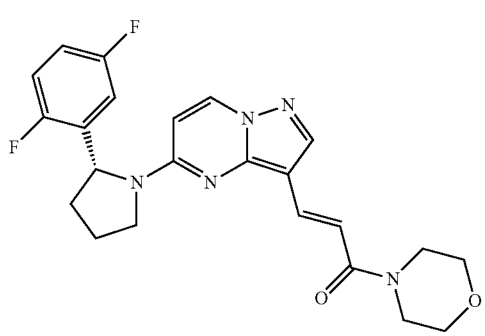 [SMILES: O=C(/C=C/c1cnn2ccc(N3CCC[C@@H]3c3cc(F)ccc3F)nc12)N1CCOCC1] | <10 | <10 | <100 |

TABLE 1-continued

| Chemical Compound No. | Structure | IC$_{50}$ (nM) | | |
|---|---|---|---|---|
| | | Enzymatic assay | Cell-based assay (TF-1) | Cell-based assay (KM12) |
| 50 | 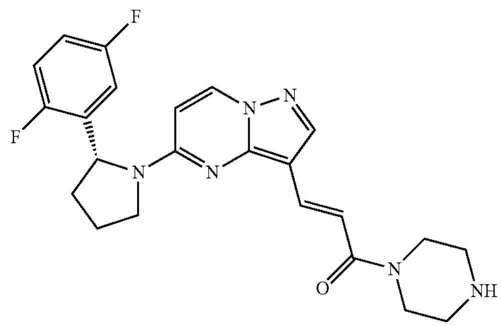 [SMILES: O=C(/C=C/c1cnn2ccc(N3CCC[C@@H]3c3cc(F)ccc3F)nc12)N1CCNCC1] | <10 | <100 | <10 |
| 51 | 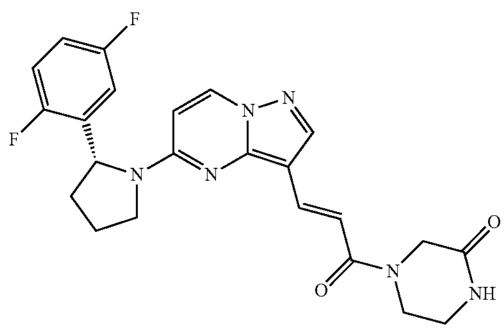 [SMILES: O=C1CN(C(=O)/C=C/c2cnn3ccc(N4CCC[C@@H]4c4cc(F)ccc4F)nc23)CCN1] | <10 | | |
| 52 | 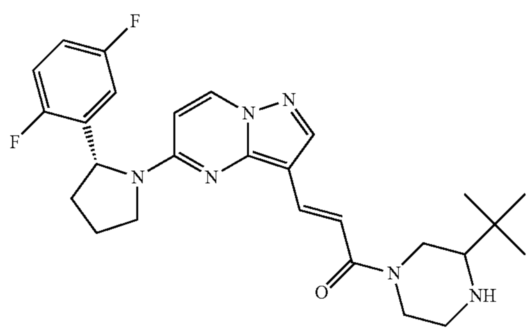 [SMILES: CC(C)(C)C1CN(C(=O)/C=C/c2cnn3ccc(N4CCC[C@@H]4c4cc(F)ccc4F)nc23)CCN1] | <10 | | |
| 53 | 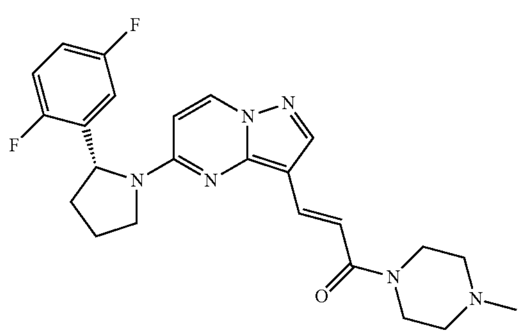 [SMILES: CN1CCN(C(=O)/C=C/c2cnn3ccc(N4CCC[C@@H]4c4cc(F)ccc4F)nc23)CC1] | <10 | | <100 |

TABLE 1-continued

| Chemical Compound No. | Structure | IC$_{50}$ (nM) Enzymatic assay | Cell-based assay (TF-1) | Cell-based assay (KM12) |
|---|---|---|---|---|
| 54 | 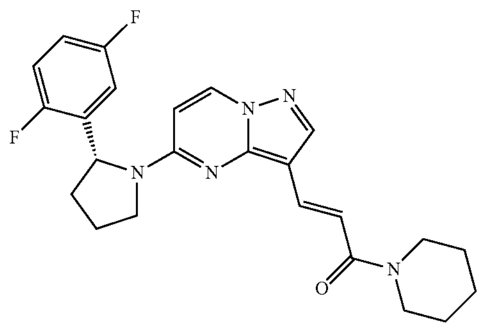 [SMILES: O=C(/C=C/c1cnn2ccc(N3CCC[C@@H]3c3cc(F)ccc3F)nc12)N1CCCCC1] | >100 | | |
| 55 | 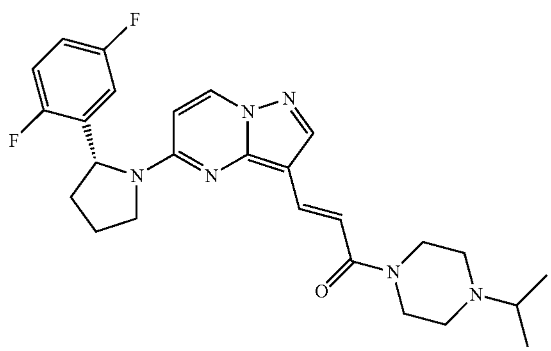 [SMILES: CC(C)N1CCN(C(=O)/C=C/c2cnn3ccc(N4CCC[C@@H]4c4cc(F)ccc4F)nc23)CC1] | <10 | | <100 |
| 56 | 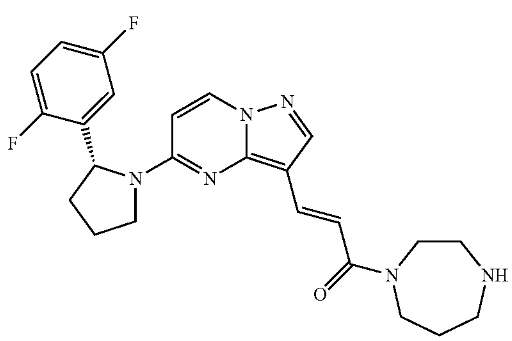 [SMILES: O=C(/C=C/c1cnn2ccc(N3CCC[C@@H]3c3cc(F)ccc3F)nc12)N1CCCNCC1] | >100 | | |
| 57 | 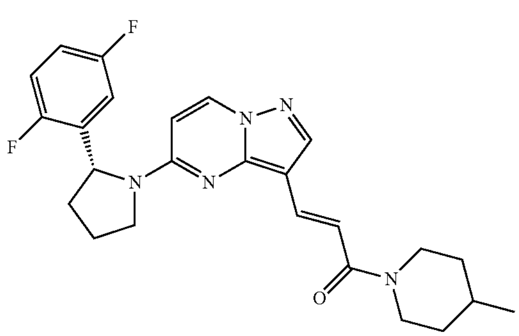 [SMILES: CC1CCN(C(=O)/C=C/c2cnn3ccc(N4CCC[C@@H]4c4cc(F)ccc4F)nc23)CC1] | <10 | | <100 |

TABLE 1-continued

| Chemical Compound No. | Structure | IC$_{50}$ (nM) | | |
| --- | --- | --- | --- | --- |
| | | Enzymatic assay | Cell-based assay (TF-1) | Cell-based assay (KM12) |
| 58 | 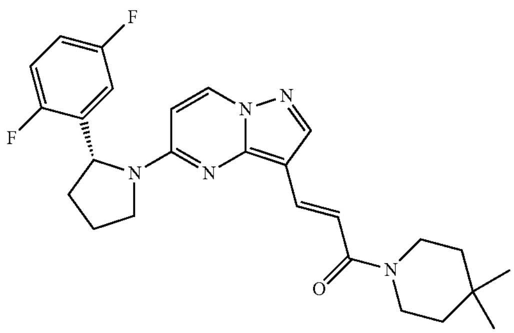 [SMILES: CC1(C)CCN(C(=O)/C=C/c2cnn3ccc(N4CCC[C@@H]4c4cc(F)ccc4F)nc23)CC1] | <10 | | <10 |
| 59 | 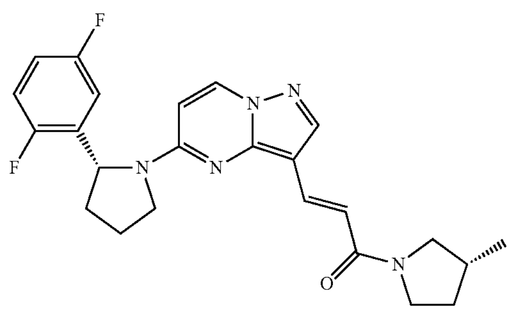 [SMILES: C[C@@H]1CCN(C(=O)/C=C/c2cnn3ccc(N4CCC[C@@H]4c4cc(F)ccc4F)nc23)C1] | <10 | | <100 |
| 60 | 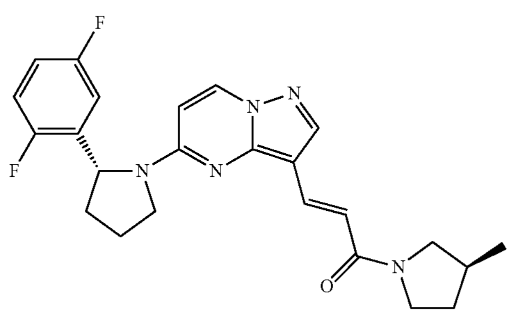 [SMILES: C[C@H]1CCN(C(=O)/C=C/c2cnn3ccc(N4CCC[C@@H]4c4cc(F)ccc4F)nc23)C1] | <10 | | <100 |
| 61 | 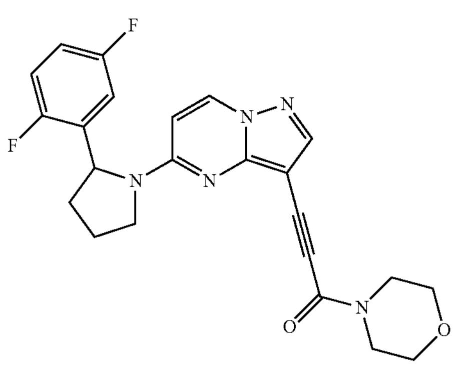 [SMILES: O=C(C#Cc1cnn2ccc(N3CCCC3c3cc(F)ccc3F)nc12)N1CCOCC1] | <10 | <100 | <100 |

What is claimed is:

1. A compound of Formula I or a salt thereof:

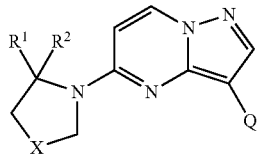

Formula I

R¹ is a 6-membered aryl or heteroaryl ring optionally substituted with one or more substituent groups independently selected from the group consisting of halogen, hydroxyl, linear C1-C4 alkyl, branched C1-C4 alkyl, linear C1-C4 alkoxy, and branched C1-C4 alkoxy;

R² is selected from the group consisting of hydrogen, linear C1-C4 alkyl and branched linear C1-C4 alkyl;

X is selected from the group consisting of —CH₂—, —CH₂CH₂—, —CH₂O— and —CH(Z)—, wherein Z is halogen; and Q is selected from the group consisting of —CH=CR³C(O)NR⁴R⁵, —C≡CC(O)NR⁴R⁵, and

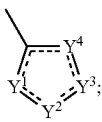

wherein R³ is hydrogen or halogen,
wherein —NR⁴R⁵ either forms a 4-7 membered heterocyclic ring or does not form a ring structure, the heterocyclic ring being either heteroaryl or heterocycloalkyl ring,
wherein when —NR⁴R⁵ forms a 4-7 membered heterocyclic ring, the 4-7 membered heterocyclic ring includes an optional second heteroatom in addition to the nitrogen of —NR⁴R⁵ and is optionally substituted with one or more substituent groups independently selected from the group consisting of linear C1-C6 alkyl, branched C1-C6 alkyl, hydroxyl, carboxylic acid, linear C1-C4 alkyl carboxylic acid, and branched C1-C4 alkyl carboxylic acid branched,
wherein when —NR⁴R⁵ does not form a ring structure, R⁴ is selected from the group consisting of hydrogen, linear C1-C6 alkyl and branched C1-C6 alkyl, and R⁵ is selected from the group consisting of hydrogen, linear C1-C6 alkyl optionally substituted with at least one fluorine or at least one hydroxyl, branched C1-C6 alkyl optionally substituted with at least one fluorine or at least one hydroxyl, and C1-C6 cycloalkyl optionally substituted with at least one fluorine or at least one hydroxyl,
wherein Y¹, Y², Y³, and Y⁴ are each independently selected from the group consisting of —CH, N, O, S, —CR⁶, and —NR⁶,
wherein R⁶ is selected from the group consisting of hydrogen, linear C1-C4 alkyl, branched C1-C4 alkyl, 5-6 membered aryl ring, 5-6 membered heteroaryl ring, 3-7 membered heterocycloalkyl ring, 3-7 membered cycloalkyl ring, —NHCO-(aryl ring), and —CH₂CO—(C3-C6 membered heterocylic ring).

2. The compound of claim 1, wherein R¹ a phenyl ring substituted with one or more substituent groups are independently selected from the group consisting of fluorine, methoxy and ethoxy, wherein R² and R³ are H, wherein R⁵ is selected from the group consisting of H, methyl, ethyl, iso-propyl, cyclopropyl, t-butyl, methoxyethyl and hydroxyethyl.

3. The compound of claim 1, wherein R¹ is a pyridine ring substituted with at least one selected from the group consisting of fluorine and methoxy, wherein R² and R³ are H, wherein R⁵ is selected from the group consisting of H, methyl, ethyl, iso-propyl, cyclopropyl, t-butyl, methoxyethyl and hydroxyethyl.

4. The compound of claim 1, wherein R¹ is a pyrid-2-on-3-yl ring optionally substituted with one or more substituent groups independently selected from the group consisting of halogen and C1-C4 alkyl.

5. The compound of claim 1, wherein when —NR⁴R⁵ does not form a ring structure, R⁴ is selected from the group consisting of hydrogen, linear C1-C6 alkyl and branched C1-C6 alkyl, and R⁵ is selected from the group consisting of linear C1-C6 fluoroalkyl, branched C1-C6 fluoroalkyl, linear C1-C6 difluoroalkyl, branched C1-C6 difluoroalkyl, linear C1-C6 trifluoroalkyl, branched C1-C6 trifluoroalkyl, linear C1-C6 hyroxyalkyl, branched C1-C6 hyroxyalkyl, linear C2-C6 difluoroalkyl, and branched C2-C6 difluoroalkyl.

6. The compound of claim 1, wherein —NR⁴R⁵ forming a 4-7 membered heterocylic ring is a 4-7 membered heterocycloalkyl ring.

7. The compound of claim 1, wherein when —NR⁴R⁵ forms a 4-7 membered heterocyclic ring, the second heteroatom in the 4-7 membered heterocyclic ring is selected from the group consisting of nitrogen, oxygen and sulfur.

8. The compound of claim 1, wherein the compound of Formula I is a compound of Formula II:

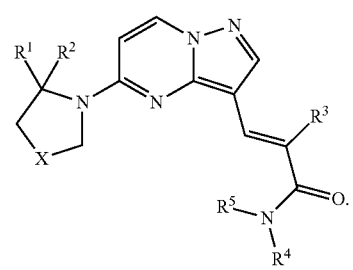

Formula II

9. The compound of claim 1, wherein the compound of Formula I is a compound of Formula III:

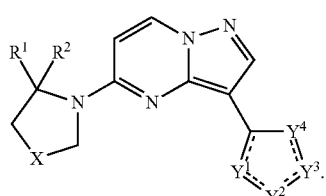

Formula III

10. The compound of claim 1, wherein the compound of Formula I is a compound of Formula IV:

Formula IV
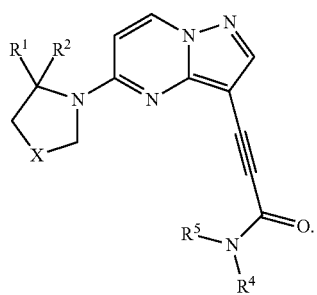
11. The compound of claim 1, wherein the compound of Formula I is selected from the group consisting of Chemical Compounds 1-10:
Chemical Compound 1
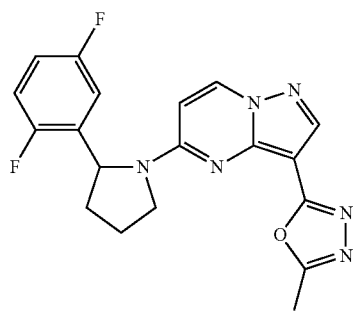
Chemical Compound 2
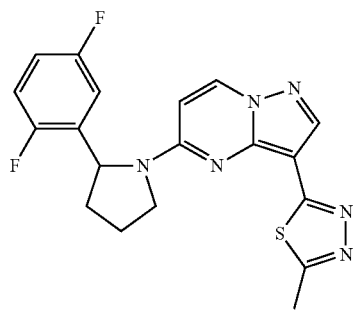
Chemical Compound 3
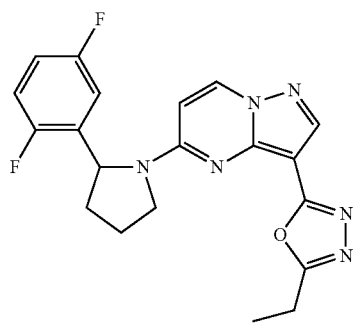
Chemical Compound 4
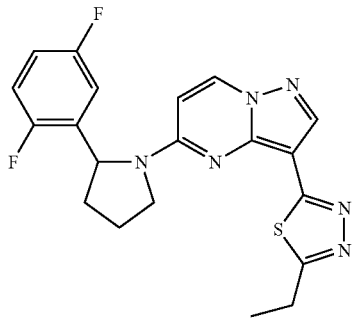
Chemical Compound 5
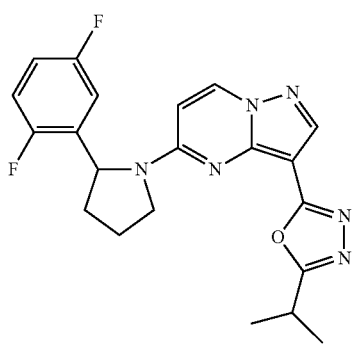
Chemical Compound 6
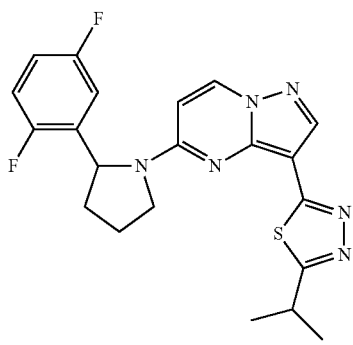
Chemical Compound 7
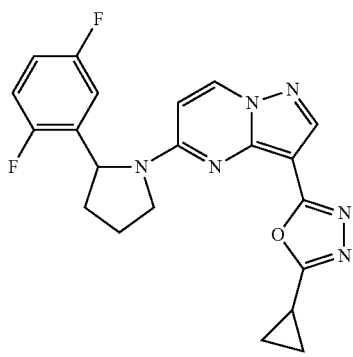

-continued
Chemical Compound 8
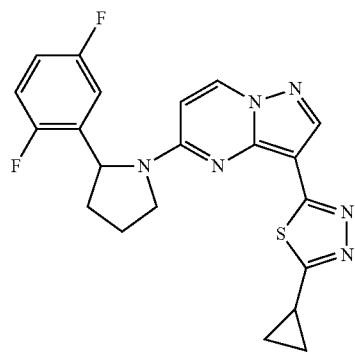
Chemical Compound 9
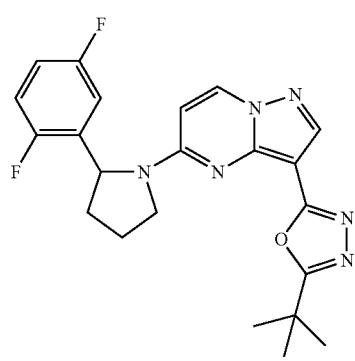
Chemical Compound 10
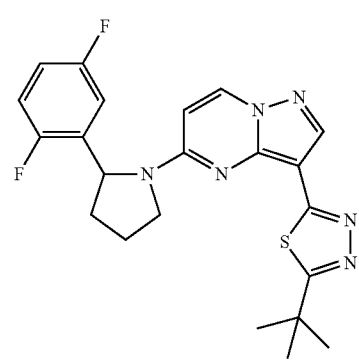
12. The compound of claim 1, wherein the compound of Formula I is selected from the group consisting of Chemical Compounds 11-20:
Chemical Compound 11
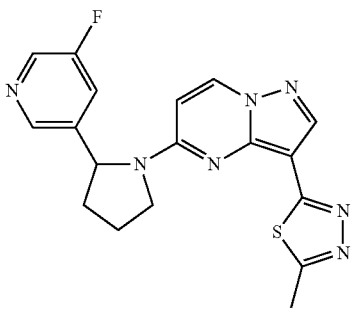
-continued
Chemical Compound 12
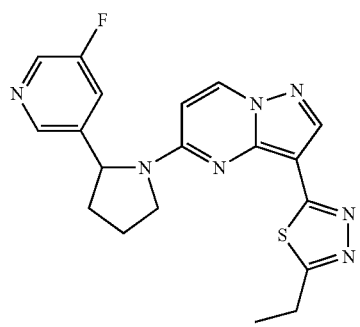
Chemical Compound 13
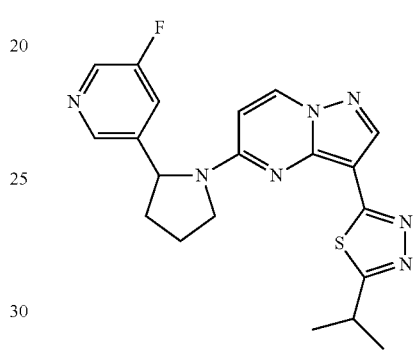
Chemical Compound 14
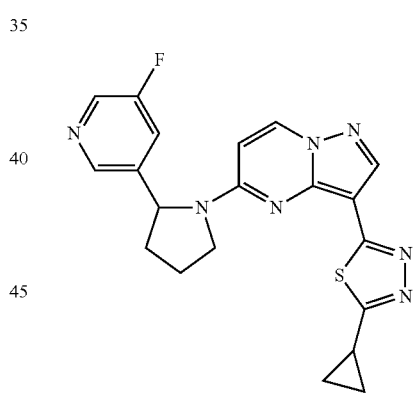
Chemical Compound 15
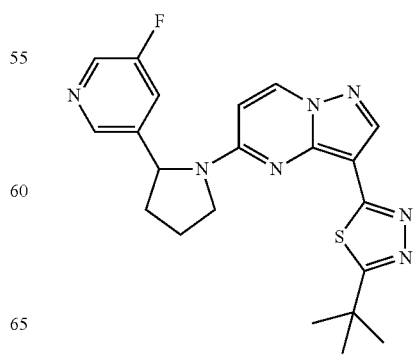

Chemical Compound 16
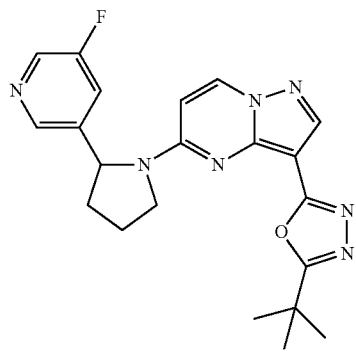
Chemical Compound 17
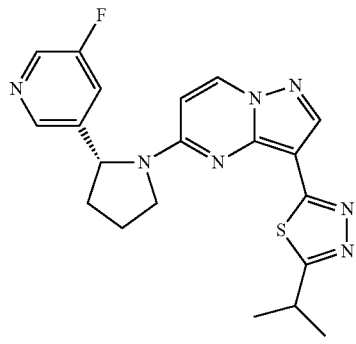
Chemical Compound 18
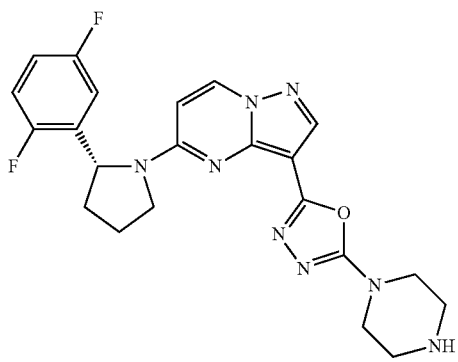
Chemical Compound 19
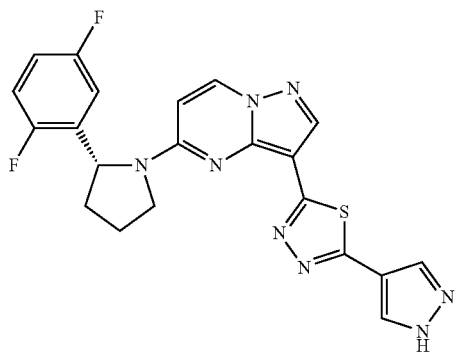
Chemical Compound 20
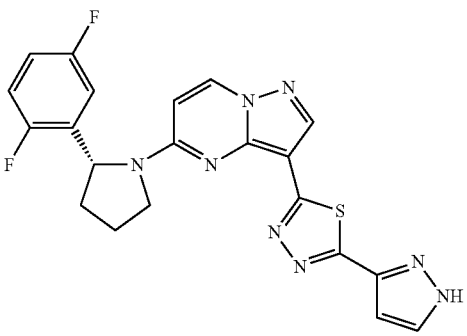
Chemical Compound 20
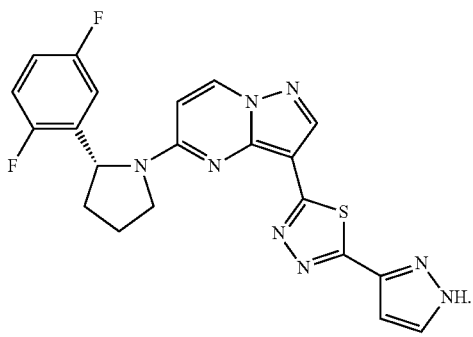
13. The compound of claim 1, wherein the compound of Formula I is selected from the group consisting of Chemical Compounds 21-30:
Chemical Compound 21
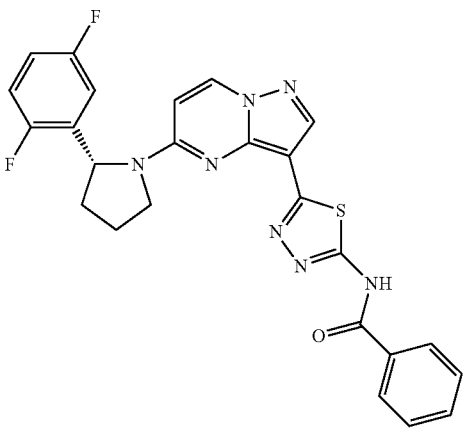

Chemical Compound 22
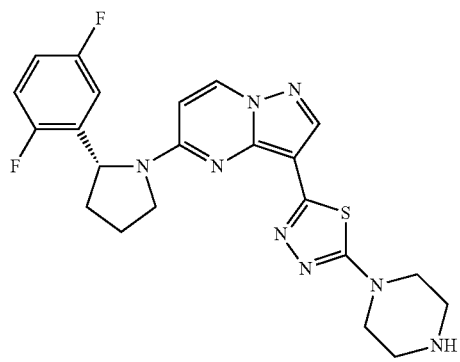
Chemical Compound 23
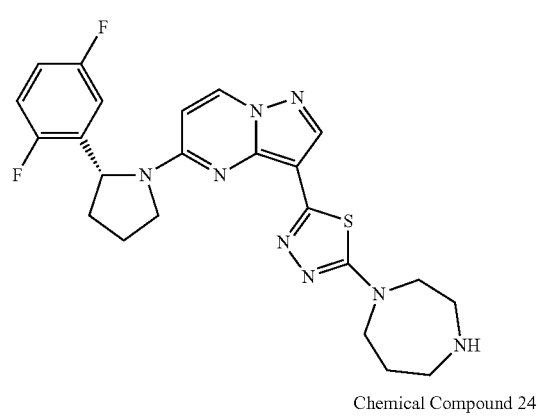
Chemical Compound 24
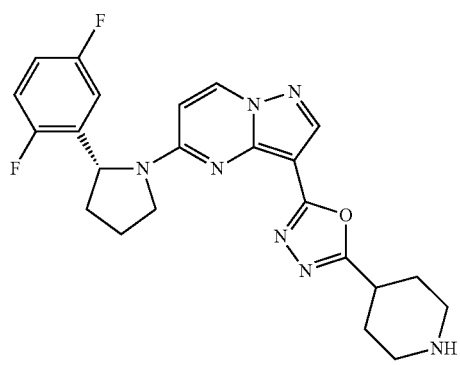
Chemical Compound 25
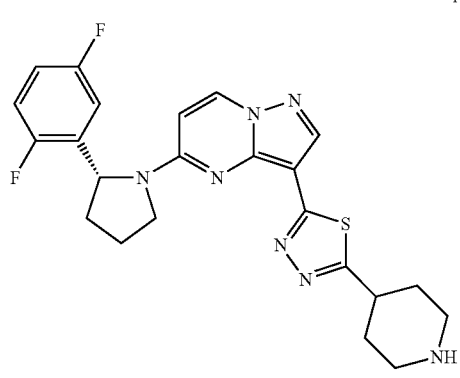
Chemical Compound 26
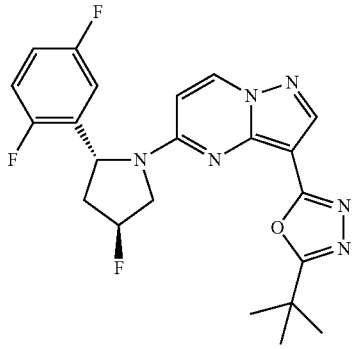
Chemical Compound 27
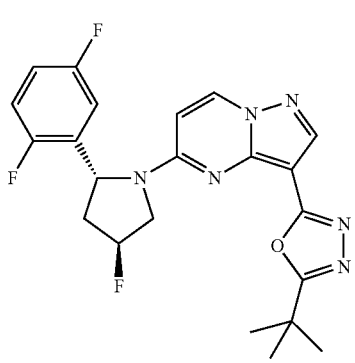
Chemical Compound 28
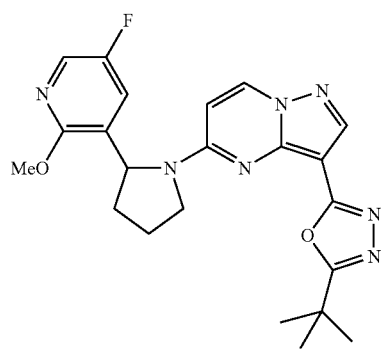
Chemical Compound 29
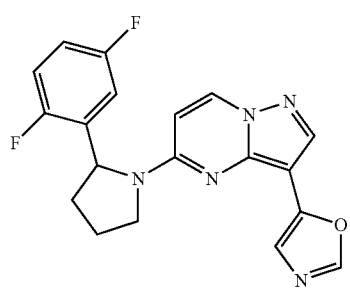

Chemical Compound 30
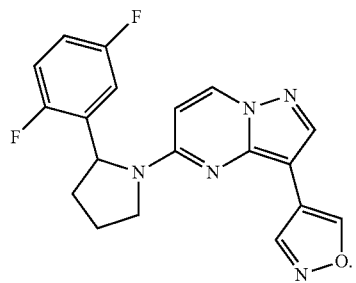
14. The compound of claim 1, wherein the compound of Formula I is selected from the group consisting of Chemical Compounds 31-40:
Chemical Compound 31
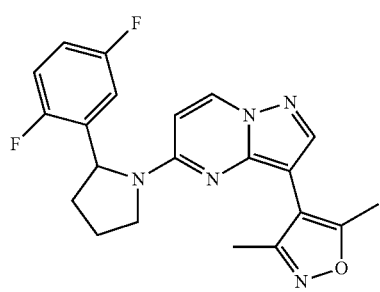
Chemical Compound 32
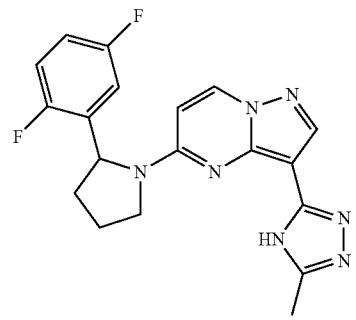
Chemical Compound 33
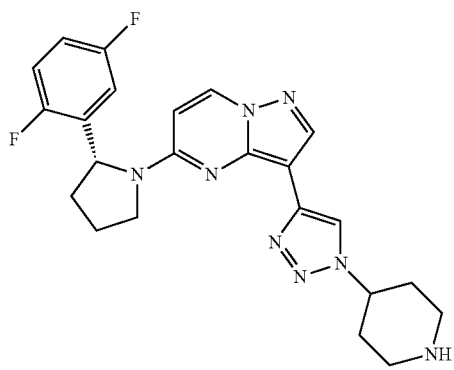
Chemical Compound 34
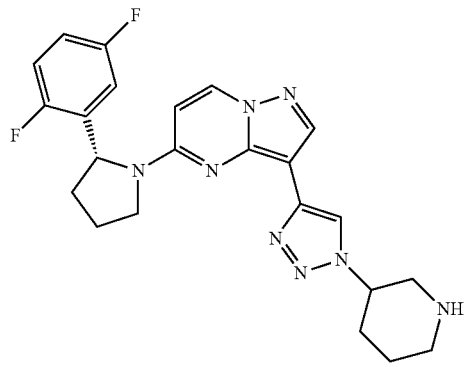
Chemical Compound 35
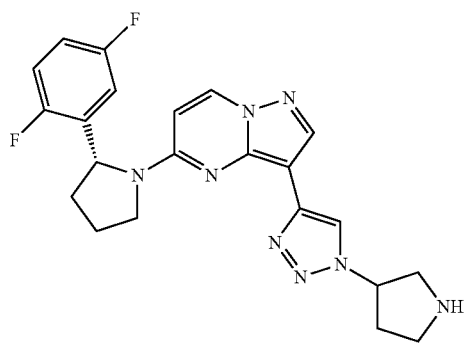
Chemical Compound 36
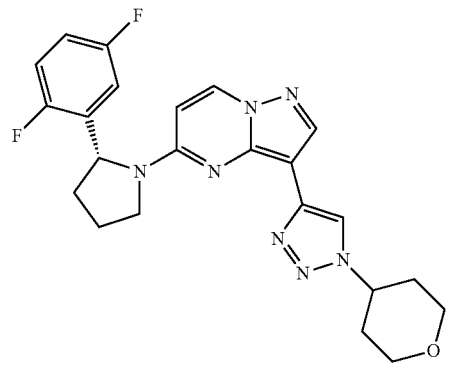
Chemical Compound 37
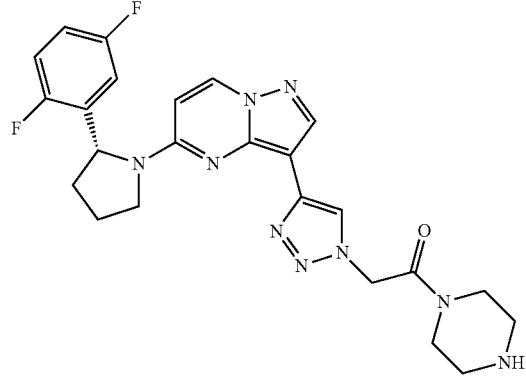

Chemical Compound 38
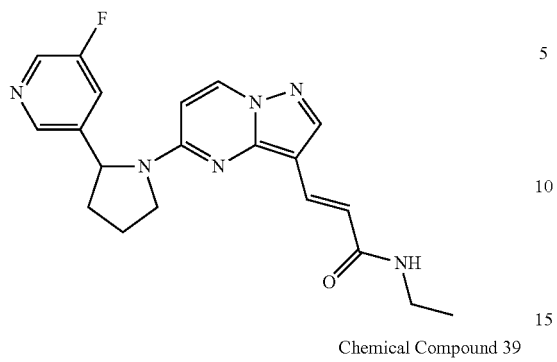
Chemical Compound 39
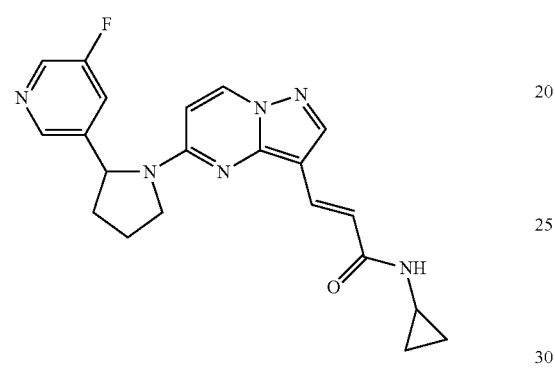
Chemical Compound 40
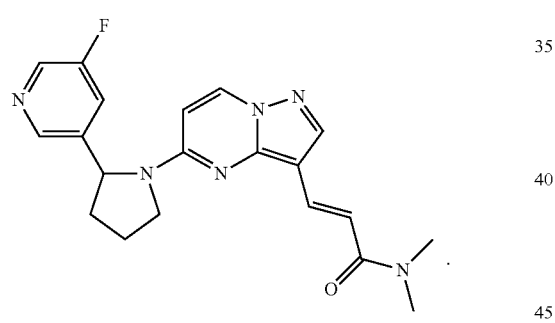
15. The compound of claim 1, wherein the compound of Formula I is selected from the group consisting of Chemical Compounds 41-50:
Chemical Compound 41
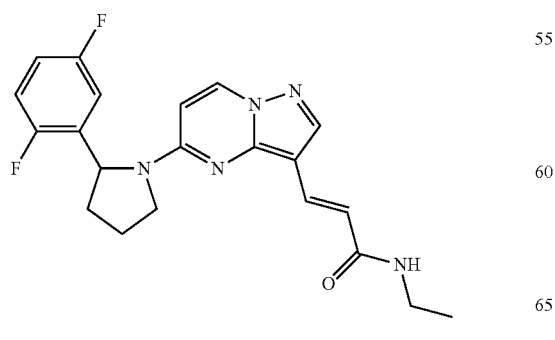
Chemical Compound 42
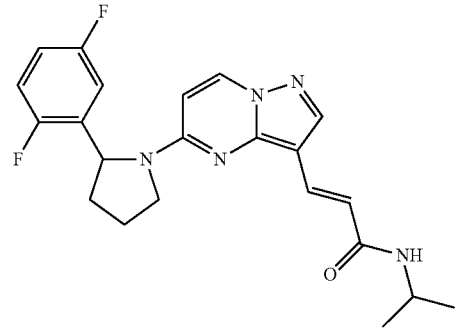
Chemical Compound 43
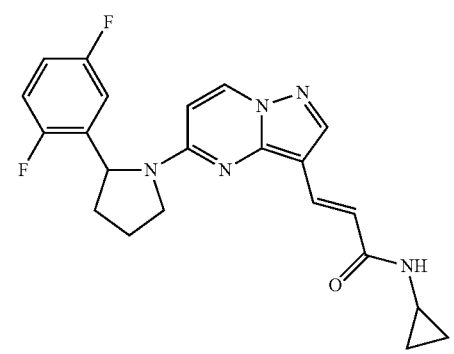
Chemical Compound 44
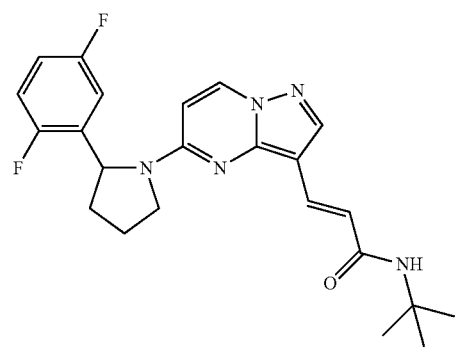
Chemical Compound 45
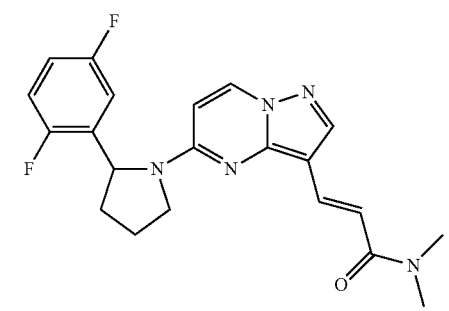

Chemical Compound 46
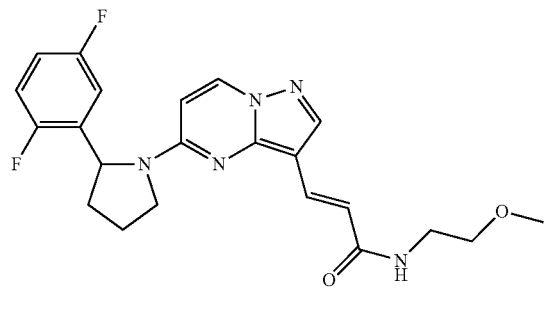
Chemical Compound 47
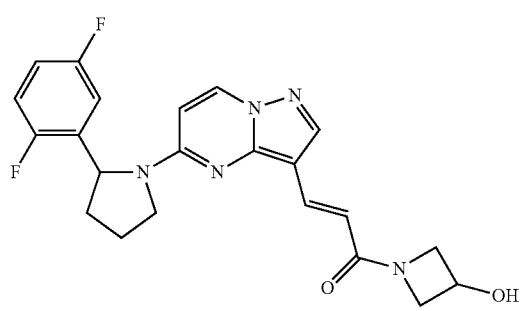
Chemical Compound 48
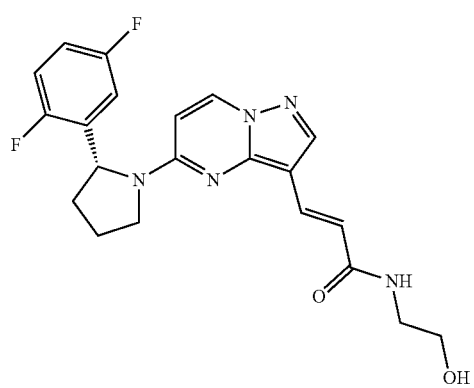
Chemical Compound 49
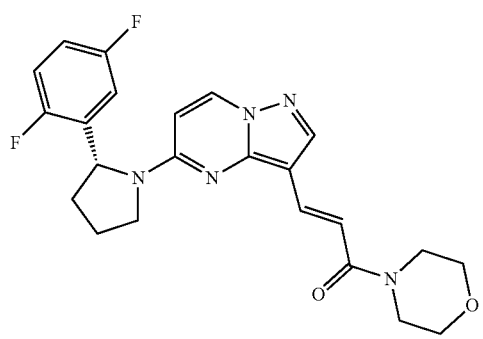
Chemical Compound 50
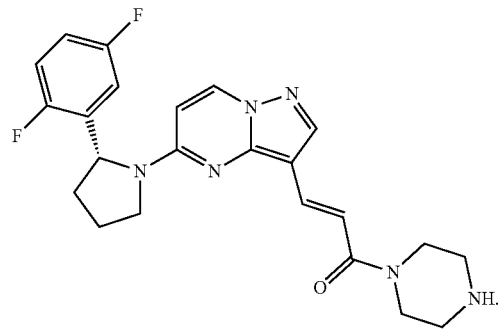
16. The compound of claim 1, wherein the compound of Formula I is selected from the group consisting of Chemical Compounds 51-61:
Chemical Compound 51
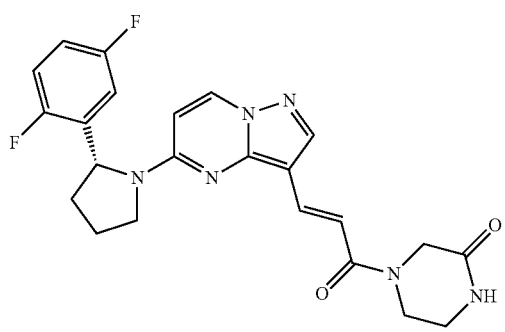
Chemical Compound 52
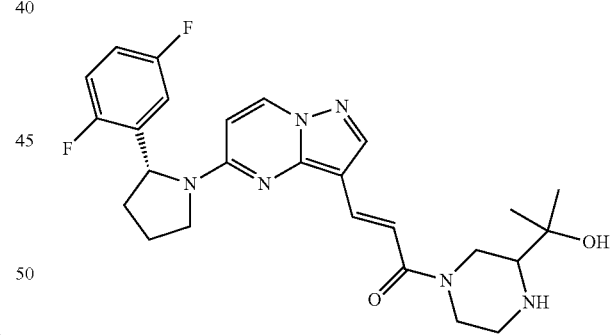
Chemical Compound 53
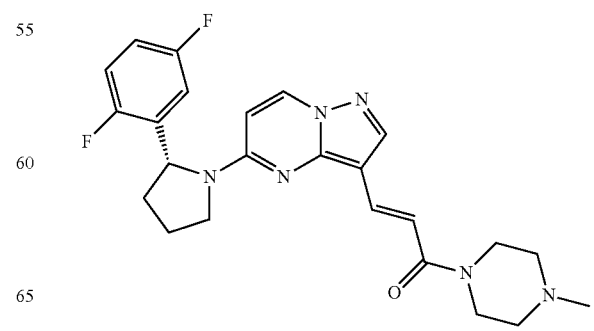

Chemical Compound 54

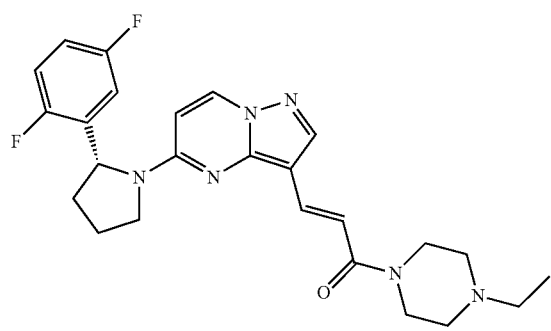

Chemical Compound 55

Chemical Compound 56

Chemical Compound 57

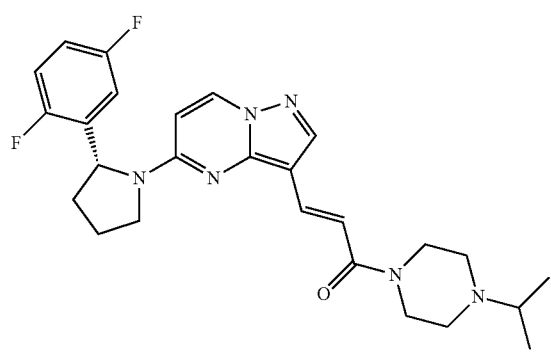

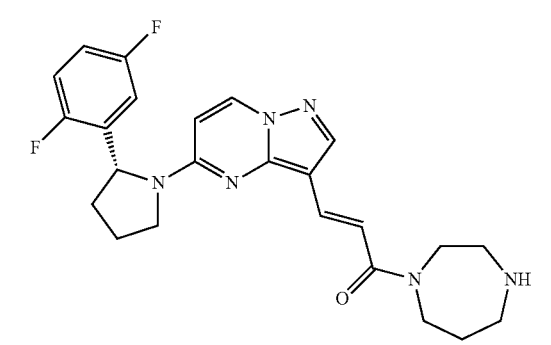

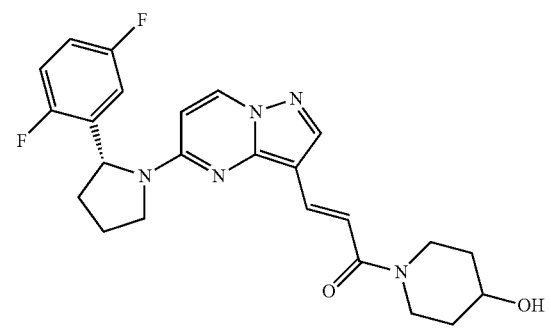

Chemical Compound 58

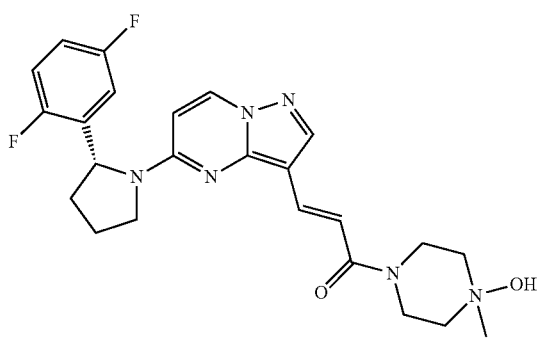

Chemical Compound 59

Chemical Compound 60

Chemical Compound 61

17. The compound of claim 1, wherein the salt is selected from the group consisting of acetate, benzoate, besylate, bitartrate, bromide, carbonate, chloride, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, oxalate, pamoate, phosphate, diphosphate, salicylate, disalicylate, stearate, succinate, sulfate, tartrate, tosylate, triethiodide, trifluoroacetate and valerate.

18. A method of treating a TRK mediated disease selected from the group consisting of papillary thyroid carcinoma, pancreatic cancer, lung cancer, colon cancer, breast carcinoma, neuroblastoma, pain, cachexia, dermatitis and asthma, the method comprising: administering a pharmaceutically effective amount of the compound of claim 1 or a pharmaceutically acceptable salt thereof to a subject having said TRK mediated disease.

19. A method of inhibiting a TRK enzyme, the method comprising:

administering a pharmaceutically effective amount of the compound of claim 1 or a pharmaceutically acceptable salt thereof to a subject in need of such inhibition.

* * * * *

UNITED STATES PATENT AND TRADEMARK OFFICE
CERTIFICATE OF CORRECTION

PATENT NO. : 9,701,681 B2
APPLICATION NO. : 14/968208
DATED : July 11, 2017
INVENTOR(S) : Kim et al.

It is certified that error appears in the above-identified patent and that said Letters Patent is hereby corrected as shown below:

On the Title Page

Item (72), (Inventors) at Line 3, change "Cheol Hwan Yoon," to --Cheolhwan Yoon,--.

Item (72), (Inventors) at Line 5, change "Je Hak Kim," to --Jay Hak Kim,--.

Item (72), (Inventors) at Line 9, change "Kinam Lee," to --Ki Nam Lee,--.

In Column 1 (page 2, item (56)) at Line 31, Under Other Publications, change "DTrKA"," to --TrkA",--.

In the Specification

In Column 1 at Line 22 (approx.), change "neutrophin" to --neurotrophin--.

In Column 1 at Line 43, change "marious" to --various--.

In Column 2 at Line 16, change "neutrophin" to --neurotrophin--.

In Column 2 at Line 25, change "Medisine" to --Medicine--.

In Column 3 at Line 18, change "heterocylic" to --heterocyclic--.

In Column 3 at Line 42, change "heterocylic" to --heterocyclic--.

In Column 3 at Line 65, change "heterocylic" to --heterocyclic--.

In Column 4 at Line 21, change "heterocylic" to --heterocyclic--.

In Column 4 at Line 47 (approx.), change "heterocylic" to --heterocyclic--.

Signed and Sealed this
Twenty-eighth Day of August, 2018

Andrei Iancu
*Director of the United States Patent and Trademark Office*

CERTIFICATE OF CORRECTION (continued)

In Column 12 at Line 14, change "undeconate" to --undecanoate--.

In Column 15 at Lines 64-65, change "sulphydryl" to --sulfhydryl--.

In Column 16 at Line 48, change "heterocylic" to --heterocyclic--.

In Column 17 at Line 8, change "heterocylic" to --heterocyclic--.

In Column 38 at Line 7, change "Formulated" to --formulated--.

In Column 38 at Line 37, change "admininstering" to --administering--.

In Column 39 at Line 63, change "epidophyllotoxins; antineopiastic" to --epipodophyllotoxins; antineoplastic--.

In Column 41 at Line 12, change "epidophyllotoxins;'" to --epipodophyllotoxins;--.

In Column 42 at Line 5, change "epidophyllotoxins;'" to --epipodophyllotoxins;--.

In Column 44 at Line 15 (approx.), change "epidophyllotoxins;'" to --epipodophyllotoxins;--.

In Column 46 at Line 50, change "epidophyllotoxins;'" to --epipodophyllotoxins;--.

In Column 48 at Line 43, change "epidophyllotoxins;'" to --epipodophyllotoxins;--.

In Column 50 at Lines 43-51 (approx.), should read -- 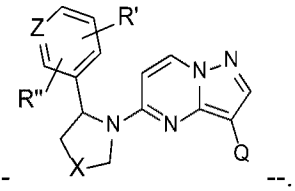 --.

In Column 87 at Line 12 (approx.), after "[Mh$^+$]" add --.--.

In Column 91 at Line 16, change "predipitated" to --precipitated--.

In Column 104 at Line 67, after "[Mh$^+$]" add --.--.

In Column 120 at Line 13 (approx.), change "(R)—N" to --(R)-N--.

In Column 120 at Line 40 (approx.), change "benzoly" to --benzoyl--.

In Column 120 at Line 46 (approx.), change "(R)—N" to --(R)-N--.

In Column 140 at Line 59 (approx.), change "N-iodosuccinamide" to --N-iodosuccinimide--.

In Column 145 at Line 25 (approx.), change "of of" to --of--.

CERTIFICATE OF CORRECTION (continued)
U.S. Pat. No. 9,701,681 B2

In Column 145 at Line 63, change "N-dimethylethanamine" to --N-dimethylmethanamine--.

In Column 152 at Line 51 (approx.), change "-11-" to -- -1- --.

In Column 174 at Lines 27-28 (approx.), change "2-methoxyethanamine" to --2-methoxyethan-1-amine--.

In Column 184 at Line 37 (approx.), after "[MH$^+$]" add --.--.

In Column 188 at Line 24, change "µl g" to --µl--.

In Column 189 at Line 7, after "[MH$^+$]" insert --.--.

In Column 192 at Line 44, change "dimethylsulfoxide(DMSO)" to --dimethyl sulfoxide (DMSO)--.

In Column 192 at Lines 60-67, replace the paragraph starting with "The protein kinase assay" with --The protein kinase assays were performed for Chemical Compounds 1-61 at 30°C for 1 hr in a final volume of 25 µL according to the following assay reaction recipe: 10 µL of diluted kinase (final concentrations are 0.4 ng/ul of TrKA, 0.5 ng/ul of TrKB and 3 ng/ul of TrKC, respectively), 5 µL of 1 ug/ul stock solution of poly(glu, Tyr), 5 µL of compounds or assay buffer, 5 µL of ATP (125 µM stock solution).--.

In Column 193 at Lines 1-10, replace the paragraph starting with "The assay was started by" with --The assay was started by incubating the reaction mixture in a 96-well plate at 30°C for 1 hr. After the incubation, the assay was terminated by the addition of 25 µL of ADP-Glo reagent. The 96-well plate was shaken and then incubated at ambient temperature for 1 hr. Then 50 µL of Kinase Detection Reagent was added, the 96-well plate was shaken and then incubated for further 30 min at ambient temperature. The 96-well reaction plate was then read on an Enspire plate reader. The IC50 values were derived through a curve fitting using SigmaPlot.--.

In the Claims

In Column 225 at Line 38 (approx.), in Claim 1, change "heterocylic" to --heterocyclic--.

In Column 225 at Line 67, in Claim 1, change "heterocylic" to --heterocyclic--.

In Column 226 at Line 30 (approx.), in Claim 6, change "heterocylic" to --heterocyclic--.